US010173971B2

(12) United States Patent
Yao et al.

(10) Patent No.: US 10,173,971 B2
(45) Date of Patent: *Jan. 8, 2019

(54) PICOLINAMIDES WITH FUNGICIDAL ACTIVITY

(71) Applicant: DOW AGROSCIENCES LLC, Indianapolis, IN (US)

(72) Inventors: Chenglin Yao, Indianapolis, IN (US); Kevin G. Meyer, Indianapolis, IN (US); Yu Lu, Indianapolis, IN (US); Brian A. Loy, Indianapolis, IN (US); David M. Jones, Indianapolis, IN (US); Ronald J. Heemstra, Indianapolis, IN (US); Jeffrey B. Epp, Indianapolis, IN (US); Johnathan E. DeLorbe, Indianapolis, IN (US); Kyle A. DeKorver, Indianapolis, IN (US); John F. Daeuble, Sr., Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/540,811

(22) PCT Filed: Dec. 21, 2015

(86) PCT No.: PCT/US2015/067199
§ 371 (c)(1),
(2) Date: Jun. 29, 2017

(87) PCT Pub. No.: WO2016/109300
PCT Pub. Date: Jul. 7, 2016

(65) Prior Publication Data
US 2017/0369421 A1   Dec. 28, 2017

Related U.S. Application Data

(60) Provisional application No. 62/098,089, filed on Dec. 30, 2014, provisional application No. 62/098,097, filed on Dec. 30, 2014, provisional application No. 62/255,144, filed on Nov. 13, 2015, provisional application No. 62/255,152, filed on Nov. 13, 2015.

(51) Int. Cl.
| | |
|---|---|
| C07C 271/22 | (2006.01) |
| C07D 213/81 | (2006.01) |
| C07C 229/36 | (2006.01) |
| A01N 43/40 | (2006.01) |
| A01N 37/44 | (2006.01) |
| A01N 47/12 | (2006.01) |
| C07C 229/08 | (2006.01) |
| C07C 229/22 | (2006.01) |

(52) U.S. Cl.
CPC .......... *C07C 271/22* (2013.01); *A01N 37/44* (2013.01); *A01N 43/40* (2013.01); *A01N 47/12* (2013.01); *C07C 229/08* (2013.01); *C07C 229/22* (2013.01); *C07C 229/36* (2013.01); *C07D 213/81* (2013.01); *C07B 2200/07* (2013.01); *C07C 2601/02* (2017.05)

(58) Field of Classification Search
CPC ... C07C 229/36; C07C 271/22; C07C 229/22; C07C 229/08; C07C 2601/02; A01N 43/40; A01N 47/12; A01N 37/44; C07D 213/81; C07B 2200/07
See application file for complete search history.

(56) References Cited

U.S. PATENT DOCUMENTS

| | | | |
|---|---|---|---|
| 4,051,173 | A | 9/1977 | Schact et al. |
| 4,588,735 | A | 5/1986 | Spatz |
| 5,342,835 | A | 8/1994 | Pepin et al. |
| 5,401,871 | A | 3/1995 | Feldmann-Krane et al. |
| 5,475,132 | A | 12/1995 | Pepin et al. |
| 5,563,165 | A | 10/1996 | Talley |
| 5,760,068 | A | 6/1998 | Talley |
| 5,852,042 | A | 12/1998 | Jakobi et al. |
| 6,355,660 | B1 | 3/2002 | Ricks et al. |
| 6,410,572 | B1 | 6/2002 | Schelberger et al. |
| 6,436,421 | B1 | 8/2002 | Schindler et al. |
| 6,521,622 | B1 | 2/2003 | Ricks et al. |
| 6,706,740 | B2 | 3/2004 | Ricks et al. |
| 6,861,390 | B2 | 3/2005 | Meyer et al. |
| 6,903,219 | B2 | 6/2005 | Niyaz et al. |

(Continued)

FOREIGN PATENT DOCUMENTS

| | | |
|---|---|---|
| CL | 2015001862 | 10/2015 |
| CN | 101530104 | 9/2009 |

(Continued)

OTHER PUBLICATIONS

Anonymous, Synergistic Fungicidal Composition of Heterocyclic Aromatic Amides and Triazoles, ip.com Journal, ip.com, Electronic Publication, West Henrietta, NY, US, Jul. 2004, 11 pages.

(Continued)

*Primary Examiner* — John M Mauro
(74) *Attorney, Agent, or Firm* — Faegre Baker Daniels LLP

(57) ABSTRACT

The invention relates to picolinamides of Formula I and their use as fungicides.

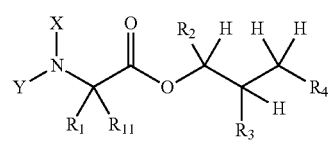

19 Claims, No Drawings

(56) References Cited

U.S. PATENT DOCUMENTS

| | | |
|---|---|---|
| 6,916,932 B2 | 7/2005 | Meyer et al. |
| 6,927,225 B2 | 8/2005 | Ricks et al. |
| 6,953,807 B2 | 10/2005 | Hutin |
| 7,034,035 B2 | 4/2006 | Ricks et al. |
| 7,183,278 B1 | 2/2007 | Imamura et al. |
| 7,241,804 B1 | 7/2007 | Hockenberry et al. |
| 7,250,389 B1 | 7/2007 | Sakanaka et al. |
| RE39,991 E | 1/2008 | Ricks et al. |
| 7,442,672 B2 | 12/2008 | Muller et al. |
| 7,459,581 B2 | 12/2008 | Derrer et al. |
| 7,560,565 B2 | 7/2009 | Bacque et al. |
| 7,927,617 B2 | 4/2011 | Koltzenburg |
| 8,008,231 B2 | 8/2011 | Leatherman |
| 8,153,819 B2 | 4/2012 | Dietz |
| 8,236,962 B2 | 8/2012 | Hoekstra et al. |
| 8,349,877 B2 | 1/2013 | Brix et al. |
| 8,415,274 B2 | 4/2013 | Wachendorff-Neumann et al. |
| 8,465,562 B2 | 6/2013 | Chen |
| 8,470,840 B2 | 6/2013 | Klittich et al. |
| 8,476,193 B2 | 7/2013 | Keeney et al. |
| 8,580,959 B2 | 11/2013 | Devasthale et al. |
| 8,586,550 B2 | 11/2013 | Lee et al. |
| 8,604,215 B2 | 12/2013 | Phiasivongsa et al. |
| 8,785,479 B2 | 7/2014 | Meyer et al. |
| 8,835,462 B2 | 9/2014 | Meyer et al. |
| 8,883,811 B2 | 11/2014 | Owen et al. |
| 8,916,579 B2 | 12/2014 | Boebel et al. |
| 9,006,259 B2 | 4/2015 | Boebel et al. |
| 9,084,418 B2 | 7/2015 | Ehr et al. |
| 9,131,690 B2 | 9/2015 | Meyer et al. |
| 9,144,239 B2 | 9/2015 | Meyer et al. |
| 9,155,305 B2 | 10/2015 | Gary |
| 9,156,816 B2 | 10/2015 | Ito et al. |
| 9,179,674 B2 | 11/2015 | Martin et al. |
| 9,185,911 B2 | 11/2015 | Inami et al. |
| 9,198,419 B2 | 12/2015 | Owen et al. |
| 9,247,741 B2 | 2/2016 | DeLorbe et al. |
| 9,265,253 B2 | 2/2016 | Li et al. |
| 9,265,255 B2 | 2/2016 | Funke |
| 9,271,496 B2 | 3/2016 | Kemmitt |
| 9,271,497 B2 | 3/2016 | Lorsbach |
| 9,414,596 B2 | 8/2016 | Hoekstra et al. |
| 9,439,422 B2 | 9/2016 | Martin et al. |
| 9,482,661 B2 | 11/2016 | Ross |
| 9,549,555 B2 | 1/2017 | DeLorbe et al. |
| 9,549,556 B2 | 1/2017 | DeKorver et al. |
| 9,629,365 B2 | 4/2017 | Li et al. |
| 9,681,664 B2 | 6/2017 | LaLonde et al. |
| 9,686,984 B2 | 6/2017 | DeKorver et al. |
| 9,700,047 B2 | 7/2017 | Lu |
| 9,750,248 B2 | 9/2017 | Ouimette et al. |
| 9,828,408 B2 | 11/2017 | Kalayanov |
| 9,840,475 B2 | 12/2017 | Lorsbach |
| 9,936,697 B2 | 4/2018 | Hopkins |
| 9,955,690 B2 | 5/2018 | Owen |
| 9,955,691 B2 | 5/2018 | Boebel |
| 9,974,304 B2 | 5/2018 | DeKorver |
| 2002/0119979 A1 | 8/2002 | Degenhardt et al. |
| 2002/0177578 A1 | 11/2002 | Ricks et al. |
| 2003/0018052 A1 | 1/2003 | Ricks et al. |
| 2003/0022902 A1 | 1/2003 | Ricks et al. |
| 2003/0022903 A1 | 1/2003 | Ricks et al. |
| 2005/0239873 A1 | 10/2005 | Hockenbery et al. |
| 2006/0167281 A1 | 7/2006 | Meijer |
| 2007/0010401 A1 | 1/2007 | Noon |
| 2007/0066629 A1 | 3/2007 | Tormo i Blasco et al. |
| 2009/0203770 A1 | 8/2009 | Hockenberry et al. |
| 2009/0306142 A1 | 12/2009 | Carson et al. |
| 2010/0016163 A1 | 1/2010 | Keiper et al. |
| 2011/0070278 A1 | 3/2011 | Lopez |
| 2011/0082162 A1 | 4/2011 | Lorsbach et al. |
| 2012/0245031 A1 | 9/2012 | Gewehr et al. |
| 2013/0296372 A1 | 11/2013 | Owen et al. |
| 2014/0051678 A1 | 2/2014 | Clement-Schatlo et al. |
| 2014/0128411 A1 | 5/2014 | Ogawa et al. |
| 2014/0187587 A1 | 7/2014 | Ouimette et al. |
| 2014/0357713 A1 | 12/2014 | Damaj et al. |
| 2015/0018374 A1 | 1/2015 | Taggi et al. |
| 2015/0065529 A1 | 3/2015 | Owen et al. |
| 2015/0181868 A1 | 7/2015 | DeKorver et al. |
| 2015/0289508 A1 | 10/2015 | Meyer et al. |
| 2015/0322051 A1 | 11/2015 | Lu et al. |
| 2016/0007601 A1 | 1/2016 | Boebel et al. |
| 2016/0037774 A1 | 2/2016 | Schulz |
| 2016/0183526 A1 | 6/2016 | Hopkins et al. |
| 2016/0183527 A1 | 6/2016 | Hopkins et al. |
| 2016/0183528 A1 | 6/2016 | Hopkins et al. |
| 2017/0037541 A1 | 2/2017 | Hoshi et al. |
| 2017/0183324 A1 | 6/2017 | Li et al. |
| 2017/0360038 A1 | 6/2017 | Yao |
| 2017/0273303 A1 | 9/2017 | DeKorver et al. |
| 2017/0273306 A1 | 9/2017 | LaLonde et al. |
| 2017/0290333 A1 | 10/2017 | Bravo-Altamirano et al. |
| 2017/0295792 A1 | 10/2017 | Bravo-Altamirano et al. |
| 2018/0000080 A1 | 1/2018 | Buchan |
| 2018/0000084 A1 | 1/2018 | Yao |
| 2018/0000085 A1 | 1/2018 | Bravo-Altamirano et al. |
| 2018/0002288 A1 | 1/2018 | Buchan |
| 2018/0002319 A1 | 1/2018 | Wilmot |

FOREIGN PATENT DOCUMENTS

| | | |
|---|---|---|
| EP | 3141118 | 9/2015 |
| FR | 2649699 | 1/1991 |
| JP | 19940026884 | 9/1995 |
| JP | 1998053583 | 2/1998 |
| JP | H10-045747 | 2/1998 |
| WO | 1996010016 | 4/1996 |
| WO | 199637472 | 11/1996 |
| WO | 1997019908 | 6/1997 |
| WO | 199741103 | 11/1997 |
| WO | 1998018751 | 5/1998 |
| WO | 1999011127 | 11/1999 |
| WO | 2000076979 | 12/2000 |
| WO | 200114339 | 3/2001 |
| WO | 2005121069 | 12/2005 |
| WO | 2008079387 | 7/2008 |
| WO | 2012016989 | 2/2012 |
| WO | 2012020777 | 2/2012 |
| WO | 2014105844 | 7/2014 |
| WO | 2016007525 | 1/2016 |
| WO | 2016109288 | 7/2016 |
| WO | 2016109289 | 7/2016 |
| WO | 2016109290 | 7/2016 |
| WO | 2016109291 | 7/2016 |
| WO | 2016109301 | 7/2016 |
| WO | 2016109302 | 7/2016 |
| WO | 2016109303 | 7/2016 |
| WO | 2016109304 | 7/2016 |
| WO | 2016109305 | 7/2016 |
| WO | 2015005355 | 3/2017 |

OTHER PUBLICATIONS

Backman, P., Fungicide Formulation: Relationship to Biological Activity, Ann. Rev. Phytopathol, 1978, 16, pp. 211-237.

BASF New Fungicide Xemium Got Full Approval in EU, Agronews, Jul. 18, 2012 [retrieved on Apr. 2, 2014]. Retrieved from the Internet: ,URL:http://news.agropages.com/News/NewsDetail---7386.htm, 1 page.

Bolton, M. et al., "Wheat leaf rust caused by Puccinia triticina," Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf.

Davari, M. et al. "Quantum Chemical Investigation of Intramolecular Thione-Thiol Tautomerism of 1, 2, 4-triazole-3-thione and its disubstituted derivatives," Journal of Molecular Modeling, Sep. 2009, 16(5), pp. 841-855.

(56) References Cited

OTHER PUBLICATIONS

FRAC Code List: Fungicides Sorted by Mode of Action (including FRAC Code numbering), Fungicide Resistance Action Committee, Dec. 2008, 10 pages.
Fungicidal Mixtures, IP.com Prior Art Database Technical Disclosure, (Jul. 5, 2005), XP055073888, DOI: http://ip.com/pdf/ipcompad/IPCOM000126160D.pdf, 12 pages.
Gisi, U., "Synergistic Interaction of Fungicides in Mixtures," The American Phytopathological Society, vol. 86, No. 11, 1996, pp. 1273-1279.
Hu, Z. et al., "Synthesis of Novel Analogues of Antimycin A3," Tetrahedron Letters 49 (2008), pp. 5192-5195.
Huang, C. et al., "Synergistic Interactions between Chitinase ChiCW and Fungicides Against Plant Fungal Pathogens," J. Microbiol. Biotechnol., 2008, 18(4), pp. 784-787.
Kissling, E., "Crop Protection Pipeline Value Jumps to Euro 2.4 Billion," BASF SE, Mar. 10, 2011 [retrieved on Apr. 4, 2014], Retrieved from the internet: ,URL:http://agro.basf.com/agri/AP-Internet/en/content/news_room/news/basf-crop-protection-pipeline-value, 4 pages.
Koyanagi, T. et al., "Bioisoterism in Agrochemicals," Synthesis and Chemistry of Agrochemicals IV; Baker, D. et al., ACS Symposium Series; American Chemical Society: Washington, D.C., 1995, pp. 15-24.
Latin, R., et al, "Re-Examining Fungicide Synergism for Dollar Spot Control," GCM, Jul. 2008, pp. 84-87.
Jeki, M., et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-643.
O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals," Applied and Environmental Microbiology, vol. 77, No. 4, Feb. 2011, pp. 1460-1465.
PubChem: Open Chemistry Database, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>, 5 pages.
Science for a Better Life, Bayer CropScience "Positioned for Growth", Jun. 2008, 22 pages.
Calcium Dodecyl Benzene Sulfonate, CAS 26264-06-2, (http://www.hichem.com/product/showproduct.php?id=334639) Mar. 28, 2013, 4 pages.
Tani, K. et al., The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from *Streptomyces* sp. 517-02," Bioorganic & Medicinal Chemistry Letters, vol. 15, No. 8, 2005, pp. 2011-2014.
Usuki, Y. et al., Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruiticola and Botrytis cinerea," 1987, Plant Disease, vol. 71, No. 4, pp. 316-319.
Written Opinion and Search Report for PCT Patent Application No. PCT/US2015/067199 dated Mar. 11, 2016, 9 pages.
Guseynov et al: "Study of the reaction of aminoacetic acid with dihydric alcohols and production of epoxy esters" Chemical Problems, 2009 (1), pp. 188-190. English Machine Translation attached.
Goellner et al. "*Phakopsora pachyrhizi*, the causal agent of Asian soybean rust." Molecular Plant Pathology, vol. 11, No. 2, pp. 169-177 (2010).
Fujita T, Ed. "Quantitative structure-activity analysis and database-aided bioisosteric structural transformation procedure as methodologies of agrochemical design"; Classical and Three Dimensional QSAR in Agrochemistry, American Chemical Society Symposium Series, Washington, D.C. vol. 606, pp. 13-34 (1995).
Patani et al. "Biosterism: A rational approach in drug design". Chemical Reviews, vol. 96, No. 8, pp. 3147-3176 (1996).
Kendall, S. et al. "Changes in sensitivity to DMI fungicides in Rhynchosporium secalis". Crop Protection, vol. 12, No. 5, pp. 357-362 (1993).
Cooke et al. "The effect of fungicide programmes based on epoxiconazole on the control and DMI sensitivity of Rhynchosporium secalis in winter barley." Crop Protection, vol. 23, No. 5, pp. 393-406 (2004).
Shimano et al. "Total synthesis of the antifungal dilactones UK-2A and UK-3A: The determination of their relative and absolute configurations, analog synthesis and antifungal activities". Tetrahedron, vol. 54, pp. 12745-12774 (1998).
Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012). (Submitted in 3 parts due to size limitations).
Lippard, S. "Chemical Synthesis:The Art of Chemistry". Nature, vol. 416, p. 587 (2002).
Hanafi et al. "UK2A, B, C, and D, Novel Antifungal Antibiotics from *Streptomyces* sp 517-02 II. Structural Elucidation." The Journal of Antibiotics, vol. 49, Issue 12, pp. 1226-1231 (1996).
Shibata et al. "UK1, A Novel Cytotoxic Metabolite from *Streptomyces* sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Ueki, M., et al., "UK-1, A Novel Cytotoxic Metabolite from *Streptomyces* sp. 517-02 I. Taxonomy, Fermentation, Isolation, Physico-chemical and Biological Properties." The Journal of Antibiotics, vol. 46, No. 7, pp. 1089-1094 (1993).
Ueki et al. "UK-3A, A Novel Antifungal Antibiotic from *Streptomyces* sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from *Streptomyces* sp. 517-02". The Journal of Antibiotics, vol. 50, Issue 12, pp. 1052-1057 (1997).
Stephenson, G., et al. "Glossary of terms relating to pesticides". Pure and Applied Chemistry, vol. 78, No. 11, pp. 2075-2154, International Union of Pure and Applied Chemistry (2006).
Chitwood, D. "Nematicides". Encyclopedia of Agrochemicals (3), pp. 1104-1115, John Wiley & Sons, New York, NY, http://naldc.nal.usda.gov/download/43874/PDF (2003).
International Searching Authority, International Search Report for PCT/US14/058070, dated Dec. 15, 2014, 4 pages.
International Searching Authority, Written Opinion for PCT/US14/058070, dated Dec. 15, 2014, 5 pages.
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report and Written Opinion for PCT/US1528407 dated Aug. 5, 2015, 8 pages.
International Searching Authority, International Search Report and Written Opinion for PCT/US1539407 dated Sep. 30, 2015, 9 pages.
International Searching Authority, International Search Report and Written Opinion for PCT/US1539409 dated Oct. 5, 2015, 10 pages.
International Searching Authority, International Search Report and Written Opinion for PCT/US1544383 dated Mar. 16, 2016, 11 pages.

(56) References Cited

OTHER PUBLICATIONS

International Searching Authority, International Search Report and Written Opinion for PCT/US1567111 dated Mar. 11, 2016, 11 pages.
International Searching Authority, International Search Report and Written Opinion for PCT/US1567113 dated Mar. 11, 2016, 10 pages.
International Searching Authority, International Search Report and Written Opinion for PCT/US1567116 dated Mar. 7, 2016, 8 pages.
International Searching Authority, International Search Report and Written Opinion for PCT/US1567199 dated Mar. 11, 2016, 9 pages.
International Searching Authority, International Search Report and Written Opinion for PCT/US1567200 dated Mar. 10, 2016, 10 pages.
International Searching Authority, International Search Report and Written Opinion for PCT/US1567201 dated Mar. 11, 2016, 8 pages.
International Searching Authority, International Search Report and Written Opinion for PCT/US1567204 dated Mar. 7, 2016, 10 pages.
International Searching Authority, International Search Report and Written Opinion for PCT/US1567206 dated Mar. 7, 2016, 8 pages.
International Searching Authority, International Search Report and Written Opinion for PCT/US1567207 dated Mar. 11, 2016, 12 pages.
International Searching Authority, International Search Report and Written Opinion for PCT/US2013039726 dated Sep. 17, 2013, 9 pages.
International Searching Authority, International Search Report and Written Opinion for PCT/US2013039735 dated Oct. 18, 2013, 8 pages.
International Searching Authority, International Search Report and Written Opinion for PCT/US2013077472 dated Apr. 16, 2014, 9 pages.
International Searching Authority, International Search Report and Written Opinion for PCT/US2014071692 dated Apr. 20, 2015, 6 pages.
International Searching Authority, International Search Report and Written Opinion for PCT/US2015/067115, dated Mar. 11, 2016, 6 pages.
International Searching Authority, International Search Report and Written Opinion for PCT/US2014071695 dated Apr. 17, 2015, 9 pages.
International Searching Authority, International Search Report and Written Opinion for PCT/US2014071699 dated Apr. 20, 2015, 6 pages.
International Searching Authority, International Search Report and Written Opinion for PCT/US2014071700 dated Apr. 17, 2015, 9 pages.
International Searching Authority, International Search Report and Written Opinion for PCT/US2015066760 dated Apr. 14, 2016, 11 pages.
International Searching Authority, International Search Report and Written Opinion for PCT/US2015066764 dated Apr. 28, 2016, 11 pages.
International Searching Authority, International Search Report and Written Opinion for PCT/US20150051598 dated Dec. 6, 2010, 5 pages.
International Searching Authority, International Search Report for PCT/US14/058067, dated Dec. 22, 2014, 4 pages.
International Searching Authority, Written Opinion for PCT/US14/058067, dated Dec. 22, 2014, 5 pages.
International Searching Authority, International Search Report and Written Opinion for PCT/US2013077537, dated Apr. 16, 2014, 11 pages.
International Searching Authority, International Search Report PCT/US2000/021523 dated Jul. 7, 2001, 7 pages.
Database Chemabs Online, Chemical Abstracts Service, Columbus Ohio, US: accession No. CA63:16300d XP002164206 (International Search Report for PCT/US2000/021523).
Cantacuzene, D., "Optimization of the papain catalyzed esterification of amino acids by alcohols and diols," Tetrahedron, vol. 45, Issue 3 (1989), pp. 741-748.
Washburn, W.N., "Identification of a nonbasic melanin hormone receptor 1 antagonist as an antiobesity clinical candidate," Journal of Medicinal Chemistry, 57, 18 (Aug. 28, 2014), pp. 7509-7522.

PICOLINAMIDES WITH FUNGICIDAL ACTIVITY

CROSS REFERENCE TO RELATED APPLICATIONS

The application is a U.S. National Phase filing of International Application No. PCT/US2015/067199, filed Dec. 21, 2015, which claims the benefit of U.S. Provisional Patent Application Ser. No. 62/098,089 filed Dec. 30, 2014, 62/098,097 filed Dec. 30, 2014, 62/255,144 filed Nov. 13, 2015 and 62/255,152 filed Nov. 13, 2015, the disclosures of which are hereby expressly incorporated by reference herein in their entirety.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to picolinamides and their use as fungicides. The compounds of the present disclosure may offer protection against ascomycetes, basidiomycetes, deuteromycetes and oomycetes.

One embodiment of the present disclosure may include compounds of Formula I:

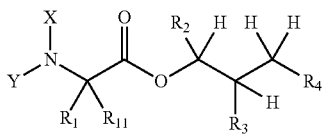

I

X is hydrogen or $C(O)R_5$;
Y is hydrogen, $C(O)R_5$, or Q;
Q is

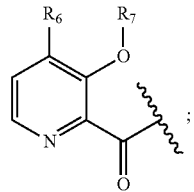

$R_1$ is $CH_2OCH_3$, or hydrogen or alkyl, where alkyl is optionally substituted with 0, 1 or multiple $R_8$;
$R_2$ is methyl;
$R_3$ is chosen from $C(O)OCH_3$ or alkyl, alkenyl, or aryl, each optionally substituted with 0, 1 or multiple $R_8$;
$R_4$ is chosen from alkyl or aryl, each optionally substituted with 0, 1 or multiple $R_8$;
$R_5$ is alkoxy, optionally substituted with 0, 1, or multiple $R_8$;
$R_6$ is chosen from hydrogen or alkoxy, each optionally substituted with 0, 1, or multiple $R_8$;
$R_7$ is chosen from hydrogen, $—C(O)R_9$, or $—CH_2OC(O)R_9$;
$R_8$ is chosen from hydrogen, alkyl, aryl, halo, alkenyl, or phenoxy, each optionally substituted with 0, 1, or multiple $R_{10}$;
$R_9$ is chosen from alkyl, alkoxy, or aryl, each optionally substituted with 0, 1, or multiple $R_8$;
$R_{10}$ is chosen from alkyl, aryl, halo, haloalkyl, haloaryl, alkenyl, or alkoxy;
$R_{11}$ is chosen from hydrogen or methyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a saturated branched, unbranched, or cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl and the like.

The term "aryl" refers to any aromatic, mono- or bi-cyclic, containing 0 heteroatoms.

The term "heterocycle" refers to any aromatic or non-aromatic ring, mono- or bi-cyclic, containing one or more heteroatoms The term "alkoxy" refers to an —OR substituent.

The term "haloalkyl" refers to an alkyl, which is substituted with Cl, F, I, or Br or any combination thereof.

The term "halogen" or "halo" refers to one or more halogen atoms, defined as F, Cl, Br, and I.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same use or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzenesulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila*, *Fusarium oxysporum*, *Gliocladium* spp., *Phlebiopsis gigantea*, *Streptomyces griseoviridis*, *Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)

phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Zymoseptoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Pyricularia oryzae*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Colletotrichum lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m$^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

GENERAL SCHEMES

The following schemes illustrate approaches to generating picolinamide compounds of Formula (I). The following descriptions and examples are provided for illustrative purposes and should not be construed as limiting in terms of substituents or substitution patterns.

Compounds of Formula 1.3, wherein $R_4$ is as originally defined, but not alkoxyaryl, can be prepared according to the methods outlined in Scheme 1, steps a-c. Compounds of Formula 1.1, wherein $R_4$ is as originally defined, but not alkoxyaryl, can be obtained by reaction of the dianion of an ester of Formula 1.0, formed by treatment with lithium diisopropylamide (LDA) at −50° C., with an alkyl halide, such as benzyl bromide, or allyl halide in a solvent such as tetrahydrofuran (THF) at cryogenic temperatures, such as −78° C., as shown in step a. Compounds of Formula 1.2, wherein $R_4$ is alkyl, can be obtained by treating compounds of Formula 1.1, wherein $R_4$ is an alkenyl functionality, with hydrogen gas in the presence of a catalyst, such as palladium on carbon (Pd/C), in a solvent such as ethyl acetate (EtOAc), as shown in step b. Compounds of Formula 1.3, wherein $R_4$ is as originally defined, but not alkoxyaryl, can be prepared from compounds of Formula 1.1, wherein $R_4$ is as defined above, but not alkoxyaryl, and Formula 1.2, wherein $R_4$ is as defined above, but not alkoxyaryl, by treating with an alkylating agent such as 4-methoxybenzyl 2,2,2-trichloroacetimidate, or benzyl 2,2,2-trichloroacetimidate, in the presence of an acid such as camphor sulfonic acid (CSA), or triflic acid, in a solvent such as dichloromethane (DCM), as depicted in step c.

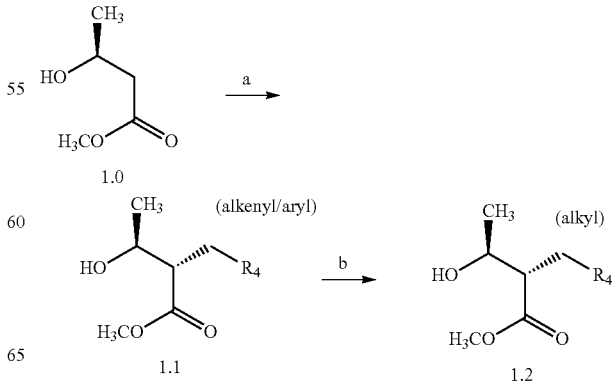

Scheme 1

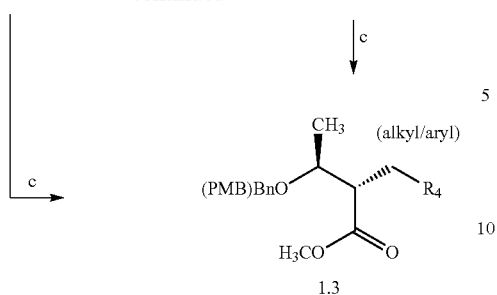

5

10

1.3

Compounds of Formulas 2.2 and 2.3 can be prepared according to the methods outlined in Scheme 2, steps a-b. Compound 2.1 can be obtained by reaction of the dianion of an ester of Formula 2.0, formed by treatment with LDA at −50° C., with alkyl halide such as 4-methoxybenzyl bromide, in a solvent such as THF at cryogenic temperatures such as −78° C., as shown in step a. Compounds of Formulas 2.2 and 2.3 can be prepared from compounds of Formula 2.1, by treating with an alkylating agent such as benzyl 2,2,2-trichloroacetimidate, in the presence of an acid such as triflic acid, in a solvent such as DCM, as depicted in step b.

Scheme 2

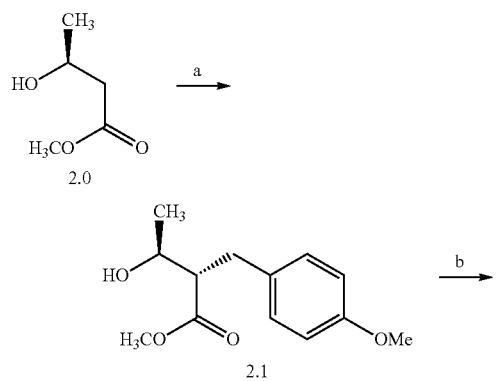

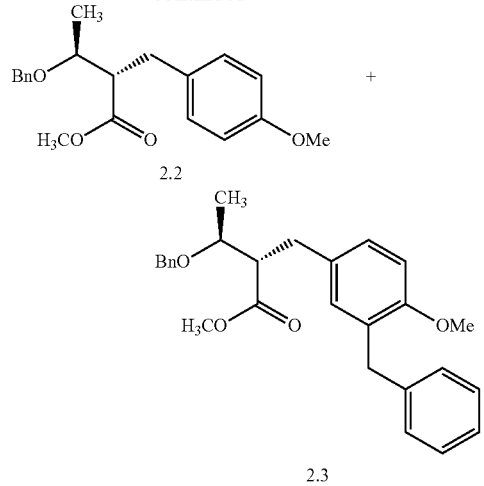

2.2

2.3

Compounds of Formulas 3.2, 3.3, 3.4, and 3.5 wherein $R_4$ is as originally defined, can be prepared according to the methods outlined in Scheme 3, steps a-d. Compounds of Formula 3.1, wherein $R_4$ is as originally defined, can be obtained by the reaction of compounds of the Formula 3.0, wherein $R_4$ is as originally defined, with a reducing agent such as diethylsilane in the presence of a transition metal catalyst such as chlorobis(cyclooctene)iridium(I) dimer in a solvent such as DCM at a temperature such as 0° C., as depicted in step a. Compounds of Formulas 3.2 and 3.3, wherein $R_4$ is as originally defined, can be prepared from compounds of the Formula 3.1, wherein $R_4$ is as originally defined, by treating with vinylmagnesium bromide at cryogenic temperatures such as −78° C. in a solvent such as THF, as shown in step b. Compounds of the Formula 3.4, wherein $R_4$ is as originally defined, can be obtained by a reaction of compounds of the Formula 3.0, wherein $R_4$ is as originally defined, with a reducing agent such as lithium aluminum hydride (LAH) in a solvent such as THF at a temperature of about −78° C. to about 23° C., as shown in step c. Additionally, compounds of Formula 3.0, wherein $R_4$ is as originally defined, can be treated with a nucleophile such as methyllithium in a solvent such as THF at a temperature of about −78° C. to about 23° C., as described is step d, to afford compounds of Formula 3.5, wherein $R_4$ is as originally defined.

Scheme 3

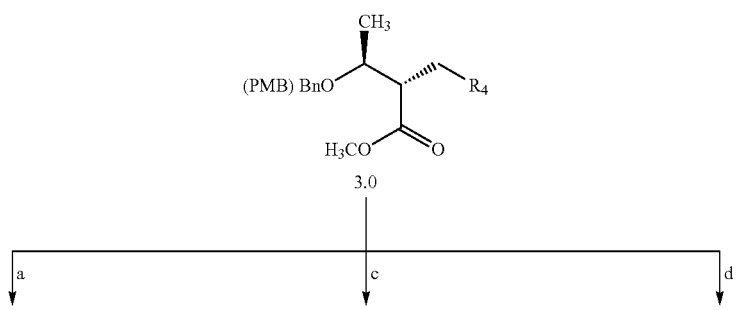

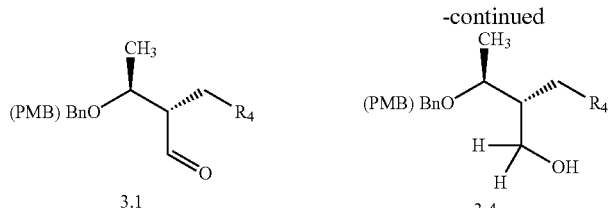
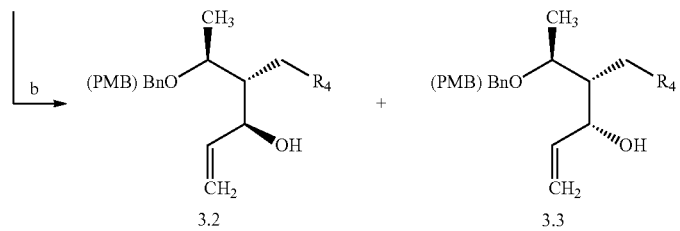

Compounds of Formulas 4.2, 4.4, and 4.7, wherein $R_4$ is as originally defined, $R_8$ is alkyl or aryl, and $R_{10}$ is alkyl, can be prepared according to the methods described in Scheme 4, steps a-g. Compounds of the Formula 4.0 can be treated with a base such as potassium t-butoxide and alkylating agent such as n-propyltosylate, in a solvent such as dimethoxyethane (DME) at a temperature of about 40° C., to afford compounds of Formula 4.1, wherein $R_4$ is as originally described and $R_8$ is alkyl, as depicted in step a. Compounds of Formula 4.2, wherein $R_4$ is as originally described and $R_8$ is alkyl, can be obtained upon treating compounds of the Formula 4.1, wherein $R_4$ is as originally described and $R_8$ is alkyl, with a transition metal catalyst, such as Pd/C, under a hydrogen ($H_2$) atmosphere in a polar solvent such as EtOAc or methanol (MeOH), as shown in step b. Additionally, compounds of the Formula 4.0, wherein $R_4$ is as originally described, can be arylated to provide compounds of the Formula 4.3, wherein $R_4$ is as originally described and $R_8$ is aryl, using a reagent such as tris(o-tolyl) bismuth(V) diacetate in the presence of an amine base such as N,N-dicyclohexyl-N-methylamine and a catalyst such as copper(II) acetate, in a solvent such as toluene at a temperature of about 65° C., as shown in step c. Compounds of Formula 4.4, wherein $R_4$ is as originally described and $R_8$ is aryl, can be obtained via hydrogenation of compounds of Formula 4.3, wherein $R_4$ is as originally described and $R_8$ is aryl, in the presence of a transition metal catalyst, such as Pd/C, under a $H_2$ atmosphere in a polar solvent such as EtOAc or MeOH, as shown in step d. Furthermore, compounds of Formula 4.3, wherein $R_4$ is as originally described and $R_8$ is aryl, can be subjected to ozone ($O_3$) in the presence of an acid scavenger, such as sodium bicarbonate ($NaHCO_3$), and an indicator, such as Sudan III, in a solvent like DCM at a temperature of about −78° C., followed by addition of a reducing agent, such as sodium borohydride, in a solvent such as methanol at a temperature of about −78° C. to about 23° C., to provide compounds of Formula 4.5, wherein $R_4$ is as originally described and $R_8$ is aryl, as shown in step e. Alkylation of compounds of Formula 4.5, wherein $R_4$ is as originally described and $R_8$ is aryl, using a base, such as sodium hydride, and an alkylating agent, such as ethyl iodide, in a solvent such as THF at temperatures from about 0° C. to 23° C., afford compounds of Formula 4.6, wherein $R_4$ is as originally described, $R_8$ is aryl and $R_{10}$ is alkyl, as depicted in step f. Compounds of Formula 4.7, wherein $R_4$ is as originally described, $R_8$ is aryl and $R_{10}$ is alkyl, can be obtained upon treating compounds of the Formula 4.6, wherein $R_4$ is as originally described, $R_8$ is aryl and $R_{10}$ is alkyl, with a 2,3-dichloro-5,6-dicyanoquinone (DDQ) in a solvent such as DCM at a temperature of about 0° C., as shown in step g.

Scheme 4

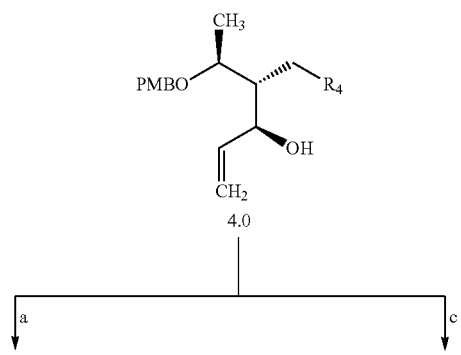

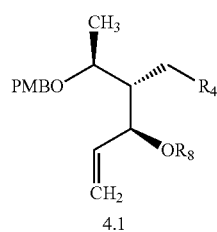
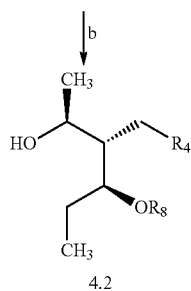
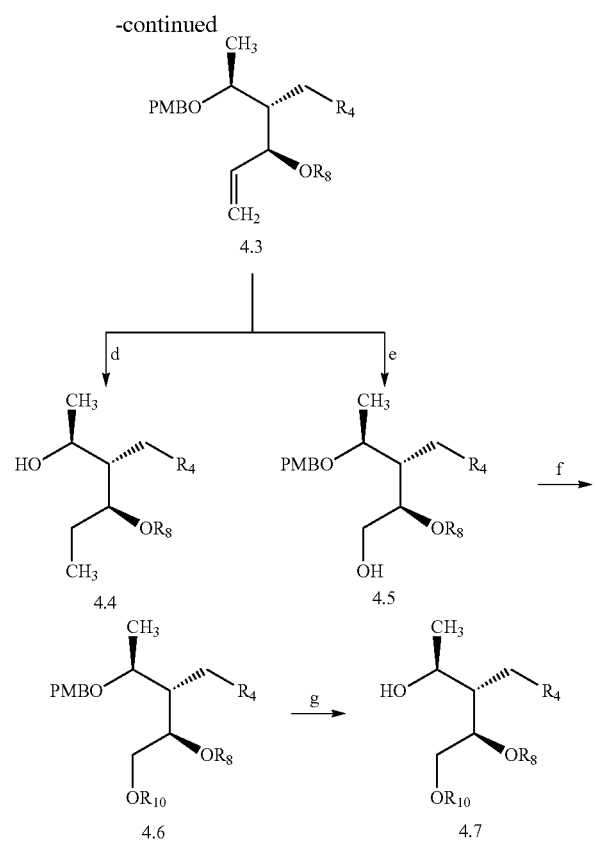

Compounds of Formulas 5.1, 5.2, and 5.3, wherein $R_4$ is as originally defined and $R_8$ is hydrogen or alkyl, and $R_{10}$ is alkyl or aryl, can be prepared according to the methods outlined in Scheme 5, steps a-c. Treatment of compounds of Formula 5.0, wherein $R_4$ is as originally defined and $R_8$ is hydrogen or methyl, with a methylating agent, trimethyloxonium tetrafluoroborate, in the presence of a base, such as 1,8-bis(dimethylamino)naphthalene, in a solvent such as DCM at a temperature of about 0° C. to 23° C., affords compounds of Formula 5.1, wherein $R_4$ is as originally defined, $R_8$ is hydrogen or methyl, and $R_{10}$ is methyl, as shown in step a. Compounds of Formula 5.2, wherein $R_4$ is as originally defined, $R_8$ is hydrogen or methyl, and $R_{10}$ is either alkyl or alkenyl, can be obtained from the reaction between compounds of a Formula 5.0, wherein $R_4$ is as originally defined and $R_8$ is hydrogen or methyl, and an appropriate alkyl or alkenyl halide, such as benzyl bromide or allyl bromide, in the presence of a base, such as sodium hydride, and a catalyst such as tetrabutylammonium iodide, in a solvent such as DMF at a temperatures of about 0° C. to 23° C., as shown in step b. Additionally, compounds of Formula 5.0, wherein $R_4$ is as originally defined and $R_8$ is hydrogen or methyl, can be treated with a base, such as sodium hydride or potassium t-butoxide, and an aryl fluoride such as 1,2,4-trifluorobenzene, with or without a crown ether such as 15-crown-5, in a solvent such as DMF at temperatures of about 0° C. to about 70° C., to provide compounds of Formula 5.3, wherein $R_4$ is as originally defined, $R_8$ is hydrogen or methyl, and $R_{10}$ is aryl, as shown in step c.

Scheme 5

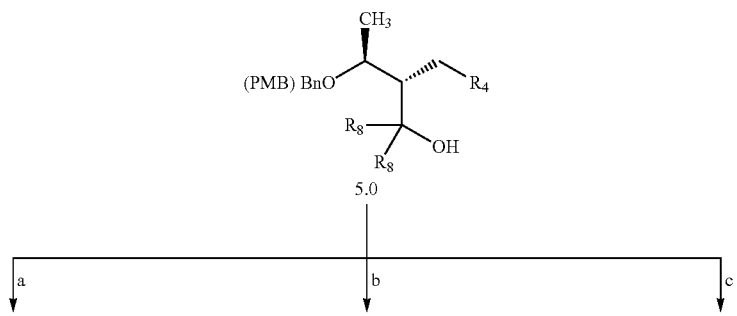

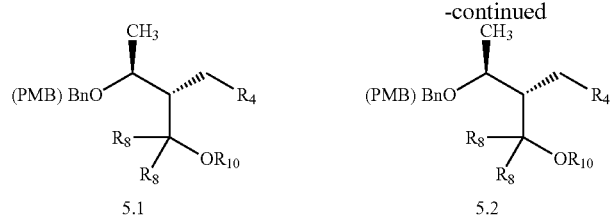
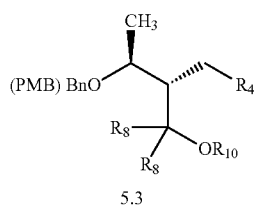

Compounds of Formula 6.2, wherein $R_4$ is as originally defined and $R_8$ is alkyl or aryl, can be prepared according to the methods depicted in Scheme 6, steps a-c. Hydrogenolysis of compounds of Formula 6.0, wherein $R_4$ is as originally defined and $R_8$ is aryl, alkenyl, or alkyl, but not benzyl, in the presence of a catalyst such as Pd/C under an atmosphere of $H_2$ in a polar solvent such as EtOAc or EtOH, or with an alternate source of hydrogen, such as cyclohexene, in a polar solvent such as EtOH, provides products of Formula 6.2, wherein $R_4$ is as originally defined and $R_8$ is alkyl or aryl, but not alkenyl, benzyl or aryl chloride, as shown in step a. Compounds of Formula 6.1, wherein $R_4$ is as originally defined and $R_8$ is alkyl, alkenyl, or aryl, but not benzyl, upon treatment with a catalyst such as Pd/C under an atmosphere of $H_2$ in a polar solvent such as EtOAc or EtOH, afford compounds of Formula 6.2, wherein $R_4$ is as originally defined and $R_8$ is alkyl or aryl, but not alkenyl, benzyl or aryl chloride, as shown in step b. Alternatively, compounds of Formula 6.2, wherein $R_4$ is as originally defined and $R_8$ is alkyl, benzyl or aryl, may be obtained by treating compounds of Formula 6.1, where $R_4$ is as originally defined and $R_8$ is alkyl, benzyl or aryl, with an oxidant, such as ceric ammonium nitrate (CAN) in a solvent such as wet acetonitrile at a temperature of about 0° C. to 23° C., as shown in step c.

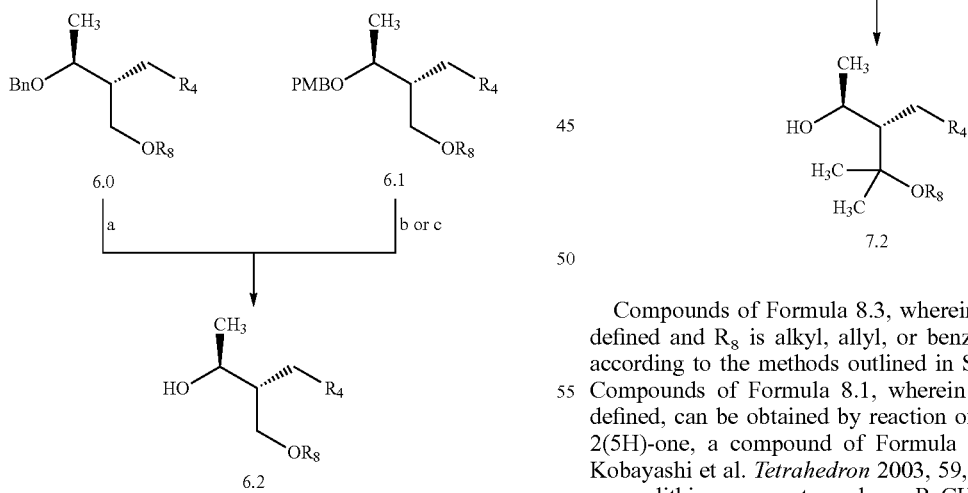

Compounds of Formula 7.2, wherein $R_4$ is as originally defined and $R_8$ is alkyl or aryl, can be prepared according to the methods depicted in Scheme 7, steps a-c. Hydrogenolysis of compounds of Formula 7.0, wherein $R_4$ is as originally defined and $R_8$ is aryl, alkenyl, or alkyl, but not benzyl, in the presence of a catalyst such as Pd/C under an atmosphere of $H_2$ in a polar solvent such as EtOAc or EtOH, provides products of Formula 7.2, wherein $R_4$ is as originally defined and $R_8$ is alkyl or aryl, but not alkenyl, benzyl or aryl chloride, as shown in step a. Compounds of Formula 7.1, wherein $R_4$ is as originally defined and $R_8$ is alkyl or alkenyl, but not benzyl, upon treatment with a catalyst such as Pd/C, under an atmosphere of $H_2$ in a polar solvent such as EtOAc or EtOH, afford compounds of Formula 7.2, wherein $R_4$ is as originally defined and $R_8$ is alkyl or aryl, but not alkenyl or benzyl, as shown in step b. Alternatively, compounds of Formula 7.2, wherein $R_4$ is as originally defined and $R_8$ is alkyl, alkenyl, benzyl or aryl, may be obtained by treating compounds of Formula 7.1, where $R_4$ is as originally defined and $R_8$ is alkyl, alkenyl, benzyl or aryl, with an oxidant, such as CAN, in a solvent such as wet acetonitrile at a temperature of about 0° C. to 23° C., as shown in step c.

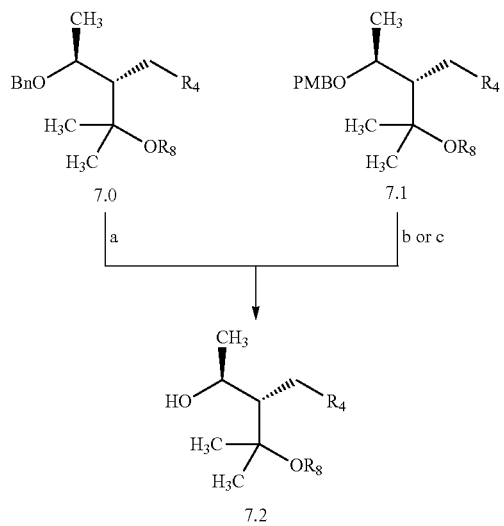

Compounds of Formula 8.3, wherein $R_4$ is as originally defined and $R_8$ is alkyl, allyl, or benzyl, can be prepared according to the methods outlined in Scheme 8, steps a-c. Compounds of Formula 8.1, wherein $R_4$ is as originally defined, can be obtained by reaction of (S)-5-methylfuran-2(5H)-one, a compound of Formula 8.0 (prepared as in Kobayashi et al. *Tetrahedron* 2003, 59, 9743-9758) with an organolithium reagent, such as $R_4CH_2Li$, or a Grignard reagent, such as $R_4CH_2MgX$, wherein $R_4$ is as originally defined and X is bromide or chloride, and copper (I) iodide in a solvent such as THF at cryogenic temperatures such as −78° C., as shown in step a. Compounds of Formula 8.2, wherein $R_4$ is as originally defined and $R_8$ is alkyl, alkenyl, or benzyl, can be obtained by treating compounds of Formula 8.1, wherein $R_4$ is as originally defined, with lithium diisopropylamide (LDA), which was generated in situ from n-butyllithium (n-BuLi) and diisopropylamine (i-Pr$_2$NH) at −20° C., followed by reacting with alkyl, allyl, or benzyl bromide or alkyl, allyl, or benzyl chloride, such as R$_8$Br, wherein R$_8$ is alkyl, allyl, or benzyl, in a solvent such as THF from −78° C. to ambient temperature, as shown in step b. Compounds of Formula 8.3, wherein R$_4$ is as originally defined and R$_8$ is alkyl, allyl, or benzyl, can be prepared from compounds of Formula 8.2, wherein R$_4$ is as originally defined and R$_8$ is alkyl, allyl, or benzyl, by treating with a reducing agent such as LAH, in a solvent such as THF from 0° C. to ambient temperature, as depicted in step c.

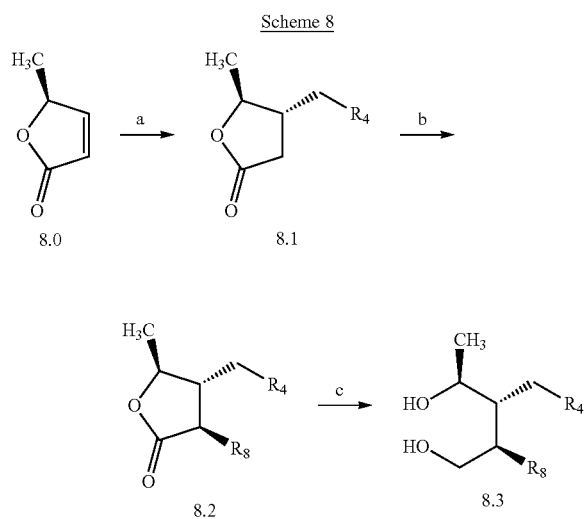

Compounds of Formula 9.3, wherein R$_4$ is as originally defined and R$_8$ is alkyl or benzyl, can be prepared as shown in Scheme 9, steps a-d. Diols of Formula 9.3, wherein R$_4$ is as originally defined and R$_8$ is alkyl, allyl, or benzyl, can be protected as bis-trimethylsilyl (TMS) ethers to give compounds of Formula 9.0, wherein R$_4$ is as originally defined and R$_8$ is alkyl, allyl, or benzyl, by reacting with a base such as triethylamine (Et$_3$N) and silylating reagent, such as chloro trimethylsilane (TMSCl), in an aprotic solvent, such as DCM, at ambient temperature, as shown in step a. Compounds of Formula 9.1, wherein R$_4$ is as originally defined and R$_8$ is alkyl, allyl, or benzyl, can be obtained by reacting compounds of Formula 9.0, wherein R$_4$ is as originally defined and R$_8$ is alkyl, allyl, or benzyl, with an oxidant, such as a solution of chromium trioxide (CrO$_3$) and pyridine in DCM, in a solvent such as DCM at low temperatures such as from about −25° C. to about −10° C., as shown in step b. Compounds of Formula 9.2, wherein R$_4$ is as originally defined and R$_7$ is alkyl, allyl, or benzyl, can be prepared by addition of compounds of Formula 9.1, is as originally defined and R$_8$ is alkyl, allyl, or benzyl, into a mixture of n-BuLi and triphenylmethylphosphonium bromide (Ph$_3$PCH$_3$Br), in a solvent such as THF at cryogenic temperatures such as −78° C., and slowly warming to ambient temperature, as shown in step c. Compounds of Formula 9.3, wherein R$_4$ is as originally defined and R$_8$ is alkyl or benzyl, can be obtained from compounds of Formula 9.2, is as originally defined and R$_8$ is alkyl, allyl, or benzyl, via hydrogenation in the presence of a catalyst, such as Pd/C, under an atmosphere of H$_2$ in a polar solvent such as EtOAc or EtOH, as shown in step d.

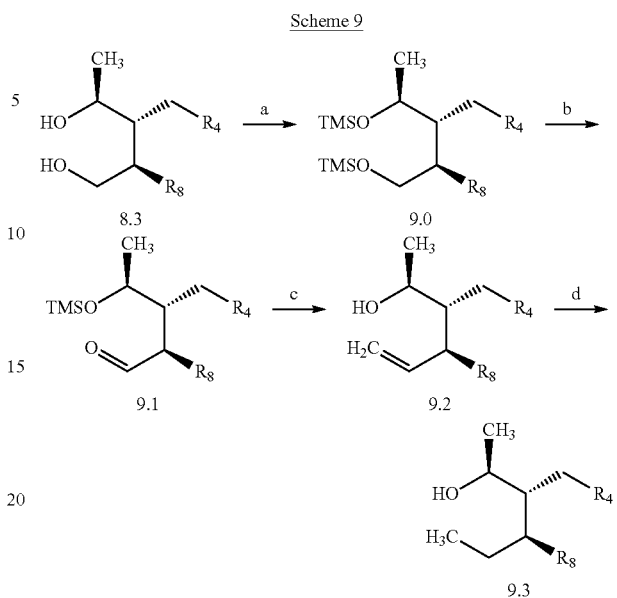

Compounds of Formula 10.1, wherein R$_4$ is as originally defined, can be prepared from the reaction between trans-2-methyl-3-phenyloxirane, a compound of Formula 10.0, with an organolithium reagent, such as R$_4$CH$_2$Li, or a Grignard reagent, such as R$_4$CH$_2$MgX, wherein R$_4$ is as originally defined and X is bromide or chloride, and copper (I) iodide in a solvent such as THF at cryogenic temperatures such as −78° C., as shown in step a.

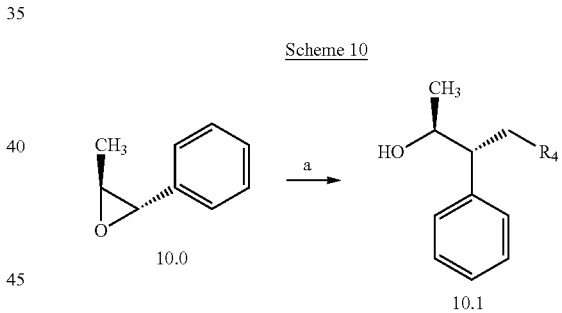

Compounds of Formula 11.3, wherein R$_4$ is aryl, can be prepared as shown in Scheme 11, steps a-c. Methyl acetoacetate, a compound of Formula 11.0, can be reacted with benzylic halides, such as R$_4$CH$_2$X, wherein R$_4$ is aryl and X is Br or Cl, in the presence of a base, such as potassium carbonate (K$_2$CO$_3$) and a phase transfer catalyst, such as 1-butyl-3-methylimidazolium tetrafluoroborate, in a polar aprotic solvent like DMF at a temperature of about 23° C. to afford compounds of Formula 11.1, wherein R$_4$ is aryl, as depicted in step a. Treatment of compounds such as 11.1, wherein R$_4$ is aryl, with a nucleophile such as 4-aminobenzenethiol in the presence of a base, such as cesium carbonate (Cs$_2$CO$_3$) in a solvent like DMF at a temperature of about 85° C. provides compounds of Formula 11.2, wherein R$_4$ is aryl, as in step b. Compounds of Formula 11.3, wherein R$_4$ is aryl, can be generated by a reduction of ketones of Formula 11.2, wherein R$_4$ is aryl, using a reductant such as borane-dimethylsulfide complex (BH$_3$·SMe$_2$) in the presence of a chiral catalyst like (R)-(+)-2-Methyl-CBS-oxazaborolidine in nonpolar solvent such as toluene at temperatures of about −78° C. to about 23° C., as shown in step c.

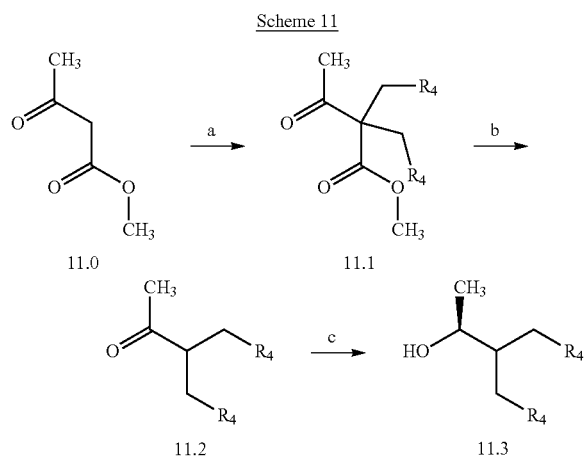

Scheme 11

Compounds of Formula 12.3, wherein $R_1$, $R_2$, $R_3$, $R_4$, and $R_{11}$ are as originally defined, can be prepared according to the methods shown in Scheme 12, steps a-b. Alcohols of Formula 12.0, wherein $R_2$, $R_3$, and $R_4$ are as originally defined, can be treated with compounds of Formula 12.1, wherein $R_1$ and $R_{11}$ are as originally defined, a coupling reagent, such as 3-ethyliminomethyleneamino)-N,N-dimethylpropan-1-amine hydrochloride (EDC) or a polymer-supported carbodiimide (PS-CDI), and a catalyst, such as N,N-dimethylaminopyridine (DMAP), in a halogenated solvent such as DCM to afford compounds of Formula 12.3, wherein $R_1$, $R_2$, $R_3$, $R_4$, and $R_{11}$ are as originally defined, as shown in step a. Alternatively, compounds of Formula 12.3, wherein $R_1$, $R_2$, $R_3$, $R_4$, and $R_{11}$ are as originally defined, can be prepared by reacting compounds of Formula 12.2, wherein $R_2$, $R_3$, and $R_4$ are as originally defined, with an activating agent, such as diisopropyl azodicarboxylate (DIAD), in the presence of phosphine reagent, such as triphenylphosphine, and a nucleophile such as compounds of Formula 12.1, wherein $R_1$ and $R_{11}$ are as originally defined, in a solvent such as tetrahydrofuran (THF) at temperatures of about 0° C. to about 23° C., as depicted in step b.

Compounds of Formula 13.4, wherein $R_1$ and $R_{11}$ are as originally defined, can be prepared according to the methods described in Scheme 13, steps a-c. Treatment of compound of Formula 13.1 (see: Hayashi, T. et al. *Tetrahedron* 1994, 50, 335) with amino acids of Formula 13.0, wherein $R_1$ and $R_{11}$ are as originally defined, under coupling conditions outlined in Scheme 12, step a, affords compounds of Formula 13.2, wherein $R_1$ and $R_{11}$ are as originally defined, as depicted in step a. Ketones of Formula 13.2, wherein $R_1$ and $R_{11}$ are as originally defined, can be treated with an olefinating reagent, such as bis(cyclopentadienyl)-μ-chloro(dimethylaluminum)-μ-methylenetitanium (Tebbe reagent), in a nonpolar solvent like toluene at temperatures of about 0° C. to about 23° C., to afford compounds of Formula 13.3, $R_1$ and $R_{11}$ are as originally defined, as shown in step b. Compounds of Formula 13.3, wherein $R_1$ and $R_{11}$ are as originally defined, can be hydrogenated under conditions outlined in Scheme 9, step d, to afford compounds of the Formula 13.4, $R_1$ and $R_{11}$ are as originally defined, as depicted in step c.

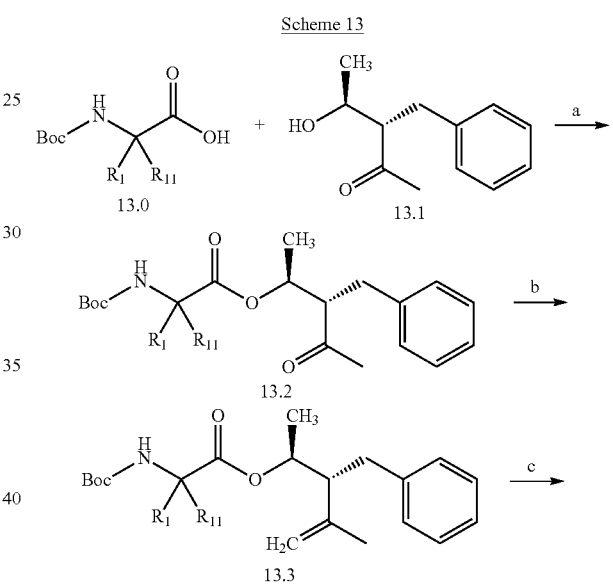

Scheme 13

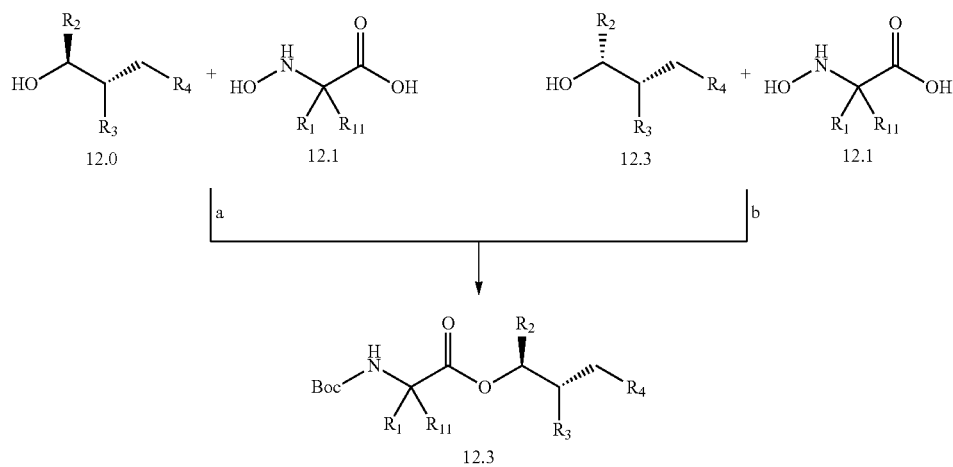

Scheme 12

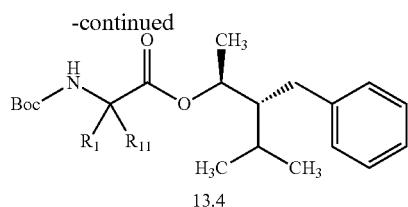

13.4

Compounds of Formula 14.4, wherein $R_1$, $R_2$, $R_3$, $R_4$, $R_6$ and $R_{11}$ are as originally defined, can be prepare according to the methods outlined in Scheme 14, steps a-c. Compounds of Formula 14.0, wherein $R_1$, $R_2$, $R_3$, $R_4$, $R_6$ and $R_{11}$ are as originally defined, but not alkenyl, can be treated with an acid, such as a 4 N solution of HCl in dioxane, to afford compounds of Formula 14.1, wherein $R_1$, $R_2$, $R_3$, $R_4$, $R_6$ and $R_{11}$ are as originally defined, but not alkenyl, as shown in step a. Alternatively, compounds of Formula 14.2, wherein $R_1$, $R_2$, $R_3$, $R_4$, $R_6$ and $R_{11}$ are as originally defined, can be obtained via treatment of compounds of Formula 14.0, wherein $R_1$, $R_2$, $R_3$, $R_4$, $R_6$ and $R_{11}$ are as originally defined, with an acid, such as 2,2,2-trifluoroacetic acid, in a solvent such as DCM, as depicted in step b. Compounds of Formulas 14.1 and 14.2, wherein $R_1$, $R_2$, $R_3$, $R_4$, $R_6$ and $R_{11}$ are as originally defined, can be treated with compound of Formula 14.3, in the presence of a base, such as diisopropylethylamine, and a peptide coupling reagent, such as benzotriazol-1-yl-oxytripyrrolidinophosphonium hexafluorophosphate (PyBOP) or O-(7-azabenzo-triazol-1-yl)-N,N,N',N'-tetramethyluronium hexafluorophosphate (HATU), in a halogenated solvent such as DCM, to afford compounds of Formula 14.4, wherein $R_1$, $R_2$, $R_3$, $R_4$, $R_6$ and $R_{11}$ are as originally defined, as shown step c.

Compounds of Formula 15.1, wherein $R_1$, $R_2$, $R_3$, $R_4$, $R_6$, $R_7$, and $R_{11}$ are as originally defined, can be prepared according to the method outlined in Scheme 15, step a. Compounds of Formula 15.0, wherein $R_1$, $R_2$, $R_3$, $R_4$, $R_6$, $R_7$, and $R_{11}$ are as previously defined, can be treated with an appropriate alkyl halide, with or without a reagent such as sodium iodide (NaI), and an alkali carbonate base, such as $Na_2CO_3$ or potassium carbonate ($K_2CO_3$), in a solvent like acetone or by treatment with an acyl halide in the presence of an amine base, such as pyridine, $NEt_3$, DMAP, or mixtures thereof, in an aprotic solvent such as DCM, to afford compounds of Formula 15.1, wherein $R_1$, $R_2$, $R_3$, $R_4$, $R_6$, $R_7$, and $R_{11}$ are as previously defined, as shown in step a.

Scheme 15

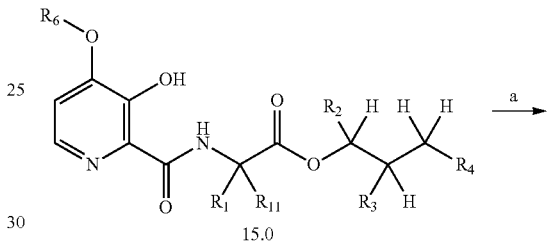

15.0

Scheme 14

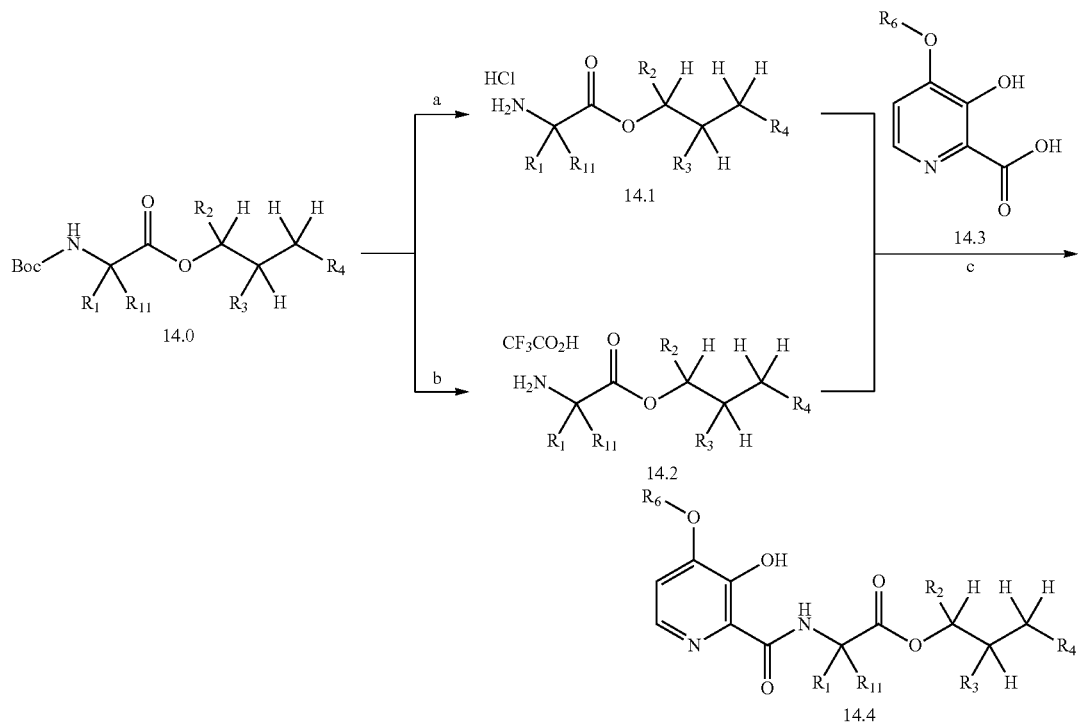

-continued

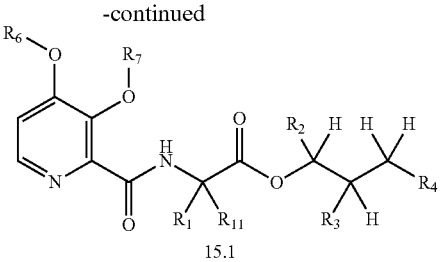

15.1

The following examples are presented to illustrate the various aspects of the compounds of the present disclosure and should not be construed as limitations to the claims.

EXAMPLES

Example 1, Step 1: Preparation of (S)-methyl 2-((S)-1-hydroxyethyl)-5-methylhex-4-enoate

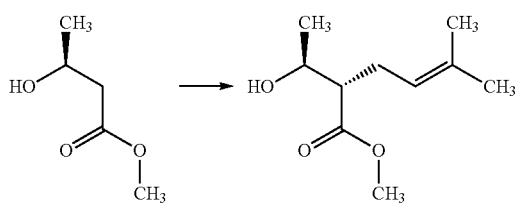

To a solution of diisopropylamine (19.93 mL, 142 mmol) in anhydrous THF (99 mL) at −50° C. (deficient dry ice/acetone bath) was added butyllithium (54.3 mL, 130 mmol). This solution was removed from the cold bath for 15 min, then re-cooled to −50° C. To this solution was added a solution of (S)-methyl 3-hydroxybutanoate (6.64 mL, 59.3 mmol) in THF (20 mL) dropwise over 15 minutes using a Teflon canula. This solution was allowed to warm to −30° C. over 30 min, then stirred at this temperature for another 1 h and cooled to −78° C. To this solution was added a solution of 1-bromo-3-methylbut-2-ene (13.69 mL, 119 mmol) in anhydrous 1,2-dimethoxyethane (20.00 mL, 193 mmol) dropwise over 15 minutes using a Teflon canula. This reaction was at −60° C. after 1 h. Removed the cold bath and stirred at room temperature for 1.5 h. The reaction was quenched with addition of sat aq. NH$_4$Cl (50 mL) then added EtOAc (50 mL) and the phases were transferred to a separatory funnel and separated. The aqueous phase was further extracted with EtOAc (2×50 mL) and the combined organic extracts were washed with brine (50 mL), dried (Na$_2$SO$_4$), filtered and concentrated to dryness. The crude residue was purified using flash chromatography on silica (120 g column, 85 mL/min, 0% EtOAc 1 min, ramp to 40% EtOAc/hexanes over 28 min) to afford (S)-methyl 2-((S)-1-hydroxyethyl)-5-methylhex-4-enoate (9.5 g, 86%) as a slightly yellow oil. $^1$H NMR (400 MHz, CDCl$_3$) δ 5.11-5.01 (m, 1H), 3.92 (p, J=6.3 Hz, 1H), 3.70 (s, 3H), 2.78 (s, 1H), 2.46-2.28 (m, 3H), 1.69 (d, J=1.4 Hz, 3H), 1.62 (s, 3H), 1.23 (d, J=6.4 Hz, 3H). $^{13}$C NMR (101 MHz, CDCl$_3$) δ 175.54, 134.14, 120.30, 67.78, 52.72, 51.52, 27.90, 25.73, 21.46, 17.64; (Thin film) 3452, 2971, 2929, 1730, 1437, 1198, 1160 cm$^{-1}$.

Example 1, Step 2: Preparation of (S)-methyl 2-((S)-1-hydroxyethyl)-5-methylhexanoate

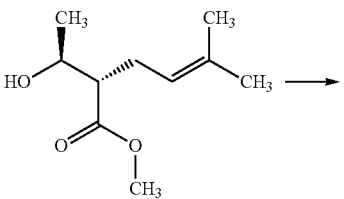

Palladium on carbon (Pd/C) (0.543 g, 5.10 mmol) (1 mol %) was added to a well stirred solution of (S)-methyl 2-((S)-1-hydroxyethyl)-5-methylhex-4-enoate (9.5 g, 51.0 mmol) in MeOH (51.0 mL). The reaction was placed under a hydrogen atmosphere (balloon) and stirred at room temperature for 20 h. The suspension was filtered through plug of celite, and the plug was washed with MeOH (20 mL). The solvent was removed under reduced pressure and then CH$_2$Cl$_2$ (50 mL) was added to the residue and the solution was passed through a phase separator. Then the solvent was removed under reduced pressure to afford (s)-methyl 2-((S)-1-hydroxyethyl)-5-methylhexanoate (9.45 g, 98%) as a slightly yellow oil. $^1$H NMR (400 MHz, CDCl$_3$) δ 3.91 (p, J=6.4 Hz, 1H), 3.72 (s, 3H), 2.77 (s, 1H), 2.36 (ddd, J=9.2, 6.3, 5.0 Hz, 1H), 1.72-1.45 (m, 3H), 1.28-1.05 (m, 5H), 0.88 (dd, J=6.6, 3.2 Hz, 6H). $^{13}$C NMR (75 MHz, CDCl$_3$) δ 176.13, 68.55, 53.29, 51.67, 36.55, 28.16, 27.37, 22.74, 22.44, 21.68. (Thin film) 3451, 2954, 2871, 1736, 1719, 1169 cm$^{-1}$.

Example 1, Step 3: Preparation of (S)-methyl 2-((S)-1-((4-methoxybenzyl)oxy)ethyl)-5-methyl-hexanoate

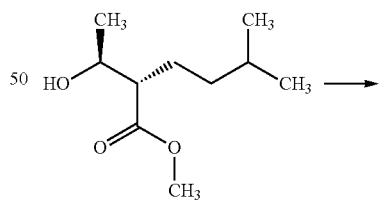

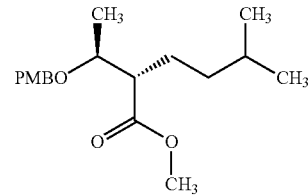

To a solution of (S)-methyl 2-((S)-1-hydroxyethyl)-5-methylhexanoate (5 g, 26.6 mmol) and ((1S,4R)-7,7-dimethyl-2-oxobicyclo[2.2.1]heptan-1-yl)methanesulfonic acid (0.617 g, 2.66 mmol) in CH$_2$Cl$_2$ (53.1 mL) at 0° C. was added 4-methoxybenzyl 2,2,2-trichloroacetimidate (8.27 mL, 39.8 mmol). The reaction mixture was removed from the cold bath and stirred at room temperature for 17 h. To the mixture was added hexanes (50 mL) and the precipitates were removed by filtration through a phase separator. The solids were washed with hexanes (2×10 mL). Celite™ (2 scoopula tip-fulls) was then added to the organic phase then the solvent was removed under reduced pressure and the resulting solid material was directly loaded onto a column and purified using flash chromatography on silica (80 g column, 60 mL/min, 0% EtOAc 1 min, ramp to 35% EtOAc/hexanes over 33 min and hold at 35% for 2 mins) to afford (S)-methyl 2-((S)-1-((4-methoxybenzyl)oxy)ethyl)-5-methylhexanoate (6.3 g, 77%) as a colorless oil. $^1$H NMR (400 MHz, CDCl$_3$) δ 7.24-7.16 (m, 2H), 6.89-6.79 (m, 2H), 4.49 (d, J=11.2 Hz, 1H), 4.33 (d, J=11.1 Hz, 1H), 3.75 (s, 3H), 3.74-3.62 (m, 4H), 2.49 (ddd, J=10.7, 8.2, 4.0 Hz, 1H), 1.62-1.40 (m, 3H), 1.23-1.16 (m, 3H), 1.16-1.03 (m, 2H), 0.87 (d, J=3.9 Hz, 3H), 0.85 (d, J=3.9 Hz, 3H). $^{13}$C NMR (101 MHz, CDCl$_3$) δ 175.03, 159.10, 130.63, 129.14, 113.62, 76.16, 70.71, 55.11, 52.64, 51.25, 36.58, 27.97, 26.00, 22.69, 22.17, 17.08. ESIMS (m/z) 331 ([M+Na]$^+$).

Example 2: Preparation of (2S,3S)-methyl 3-(benzyloxy)-2-(4-methoxybenzyl)butanoate and (2S,3S)-methyl 2-(3-benzyl-4-methoxybenzyl)-3-(benzyloxy)butanoate

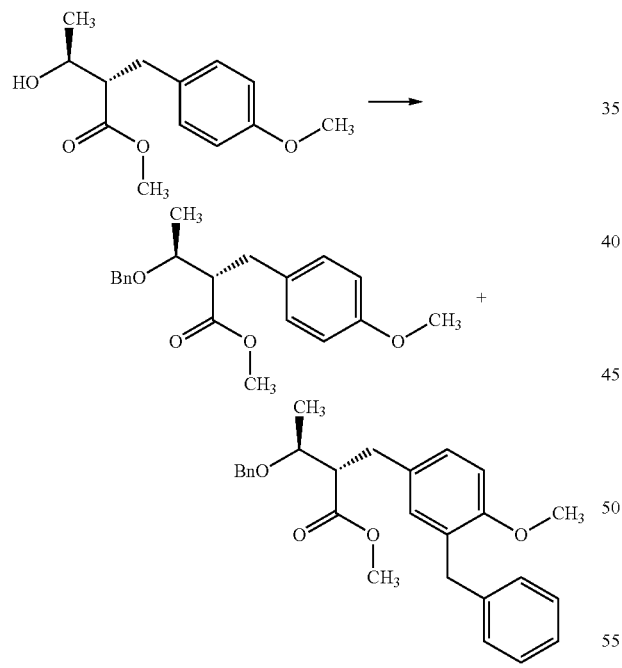

To a solution of (2S,3S)-methyl 3-hydroxy-2-(4-methoxybenzyl)butanoate (7.6 g, 31.9 mmol) in DCM (100 mL) at 0° C. was added benzyl 2,2,2-trichloroacetimidate (12.08 g, 47.8 mmol). To the mixture was then added trifluoromethanesulfonic acid (0.282 mL, 3.19 mmol) dropwise. The mixture was allowed to slowly warm to room temperature and stirred overnight. To the mixture was then added hexanes. The solution was stirred for 20 min, filtered through celite and the filter cake washed with hexanes. The filtrate was then treated with sat. NaHCO$_3$, and the products extracted with DCM. The organics were then washed with water and brine, dried with Na$_2$SO$_4$, filtered and concentrated. Purification via flash chromatography (120 g silica column, 0-30% acetone/hexanes) provided 5.76 g of a pale yellow oil. Subsequent reverse phase chromatography (C18 stationary phase column, 5-100% acetonitrile/water) provided (2S,3S)-methyl 3-(benzyloxy)-2-(4-methoxybenzyl)butanoate (3.009 g, 28%) as viscous yellow/orange oil. $^1$N HMR (400 MHz, CDCl$_3$) δ 7.38-7.20 (m, 5H), 7.13-6.97 (m, 2H), 6.88-6.70 (m, 2H), 4.59 (d, J=11.7 Hz, 1H), 4.46 (d, J=11.6 Hz, 1H), 3.80 (dq, J=10.8, 6.3 Hz, 1H), 3.76 (s, 3H), 3.53 (s, 3H), 2.93-2.71 (m, 3H), 1.28 (d, J=6.2 Hz, 3H). $^{13}$C NMR (101 MHz, CDCl$_3$) δ 174.13, 158.09, 138.48, 131.28, 129.76, 128.33, 127.63, 127.54, 113.82, 75.98, 71.04, 55.20, 54.37, 51.44, 33.09, 17.23. (Thin film) 2948.79, 1731.78, 1511.90, 1244.97, 1028.55 cm$^{-1}$. HRMS-ESI (m/z) ([M+H]$^+$) calcd for C$_{20}$H$_{25}$O$_4$, 329.1747; found, 329.1731. And, (2S,3S)-methyl 2-(3-benzyl-4-methoxybenzyl)-3-(benzyloxy)butanoate (1.314 g, 2.51 mmol, 8%, ~80% purity) as a viscous orange oil. $^1$N HMR (400 MHz, CDCl$_3$) δ 7.40-7.21 (m, 6H), 7.21-7.00 (m, 3H), 6.96 (dt, J=8.3, 1.6 Hz, 1H), 6.93-6.81 (m, 1H), 6.81-6.61 (m, 2H), 4.57 (d, J=11.6 Hz, 1H), 4.43 (d, J=11.5 Hz, 1H), 4.06 3.84 (m, 2H), 3.77 (s, 3H), 3.54-3.49 (m, 1H), 3.46 (s, 3H), 2.87-2.70 (m, 3H), 1.25 (d, J=6.2 Hz, 3H). $^{13}$C NMR (101 MHz, CDCl$_3$) δ 174.14, 155.90, 141.13, 138.48, 130.87, 129.47, 128.85, 128.45, 128.30, 128.21, 127.63, 127.55, 127.52, 125.73, 110.46, 76.03, 71.04, 55.43, 54.42, 51.36, 35.83, 33.21, 17.25. (Thin film) 2947, 1732, 1495, 1248, 1028 cm$^{-1}$. HRMS-ESI (m/z) ([M+H]$^+$) calcd for C$_{27}$H$_{31}$O$_4$, 419.2217; found, 419.2219.

Example 3A, Step 1: Preparation of (2S,3S)-2-benzyl-3-((4-methoxybenzyl)oxy)butanal

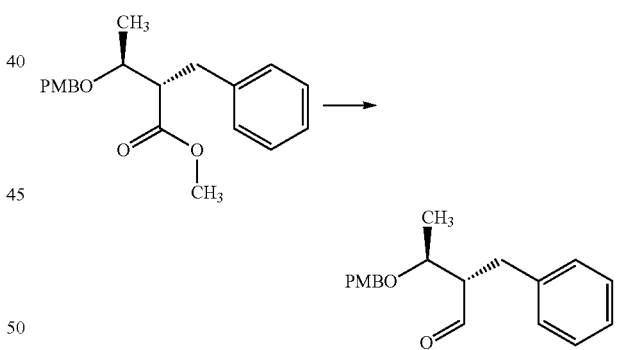

To a magnetically stirred 50 mL RB flask was added (2S,3S)-methyl 2-benzyl-3-((4-methoxybenzyl)oxy)butanoate (5 g, 15.23 mmol) and DCM (7.61 mL). Then, Ir$_2$Cl$_2$(coe)$_4$ (0.273 g, 0.305 mmol) was added and the flask was cooled to 0° C. Over 5 min, diethylsilane (2.95 mL, 22.84 mmol) was added via syringe with much gas evolution. Once the addition was complete, the flask was removed from the cold bath and allowed to warm to rt overnight. The reaction was poured into a well-stirred Erlenmeyer flask containing a mixture of 50 mL Et$_2$O and 15 mL 2 N HCl at 0° C. The flask was stirred vigorously at 0° C. for 1.5 h, then the mixture was transferred to a separatory funnel and diluted with 25 mL H$_2$O. The phases were separated and the aqueous phase was extracted with Et$_2$O×3. The organic phases were washed with sat. NaHCO$_3$ and then brine. The solvent was removed and the resulting oil was purified by flash chromatography on silica (gradient eluent: 1-15% acetone in hexanes) to afford (2S,3S)-2-benzyl-3-((4-methoxybenzyl)-oxy)butanal (4.25 g, 94%) as a colorless oil. ¹H NMR (400 MHz, CDCl₃) δ 9.78 (d, J=2.8 Hz, 1H), 7.29-7.22 (m, 4H), 7.22-7.14 (m, 1H), 7.11-7.05 (m, 2H), 6.93-6.85 (m, 2H), 4.56 (d, J=11.3 Hz, 1H), 4.34 (d, J=11.3 Hz, 1H), 3.81 (s, 3H), 3.81-3.75 (m, 1H), 3.03 (dd, J=14.0, 8.2 Hz, 1H), 2.87 (dd, J=14.0, 6.3 Hz, 1H), 2.70 (dddd, J=8.2, 6.4, 4.5, 2.8 Hz, 1H), 1.29 (d, J=6.4 Hz, 3H).

Example 3A, Step 2: Preparation of (3S,4R,5S)-4-benzyl-5-((4-methoxybenzyl)oxy)hex-1-en-3-ol and (3R,4R,5S)-4-benzyl-5((4-methoxybenzyl)oxy)hex-1-en-3-ol

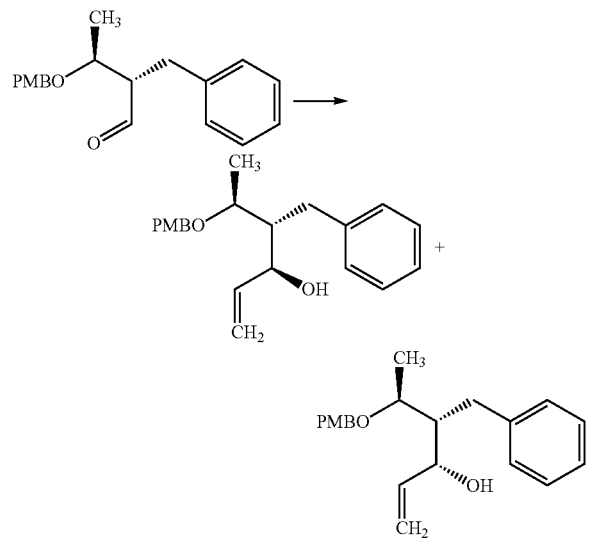

To a magnetically stirred 100 mL round-bottomed (rb) flask was added (2S,3S)-2-benzyl-3-((4-methoxybenzyl) oxy)butanal (1.987 g, 6.66 mmol) and THF (13 mL). The flask was cooled to −78° C. and vinylmagnesium bromide (1.0 M in THF) (13.3 mL, 13.3 mmol) was added in a slow stream via syringe. The reaction was maintained at −78° C. for 1.5 h. The reaction was quenched with sat. NH₄Cl at −78° C. (20 mL) and then removed from the cold bath. After warming to rt, the biphasic solution was diluted with EtOAc (50 mL). The solution was washed with brine (15 mL), dried over MgSO₄, filtered and concentrated. The oil was purified by flash chromatography on silica (40 g column, 40 mL/min, gradient eluent: 0-15% acetone in hexanes over 20 min) to afford clean separation of the two isomers: (3S,4R,5S)-4-benzyl-5-((4-methoxy-benzyl)oxy)hex-1-en-3-ol (1.15 g, 51%). ¹H NMR (400 MHz, CDCl₃) δ 7.28-7.17 (m, 5H), 7.05-6.98 (m, 2H), 6.92-6.84 (m, 2H), 5.91 (ddd, J=17.1, 10.6, 4.4 Hz, 1H), 5.36 (dt, J=17.2, 1.9 Hz, 1H), 5.23 (dt, J=10.6, 1.8 Hz, 1H), 4.65-4.59 (m, 1H), 4.56 (d, J=10.9 Hz, 1H), 4.21 (d, J=11.0 Hz, 1H), 3.89 (d, J=2.7 Hz, 1H), 3.78 (s, 3H), 3.65 (qd, J=6.3, 3.7 Hz, 1H), 2.72 (d, J=7.3 Hz, 2H), 1.78-1.70 (m, 1H), 1.25 (d, J=6.2 Hz, 3H). ¹³C NMR (101 MHz, CDCl₃) δ 159.46, 141.10, 139.22, 130.09, 129.57, 129.23, 128.39, 125.91, 115.02, 114.01, 75.38, 70.99, 70.74, 55.33, 50.95, 31.46, 17.72. ESIMS (m/z) 349 ([M+Na]⁺). And, (3R,4R,5S)-4-benzyl-5-((4-methoxybenzyl)oxy)hex-1-en-3-ol (0.5 g, 22%). ¹H NMR (400 MHz, CDCl₃) δ 7.29-7.22 (m, 5H), 7.16-7.10 (m, 2H), 6.92-6.85 (m, 2H), 5.95 (ddd, J=17.2, 10.5, 5.5 Hz, 1H), 5.24 (dt, J=17.2, 1.7 Hz, 1H), 5.10 (dt, J=10.5, 1.6 Hz, 1H), 4.55 (d, J=11.3 Hz, 1H), 4.30 (d, J=11.3 Hz, 1H), 4.28-4.20 (m, 1H), 3.81 (s, 3H), 3.69 (qd, J=6.4, 4.1 Hz, 1H), 2.85 (dd, J=5.4, 1.1 Hz, 1H), 2.80 (dd, J=14.0, 7.1 Hz, 1H), 2.71 (dd, J=14.0, 7.0 Hz, 1H), 2.04-1.96 (m, 1H), 1.26 (d, J=6.4 Hz, 3H).

Example 3B: Preparation of (2R,3S)-2-benzyl-3-((4-methoxybenzyl)oxy)butan-1-ol

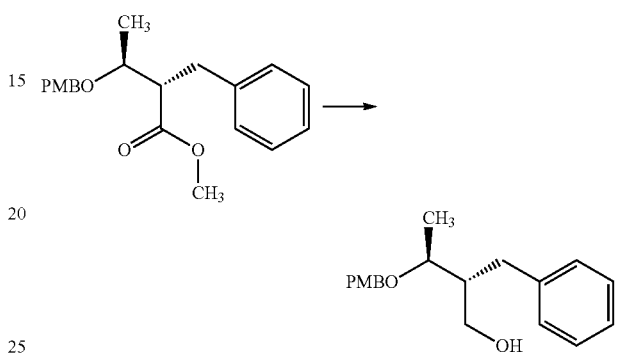

To a suspension of lithium aluminum hydride (0.844 g, 22.23 mmol) in THF (50 mL) at −78° C. was added a solution of (2S,3S)-methyl 2-benzyl-3-((4-methoxybenzyl) oxy)butanoate (3.65 g, 11.11 mmol) in THF (5 mL) dropwise. The mixture was then warmed to room temperature and stirred overnight. The mixture was cooled to 0° C. and the reaction was quenched via the CAREFUL addition of water (0.84 mL) followed by the addition of 15% NaOH (0.84 mL), and then more water (2.52 mL). The solution was then allowed to warm to room temperature and stirred an additional 1 h. The solids were then filtered off and the filter cake washed with ether. The collected filtrate was then concentrated and the residue purified via flash chromatography (80 g silica column, 0-30% acetone/hexanes) to provide (2R,3S)-2-benzyl-3-((4-methoxybenzyl)oxy)butan-1-ol (2.94 g, 88%) as a clear colorless oil. ¹N HMR (400 MHz, CCDCl₃) δ 7.30-7.23 (m, 4H), 7.21-7.12 (m, 3H), 6.92-6.86 (m, 2H), 4.60 (d, J=11.2 Hz, 1H), 4.31 (d, J=11.2 Hz, 1H), 3.90 (ddd, J=11.3, 3.9, 2.6 Hz, 1H), 3.81 (s, 3H), 3.66 (qd, J=6.2, 4.3 Hz, 1H), 3.56-3.43 (m, 1H), 2.86 (ddd, J=7.6, 3.9, 1.3 Hz, 1H), 2.84-2.68 (m, 2H), 1.82-1.71 (m, 1H), 1.30 (d, J=6.2 Hz, 3H). ¹³C NMR (101 MHz, CDCl₃) δ 159.30, 140.56, 130.31, 129.36, 129.17, 128.34, 125.95, 113.90, 70.68, 62.36, 55.29, 47.79, 35.13, 17.66. (Thin film) 3432.14, 2932.00, 1611.60, 1512.16, 1245.18, 1030.65 cm⁻¹. HRMS-ESI (m/z) ([M+Na]⁺) calcd for C₁₉H₂₄NaO₃, 323.1623; found, 323.1625.

Example 3C: Preparation of (3S,4S)-3-(4-fluorobenzyl)-4-((4-methoxybenzyl)oxy)-2-methylpentan-2-ol

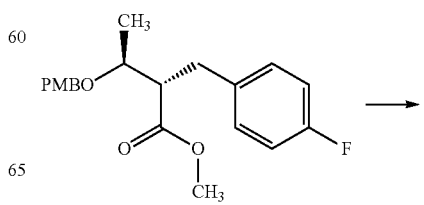

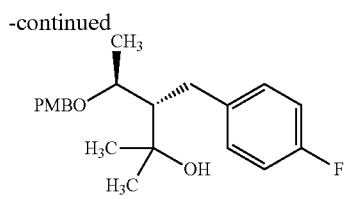

In a 250 mL round-bottom flask, a solution of (2S,3S)-methyl 2-(4-fluorobenzyl)-3-((4-methoxybenzyl)oxy)butanoate (3.55 g, 10.25 mmol) was prepared in THF (41.0 mL) and cooled to −78° C. in an acetone/dry ice bath. After ~15 min, methyllithium (1.6 M in Et$_2$O) (19.22 mL, 30.7 mmol) was added via syringe over 1 h. The reaction was allowed to slowly warm to room temperature and stirred overnight. The reaction was cooled to 0° C. and carefully quenched with sat. aq. NH$_4$Cl (60 mL) and extracted with EtOAc (3×60 mL). The combined organic phases were dried over Na$_2$SO$_4$, filtered and concentrated to afford a yellow oil. The oil was purified via flash chromatography on silica (120 g column, 85 mL/min, 100% hexanes for 2 column volumes, 100% hexanes to 40% acetone:hexanes over 12 column volumes, hold at 40% acetone:hexanes for 2 column volumes) to afford (3S,4S)-3-(4-fluorobenzyl)-4-((4-methoxybenzyl)oxy)-2-methylpentan-2-ol (1.706 g, 48%) as a yellow oil. $^1$H NMR (400 MHz, CDCl$_3$) δ 7.30-7.21 (m, 2H), 7.11-7.01 (m, 2H), 6.99-6.82 (m, 4H), 4.60 (d, J=10.9 Hz, 1H), 4.45 (s, 1H), 4.30 (d, J=11.0 Hz, 1H), 3.80 (s, 3H), 3.75-3.65 (m, 1H), 2.76-2.65 (m, 1H), 2.39 (dd, J=15.3, 7.2 Hz, 1H), 1.95 (td, J=7.0, 4.1 Hz, 1H), 1.27-1.20 (m, 9H). $^{13}$C NMR (101 MHz, CDCl$_3$) δ 161.15 (d, J=243.8 Hz), 159.42, 137.58 (d, J=3.2 Hz), 129.99 (d, J=7.7 Hz), 129.73, 129.65, 115.10 (d, J=21.1 Hz), 113.96, 78.02, 73.70, 70.27, 55.30, 55.14, 34.78, 30.31, 26.29, 18.99. $^{19}$F NMR (376 MHz, CDCl$_3$) δ−117.71. (Thin film) 3441, 2971, 2935, 1612, 1586, 1509, 1464, 1377, 1302, 1247, 1218, 1172, 1157, 1071, 986, 942, 900, 819, 749 cm$^{-1}$. HRMS-ESI (m/z) ([M+Na]$^+$) calcd for C$_{21}$H$_{27}$FNaO$_3$, 369.1836; found, 369.1845.

Example 4A: Preparation of 1-((((2S,3S,4S)-3-benzyl-4-propoxyhex-5-en-2-yl)oxy)-methyl)-4-methoxybenzene

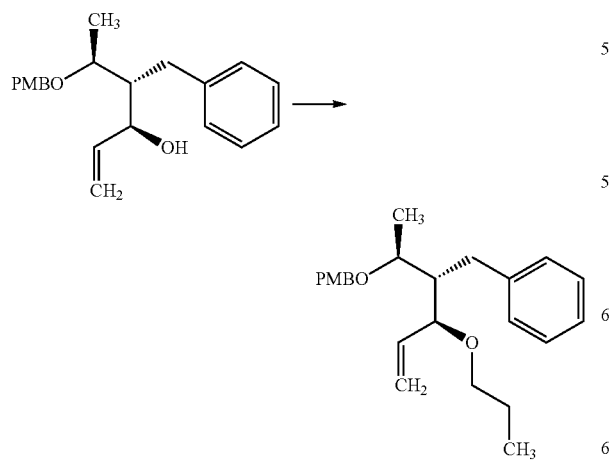

To a solution of (3S,4R,5S)-4-benzyl-5-((4-methoxybenzyl)oxy)hex-1-en-3-ol (390 mg, 1.195 mmol) in THF (7965 µL) at room temperature was added t-BuOK (161 mg, 1.434 mmol). The mixture then became orange. After stirring at this temperature for 10 min n-propyl tosylate (337 µL, 1.792 mmol) was added to the solution and the mixture was stirred at room temperature for 20 h. The mixture became slurry-like. Alcohol remained so additional tosylate (100 µL) and potassium t-BuOK (40.2 mg, 0.358 mmol) were added and the reaction was allowed to stir at room temperature for 14 h. H$_2$O (10 mL) was added and the reaction was transferred to a separatory funnel. The aq. phase was extracted with EtOAc (3×10 mL), and the combined organics were dried (Na$_2$SO$_4$), filtered, and concentrated to dryness. Took up in CH$_2$Cl$_2$ (10 mL) then Celite™ (2 scoopula tip-fulls) was added to the organic phase then the solvent was removed under reduced pressure and the resulting solid material was directly loaded onto a column and purified via flash chromatography on silica (24 g column, 35 mL/min, 0% EtOAc 1 min, ramp to 30% EtOAc/hexanes over 12 min and hold at 30% for 2 mins) to afford recovered (3S,4R,5S)-4-benzyl-5-((4-methoxybenzyl)oxy)hex-1-en-3-ol (60 mg, 15%) and 1-((((2S,3S,4S)-3-benzyl-4-propoxyhex-5-en-2-yl)oxy)methyl)-4-methoxybenzene (315 mg, 72%). $^1$H NMR (400 MHz, CDCl$_3$) δ 7.27-7.16 (m, 6H), 7.16-7.08 (m, 1H), 6.90-6.80 (m, 2H), 5.67 (ddd, J=17.4, 10.3, 7.2 Hz, 1H), 5.21-5.10 (m, 2H), 4.43 (d, J=11.3 Hz, 1H), 4.33 (d, J=11.3 Hz, 1H), 3.87-3.79 (m, 1H), 3.77 (s, 3H), 3.73-3.62 (m, 1H), 3.40 (app dt, J=9.1, 6.6 Hz, 1H), 3.11 (app dt, J=9.1, 6.6 Hz, 1H), 2.83 (dd, J=14.4, 6.1 Hz, 1H), 2.68 (dd, J=14.4, 6.2 Hz, 1H), 2.16 (qd, J=6.0, 4.7 Hz, 1H), 1.60-1.46 (m, 2H), 1.13 (d, J=6.4 Hz, 3H), 0.90 (t, J=7.4 Hz, 3H). $^{13}$C NMR (101 MHz, CDCl$_3$) δ 159.06, 142.74, 138.35, 131.27, 129.22, 129.20, 128.12, 125.44, 116.55, 113.74, 81.12, 75.17, 70.52, 70.13, 55.28, 49.99, 32.01, 23.25, 17.35, 10.92. ESIMS (m/z) 391 ([M+Na]$^+$).

Example 4B, Step 1: Preparation of 1-fluoro-4-((2S,3S)-2-((S)-1-((4-methoxybenzyl)oxy)ethyl)-3-(p-tolyloxy)pent-4-en-1-yl)benzene

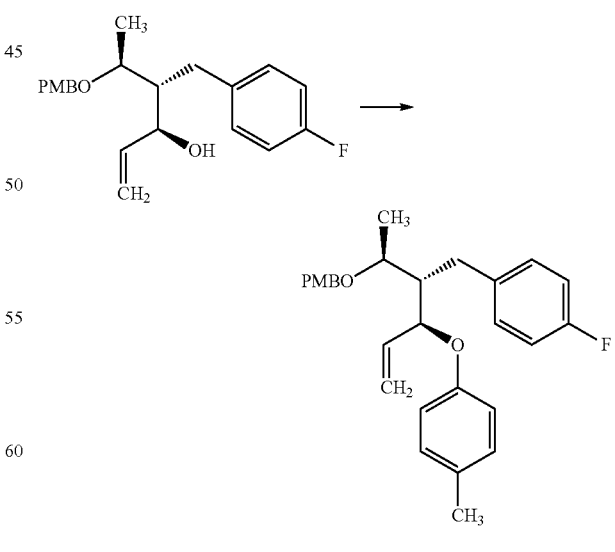

To a magnetically stirred 100 mL Schlenk tube was added (3S,4R,5S)-4-(4-fluorobenzyl)-5-((4-methoxybenzyl)oxy)hex-1-en-3-ol (1.2 g, 3.48 mmol) and toluene (11.61 mL), followed by copper(II) acetate (0.127 g, 0.697 mmol), tri(p-tolyl)bismuth(V) acetate (2.51 g, 4.18 mmol), and N-cyclohexyl-N-methylcyclohexanamine (0.887 mL, 4.18 mmol). The flask was evacuated under vacuum and back-filled with $N_2$ four times, then heated to 65° C. and left to stir over the weekend. The reaction was filtered through Celite™ with EtOAc and then concentrated. The crude green oil was purified via flash chromatography on silica (gradient eluent: 1-10% acetone in hexanes) to afford 1-fluoro-4-((2S,3S)-2-((S)-1-((4-methoxybenzyl)oxy)ethyl)-3-(p-tolyloxy)pent-4-en-1-yl)benzene (798 mg, 53%). $^1$H NMR (400 MHz, $CDCl_3$) δ 7.17-7.11 (m, 2H), 7.08-7.00 (m, 4H), 6.99-6.89 (m, 2H), 6.80-6.71 (m, 4H), 5.78 (ddd, J=17.3, 10.7, 5.2 Hz, 1H), 5.22 (dt, J=17.5, 1.6 Hz, 1H), 5.18 (dt, J=10.6, 1.5 Hz, 1H), 4.99 (td, J=3.6, 1.8 Hz, 1H), 4.40 (d, J=10.8 Hz, 1H), 4.15 (d, J=10.9 Hz, 1H), 3.78 (s, 3H), 3.69 (p, J=6.4 Hz, 1H), 2.95 (dd, J=15.0, 5.8 Hz, 1H), 2.68 (dd, J=14.8, 6.3 Hz, 1H), 2.28 (s, 3H), 2.17 (qd, J=6.4, 3.5 Hz, 1H), 1.15 (d, J=6.2 Hz, 3H). $^{19}$F NMR (376 MHz, $CDCl_3$) δ−117.98.

Example 4B, Step 2: Preparation of (2R,3S,4S)-3-(4-fluorobenzyl)-4-((4-methoxybenzyl)oxy)-2-(p-tolyloxy)pentan-1-ol reaction was quenched with sat. $NH_4Cl$ and extracted with DCM×3. The organic phases were passed through a phase separator and then the solvent was removed. The crude oil was purified via flash chromatography on silica (gradient eluent: 1-25% acetone in hexanes) to afford (2R,3S,4S)-3-(4-fluorobenzyl)-4-((4-methoxybenzyl)oxy)-2-(p-tolyloxy)pentan-1-ol (602 mg, 80%) as a colorless oil. $^1$N NMR (400 MHz, $CDCl_3$) δ 7.19 (d, J=8.5 Hz, 2H), 7.10 (dd, J=8.3, 5.7 Hz, 2H), 7.03-6.99 (m, 2H), 6.95 (t, J=8.6 Hz, 2H), 6.87 (d, J=8.6 Hz, 2H), 6.69 (dd, J=8.4, 1.4 Hz, 2H), 4.51 (d, J=11.0 Hz, 1H), 4.52-4.47 (m, 1H), 4.18 (d, J=11.1 Hz, 1H), 3.81 (s, 3H), 3.81-3.74 (m, 2H), 3.64-3.55 (m, 1H), 2.83 (dd, J=14.3, 7.3 Hz, 1H), 2.74 (dd, J=14.2, 6.9 Hz, 1H), 2.47-2.35 (m, 1H), 2.27 (s, 3H), 2.27-2.20 (m, 1H), 1.29 (d, J=6.4 Hz, 3H). $^{13}$C NMR (101 MHz, $CDCl_3$) δ 161.36 (d, J=244.0 Hz), 159.20, 155.88, 136.70 (d, J=2.2 Hz), 130.51 (d, J=7.8 Hz), 130.46, 130.31, 130.00, 129.28, 115.80, 115.14 (d, J=21.0 Hz), 113.83, 78.80, 74.95, 70.40, 62.78, 55.30, 46.83, 33.68, 20.49, 17.68. $^{19}$F NMR (376 MHz, $CDCl_3$) δ−117.22.

Example 4B, Step 3: Preparation of 1-((2S,3R)-4-ethoxy-2-((S)-1-((4-methoxy-benzyl)oxy)ethyl)-3-(p-tolyloxy)butyl)-4-fluorobenzene

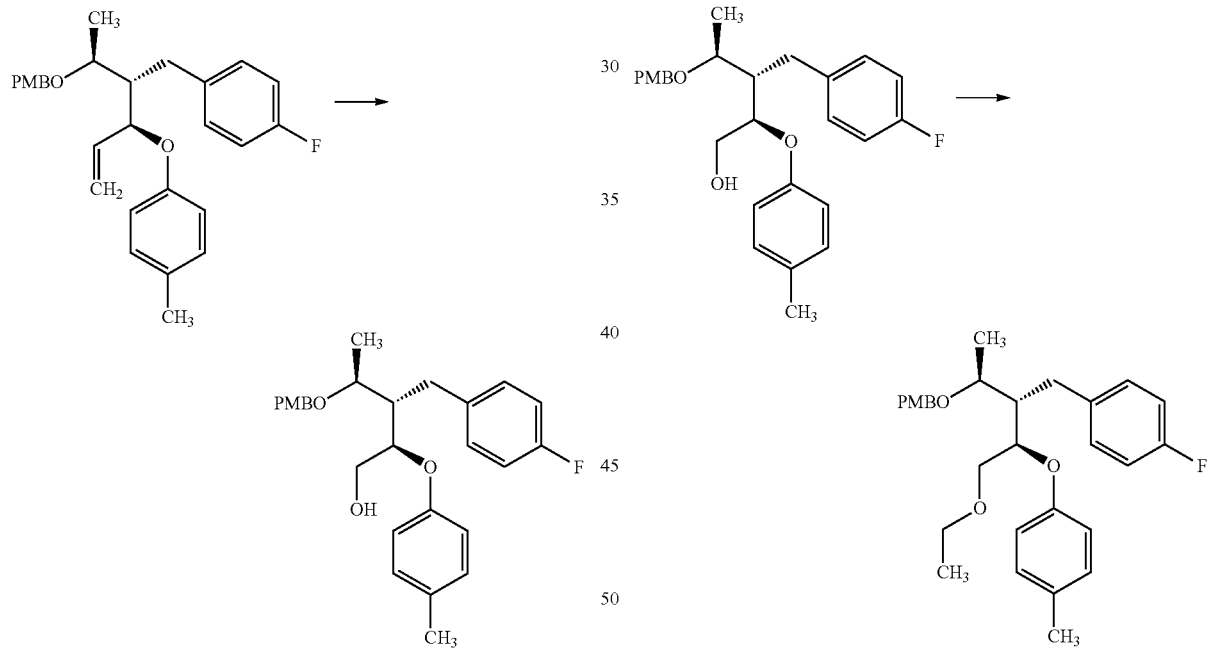

To a magnetically stirred 100 mL three-necked flask was added 1-fluoro-4-((2S,3S)-2-((S)-1-((4-methoxybenzyl)oxy)ethyl)-3-(p-tolyloxy)pent-4-en-1-yl)benzene (748 mg, 1.721 mmol), DCM (20 mL), MeOH (5 mL), and 2 drops of 0.1% Sudan III in DCM. Then, the flask was connected to the ozonator and cooled to −78° C. Ozone was bubbled into the flask (ozone pressure=1.0, 6 psi) for ~10 min until the color turned from red to colorless. Then, the ozone was shut off and $O_2$ was bubbled through the reaction to purge remaining ozone for ~5 min. While still at −78° C., sodium borohydride (195 mg, 5.16 mmol) was added in one portion, and then the flask was removed from the cold bath, fitted to a nitrogen inlet, and let warm to rt. Another 10 mL MeOH was added and the reaction was left to stir overnight. The To a magnetically stirred 25 mL screw-cap vial was added (2R,3S,4S)-3-(4-fluorobenzyl)-4-((4-methoxybenzyl)oxy)-2-(p-tolyloxy)pentan-1-ol (142 mg, 0.324 mmol) and THF (3238 µL). Then, the vial was cooled to 0° C. and sodium hydride (32.4 mg, 0.810 mmol) was added. The reaction was stirred for 30 min at 0° C., then ethyl iodide (78 µL, 0.971 mmol) was added. The reaction was removed from the cold bath and allowed to warm to rt overnight. In the morning, a small amount of alcohol remained by TLC, so another 15 mg NaH and 40 µL ethyl iodide was added. The reaction was left for another 3 h, then quenched with sat. $NH_4Cl$. The aqueous phase was extracted with EtOAc (3×) and then the organic phase was washed with brine and dried over $Na_2SO_4$. The solvent was removed and the crude oil was purified via flash chromatography on silica (gradient eluent: 1-15% acetone in hexanes) to afford 1-((2S,3R)-4-ethoxy-2-((S)-1-((4-methoxybenzyl)oxy)ethyl)-3-(p-tolyloxy)butyl)-4-fluorobenzene (108 mg, 72%) as a colorless oil. $^1$H NMR (400 MHz, CDCl$_3$) δ 7.17 (dd, J=8.5, 5.6 Hz, 2H), 7.12 (d, J=8.6 Hz, 2H), 7.05-7.01 (m, 2H), 6.94 (t, J=8.7 Hz, 2H), 6.80 (t, J=8.9 Hz, 4H), 4.65 (td, J=5.9, 3.1 Hz, 1H), 4.41 (d, J=11.1 Hz, 1H), 4.14 (d, J=11.2 Hz, 1H), 3.79 (s, 3H), 3.59 (p, J=6.2 Hz, 1H), 3.51 (dd, J=10.3, 5.7 Hz, 1H), 3.44-3.33 (m, 2H), 3.33-3.25 (m, 1H), 2.92 (dd, J=14.5, 6.9 Hz, 1H), 2.73 (dd, J=14.5, 5.9 Hz, 1H), 2.34 (dtd, J=7.0, 5.9, 3.1 Hz, 1H), 2.27 (s, 3H), 1.19 (d, J=6.2 Hz, 3H), 1.10 (t, J=7.0 Hz, 3H). $^{13}$C NMR (101 MHz, CDCl$_3$) δ 161.22 (d, J=243.3 Hz), 159.01, 156.47, 137.70 (d, J=3.2 Hz), 130.97, 130.50 (d, J=7.7 Hz), 130.02, 129.87, 129.21, 115.97, 114.92 (d, J=21.0 Hz), 113.65, 76.76, 75.17, 70.36, 70.16, 66.62, 55.27, 46.88, 31.49, 20.52, 17.54, 15.16. ESIMS (m/z) 467 [(M+H)$^+$].

Example 4C: Preparation of 1-fluoro-4-((S)-3-methoxy-2-((S)-1-((4-methoxybenzyl)oxy)ethyl)-3-methylbutyl)benzene

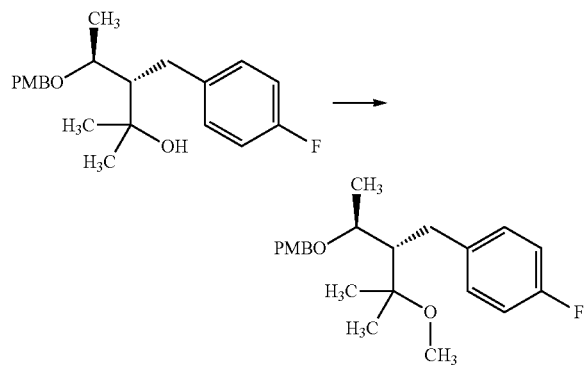

To a solution of (3S,4S)-3-(4-fluorobenzyl)-4-((4-methoxybenzyl)oxy)-2-methylpentan-2-ol (300 mg, 0.866 mmol) in DCM (4330 μL) was added N,N,N',N'-tetramethylnaphthalene-1,8-diamine (371 mg, 1.732 mmol), in one portion, followed by the addition of trimethyloxonium tetrafluoroborate (167 mg, 1.126 mmol). The resulting clear, colorless solution was stirred at room temperature overnight. The reaction was carefully quenched with sat. aq. NaHCO$_3$ (20 mL) and extracted with DCM (3×20 mL). The combined organic layers were washed with 1 N HCl (2×20 mL) and then brine (20 mL). The organic layer was filtered through a phase separator and concentrated to afford a pale yellow oil. The oil was purified via flash chromatography on silica (40 g column, 40 mL/min, 100% hexanes for 2 column volumes, 100% hexanes to 30% ethyl acetate:hexanes over 12 column volumes, hold at 30% ethyl acetate:hexanes for 2 column volumes) to afford 1-fluoro-4-((S)-3-methoxy-2-((S)-1-((4-methoxybenzyl)oxy)ethyl)-3-methylbutyl)benzene (232.6 mg, 74%) as a clear, colorless oil. $^1$H NMR (400 MHz, CDCl$_3$) δ 7.15 (dt, J=8.5, 2.7 Hz, 4H), 6.95-6.80 (m, 4H), 4.41 (d, J=11.4 Hz, 1H), 4.29 (d, J=11.5 Hz, 1H), 3.86-3.72 (m, 4H), 3.12 (s, 3H), 2.76 (dd, J=6.1, 2.8 Hz, 2H), 2.23 (ddd, J=6.4, 5.6, 2.9 Hz, 1H), 1.24 (d, J=6.4 Hz, 3H), 1.17 (s, 3H), 1.14 (s, 3H). $^{13}$C NMR (101 MHz, CDCl$_3$) δ 160.94 (d, J=242.6 Hz), 158.96, 139.33 (d, J=3.3 Hz), 131.28, 130.36 (d, J=7.7 Hz), 128.90, 114.72 (d, J=20.9 Hz), 113.66, 76.80, 74.64, 69.84, 55.26, 52.32, 48.73, 30.83, 24.31, 24.25, 17.52. $^{19}$F NMR (376 MHz, CDCl$_3$) δ−118.64. (Thin film) 2972, 2936, 2833, 1612, 1586, 1509, 1464, 1381, 1365, 1301, 1245, 1219, 1172, 1156, 1143, 1109, 1069, 1035, 929, 895, 812, 772, 753 cm$^{-1}$. HRMS-ESI (m/z) ([M+Na]$^+$) calcd for C$_{22}$H$_{29}$FNaO$_3$, 383.1993; found, 383.1997.

Example 4D: Preparation of 1-((((2S,3S)-4-(allyloxy)-3-benzyl-4-methylpentan-2-yl)-oxy)methyl)-4-methoxybenzene

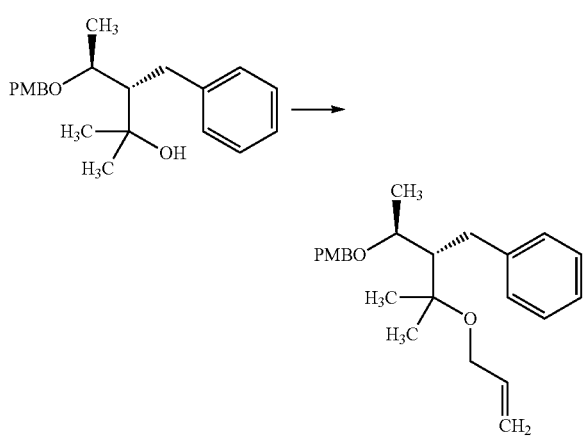

To a suspension of sodium hydride (0.046 g, 1.142 mmol) in THF (3.04 mL) was added a solution of ((3S,4S)-3-benzyl-4-((4-methoxybenzyl)oxy)-2-methylpentan-2-ol (0.250 g, 0.761 mmol) in THF (1 mL). To the mixture was added tetrabutylammonium iodide (0.028 g, 0.076 mmol) followed by allyl bromide (0.079 mL, 0.913 mmol). The mixture was then heated to reflux and stirred overnight. The reaction was quenched with NH$_4$Cl and extracted with ether (2×). The combined organics were then washed with water and brine (2×), dried with Na$_2$SO$_4$, filtered and concentrated. The crude mixture was purified via flash chromatography on silica (12 g silica column, 0-30% acetone in hexanes) to provide 1-((((2S,3S)-4-(allyloxy)-3-benzyl-4-methylpentan-2-yl)oxy)methyl)-4-methoxybenzene (132 mg, 47%) as a pale yellow oil. $^1$H NMR (400 MHz, CDCl$_3$) δ 7.29-7.21 (m, 4H), 7.21-7.08 (m, 3H), 6.91-6.80 (m, 2H), 5.94-5.80 (m, 1H), 5.32-5.18 (m, 1H), 5.14-5.02 (m, 2H), 4.41 (d, J=11.5 Hz, 1H), 4.33 (d, J=11.4 Hz, 1H), 3.90-3.85 (m, 2H), 3.80 (s, 3H), 2.85 (dd, J=6.0, 1.1 Hz, 2H), 2.37-2.29 (m, 1H), 1.26 (d, J=6.4 Hz, 3H), 1.21 (s, 3H), 1.17 (s, 3H). $^{13}$C NMR (101 MHz, CDCl$_3$) δ 158.88, 143.75, 136.14, 131.40, 129.11, 128.89, 128.09, 125.21, 115.10, 113.64, 77.18, 74.74, 69.84, 62.15, 55.28, 52.46, 31.67, 25.07, 24.86, 17.70. (Thin film) 2972.71, 1611.99, 1512.34, 1245.18, 1062.24, 1033.31 cm$^{-1}$. HRMS-ESI (m/z) ([M+Na]$^+$) calcd for C$_{24}$H$_{32}$NaO$_3$, 391.2244; found, 391.2249.

Example 4E: Preparation of 1-(((3S,4S)-3-benzyl-4-((4-methoxybenzyl)oxy)-2-methylpentan-2-yl)oxy)-2,4-dichlorobenzene

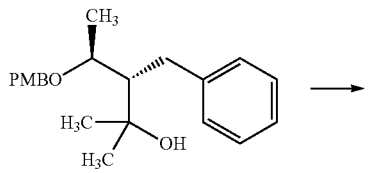

-continued

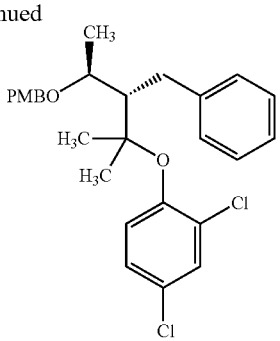

To a solution of (3S,4S)-3-benzyl-4-((4-methoxybenzyl)oxy)-2-methylpentan-2-ol (0.445 g, 1.355 mmol) in DMF (6.77 mL) was added 15-crown-5 (0.030 g, 0.135 mmol), 2,4-dichloro-1-fluorobenzene (0.476 mL, 4.06 mmol), and sodium hydride (0.081 g, 2.032 mmol). The mixture was then warmed to 70° C. and stirred overnight. The reaction was quenched with NH$_4$Cl and extracted with ether (2×). The combined organics were then washed with water and brine (2×), dried with Na$_2$SO$_4$, filtered and concentrated. The crude mixture was purified via flash chromatography on silica (24 g silica column, 0-30% acetone in hexanes) to provide 1-(((3S,4S)-3-benzyl-4-((4-methoxybenzyl)oxy)-2-methylpentan-2-yl)oxy)-2,4-dichlorobenzene (318 mg, 50%) as a pale yellow oil. $^1$H NMR (400 MHz, CDCl$_3$) δ 7.37 (d, J=2.6 Hz, 1H), 7.28-7.23 (m, 4H), 7.21-7.13 (m, 3H), 7.09 (dd, J=8.8, 2.6 Hz, 1H), 6.95 (d, J=8.8 Hz, 1H), 6.89-6.83 (m, 2H), 4.48 (d, J=11.5 Hz, 1H), 4.36 (d, J=11.6 Hz, 1H), 4.02 (qd, J=6.5, 3.0 Hz, 1H), 3.80 (s, 3H), 3.08 (dd, J=14.5, 5.7 Hz, 1H), 2.97 (dd, J=14.6, 6.3 Hz, 1H), 2.53 (td, J=6.0, 3.0 Hz, 1H), 1.35 (d, J=6.4 Hz, 3H), 1.33 (s, 3H), 1.31 (s, 3H). $^{13}$C NMR (101 MHz, CDCl$_3$) δ 158.97, 150.31, 143.27, 131.22, 130.09, 129.93, 129.07, 129.01, 128.21, 128.19, 127.11, 125.43, 125.16, 113.69, 86.22, 74.55, 69.96, 55.29, 54.62, 32.10, 26.26, 25.93, 17.86. (Thin film) 2975.24, 1512.04, 1494.87, 1471.70, 1245.00, 1055.68 cm$^{-1}$. HRMS-ESI (m/z) ([M+Na]$^+$) calcd for C$_{27}$H$_{30}$Cl$_2$NaO$_3$, 495.1464; found, 495.146.

Example 5A: Preparation of (2S,3S)-3-(4-methoxybenzyl)-4-methyl-4-propoxypentan-2-ol

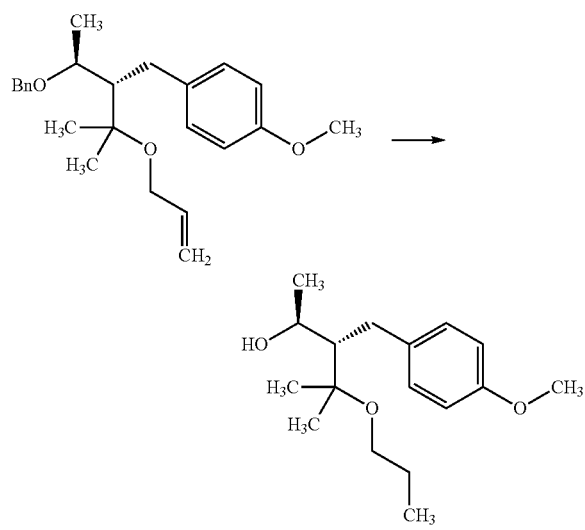

To a solution of 1-((S)-3-(allyloxy)-2-((S)-1-(benzyloxy)ethyl)-3-methylbutyl)-4-methoxybenzene (0.300 g, 0.814 mmol) in EtOAc (4.07 mL) was added palladium (5% wt on carbon, dry basis) (0.347 g, 0.081 mmol). The mixture was then stirred overnight under an atmosphere of hydrogen. The mixture was filtered through Celite™, and the filter cake was washed with EtOAc. The combined filtrate was concentrated and the residue purified via flash chromatography (12 g silica column, 0-30% acetone in hexanes) to provide (2S,3S)-3-(4-methoxybenzyl)-4-methyl-4-propoxypentan-2-ol (90 mg, 39%) as a clear oil. $^1$H NMR (400 MHz, CDCl$_3$) δ 7.19-7.09 (m, 2H), 6.87-6.65 (m, 2H), 5.42 (s, 1H), 4.00 3.90 (m, 1H), 3.79 (s, 3H), 3.41 (ddt, J=28.2, 8.5, 6.6 Hz, 2H), 2.52 (dd, J=15.6, 4.0 Hz, 1H), 2.35 (dd, J=15.7, 6.3 Hz, 1H), 2.02 (ddd, J=8.7, 6.3, 4.0 Hz, 1H), 1.61-1.51 (m, 2H), 1.29 (s, 3H), 1.25 (s, 3H), 1.13 (d, J=6.2 Hz, 3H), 0.92 (t, J=7.4 Hz, 3H). $^{13}$C NMR (101 MHz, CDCl$_3$) δ 157.69, 133.99, 129.41, 113.78, 80.84, 70.43, 62.83, 55.24, 54.15, 34.13, 25.10, 23.48, 22.96, 20.42, 10.76. (Thin film) 3418.41, 2967.62, 1511.47, 1245.36, 1069.93, 1035.76 cm$^{-1}$.

Example 5B: Preparation of (2S,3R)-3-benzyl-4-phenoxybutan-2-ol

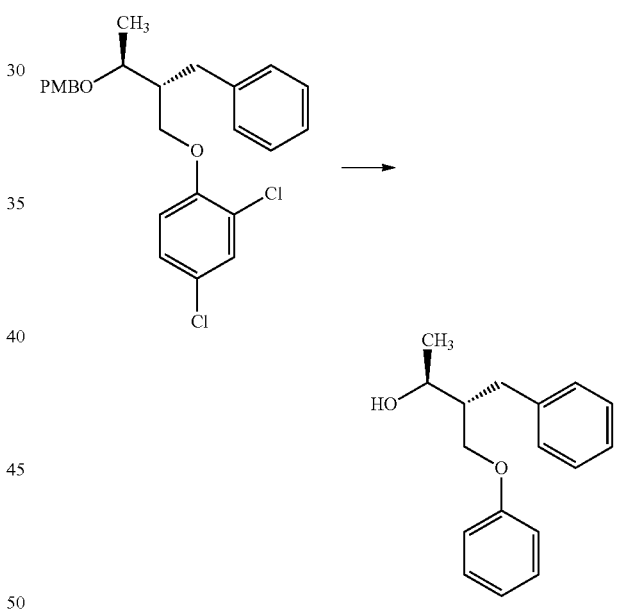

To a solution of 1-((2R,3S)-2-benzyl-3-((4-methoxybenzyl)oxy)butoxy)-2,4-dichlorobenzene (0.275 g, 0.617 mmol) in MeOH (1.544 mL) and ethyl acetate (1.544 mL) was added palladium (5% wt on carbon, dry basis) (0.131 g, 0.031 mmol). The mixture was then stirred under an atmosphere of hydrogen overnight. The reaction was incomplete as determined by UPLC. An additional portion of palladium (5% wt on carbon, dry basis) (0.131 g, 0.031 mmol) was then added and the mixture was warmed to 50° C. and stirred under hydrogen for an additional 8 h. The mixture was cooled to rt and filtered through Celite™. The filter cake was washed with EtOAc and the filtrate concentrated. The residue was then purified via flash chromatography on silica (4 g silica column, 0-20% acetone in hexanes) to provide (2S,3R)-3-benzyl-4-phenoxybutan-2-ol (110 mg, 70%) as a clear oil. $^1$H NMR (400 MHz, CDCl$_3$) δ 7.32-7.23 (m, 4H), 7.23-7.16 (m, 3H), 6.98-6.91 (m, 1H), 6.89-6.82 (m, 2H), 4.09 (dd, J=9.5, 3.9 Hz, 1H), 4.06-3.97 (m, 1H), 3.91 (ddd, J=9.6, 4.9, 1.0 Hz, 1H), 2.92 (dd, J=13.7, 6.0 Hz, 1H), 2.79 (dd, J=13.7, 9.2 Hz, 1H), 2.28 (s, 1H), 2.11-1.98 (m, 1H), 1.32 (dd, J=6.4, 0.9 Hz, 3H). $^{13}$C NMR (101 MHz, CDCl$_3$) δ 158.59, 140.19, 129.49, 129.22, 128.49, 126.14, 121.03, 114.54, 68.92, 67.07, 46.84, 34.62, 21.54. (Thin film) 3382.25, 2929.09, 1598.48, 1495.02, 1240.62 cm$^{-1}$. HRMS-ESI (m/z) ([M+Na]$^+$) calcd for C$_{17}$H$_{20}$NaO$_2$, 279.1356; found, 279.1351.

Example 5C: (2S,3R)-4-(2,4-difluorophenoxy)-3-(4-methoxybenzyl)butan-2-ol

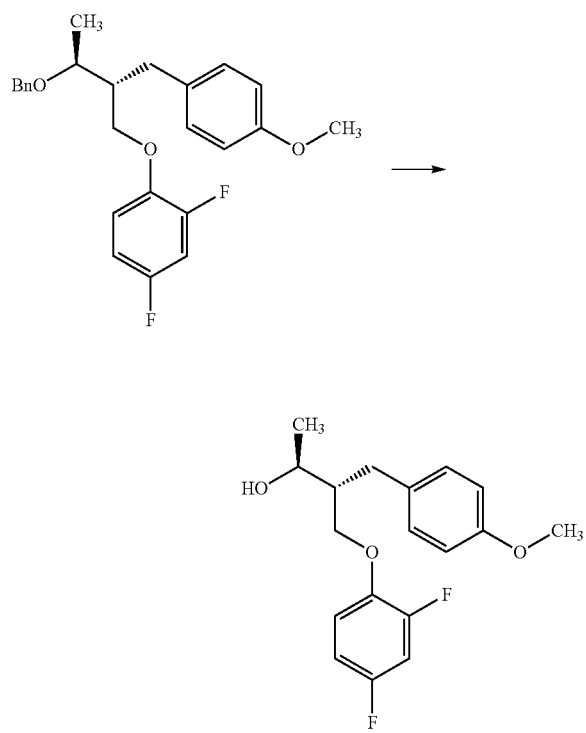

To a solution of 1-((2R,3S)-3-(benzyloxy)-2-(4-methoxybenzyl)butoxy)-2,4-difluorobenzene (0.298 g, 0.722 mmol) in EtOH (4.82 mL) and cyclohexene (2.408 mL) was added palladium (5% wt on carbon, dry basis) (0.154 g, 0.036 mmol). The mixture was then heated to 65° C. and stirred for 3 h. The mixture was filtered through Celite™ and the filter cake washed with EtOAc. The filtrate was then concentrated to provide (2S,3R)-4-(2,4-difluorophenoxy)-3-(4-methoxybenzyl)butan-2-ol (232 mg, 100%) as a clear oil. $^1$H NMR (400 MHz, CDCl$_3$) δ 7.14-7.08 (m, 2H), 7.04-6.96 (m, 1H), 6.85-6.79 (m, 2H), 6.62-6.51 (m, 2H), 4.09 (dd, J=9.3, 3.9 Hz, 1H), 4.06-3.98 (m, 1H), 3.91 (dd, J=9.3, 4.7 Hz, 1H), 3.78 (s, 3H), 2.87 (dd, J=13.8, 6.0 Hz, 1H), 2.74 (dd, J=13.8, 9.4 Hz, 1H), 2.12 (s, 1H), 2.07-1.98 (m, 1H), 1.34 (d, J=6.4 Hz, 3H). $^{13}$C NMR (101 MHz, CDCl$_3$) δ 158.70 (dd, J=242.1, 2.5 Hz), 158.06, 148.94 (dd, J=241.1, 3.3 Hz), 147.44 (dd, J=12.7, 10.4 Hz), 131.74, 130.06, 116.07 (dd, J=20.6, 10.2 Hz), 113.96, 106.68 (dd, J=23.8, 6.9 Hz), 102.58 (dd, J=27.7, 1.9 Hz), 68.41, 68.35, 55.24, 47.02, 33.43, 21.59. HRMS-ESI (m/z) (([M+Na]$^+$)) calcd for C$_{18}$H$_{20}$F$_2$NaO$_3$, 345.1273; found, 345.126.

Example 5D: Preparation of (2S,3R)-3-benzyl-4-(2,4-dichlorophenoxy)butan-2-ol

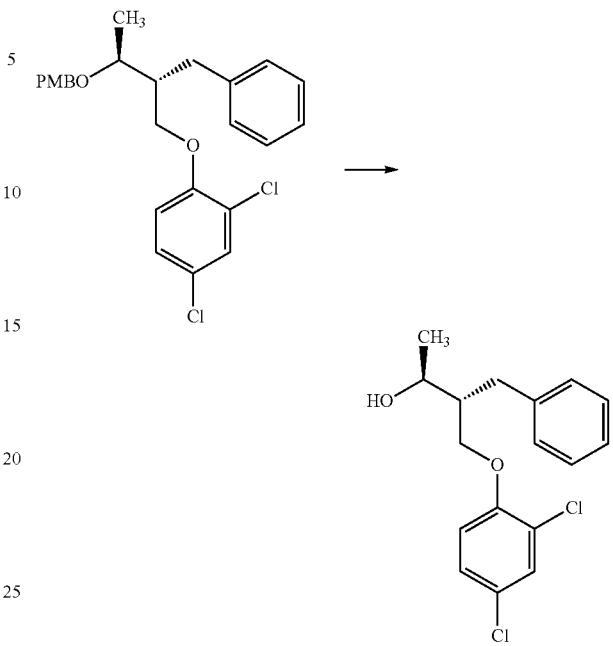

To a solution of 1-((2R,3S)-2-benzyl-3-((4-methoxybenzyl)oxy)butoxy)-2,4-dichlorobenzene (0.280 g, 0.629 mmol) in acetonitrile (5.72 mL) and water (0.572 mL) was added ceric ammonium nitrate (0.758 g, 1.383 mmol) at room temperature. The mixture was stirred for 45 min and then was quenched with NaHCO$_3$ (some gas evolution). The mixture was then diluted with water and ether. The products were extracted with Et$_2$O (2×), and the combined organics were washed with water and brine (2×), dried with Na$_2$SO$_4$, filtered and concentrated. The crude was purified via flash chromatography on silica (24 g silica column, 0-25% acetone in hexanes) to afford (2S,3R)-3-benzyl-4-(2,4-dichlorophenoxy)butan-2-ol (172 mg, 84%) as a clear, slightly pink oil. $^1$N NMR (400 MHz, CDCl$_3$) δ 7.37 (d, J=2.5 Hz, 1H), 7.31-7.26 (m, 2H), 7.24-7.16 (m, 3H), 7.13 (dd, J=8.8, 2.6 Hz, 1H), 6.71 (d, J=8.8 Hz, 1H), 4.13 (dd, J=9.2, 3.7 Hz, 1H), 4.09-3.99 (m, 1H), 3.89 (dd, J=9.3, 4.4 Hz, 1H), 2.95 (dd, J=13.6, 6.0 Hz, 1H), 2.85 (dd, J=13.6, 9.5 Hz, 1H), 2.30 (s, 1H), 2.12-1.99 (m, 1H), 1.36 (d, J=6.4 Hz, 3H). $^{13}$C NMR (101 MHz, CDCl$_3$) δ 152.96, 139.92, 129.86, 129.16, 128.53, 127.61, 126.23, 125.91, 123.57, 113.65, 68.69, 68.12, 46.86, 34.57, 21.74. (Thin film) 3377.21, 2929.96, 1483.11, 1461.63, 1245.26, 1058.96 cm$^{-1}$. HRMS-ESI (m/z) ([M+H]$^+$) calcd for C$_{17}$H$_{19}$Cl$_2$O$_2$, 325.0757; found, 325.0756.

Example 6, Step 1: Preparation of (4R,5S)-4-(4-fluorobenzyl)-5-methyldihydrofuran-2(3H)-one

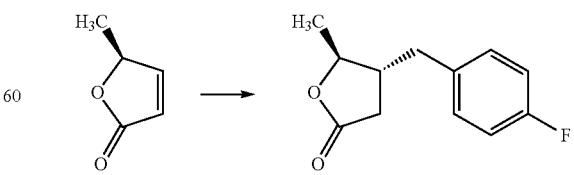

To a flame-dried 3-neck 2 L rb flask charged with Mg-turnings (66.9 g, 2752.2 mmol) that were activated by stirring half an hour under nitrogen, was added dry ether (900 mL). This was allowed to stir for 15 min. Para-fluorobenzyl chloride (66.4 g, 458.7 mmol) was then added as an ether (200 mL) solution drop-wise over ~1.5 h, maintaining an internal temperature below 30° C. A water cooling bath was applied when required. After completion of the addition, the reaction mixture was stirred for a further 2 h at room temperature. A separate flame dried 3-neck flask was charged with CuI (dried in a vac oven at 60° C. overnight, 40.8 g, 214.06 mmol) under nitrogen to which was added dry ether (450 mL), stirred for 10 min, and cooled to −78° C. The Grignard reagent (prepared above) was transferred to the dropping funnel using a cannula and added slowly over 1 h (the temperature increased to −63° C.) and the reaction mixture was stirred for a further 2.5 h. The reaction mixture was also allowed to warm up to −33° C. and the gray color reaction mixture turned to a black solution with black suspension indicating the formation of the organo-copper reagent. A pre-mixed mixture of compound 8 and TMSCl (16.6 g, 152.9 mmol) in ether (100 mL) was added using a addition funnel over 20 min. The reaction mixture was stirred for 2 h at −78° C. and the HPLC showed no starting material (confirmed by TLC 40% EA in hexane). The formation of the product was confirmed by GC. The reaction mixture was quenched with a saturated NH₄Cl solution and extracted with ethyl acetate (3 times). The combined organic layers were further washed with a NH₄Cl solution (3 times) to remove CuI. The organic layers were dried over Na₂SO₄, filtered, and evaporated to give a crude material (41 g), which was purified by silica gel flash chromatography (0-30% ethyl acetate in hexanes) to give (4R,5S)-4-(4-fluorobenzyl)-5-methyldihydrofuran-2(3H)-one (17.0 g, 53%). ¹H NMR (400 MHz, CDCl₃) δ 7.14-7.08 (m, 2H), 7.01-6.97 (m, 2H), 4.31 (m, 1H), 2.80 (m, 1H), 2.71-2.52 (m, 2H), 2.39-2.23 (m, 2H), 1.31 (d, J=4 Hz, 3H).

Example 6, Step 2: Preparation of (3R,4R,5S)-3-benzyl-4-(4-fluorobenzyl)-5-methyl-dihydrofuran-2(3H)-one To a solution of (4R,5S)-4-(4-fluorobenzyl)-5-methyldihydrofuran-2(3H)-one (1.2 g, 5.76 mmol) in dry THF (30 mL) at −78° C. was added LDA (2.0 M, 17.29 mmol, 8.15 mL) drop-wise. After complete addition, the reaction mixture was stirred for a further 30 min at −78° C. Hexamethylphosphoramide (155 mg, 0.864 mmol) was added and the reaction was stirred for 0.5 h. Benzylbromide (2.9 g, 17.29 mmol) was added drop-wise as a THF (10 mL) solution at −78° C. The reaction mixture was then stirred at −78° C. for 30 min. The cooling bath was then removed to allow the mixture to come up to room temperature and stirred overnight. The reaction mixture was quenched with a saturated aq. NH₄Cl solution and extracted with ethyl acetate (3 times). The combined organic layers were washed with brine, dried (Na₂SO₄), filtered, and evaporated to give a crude product which was purified via flash chromatography on silica to give the (3R,4R,5S)-3-benzyl-4-(4-fluorobenzyl)-5-methyldihydrofuran-2(3H)-one (0.99 g, 58%). ¹H NMR (400 MHz, CDCl₃) δ 7.34-7.26 (m, 3H), 7.15 (d, J=8 Hz, 2H), 7.01-6.92 (m, 4H), 4.17 (m, 1H), 3.06-2.95 (m, 2H), 2.67 (m, 1H), 2.51 (m, 1H), 2.04 (m, 1H), 1.01 (d, J=4 Hz, 3H).

Example 6, Step 3: Preparation of (2R,3R,4S)-2-benzyl-3-(4-fluorobenzyl)pentane-1,4-diol

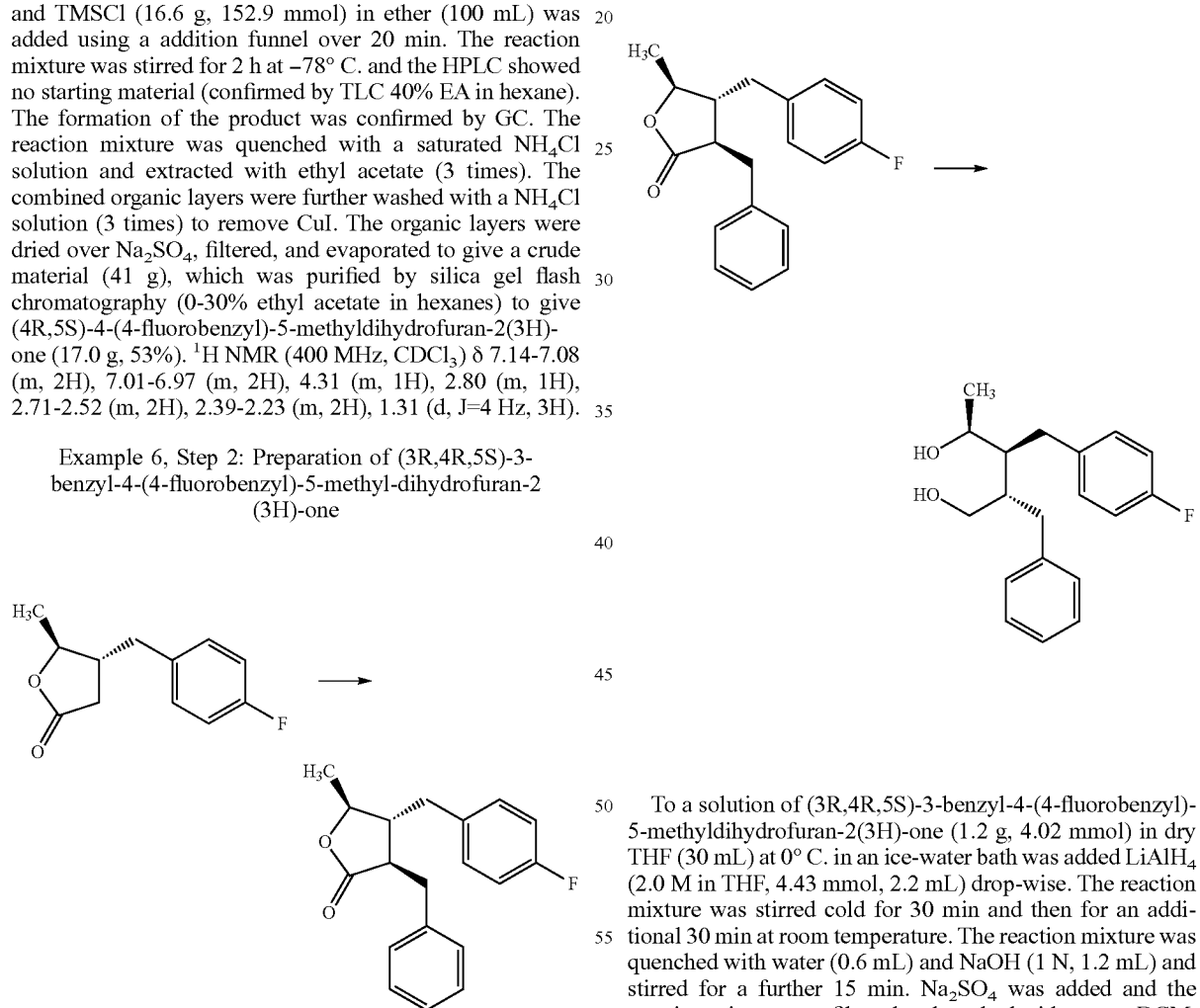

To a solution of (3R,4R,5S)-3-benzyl-4-(4-fluorobenzyl)-5-methyldihydrofuran-2(3H)-one (1.2 g, 4.02 mmol) in dry THF (30 mL) at 0° C. in an ice-water bath was added LiAlH₄ (2.0 M in THF, 4.43 mmol, 2.2 mL) drop-wise. The reaction mixture was stirred cold for 30 min and then for an additional 30 min at room temperature. The reaction mixture was quenched with water (0.6 mL) and NaOH (1 N, 1.2 mL) and stirred for a further 15 min. Na₂SO₄ was added and the reaction mixture was filtered and washed with excess DCM. The filtrate was evaporated to give the crude material which was purified via flash chromatography on silica to afford (2R,3R,4S)-2-benzyl-3-(4-fluorobenzyl)pentane-1,4-diol (1.2 g, 98%) which was used in the next step without further purification. ¹H NMR (400 MHz, CDCl₃) δ 7.23-7.21 (m, 2H), 7.16 (m, 1H), 7.05-7.01 (m, 4H), 6.92-6.90 (m, 2H), 3.91 (m, 1H), 3.79 (m, 1H), 3.57 (m, 1H), 2.87 (dd, J=8 Hz, 4 Hz, 1H), 2.74-2.70 (m, 2H), 2.61-2.54 (m, 2H), 2.26 (br-s, 1H), 2.03 (m, 1H), 1.88 (m, 1H), 1.33 (d, J=8 Hz, 3H).

Example 6, Step 4: Preparation of (4S,5S,6S)-6-benzyl-5-(4-fluorobenzyl)-2,2,4,9,9-pentamethyl-3,8-dioxa-2,9-disiladecane

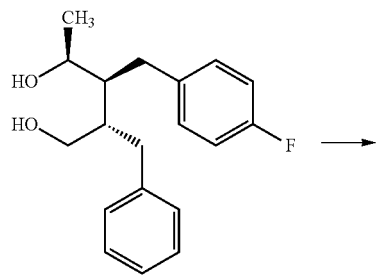

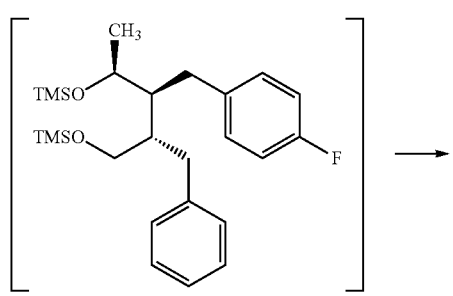

(2R,3R,4S)-2-benzyl-3-(4-fluorobenzyl)pentane-1,4-diol (2.6 g, 8.6 mmol) was dissolved in dry DCM (90 mL) to which was added Et₃N (4.4 g, 43.0 mmol) followed by TMSCl (2.3 g, 21.5 mmol) drop-wise. The reaction mixture was stirred at room temperature for 1 h. Hexane was added to precipitate the triethyl amine salt, which was filtered through a Celite™ pad and washed with hexane-ethyl acetate (440 mL, 10:1). The filtrate was evaporated to give (4S,5S,6S)-6-benzyl-5-(4-fluorobenzyl)-2,2,4,9,9-pentamethyl-3,8-dioxa-2,9-disiladecane (3.6 g) as an colorless oil which was used in the next step without further purification or characterization.

Example 6, Step 5: Preparation of (2S,3S,4S)-2-benzyl-3-(4-fluorobenzyl)-4-((trimethyl silyl)oxy)pentanal

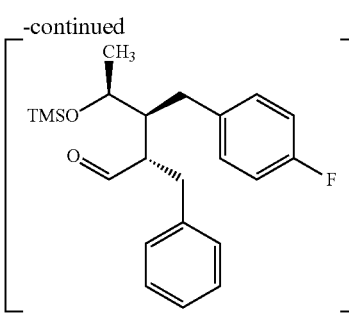

Dry chromium(VI) oxide (3.9 g, 38.7 mmol) was dissolved in dry DCM (80 mL) at room temperature, to which pyridine (6.1 g, 77.4 mmol) was added slowly and stirred at room temperature for 30 min. The reaction mixture was then cooled to −20° C. The (4S,5S,6S)-6-benzyl-5-(4-fluorobenzyl)-2,2,4,9,9-pentamethyl-3,8-dioxa-2,9-disiladecane (3.6 g crude) was added as a DCM (30 mL) solution slowly. The reaction mixture was allowed to stir at a temperature of between −10° C. and −20° C. for 2 h. The cold reaction mixture was filtered quickly through a pad of silica gel and the silica was further washed with Hex-EA (5:1, checked by TLC). The clear filtrate was evaporated to give (2S,3S,4S)-2-benzyl-3-(4-fluorobenzyl)-4-((trimethylsilyl)oxy)pentanal (2.9 g) which was used in the next step without further purification or characterization.

Example 6, Step 6: Preparation of (2S,3S,4R)-4-benzyl-3-(4-fluorobenzyl)hex-5-en-2-ol

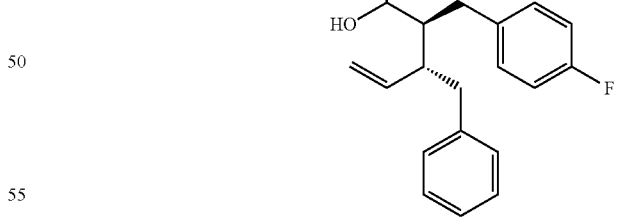

To a suspension of bromo(methyl)triphenylphosphorane (10.4 g, 29.24 mmol) in dry THF (110 mL) was added n-BuLi (2.5 M, 28.38 mmol, 11.4 mL) drop-wise at 0° C. and stirred for 30 min (colour changed from white to yellow). The reaction mixture was then cooled to −78° C. and (2S,3S,4S)-2-benzyl-3-(4-fluorobenzyl)-4-((trimethylsilyl)oxy)pentanal (2.9 g) was added as a THF (30 mL) solution drop-wise. The reaction mixture was allowed to warm up to room temperature overnight. The reaction mixture was quenched with water, then the pH was adjusted to 1 using 1 N HCl, stirred for 15 min and then extracted with EtOAc (3 times). The organic layers were washed with brine, dried over Na$_2$SO$_4$ and evaporated to give an colorless oil which was purified via flash chromatography on silica to afford (2S,3S,4R)-4-benzyl-3-(4-fluorobenzyl)hex-5-en-2-ol (1.2 g, 47%). $^1$N NMR (400 MHz, CDCl3) δ 7.25-7.22 (m, 2H), 7.14 (m, 1H), 7.05-7.02 (m, 2H), 7.00-6.98 (m, 2H), 6.94-6.90 (m, 2H), 5.85 (m, 1H), 5.03 (dd, J=8 Hz, 0.8 Hz, 1H), 4.88 (dd, J=12 Hz, 0.8 Hz, 1H), 3.92 (m, 1H), 2.95 (dd, J=8 Hz, 4 Hz, 1H), 2.72 (dd, J=8 Hz, 4 Hz, 1H), 2.64 (dd, J=8 Hz, 4 Hz, 1H), 2.54 (dd, J=8 Hz, 4 Hz, 1H), 1.84 (m, 1H), 1.29 (d, J=4 Hz, 1H), 1.23 (d, J=8 Hz, 3H).

Example 7: (2S,3R)-4-(3,4-dichlorophenyl)-3-phenylbutan-2-ol

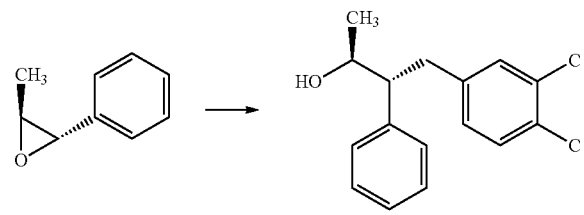

To magnesium turnings (219 mg, 9.00 mmol) in 2 mL Et$_2$O was added a solution of 4-(bromomethyl)-1,2-dichlorobenzene (1080 mg, 4.50 mmol) in 2 mL Et$_2$O at rt, followed by 5 μL of MeI. The mixture was warmed to rt, heated by heat gun to gentle boil, and then stirred at rt for 1 hr. The clear solution was transferred into a suspension of copper(I) iodide (429 mg, 2.250 mmol) in 3.5 mL Et$_2$O at −78° C. The reaction was stirred at −30° C. for 30 min, then cooled to −78° C., (2S,3S)-2-methyl-3-phenyloxirane (201 μl, 1.5 mmol) was added. The reaction was slowly warmed to rt overnight. The reaction was then quenched with saturated aq. NH$_4$Cl and extracted with EtOAc. Combined organic phases dried over Na$_2$SO$_4$, concentrated and purified by flash chromatography on silica (0-10% acetone in hexanes) to provide (2S,3R)-4-(3,4-dichlorophenyl)-3-phenylbutan-2-ol (370 mg, 79%) as a colorless oil. $^1$N HMR (400 MHz, CDCl$_3$) δ 7.32-7.25 (m, 2H), 7.25-7.19 (m, 2H), 7.19-7.11 (m, 3H), 6.85 (dd, J=8.2, 2.1 Hz, 1H), 4.03-3.91 (m, 1H), 3.11 (dd, J=13.6, 6.3 Hz, 1H), 2.88 (dd, J=13.5, 9.0 Hz, 1H), 2.76 (ddd, J=9.1, 6.4, 5.2 Hz, 1H), 1.35 (s, 1H), 1.16 (d, J=6.3 Hz, 3H). $^{13}$C NMR (101 MHz, CDCl$_3$) δ 140.70, 139.68, 131.98, 130.97, 130.00, 129.80, 129.05, 128.55, 128.52, 127.10, 69.48, 54.91, 37.66, 21.63. ESIMS m/z 318.2 ([M+Na]$^+$).

Example 8, Step 1: Preparation of methyl 2,2-bis(4-fluorobenzyl)-3-oxobutanoate

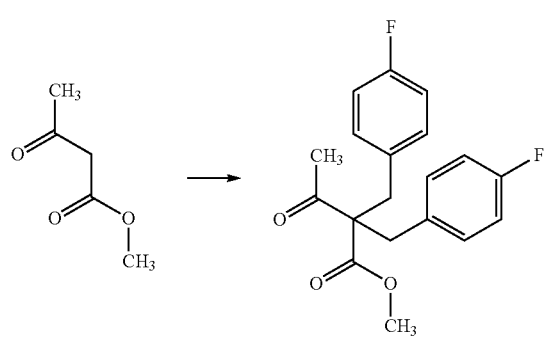

To a stirred solution of methyl 3-oxobutanoate (0.929 mL, 8.61 mmol) in DMF (20 mL) was added potassium carbonate (2.98 g, 21.53 mmol), 1-(bromomethyl)-4-fluorobenzene (2.361 mL, 18.95 mmol) and 1-butyl-3-methyl-1H-imidazolium tetrafluoroborate (0.161 mL, 0.861 mmol). The reaction was stirred at rt for two hours at room temperature. The reaction was filtered and the solid was washed with diethyl ether. The filtrate was diluted with water and extracted with diethyl ether. The organic layers were combined and washed with brine solution and dried over Mg$_2$SO$_4$. The residue is purified via flash chromatography on silica to yield methyl 2,2-bis(4-fluorobenzyl)-3-oxobutanoate (2.786 g, 97%) as a white solid. $^1$H NMR (400 MHz, CDCl$_3$) δ 7.14-7.01 (m, 4H), 7.01-6.89 (m, 4H), 3.66 (s, 3H), 3.15 (s, 4H), 1.93 (s, 3H). $^{13}$C NMR (101 MHz, CDCl$_3$) δ 205.44, 172.01, 161.93 (d, J=245.7 Hz), 131.76 (d, J=3.4 Hz), 131.48 (d, J=7.9 Hz), 115.24 (d, J=21.2 Hz), 66.14, 52.12, 39.31, 29.32. HRMS-ESI (m/z) (([M+H]$^+$)) calcd for C$_{19}$H$_{18}$F$_2$O$_3$, 332.341; found, 355.1115.

Example 8, Step 2: Preparation of 3-(4-fluorobenzyl)-4-(4-fluorophenyl)butan-2-one

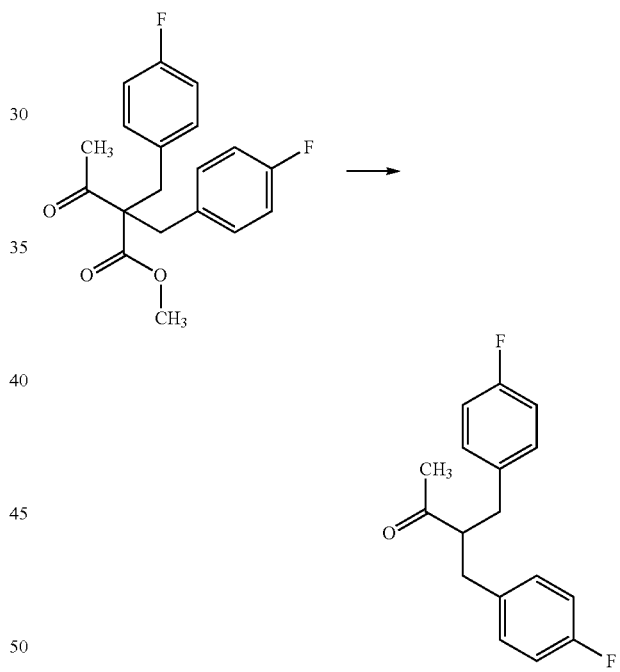

To a stirred solution of methyl 2,2-bis(4-fluorobenzyl)-3-oxobutanoate (2.736 g, 8.23 mmol) and cesium carbonate (0.805 g, 2.470 mmol) in DMF (10 mL) was added 4-aminobenzenethiol (2.061 g, 16.47 mmol). The reaction was partitioned between ether and water, and the aqueous layer was thoroughly extracted with ether. The organic layers were combined and washed with brine solution, and dried over Na$_2$SO$_4$. The ether was evaporated to yield an oil, which was purified via flash chromatography on silica to yield 3-(4-fluorobenzyl)-4-(4-fluorophenyl)butan-2-one (2.235 g, 99%) as an oil. $^1$H NMR (400 MHz, CDCl$_3$) δ 7.12-7.04 (m, 4H), 7.01-6.92 (m, 4H), 3.08 (tt, J=8.8, 5.9 Hz, 1H), 2.88 (dd, J=13.6, 8.9 Hz, 2H), 2.68 (dd, J=13.6, 5.8 Hz, 2H), 1.78 (s, 3H). $^{13}$C NMR (101 MHz, CDCl$_3$) δ 211.68, 161.56 (d, J=244.6 Hz), 134.79 (d, J=3.3 Hz), 130.26 (d, J=7.9 Hz), 115.38 (d, J=21.2 Hz), 56.62, 37.24, 31.68. $^{19}$F NMR (376 MHz, CDCl$_3$) δ –116.54.

Example 8, Step 3: Preparation of (S)-3-(4-fluorobenzyl)-4-(4-fluorophenyl)butan-2-ol

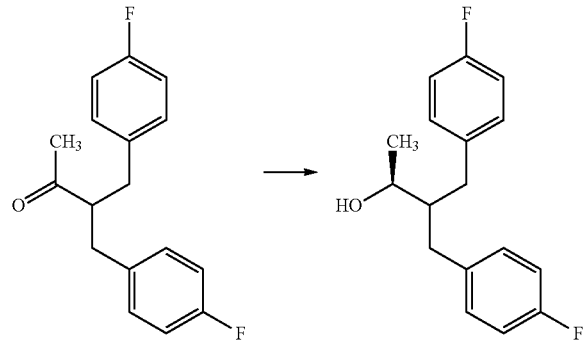 [SMILES: CC(=O)C(Cc1ccc(F)cc1)Cc1ccc(F)cc1 ; C[C@H](O)C(Cc1ccc(F)cc1)Cc1ccc(F)cc1]

To a stirred solution of 3-(4-fluorobenzyl)-4-(4-fluorophenyl)butan-2-one (2.195 g, 8.00 mmol) and (R)-1-methyl-3,3-diphenylhexahydropyrrolo[1,2-c][1,3,2]oxazaborole (0.800 mL, 0.800 mmol) in toluene (53.3 mL) under nitrogen at –78° C. was added 1 M borane-THF complex in THF (8.80 mL, 8.80 mmol) dropwise. The reaction was allowed to warm to rt and was stirred for 1 h. The reaction mixture was partitioned between EtOAc (50 mL) and water (50 mL), and the aqueous phase was extracted with EtOAc (2×, 40 mL). The organic layers were combined, washed with brine, and dried over Na$_2$SO$_4$. The organic phase was concentrated to yield a semi-solid which was purified via flash chromatography on silica to yield (S)-3-(4-fluorobenzyl)-4-(4-fluorophenyl)butan-2-ol (2.127 g, 96%) as an oil. $^1$H NMR (400 MHz, CDCl$_3$) δ 7.12-7.02 (m, 4H), 7.02-6.89 (m, 4H), 3.84-3.72 (m, 1H), 2.75 (dd, J=13.8, 7.4 Hz, 1H), 2.67 (dd, J=14.0, 6.6 Hz, 1H), 2.53 (dd, J=14.0, 7.8 Hz, 1H), 2.43 (dd, J=13.8, 7.1 Hz, 1H), 1.95 (ddq, J=11.1, 7.3, 3.7 Hz, 1H), 1.22 (d, J=6.4 Hz, 3H). $^{19}$F NMR (471 MHz, CDCl$_3$) δ –117.48. (Thin film) 3353, 2929, 1600, 1507, 1218, 823 cm$^{-1}$.

Example 9A: Preparation of (S)-(2S,3S)-3-benzyl-4-methyl-4-propoxypentan-2-yl 2-((tert-butoxycarbonyl)amino)propanoate

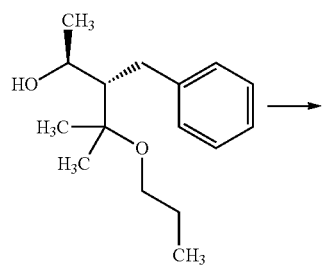

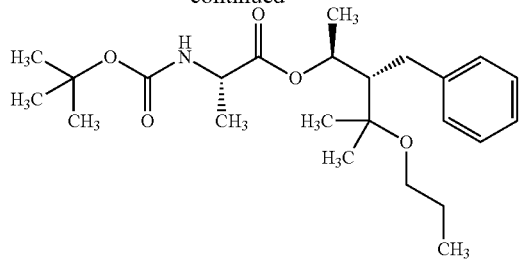

To a solution of (2S,3S)-3-benzyl-4-methyl-4-propoxypentan-2-ol (0.044 g, 0.176 mmol) in DCM (0.879 mL) at rt was added N-ethyl-N-isopropylpropan-2-amine (0.061 ml, 0.351 mmol), N,N-dimethylpyridin-4-amine (2.147 mg, 0.018 mmol), (S)-2-((tert-butoxycarbonyl)-amino)propanoic acid (0.037 g, 0.193 mmol), and 3-(((ethylimino)methylene)amino)-N,N-dimethylpropan-1-aminium chloride (EDC) (0.040 g, 0.211 mmol), in that order. The mixture was stirred at room temperature overnight. The mixture was concentrated onto Celite™ and purified via flash chromatography on silica to provide (S)-(2S,3S)-3-benzyl-4-methyl-4-propoxypentan-2-yl 2-((tert-butoxycarbonyl)amino)propanoate (55 mg, 53% yield) (~71% pure by wt) as a clear oil. $^1$H NMR (400 MHz, CDCl$_3$) δ 7.31-7.12 (m, 5H), 5.35 (qd, J=6.6, 2.8 Hz, 1H), 4.84 (s, 1H), 4.12-3.99 (m, 1H), 3.29 (td, J=6.5, 1.0 Hz, 2H), 2.96 (dd, J=14.7, 4.7 Hz, 1H), 2.74 (dd, J=14.7, 7.8 Hz, 1H), 2.23 (ddd, J=7.7, 4.8, 2.8 Hz, 1H), 1.61-1.48 (m, 2H), 1.44 (s, 9H), 1.34 (d, J=6.5 Hz, 3H), 1.23 (s, 3H), 1.18 (s, 3H), 1.07 (d, J=7.2 Hz, 3H), 0.92 (t, J=7.4 Hz, 3H). $^{13}$C NMR (101 MHz, CDCl$_3$) δ 172.4, 155.0, 143.0, 128.9, 128.2, 125.5, 79.6, 75.9, 73.0, 62.5, 52.9, 49.5, 31.0, 28.4, 24.8, 24.6, 23.7, 18.4, 17.0, 11.0. (Thin film) 3432, 2974, 1715, 1496, 1366, 1167 cm$^{-1}$. HRMS-ESI (m/z) ([M+Na]$^+$) calcd for C$_{24}$H$_{39}$NNaO$_5$, 444.272; found, 444.2723.

Example 9B: (S)-(2S,3S)-3-phenylpentan-2-yl 2-((tert-butoxycarbonyl)amino)propanoate

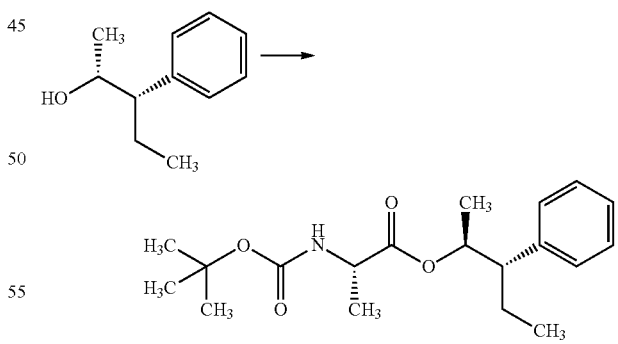

To a solution of triphenylphosphine (399 mg, 1.522 mmol) in 4 mL of THF at 0° C. was added (E)-diisopropyl diazene-1,2-dicarboxylate (300 µl, 1.522 mmol). The solution was stirred at 0° C. for 30 min. A mixture of (S)-2-((tert-butoxycarbonyl)amino)propanoic acid (288 mg, 1.522 mmol) and (2R,3S)-3-phenylpentan-2-ol (125 mg, 0.761 mmol) in 4 mL THF was added dropwise. The reaction was slowly warmed to rt overnight. The reaction was quenched with saturated aq. NaHCO$_3$ and was extracted with Et$_2$O.

The organic phases were combined, dried over Na$_2$SO$_4$, concentrated and purified via flash chromatography on silica to provide (S)-(2S,3S)-3-phenylpentan-2-yl 2-((tert-butoxycarbonyl)amino)propanoate (94 mg, 36%) as a colorless oil. $^1$H NMR (300 MHz, CDCl$_3$) δ 7.34-7.19 (m, 3H), 7.17-7.11 (m, 2H), 5.21-5.01 (m, 2H), 4.42-4.22 (m, 1H), 2.63 (ddd, J=11.0, 8.6, 3.8 Hz, 1H), 1.84 (dqd, J=13.4, 7.5, 3.9 Hz, 1H), 1.69-1.51 (m, 1H), 1.45 (s, 9H), 1.41 (d, J=7.2 Hz, 3H), 1.04 (d, J=6.3 Hz, 3H), 0.72 (t, J=7.4 Hz, 3H). $^{13}$C NMR (101 MHz, CDCl$_3$) δ 172.91, 155.04, 140.84, 128.60, 128.42, 126.76, 79.72, 75.34, 53.05, 49.54, 28.34, 24.58, 18.83, 18.38, 11.84. ESIMS m/z 336 [(M+H)$^+$].

Example 10, Step 1: Preparation of (S)-(2S,3S)-3-benzyl-4-oxopentan-2-yl 2-((tert-butoxycarbonyl)amino)propanoate

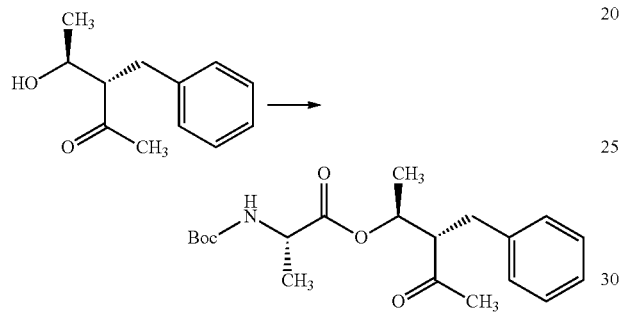

To a solution of (3S,4S)-3-benzyl-4-hydroxypentan-2-one (300 mg, 1.560 mmol) (for preparation see: see: Hayashi, T. et al. *Tetrahedron* 1994, 50, 335) in DCM (7.80 mL) at 0° C. was added (S)-2-((tert-butoxycarbonyl)amino)propanoic acid (354 mg, 1.873 mmol), EDC (598 mg, 3.12 mmol), and N,N-dimethylpyridin-4-amine (19.06 mg, 0.156 mmol). The mixture was then slowly warmed to room temperature overnight. The reaction was quenched with saturated aq. NH$_4$Cl and the product was extracted with DCM. The organics were then washed with saturated aq. NaHCO$_3$ and brine, dried with Na$_2$SO$_4$, filtered and concentrated to provide a yellow oil. The crude material was purified via flash chromatography on silica to provide (S)-(2S,3S)-3-benzyl-4-oxopentan-2-yl 2-((tert-butoxycarbonyl)amino)propanoate (540 mg, 81%) (~85% purity) as a colorless oil. $^1$H MR (400 MHz, CDCl$_3$) δ 7.34-7.23 (m, 2H), 7.24-7.17 (m, 1H), 7.16-7.09 (m, 2H), 5.16 (dq, J=7.3, 6.3 Hz, 1H), 5.02 (d, J=8.0 Hz, 1H), 4.33-4.18 (m, 1H), 3.11 (ddd, J=10.0, 7.4, 5.1 Hz, 1H), 2.93-2.75 (m, 2H), 1.92 (s, 3H), 1.44 (s, 9H), 1.34 (d, J=6.4 Hz, 3H), 1.33 (d, J=7.2 Hz, 3H). ESIMS (m/z) 387 ([M+Na]$^+$).

Example 10, Step 2: Preparation of (S)-(2S,3R)-3-benzyl-4-methylpent-4-en-2-yl 2-((tert-butoxycarbonyl)amino)propanoate

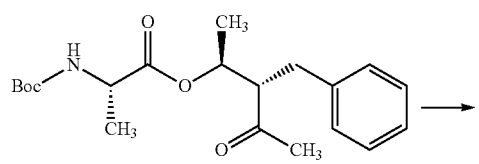

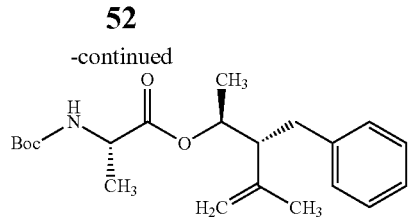

To a solution of (S)-(2S,3S)-3-benzyl-4-oxopentan-2-yl 2-((tert-butoxycarbonyl)-amino)propanoate (350 mg, 0.963 mmol) in THF (9.63 mL) at −78° C. was added pyridine (15.51 µL, 0.193 mmol) and Tebbe reagent (0.5 M in toluene) (3.85 mL, 1.926 mmol). The reaction was stirred at 0° C. for 3 hr. The reaction was quenched carefully with 1 N NaOH at 0° C., and was extracted with EtOAc. The organic phases were combined, concentrated and purified via flash chromatography on silica to provide (S)-(2S,3R)-3-benzyl-4-methylpent-4-en-2-yl 2-((tert-butoxycarbonyl)amino)propanoate (144 mg, 35%) as a colorless oil. $^1$H NMR (400 MHz, CDCl$_3$) δ 7.29-7.22 (m, 2H), 7.21-7.08 (m, 3H), 5.15-4.96 (m, 2H), 4.84-4.76 (m, 1H), 4.71-4.61 (m, 1H), 4.29 (p, J=7.6 Hz, 1H), 2.80 (dd, J=13.6, 5.6 Hz, 1H), 2.64 (dd, J=13.6, 9.5 Hz, 1H), 2.53 (dt, J=9.5, 5.8 Hz, 1H), 1.68 (dd, J=1.5, 0.8 Hz, 3H), 1.45 (s, 9H), 1.39 (d, J=7.2 Hz, 3H), 1.27 (d, J=6.3 Hz, 3H). ESIMS (m/z) 362.4 ([M+H]$^+$).

Example 10, Step 3: Preparation of (S)-(2S,3R)-3-benzyl-4-methylpentan-2-yl 2-((tert-butoxycarbonyl)amino)propanoate

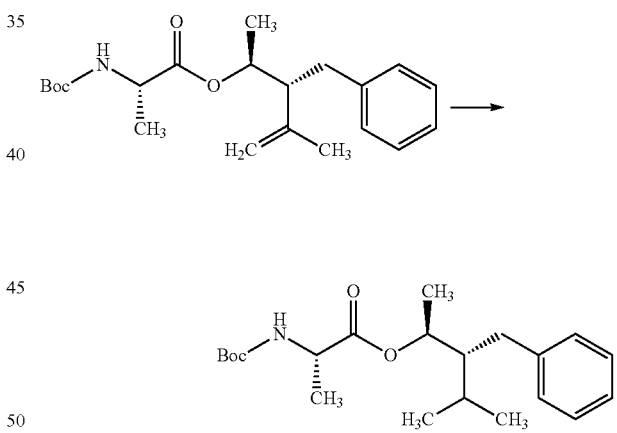

A mixture of (S)-(2S,3R)-3-benzyl-4-methylpent-4-en-2-yl 2-((tert-butoxycarbonyl)-amino)propanoate (160 mg, 0.443 mmol) and palladium on carbon (5% w/w) (94 mg, 0.044 mmol) in EtOAc (4.43 mL) was stirred under H$_2$ (100 psi) at rt overnight. The crude material was used directly in next step. $^1$H NMR (400 MHz, CDCl$_3$) δ 7.31-7.24 (m, 2H), 7.22-7.12 (m, 3H), 5.06-4.95 (m, 2H), 4.32-4.20 (m, 1H), 2.68 (dd, J=14.3, 5.2 Hz, 1H), 2.52 (dd, J=14.2, 8.2 Hz, 1H), 2.03-1.89 (m, 1H), 1.83-1.73 (m, 1H), 1.45 (s, 9H), 1.36 (d, J=7.2 Hz, 3H), 1.19 (d, J=6.5 Hz, 3H), 1.01 (d, J=6.9 Hz, 3H), 0.95 (d, J=6.8 Hz, 3H). ESIMS (m/z) 364 [(M+H)$^+$].

Example 11A, Step 1: Preparation of (S)-(2S,3R)-3-benzyl-4-phenoxybutan-2-yl 2-aminopropanoate hydrochloride

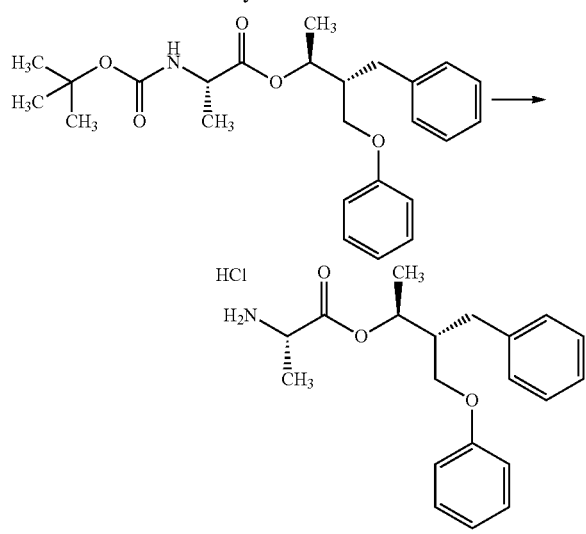

To neat (S)-(2S,3R)-3-benzyl-4-phenoxybutan-2-yl 2-((tert-butoxycarbonyl)amino)propanoate (0.111 g, 0.260 mmol) was added hydrogen chloride (4 M in dioxane) (1.298 mL, 5.19 mmol). The mixture was then stirred for 2 h. The solution was concentrated under a stream of nitrogen to provide (S)-(2S,3R)-3-benzyl-4-phenoxybutan-2-yl 2-aminopropanoate hydrochloride (0.094 g, 100%) as a clear glass. The solid was used in the next step without further purification or characterization. ESIMS (m/z) 328.4 [(M+H)$^+$].

Example 11A, Step 2: Preparation of (S)-(2S,3R)-3-benzyl-4-phenoxybutan-2-yl 2-(3-hydroxy-4-methoxypicolinamido)propanoate

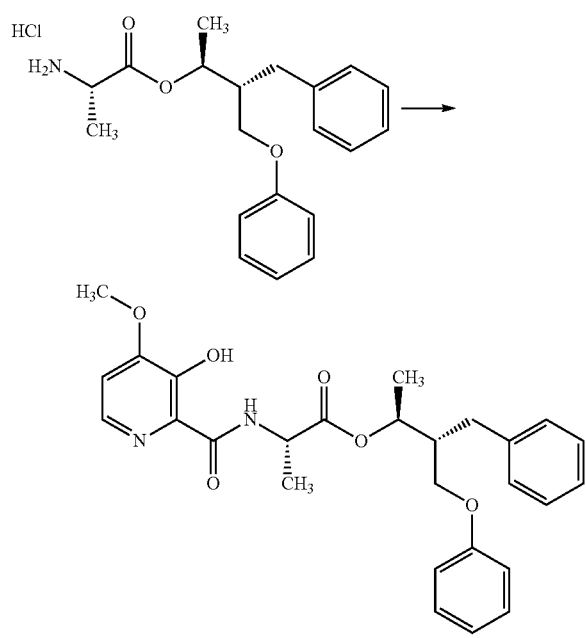

To a solution of (S)-(2S,3R)-3-benzyl-4-phenoxybutan-2-yl 2-aminopropanoate hydrochloride (0.094 g, 0.258 mmol) in DCM (2.58 mL) was added N-ethyl-N-isopropylpropan-2-amine (0.135 mL, 0.775 mmol), 3-hydroxy-4-methoxypicolinic acid (0.048 g, 0.284 mmol), and ((1H-benzo[d][1,2,3]triazol-1-yl)oxy)tri(pyrrolidin-1-yl)phosphonium hexafluorophosphate(V) (PyBOP) (0.148 g, 0.284 mmol). The mixture was then stirred at room temperature overnight. The mixture was concentrated and purified via flash chromatography on silica to provide (S)-(2S,3R)-3-benzyl-4-phenoxybutan-2-yl 2-(3-hydroxy-4-methoxypicolinamido)propanoate (80 mg, 62%) (~95% pure) as a white foam. $^1$H NMR (400 MHz, CDCl$_3$) δ 12.13 (s, 1H), 8.49 (d, J=8.0 Hz, 1H), 7.97 (d, J=5.2 Hz, 1H), 7.30-7.17 (m, 5H), 7.17-7.12 (m, 2H), 6.92 (tt, J=7.4, 1.1 Hz, 1H), 6.85 (d, J=4.7 Hz, 1H), 6.83 6.79 (m, 2H), 5.26 (qd, J=6.4, 5.0 Hz, 1H), 4.78 4.61 (m, 1H), 3.93 (s, 3H), 3.91-3.86 (m, 2H), 2.84-2.75 (m, 2H), 2.36-2.25 (m, 1H), 1.50 (d, J=7.2 Hz, 3H), 1.40 (d, J=6.5 Hz, 3H). $^{13}$C NMR (101 MHz, CDCl$_3$) δ 171.35, 168.74, 158.67, 155.38, 148.77, 140.51, 139.41, 130.42, 129.40, 129.15, 128.52, 126.30, 120.80, 114.44, 109.47, 72.36, 65.70, 56.06, 48.12, 45.32, 33.66, 18.36, 17.53. (Thin film) 3368.01, 2937.00, 1734.91, 1648.24, 1527.51, 1240.25, 1147.60 cm$^{-1}$. HRMS-ESI (m/z) ([M+H]$^+$) calcd for C$_{27}$H$_{31}$N$_2$O$_6$, 480.2209; found, 480.221.

Example 11B, Step 1: Preparation of (2S,3R,4S)-3-(4-fluorobenzyl)-4-(4-(trifluoro-methyl)benzyl)hex-5-en-2-yl L-alaninate 2,2,2-trifluoroacetate

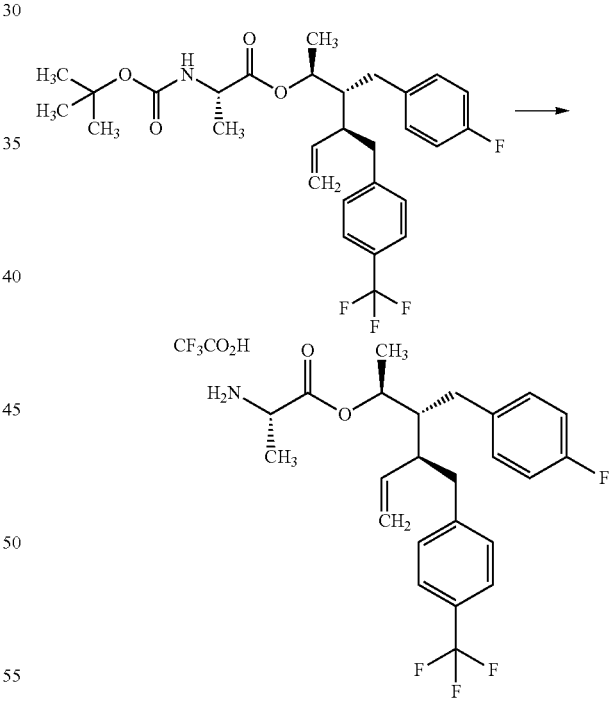

To a solution of (2S,3R,4S)-3-(4-fluorobenzyl)-4-(4-(trifluoromethyl)benzyl)hex-5-en-2-yl (tert-butoxycarbonyl)-L-alaninate (328 mg, 0.595 mmol) in DCM (3 mL) was added trifluoroacetic acid (0.46 mL, 5.95 mmol). After stirring at room temperature for 4 h, the mixture was concentrated in vacuo, to provide (2S,3R,4S)-3-(4-fluorobenzyl)-4-(4-(trifluoromethyl)-benzyl)hex-5-en-2-yl L-alaninate 2,2,2-trifluoroacetate (328 mg, 100%) as a clear, light yellow oil. $^1$H NMR (400 MHz, d$_6$-DMSO) δ 8.30 (bs, 3H), 7.55 (d, J=7.9 Hz, 2H), 7.24 (d, J=7.9 Hz, 2H), 7.17

(dd, J=8.7, 5.6 Hz, 2H), 7.08 (t, J=8.9 Hz, 2H), 5.75 (m, 1H), 5.10 (m, 1H), 4.98 (dd, J=10.3, 1.6 Hz, 1H), 4.83 (d, J=17.2 Hz, 1H), 4.10 (m, 1H), 2.94 (dd, J=13.6, 4.4 Hz, 1H), 2.73 (m, 2H), 2.65 (m, 1H), 2.46 (m, 1H), 2.05 (m, 1H), 1.36 (d, J=7.3 Hz, 3H), 1.25 (d, J=6.4 Hz, 3H). $^{19}$F NMR (376 MHz, d$_6$-DMSO)) δ−55.96, −69.59, −112.58. ESIMS (m/z) 438 [(M+H)$^+$].

Example 11B, Step 2: Preparation of (2S,3R,4S)-3-(4-fluorobenzyl)-4-(4-(trifluoro-methyl)benzyl)hex-5-en-2-yl (3-hydroxy-4-methoxypicolinoyl)-L-alaninate

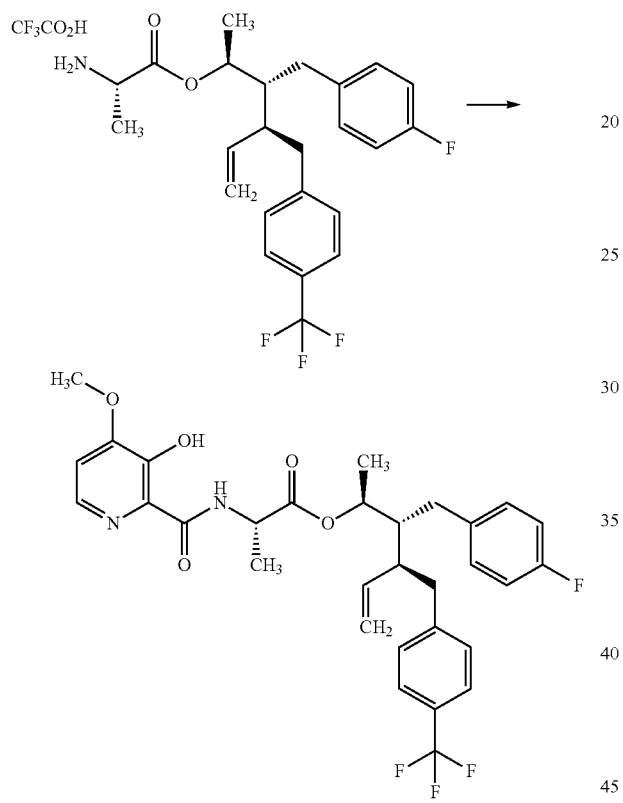

To a mixture of (2S,3R,4S)-3-(4-fluorobenzyl)-4-(4-(trifluoromethyl)benzyl)hex-5-en-2-yl L-alaninate 2,2,2-trifluoroacetate (328 mg, 0.595 mmol), 3-hydroxy-4-methoxypicolinic acid (126 mg, 0.744 mmol), and PyBOP (465 mg, 0.893 mmol) were added DCM (3 mL) and N,N-diisopropyl-N-ethylamine (0.31 mL, 1.79 mmol). The mixture was stirred for ~40 h. The mixture was concentrated in vacuo, and the residue partitioned between water and EtOAc. The layers were separated and the organics dried with Na$_2$SO$_4$, filtered and concentrated. The crude residue was purified via silica gel column chromatography (CH$_2$Cl$_2$/MeOH 100:1) to provide (2S,3R,4S)-3-(4-fluorobenzyl)-4-(4-(trifluoromethyl)benzyl)hex-5-en-2-yl (3-hydroxy-4-methoxypicolinoyl)-L-alaninate (233 mg, 67%) as a clear colorless oil. $^1$H NMR (400 MHz, CDCl$_3$) δ 12.09 (s, 1H), 8.43 (d, J=7.9 Hz, 1H), 7.87 (d, J=5.1 Hz, 1H), 7.39 (d, J=7.9 Hz, 2H), 7.04-6.96 (m, 4H), 6.91 (t, J=8.7 Hz, 2H), 6.77 (d, J=5.1 Hz, 1H), 5.69 (ddd, J=17.2, 10.3, 8.5 Hz, 1H), 5.17 (m, 1H), 5.03 (dd, J=10.3, 1.3 Hz, 1H), 4.84 (d, J=20 Hz, 1H), 4.73 (m, 1H), 3.91 (s, 3H), 2.90 (dd, J=13.1, 5.1 Hz, 1H), 2.72 (dd, J=14.1, 6.3 Hz, 1H), 2.60 (dd, J=14.1, 7.8 Hz, 1H), 2.56 2.48 (m, 1H), 2.46 (m, 1H), 1.97 (m, 1H), 1.56 (d, J=7.3 Hz, 3H), 1.31 (d, J=6.4 Hz, 3H). $^{13}$C NMR (101 MHz, CDCl$_3$) δ 171.33, 168.83, 161.34 (d, J=243 Hz), 155.36, 148.76, 144.44, 140.49, 138.45, 135.83 (d, J=3 Hz), 130.23, 130.22 (d, J=7 Hz), 129.32, 127.93 (q, J=32 Hz), 124.81 (q, J=4 Hz), 124.36 (q, J=270 Hz), 116.99, 115.18, (d, J=21 Hz), 109.40, 72.63, 56.02, 48.13, 45.33, 37.96, 32.69, 18.10, 17.63. $^{19}$F NMR (376 MHz, CDCl$_3$) δ−62.27, −117.06. ESIMS (m/z) 589 [(M+H)$^+$].

Example 11C, Step 1: Preparation of (S)-(2S,3S)-3-benzyl-4-(2,4-dichlorophenoxy)-4-methylpentan-2-yl 2-aminopropanoate hydrochloride and (S)-(2S,3R)-3-benzyl-4-methylpent-4-en-2-yl 2-aminopropanoate hydrochloride

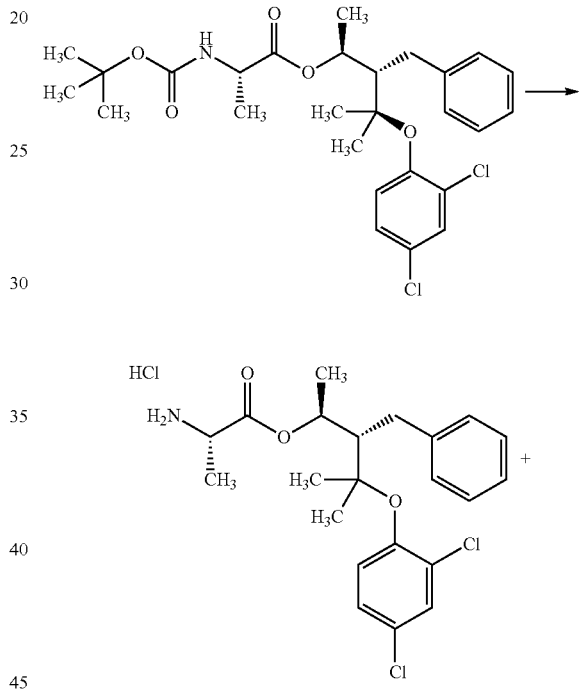

To neat (S)-(2S,3S)-3-benzyl-4-(2,4-dichlorophenoxy)-4-methylpentan-2-yl 2-((tert-butoxycarbonyl)amino)propanoate (0.095 g, 0.181 mmol) was added hydrogen chloride (4 M in dioxane) (0.906 ml, 3.62 mmol). The mixture was stirred at room temperature for 2.5 h. The mixture was concentrated under a stream of nitrogen to provide a 2:3 mixture of compounds (S)-(2S,3R)-3-benzyl-4-methylpent-4-en-2-yl 2-aminopropanoate hydrochloride (21 mg, 40%). ESIMS (m/z) 424.4 ([M+H]$^+$), and (S)-(2S,3S)-3-benzyl-4-(2,4-dichlorophenoxy)-4-methylpentan-2-yl 2-aminopropanoate hydrochloride (50 mg, 60%). ESIMS (m/z) 262.4 ([M+H]$^+$).

Example 11C, Step 2: Preparation of (S)-(2S,3S)-3-benzyl-4-(2,4-dichlorophenoxy)-4-methylpentan-2-yl 2-(3-hydroxy-4-methoxypicolinamido)propanoate and (S)-(2S,3R)-3-benzyl-4-methylpent-4-en-2-yl 2-(3-hydroxy-4-methoxypicolinamido)propanoate

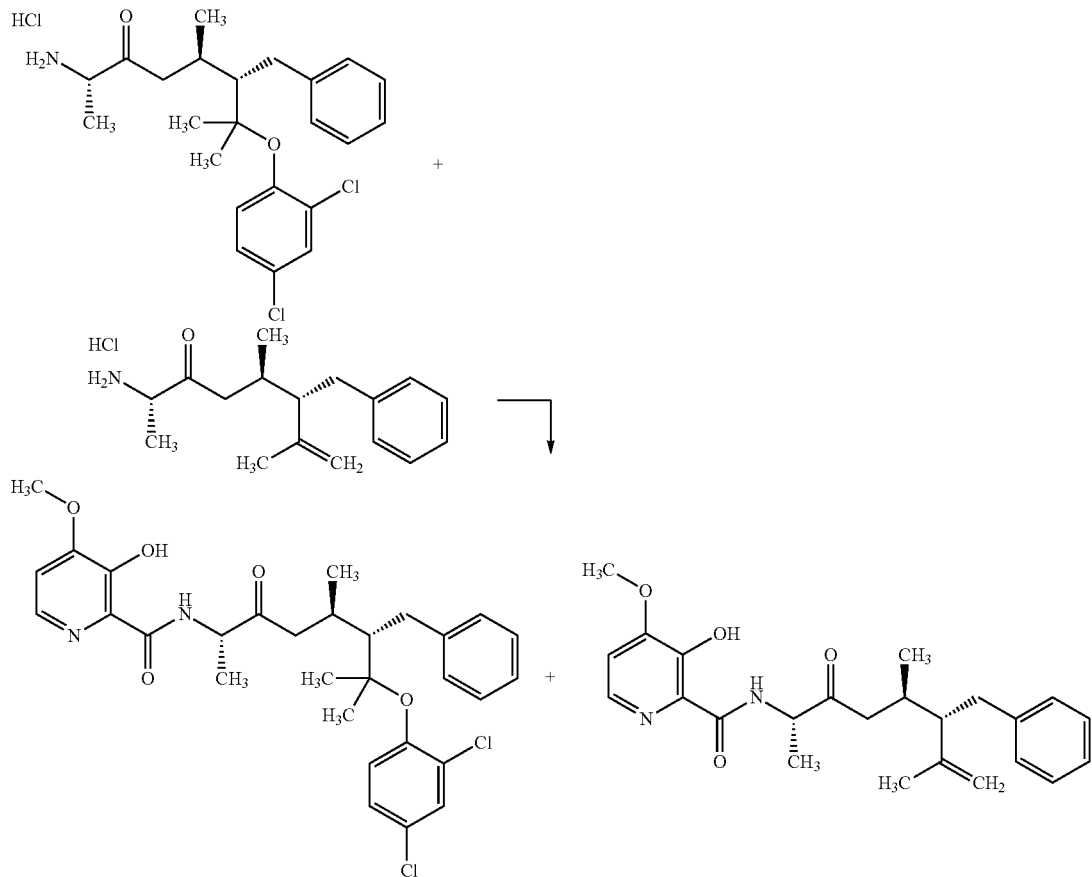

To a solution of a mixture of (S)-(2S,3S)-3-benzyl-4-(2,4-dichlorophenoxy)-4-methylpentan-2-yl 2-aminopropanoate hydrochloride (0.050 g, 0.109 mmol) and (S)-(2S,3R)-3-benzyl-4-methylpent-4-en-2-yl 2-aminopropanoate hydrochloride (21 mg, 0.071 mmol) in DCM (1.085 ml) were added N-ethyl-N-isopropylpropan-2-amine (0.094 ml, 0.543 mmol), 3-hydroxy-4-methoxypicolinic acid (0.032 g, 0.189 mmol), and PyBOP (0.098 g, 0.189 mmol). The mixture was stirred overnight at room temperature. The mixture was then concentrated and purified via reverse phase chromatography (5.5 g C18 column, 5-100% acetonitrile in water) to afford: (S)-(2S,3R)-3-benzyl-4-methylpent-4-en-2-yl 2-(3-hydroxy-4-methoxypicolinamido)propanoate (18 mg, 62%) as a sticky wax. $^1$H NMR (400 MHz, CDCl$_3$) δ 12.15 (s, 1H), 8.50 (d, J=7.9 Hz, 1H), 7.99 (d, J=5.2 Hz, 1H), 7.28-7.22 (m, 2H), 7.20-7.14 (m, 1H), 7.14-7.07 (m, 2H), 6.87 (d, J=5.3 Hz, 1H), 5.08 (p, J=6.3 Hz, 1H), 4.78-4.76 (m, 1H), 4.75-4.66 (m, 1H), 4.66-4.63 (m, 1H), 3.94 (s, 3H), 2.81 (dd, J=13.5, 5.4 Hz, 1H), 2.68-2.60 (m, 1H), 2.59-2.50 (m, 1H), 1.65 (dd, J=1.5, 0.8 Hz, 3H), 1.56 (d, J=7.2 Hz, 3H), 1.30 (d, J=6.3 Hz, 3H). $^{13}$C NMR (101 MHz, CDCl$_3$) δ 171.54, 168.73, 155.38, 148.76, 143.19, 140.46, 139.73, 130.50, 128.85, 128.22, 126.04, 114.84, 109.45, 73.11, 56.08, 53.85, 48.20, 35.81, 20.59, 18.37, 18.15. (Thin film) 3368.25, 2978.89, 1732.44, 1647.36, 1526.67, 1451.05, 1262.62 cm$^{-1}$. HRMS-ESI (m/z)([M+H]$^+$) calcd for C$_{23}$H$_{29}$N$_2$O$_5$, 413.2071; found, 413.2071, and (S)-(2S,3S)-3-benzyl-4-(2,4-dichlorophenoxy)-4-methylpentan-2-yl 2-(3-hydroxy-4-methoxypicolinamido)propanoate (31 mg, 50%) as a sticky wax. $^1$H NMR (400 MHz, CDCl$_3$) δ 12.14 (s, 1H), 8.40 (d, J=7.9 Hz, 1H), 7.97 (d, J=5.2 Hz, 1H), 7.39 (d, J=2.6 Hz, 1H), 7.30-7.18 (m, 4H), 7.18-7.11 (m, 2H), 7.01 (d, J=8.8 Hz, 1H), 6.86 (d, J=5.2 Hz, 1H), 5.60 (qd, J=6.5, 2.9 Hz, 1H), 4.56-4.44 (m, 1H), 3.94 (s, 3H), 3.24 (dd, J=14.9, 5.2 Hz, 1H), 2.93 (dd, J=14.9, 7.0 Hz, 1H), 2.51 (ddd, J=7.0, 5.2, 3.0 Hz, 1H), 1.49 (d, J=6.5 Hz, 3H), 1.43 (s, 3H), 1.31 (s, 3H), 1.29 (d, J=7.2 Hz, 3H). $^{13}$C NMR (101 MHz, CDCl$_3$) δ 171.44, 168.67, 155.37, 149.85, 148.75, 142.20, 140.46, 130.47, 130.21, 129.94, 128.75, 128.63, 128.42, 127.24, 125.80, 125.27, 109.44, 85.33, 73.24, 56.08, 54.16, 48.09, 31.34, 26.30, 25.82, 17.88, 17.30. (Thin film) 3366.01, 2977.63, 1732.01, 1648.45, 1472.90, 1261.08, cm$^{-1}$. HRMS-ESI (m/z) ([M+H]$^+$) calcd for C$_{29}$H$_{33}$Cl$_2$N$_2$O$_6$, 575.171; found, 575.171.

Example 11D, Step 1: Preparation of (S)-(2S,3S)-3-(4-fluorobenzyl)-4-((4-fluorobenzyl)oxy)-4-methyl-pentan-2-yl 2-aminopropanoate

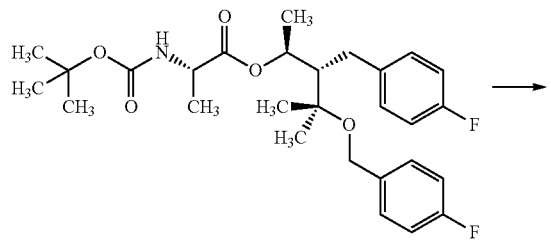

To a solution of (S)-(2S,3S)-3-(4-fluorobenzyl)-4-((4-fluorobenzyl)oxy)-4-methylpentan-2-yl 2-((tert-butoxycarbonyl)amino)propanoate (213.1 mg, 0.421 mmol) in DCM (4.215 mL) was added 2,6-dimethylpyridine (292 µL, 2.53 mmol) in one portion via syringe, followed by trimethylsilyl trifluoromethanesulfonate (305 µL, 1.686 mmol). The resulting clear, colorless solution was then stirred at room temperature for 3 h. Methanol (3 mL) was then added, and the solution was stirred at room temperature for 30 min. After 30 min, the solution was concentrated under a stream of $N_2$ to yield the title compound as a pale orange oil that was used directly in the next step without further purification. $^{19}$F NMR (376 MHz, CDCl$_3$) δ −115.97, −118.05; (Thin film) 3488, 2981, 1742, 1647, 1510, 1222, 1158, 1027 cm$^{-1}$; HRMS-ESI (m/z) calc'd for [C$_{23}$H$_{30}$F$_2$NO$_3$]$^+$, 406.2188; found, 406.2196.

Example 11D, Step 2: Preparation of (S)-(2S,3R)-3-benzyl-4-phenoxybutan-2-yl 2-(3-hydroxy-4-methoxypicolinamido)propanoate

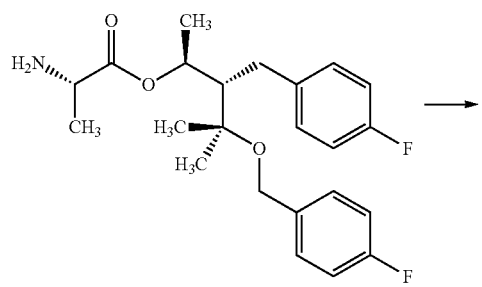

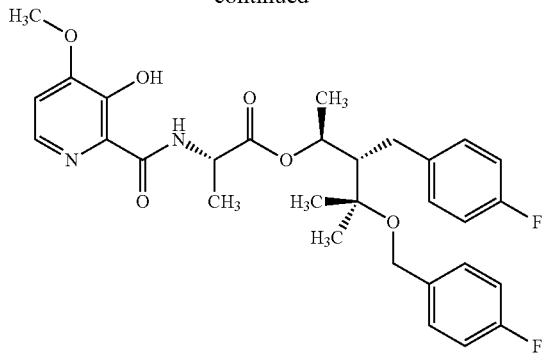

To a solution of (S)-(2S,3S)-3-(4-fluorobenzyl)-4-((4-fluorobenzyl)oxy)-4-methylpentan-2-yl 2-aminopropanoate (173.0 mg, 0.427 mmol) was added 3-hydroxy-4-methoxypicolinic acid (87 mg, 0.512 mmol) and ((1H-benzo[d][1,2,3]triazol-1-yl)oxy)tri(pyrrolidin-1-yl)phosphonium hexafluorophosphate(V) (266 mg, 0.512 mmol) in DCM (4.27 mL) was added N-ethyl-N-isopropylpropan-2-amine (297 µL, 1.707 mmol) dropwise over 45 seconds. The resultant pale orange colored reaction was stirred at rt overnight. The reaction was concentrated under reduced pressure to yield an orange colored oil which was purified via flash chromatography on silica to afford the title compound (174.6 mg, 73% yield over two steps) as a clear, colorless oil. $^1$H NMR (400 MHz, CDCl$_3$) δ 12.13 (s, 1H), 8.38 (d, J=7.9 Hz, 1H), 7.96 (d, J=5.2 Hz, 1H), 7.36-7.20 (m, 2H), 7.20-7.06 (m, 2H), 7.06-6.95 (m, 2H), 6.94-6.87 (m, 2H), 6.85 (d, J=5.3 Hz, 1H), 5.45 (qd, J=6.5, 2.8 Hz, 1H), 4.59-4.46 (m, 1H), 4.45-4.32 (m, 2H), 3.93 (d, J=2.0 Hz, 3H), 2.96 (dd, J=14.8, 5.3 Hz, 1H), 2.78 (dd, J=14.9, 7.0 Hz, 1H), 2.29 (ddd, J=7.0, 5.4, 2.8 Hz, 1H), 1.93 (dddd, J=31.2, 13.0, 7.3, 5.9 Hz, 1H), 1.36 (d, J=6.6 Hz, 3H), 1.33 (s, 3H), 1.30 (d, J=7.2 Hz, 3H), 1.26 (s, 3H); $^{19}$F NMR (376 MHz, CDCl$_3$) δ−115.67, −117.79; (Thin film) 3369, 2976, 1732, 1649, 1528, 1218, 1141, 1040, 729 cm$^{-1}$; HRMS-ESI (m/z) calc'd for [C$_{30}$H$_{35}$F$_2$N$_2$O$_6$]$^+$, 557.2458; found, 557.2471.

Example 12A: Preparation of (S)-(2S,3R)-3-phenyl-heptan-2-yl 2-(3-(acetoxymethoxy)-4-methoxypicolinamido)propanoate

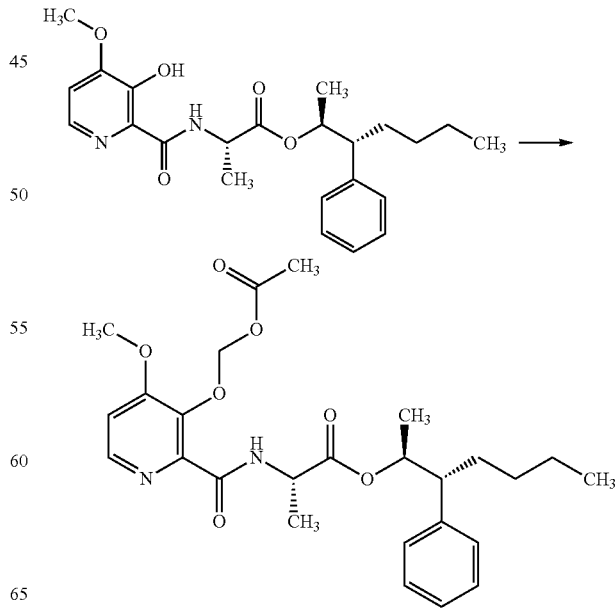

To a solution of (S)-(2S,3R)-3-phenylheptan-2-yl 2-(3-hydroxy-4-methoxypicolinamido)propanoate (98 mg, 0.236 mmol) and K$_2$CO$_3$ (98 mg, 0.709 mmol) in acetone (4.73 mL) was added bromomethyl acetate (34.8 µL, 0.355 mmol). The solution was heated to 50° C. for 3 hr. The solution was cooled to rt and concentrated. Purification via flash chromatography on silica yielded (S)-(2S,3R)-3-phenylheptan-2-yl 2-(3-(acetoxymethoxy)-4-methoxypicolinamido)propanoate (84 mg, 69%) as a colorless oil. $^1$H NMR (400 MHz, CDCl$_3$) δ 8.43-8.14 (m, 2H), 7.31-7.21 (m, 2H), 7.22-7.11 (m, 3H), 6.94 (d, J=5.4 Hz, 1H), 5.86-5.60 (m, 2H), 5.31-5.14 (m, 1H), 4.75-4.49 (m, 1H), 3.90 (s, 3H), 2.71 (ddd, J=10.3, 7.0, 4.6 Hz, 1H), 2.06 (s, 3H), 1.73-1.58 (m, 2H), 1.37-1.19 (m, 2H), 1.24 (d, J=6.3 Hz, 3H), 1.17-1.04 (m, 2H), 1.14 (d, J=7.1 Hz, 3H). 0.81 (t, J=7.2 Hz, 3H). $^{13}$C NMR (101 MHz, CDCl$_3$) d 172.23, 170.23, 162.87, 160.26, 145.68, 143.96, 142.56, 141.28, 128.62, 128.18, 126.49, 109.54, 89.55, 74.79, 56.17, 51.14, 48.18, 31.40, 29.46, 22.60, 20.85, 18.35, 18.12, 13.89. HRMS-ESI (m/z) ([M+H]$^+$) calcd for C$_{26}$H$_{35}$N$_2$O$_7$, 487.2444; found, 487.2437.

Example 12B: Preparation of ((4-methoxy-2-(((S)-1-oxo-1-(((2S,3R)-3-phenylheptan-2-yl)oxy)propan-2-yl)carbamoyl)pyridin-3-yl)oxy)methyl isobutyrate

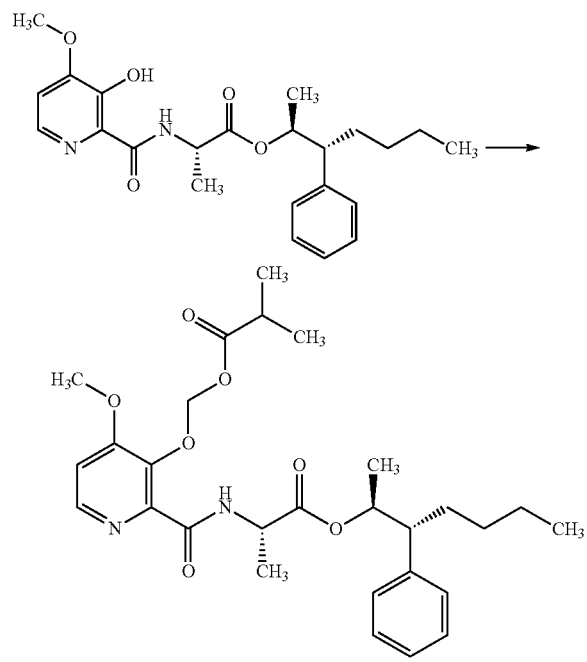

To a solution of (S)-(2S,3R)-3-phenylheptan-2-yl 2-(3-hydroxy-4-methoxy-picolinamido)propanoate (98 mg, 0.236 mmol), sodium iodide (7.09 mg, 0.047 mmol) and sodium carbonate (75 mg, 0.709 mmol) in acetone (4729 µl) was added chloromethyl isobutyrate (48.4 mg, 0.355 mmol). The solution was heated to 55° C. and stirred overnight. The solution was cooled to room temperature and concentrated. Purification via flash chromatography on silica yielded ((4-methoxy-2-(((S)-1-oxo-1-(((2S,3R)-3-phenylheptan-2-yl)oxy)propan-2-yl)carbamoyl)pyridin-3-yl)-oxy)methyl isobutyrate (94 mg, 73%) as a colorless oil. $^1$N HMR (400 MHz, CDCl$_3$) δ 8.34 (d, J=7.8 Hz, 1H), 8.26 (d, J=5.4 Hz, 1H), 7.27-7.15 (m, 5H), 6.94 (d, J=5.4 Hz, 1H), 5.76 (q, J=6.4 Hz, 2H), 5.33-5.10 (m, 1H), 4.65-4.51 (m, 1H), 3.88 (s, 3H), 2.72 (ddd, J=10.3, 7.0, 4.7 Hz, 1H), 2.54 (hept, J=7.0 Hz, 1H), 1.76-1.55 (m, 2H), 1.32-1.21 (m, 2H), 1.24 (d, J=6.3 Hz, 3H), 1.20-1.02 (m, 2H), 1.14 (d, J=7.2 Hz, 3H), 1.14 (d, J=7.0 Hz, 6H), 0.81 (t, J=7.2 Hz, 3H). $^{13}$C NMR (101 MHz, CDCl$_3$) δ 176.19, 172.23, 162.84, 160.25, 145.53, 144.19, 142.19, 141.27, 128.62, 128.17, 126.48, 109.48, 89.91, 74.77, 56.12, 51.13, 48.17, 33.84, 31.39, 29.46, 22.60, 18.66, 18.34, 18.12, 13.88. HRMS-ESI (m/z) ([M+H]$^+$) calcd for C$_{28}$H$_{39}$N$_2$O$_7$, 515.2764; found, 515.2759.

Example 12C: Preparation of (S)-(2S,3R)-3-phenylheptan-2-yl 2-(3-acetoxy-4-methoxypicolinamido)propanoate

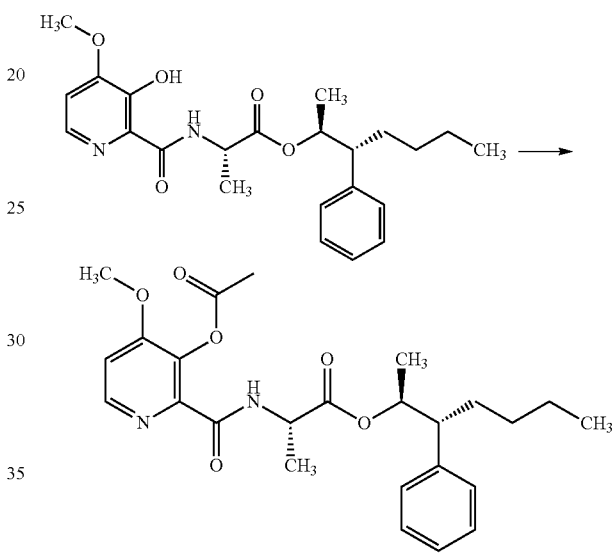

To (S)-(2S,3R)-3-phenylheptan-2-yl 2-(3-hydroxy-4-methoxypicolinamido)propanoate (98 mg, 0.236 mmol), N,N-dimethylpyridin-4-amine (5.78 mg, 0.047 mmol) and triethylamine (99 µL, 0.709 mmol) in DCM (4.73 mL) was added acetyl chloride (33.6 µl, 0.473 mmol) at rt. The reaction gradually turned orange. The reaction was stirred at rt for 2 hr. The reaction mixture was purified via flash chromatography on silica to provide (S)-(2S,3R)-3-phenylheptan-2-yl 2-(3-acetoxy-4-methoxypicolinamido)propanoate (85 mg, 71%) as a colorless oil. $^1$H NMR (400 MHz, CDCl$_3$) δ 8.46 (d, J=8.3 Hz, 1H), 8.32 (d, J=5.4 Hz, 1H), 7.33-7.14 (m, 5H), 6.99 (d, J=5.5 Hz, 1H), 5.20 (p, J=6.4 Hz, 1H), 4.58 (dq, J=8.2, 7.2 Hz, 1H), 3.89 (s, 3H), 2.70 (ddd, J=10.3, 6.9, 4.9 Hz, 1H), 2.38 (s, 3H), 1.75-1.56 (m, 2H), 1.33-1.23 (m, 2H), 1.22 (d, J=6.3 Hz, 3H), 1.13 (d, J=7.2 Hz, 3H), 1.12-0.99 (m, 2H), 0.81 (t, J=7.2 Hz, 3H). $^{13}$C NMR (101 MHz, CDCl$_3$) δ 172.13, 168.87, 162.28, 159.44, 146.64, 141.56, 141.22, 137.47, 128.65, 128.17, 126.50, 109.73, 74.81, 56.27, 51.11, 47.97, 31.39, 29.48, 22.61, 20.73, 18.32, 18.30, 13.90. HRMS-ESI (m/z) ([M+H]$^+$) calcd for C$_{25}$H$_{33}$N$_2$O$_6$, 457.2338; found, 457.2345.

Example A: Evaluation of Fungicidal Activity: Leaf Blotch of Wheat (*Zymoseptoria tritici*; Bayer code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases. Wheat leaf blotch and brown rust activity were also evaluated using track spray applications, in which case the fungicides were formulated as EC formulations, containing 0.1% Trycol 5941 in the spray solutions.

Wheat plants (variety *Yuma*) were grown from seed in a greenhouse in 50% mineral soil/50% soil-less Metro mix until the first leaf was fully emerged, with 7-10 seedlings per pot. These plants were inoculated with an aqueous spore suspension of *Zymoseptoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the $1^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity:
Wheat Brown Rust (*Puccinia triticina*; Synonym:
*Puccinia recondita* f. sp. *tritici*; Bayer code
PUCCRT)

Wheat plants (variety *Yuma*) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C: Evaluation of Fungicidal Activity:
Asian Soybean Rust (*Phakopsora pachyrhizi*; Bayer
code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% RH then transferred to a growth room at 23° C. for disease to develop. Disease severity was assessed on the sprayed leaves.

TABLE 1

| | Compound Structure and Appearance | | | |
|---|---|---|---|---|
| *Cmpd. No. | Structure | | Prepared According to Example | Appearance |
| 1 | | | Example 6, Step 1-6; Example 5A; Example 9A | Colorless Oil |
| 2 | | | Example 6, Step 1, 3-6; Example 5A; Example 9A | Colorless Oil |

TABLE 1-continued
Compound Structure and Appearance
| *Cmpd. No. | Structure | Prepared According to Example | Appearance |
|---|---|---|---|
| 3 | 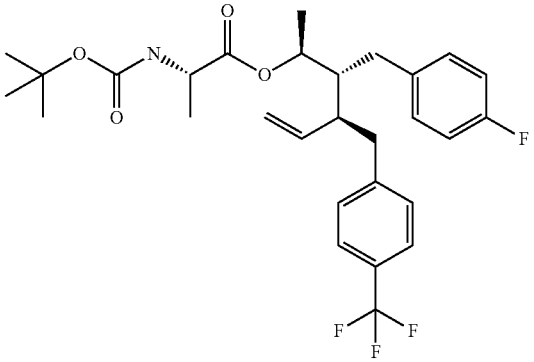 [SMILES: C=C[C@H](Cc1ccc(C(F)(F)F)cc1)[C@@H](Cc1ccc(F)cc1)[C@H](C)OC(=O)[C@H](C)NC(=O)OC(C)(C)C] | Example 6, Steps 1-6; Example 9A | Colorless Oil |
| 4 | 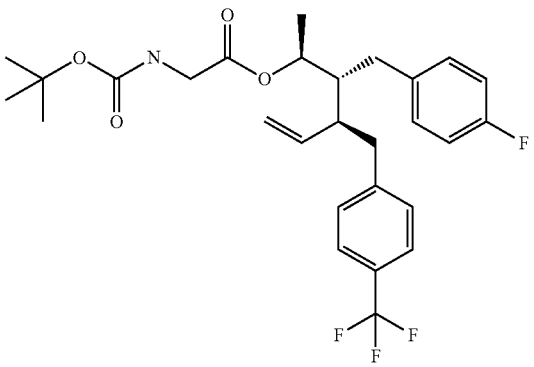 [SMILES: C=C[C@H](Cc1ccc(C(F)(F)F)cc1)[C@@H](Cc1ccc(F)cc1)[C@H](C)OC(=O)CNC(=O)OC(C)(C)C] | Example 6, Steps 1-6; Example 9A | Colorless Oil |
| 5 | 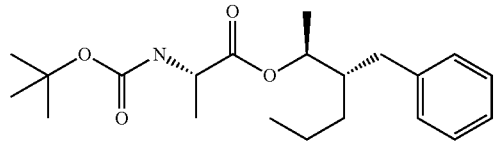 [SMILES: CCC[C@@H](Cc1ccccc1)[C@H](C)OC(=O)[C@H](C)NC(=O)OC(C)(C)C] | Example 6, Step 1, 3-6; Example 5A; Example 9A | Colorless Oil |
| 6 | 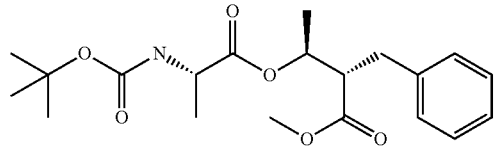 [SMILES: COC(=O)[C@@H](Cc1ccccc1)[C@H](C)OC(=O)[C@H](C)NC(=O)OC(C)(C)C] | Example 1, Step 1; Example 9A | Colorless Oil |
| 7 | 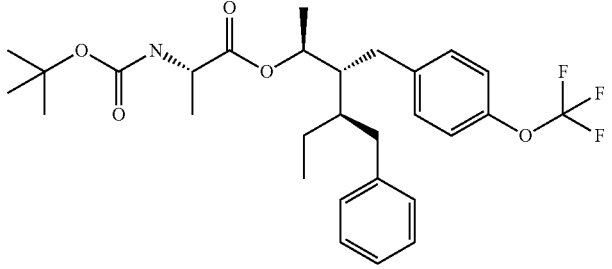 [SMILES: CC[C@H](Cc1ccccc1)[C@@H](Cc1ccc(OC(F)(F)F)cc1)[C@H](C)OC(=O)[C@H](C)NC(=O)OC(C)(C)C] | Example 6, Steps 1-6; Example 9A; Example 10B, Step 3 | Colorless Oil |

TABLE 1-continued

Compound Structure and Appearance

| *Cmpd. No. | Structure | Prepared According to Example | Appearance |
|---|---|---|---|
| 8 | 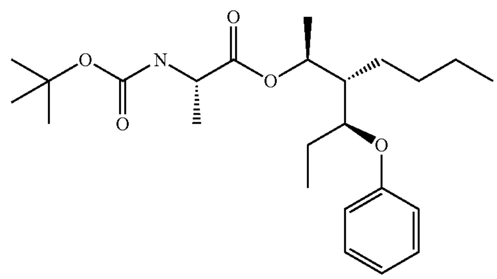 [SMILES: CCCC[C@@H]([C@H](C)OC(=O)[C@H](C)NC(=O)OC(C)(C)C)[C@H](CC)Oc1ccccc1] | Example 1, Steps 1-3; Example 3A, Steps 1-2; Example 4B; Example 5A; Example 9A | Colorless Oil |
| 9 | 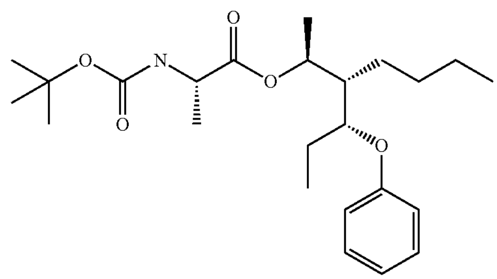 [SMILES: CCCC[C@@H]([C@H](C)OC(=O)[C@H](C)NC(=O)OC(C)(C)C)[C@@H](CC)Oc1ccccc1] | Example 1, steps 1-3; Example 3A steps 1-2; Example 4B; Example 5A; Example 9A | Red Oil |
| 10 | 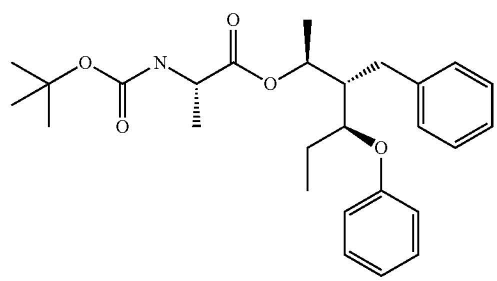 [SMILES: CC[C@H](Oc1ccccc1)[C@@H](Cc1ccccc1)[C@H](C)OC(=O)[C@H](C)NC(=O)OC(C)(C)C] | Example 1, steps 1 and 3; Example 3A steps 1-2; Example 4B; Example 5A; Example 9A | Light Yellow Oil |
| 11 | 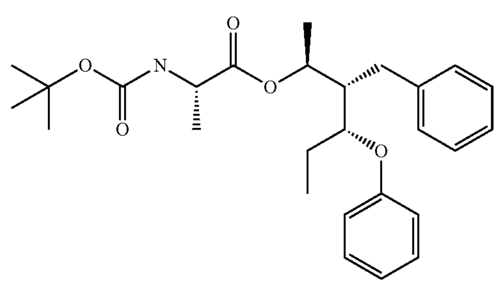 [SMILES: CC[C@@H](Oc1ccccc1)[C@@H](Cc1ccccc1)[C@H](C)OC(=O)[C@H](C)NC(=O)OC(C)(C)C] | Example 1, steps 1 and 3; Example 3A steps 1-2; Example 4B; Example 5A; Example 9A | Light Yellow Oil |
| 12 | 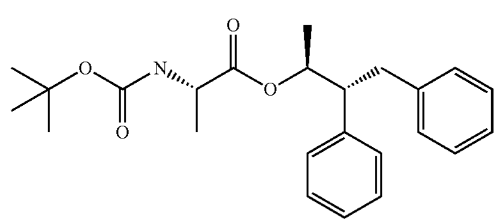 [SMILES: C[C@H](NC(=O)OC(C)(C)C)C(=O)O[C@@H](C)[C@H](Cc1ccccc1)c1ccccc1] | Example 7; Example 9A | Colorless Oil |
| 13 | 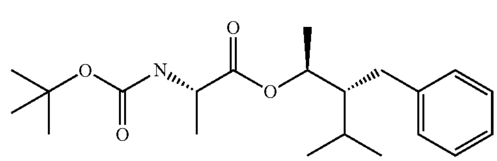 [SMILES: CC(C)[C@@H](Cc1ccccc1)[C@H](C)OC(=O)[C@H](C)NC(=O)OC(C)(C)C] | Example 10, Step 1-3 | Colorless Oil |

TABLE 1-continued

Compound Structure and Appearance

| *Cmpd. No. | Structure | Prepared According to Example | Appearance |
|---|---|---|---|
| 14 | 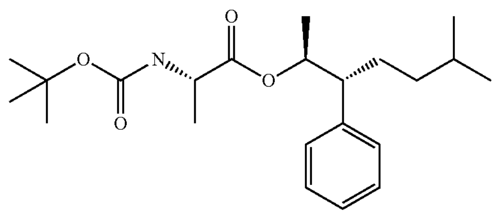 [SMILES: CC(C)CC[C@H](c1ccccc1)[C@H](C)OC(=O)[C@H](C)NC(=O)OC(C)(C)C] | Example 7; Example 9A | Colorless Oil |
| 15 | 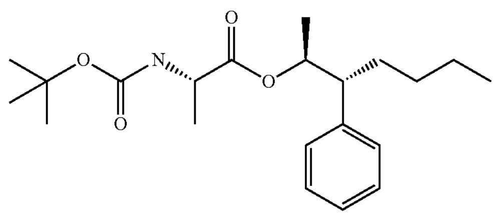 [SMILES: CCCC[C@H](c1ccccc1)[C@H](C)OC(=O)[C@H](C)NC(=O)OC(C)(C)C] | Example 7; Example 9A | Colorless Oil |
| 16 | 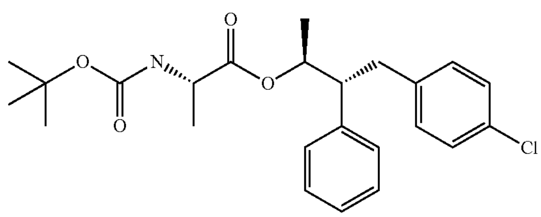 [SMILES: C[C@H](NC(=O)OC(C)(C)C)C(=O)O[C@@H](C)[C@H](Cc1ccc(Cl)cc1)c1ccccc1] | Example 7; Example 9A | Colorless Oil |
| 17 | 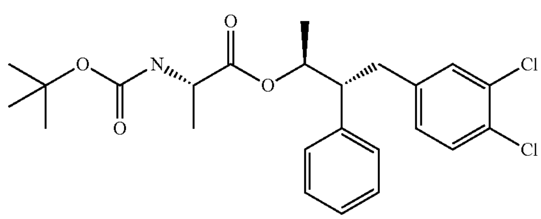 [SMILES: C[C@H](NC(=O)OC(C)(C)C)C(=O)O[C@@H](C)[C@H](Cc1ccc(Cl)c(Cl)c1)c1ccccc1] | Example 7; Example 9A | Colorless Oil |
| 18 | 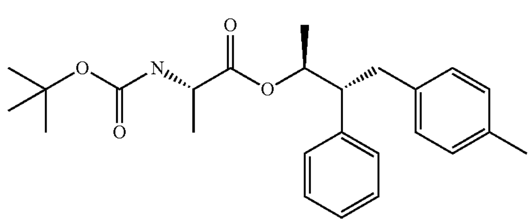 [SMILES: Cc1ccc(C[C@H](c2ccccc2)[C@H](C)OC(=O)[C@H](C)NC(=O)OC(C)(C)C)cc1] | Example 7; Example 9A | Colorless Oil |
| 19 | 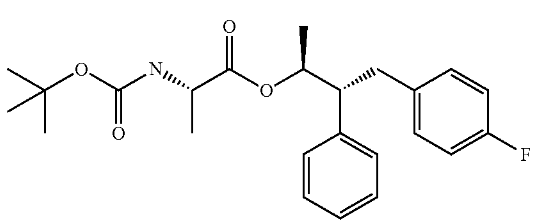 [SMILES: C[C@H](NC(=O)OC(C)(C)C)C(=O)O[C@@H](C)[C@H](Cc1ccc(F)cc1)c1ccccc1] | Example 7; Example 9A | Colorless Oil |

TABLE 1-continued

Compound Structure and Appearance

| *Cmpd. No. | Structure | Prepared According to Example | Appearance |
|---|---|---|---|
| 20 | 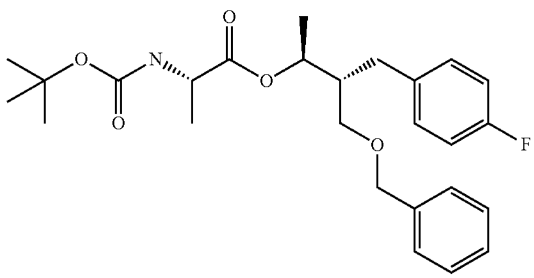 [SMILES: C[C@H](NC(=O)OC(C)(C)C)C(=O)O[C@@H](C)[C@@H](COCc1ccccc1)Cc1ccc(F)cc1] | Example 1, Steps 1 and 3; Example 3B; Example 4D; Example 5D; Example 9A | Clear, Colorless Oil |
| 21 | 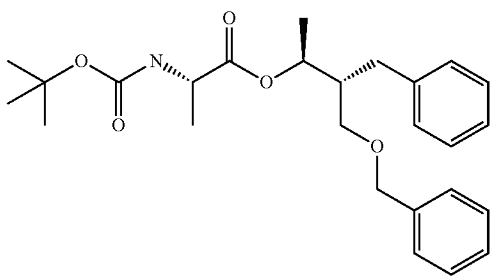 [SMILES: C[C@H](NC(=O)OC(C)(C)C)C(=O)O[C@@H](C)[C@@H](COCc1ccccc1)Cc1ccccc1] | Example 1, Steps 1 and 3; Example 3B; Example 4D; Example 5D; Example 9A | Clear, Colorless Oil |
| 22 | 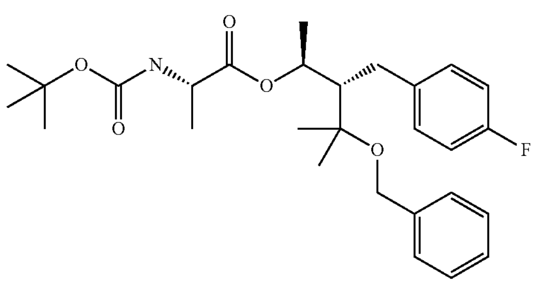 [SMILES: C[C@H](NC(=O)OC(C)(C)C)C(=O)O[C@@H](C)[C@H](Cc1ccc(F)cc1)C(C)(C)OCc1ccccc1] | Example 1, Steps 1 and 3; Example 3C; Example 4D; Example 5D; Example 9A | Clear, Colorless Oil |
| 23 | 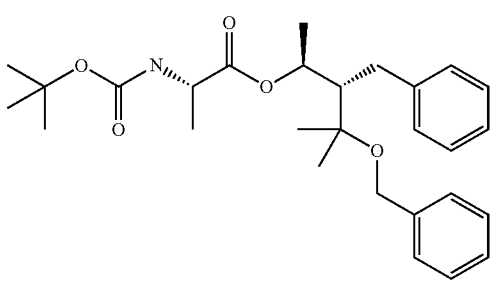 [SMILES: C[C@H](NC(=O)OC(C)(C)C)C(=O)O[C@@H](C)[C@H](Cc1ccccc1)C(C)(C)OCc1ccccc1] | Example 1, Steps 1 and 3; Example 3C; Example 4D; Example 5D; Example 9A | Clear, Colorless Oil |
| 24 | 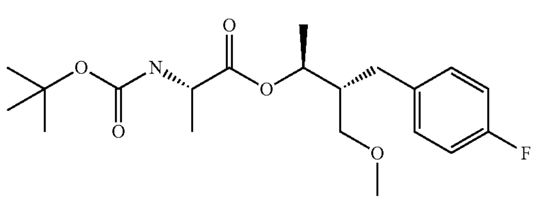 [SMILES: COC[C@@H](Cc1ccc(F)cc1)[C@H](C)OC(=O)[C@H](C)NC(=O)OC(C)(C)C] | Example 1, Steps 1 and 3; Example 3B; Example 4C; Example 5D; Example 9A | White Semi-Solid |

TABLE 1-continued

Compound Structure and Appearance

| *Cmpd. No. | Structure | Prepared According to Example | Appearance |
|---|---|---|---|
| 25 | 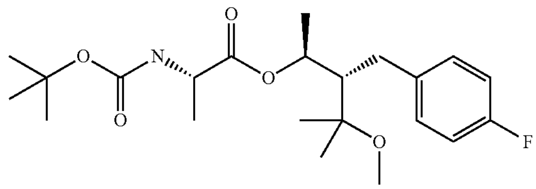 [SMILES: COC(C)(C)[C@@H](Cc1ccc(F)cc1)[C@H](C)OC(=O)[C@H](C)NC(=O)OC(C)(C)C] | Example 1, Steps 1 and 3; Example 3C; Example 4C; Example 5D; Example 9A | Clear, Colorless Oil |
| 26 | 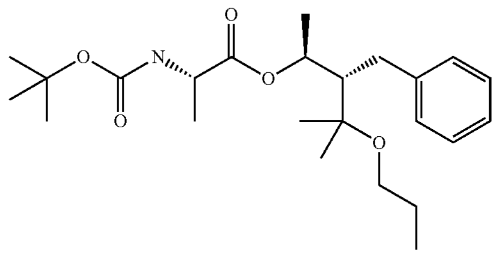 [SMILES: CCCOC(C)(C)[C@@H](Cc1ccccc1)[C@H](C)OC(=O)[C@H](C)NC(=O)OC(C)(C)C] | Example 1, steps 1 and 3; Example 3C; Example 4D; Example 5A; Example 9A | Clear Oil |
| 27 | 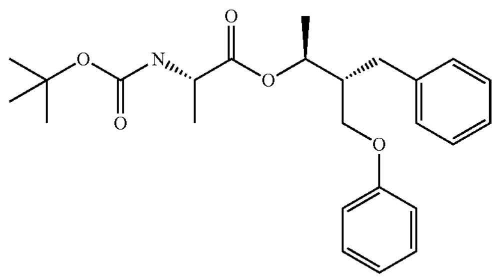 [SMILES: C[C@H](NC(=O)OC(C)(C)C)C(=O)O[C@@H](C)[C@@H](COc1ccccc1)Cc1ccccc1] | Example 1, steps 1 and 3; Example 3B; Example 4E; Example 5B; Example 9A | White Solid |
| 28 | 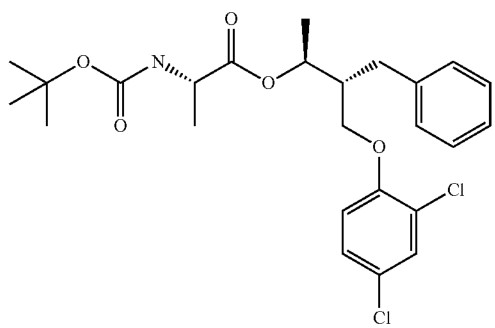 [SMILES: C[C@H](NC(=O)OC(C)(C)C)C(=O)O[C@@H](C)[C@@H](COc1ccc(Cl)cc1Cl)Cc1ccccc1] | Example 1, steps 1 and 3; Example 3B; Example 4E; Example 5D; Example 9A | Sticky Wax |
| 29 | 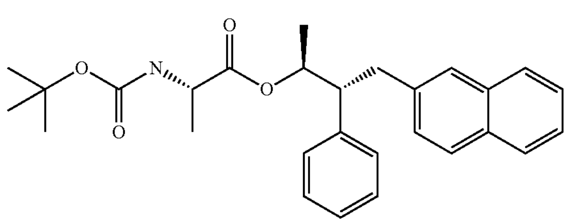 [SMILES: C[C@H](NC(=O)OC(C)(C)C)C(=O)O[C@@H](C)[C@H](Cc1ccc2ccccc2c1)c1ccccc1] | Example 7; Example 9A | Colorless Oil |
| 30 | 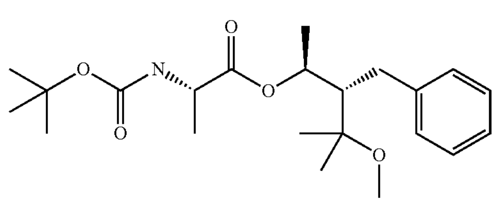 [SMILES: COC(C)(C)[C@@H](Cc1ccccc1)[C@H](C)OC(=O)[C@H](C)NC(=O)OC(C)(C)C] | Example 1, Step 1, 3; Example 3C; Example 4C; Example 5D; Example 9A | Colorless Oil |

TABLE 1-continued

Compound Structure and Appearance

| *Cmpd. No. | Structure | Prepared According to Example | Appearance |
|---|---|---|---|
| 31 | 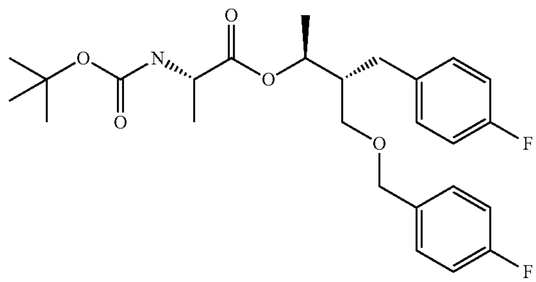 [SMILES: C[C@H](NC(=O)OC(C)(C)C)C(=O)O[C@@H](C)[C@@H](COCc1ccc(F)cc1)Cc1ccc(F)cc1] | Example 1, Steps 1 and 3; Example 3B; Example 4D; Example 5D; Example 9A | Clear, Colorless Oil |
| 32 | 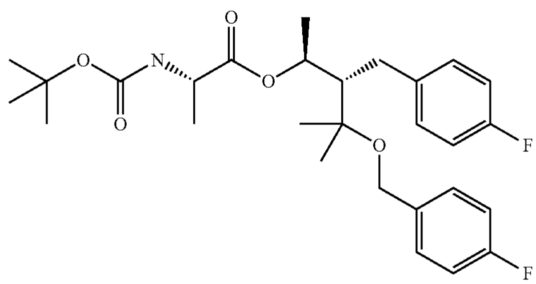 [SMILES: C[C@H](NC(=O)OC(C)(C)C)C(=O)O[C@@H](C)[C@H](Cc1ccc(F)cc1)C(C)(C)OCc1ccc(F)cc1] | Example 1, Steps 1 and 3; Example 3C; Example 4D; Example 5D; Example 9A | Clear, Colorless Oil |
| 33 | 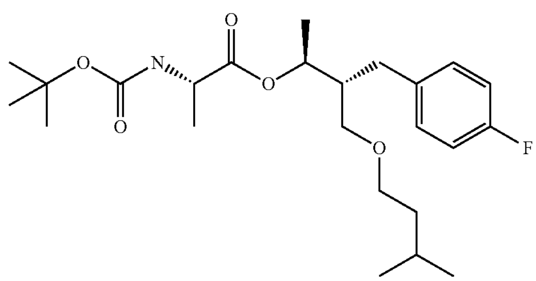 [SMILES: CC(C)CCOC[C@@H](Cc1ccc(F)cc1)[C@H](C)OC(=O)[C@H](C)NC(=O)OC(C)(C)C] | Example 1, Steps 1 and 3; Example 3B; Example 4D; Example 5B; Example 9A | Clear, Colorless Oil |
| 34 | 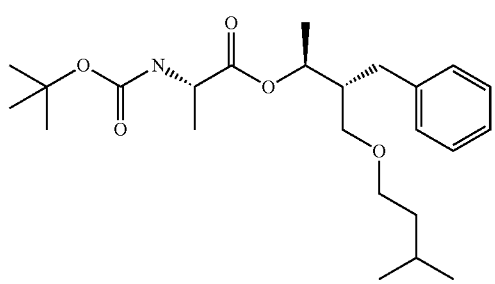 [SMILES: CC(C)CCOC[C@@H](Cc1ccccc1)[C@H](C)OC(=O)[C@H](C)NC(=O)OC(C)(C)C] | Example 1, Steps 1 and 3; Example 3B; Example 4D; Example 5B; Example 9A | Clear, Colorless Oil |
| 35 | 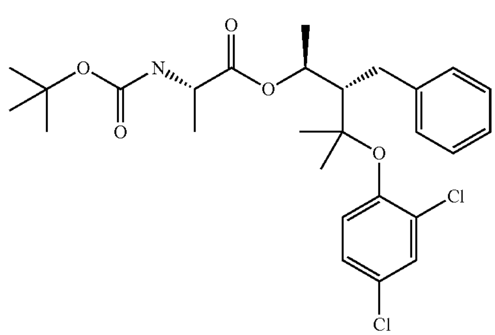 [SMILES: C[C@H](NC(=O)OC(C)(C)C)C(=O)O[C@@H](C)[C@H](Cc1ccccc1)C(C)(C)Oc1ccc(Cl)cc1Cl] | Example 1, steps 1 and 3; Example 3C; Example 4E; Example 5D; Example 9A | Sticky Wax |

TABLE 1-continued

Compound Structure and Appearance

| *Cmpd. No. | Structure | Prepared According to Example | Appearance |
|---|---|---|---|
| 36 | 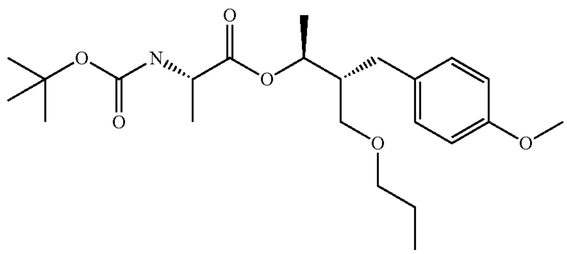 [SMILES: CCCOC[C@@H](Cc1ccc(OC)cc1)[C@H](C)OC(=O)[C@H](C)NC(=O)OC(C)(C)C] | Example 1, step 1; Example 2; Example 3B; Example 4D; Example 5A; Example 9A | Clear Oil |
| 37 | 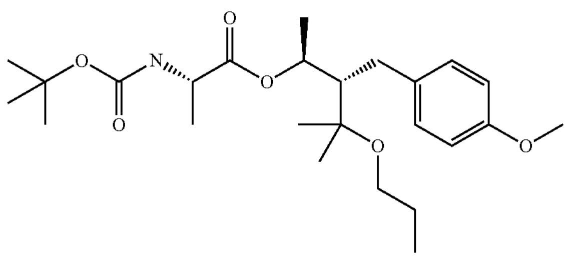 [SMILES: CCCOC(C)(C)[C@@H](Cc1ccc(OC)cc1)[C@H](C)OC(=O)[C@H](C)NC(=O)OC(C)(C)C] | Example 1, step 1; Example 2; Example 3C; Example 4D; Example 5A; Example 9A | Clear Oil |
| 38 | 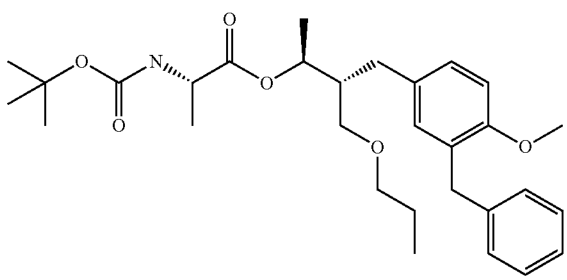 [SMILES: CCCOC[C@@H](Cc1ccc(OC)c(Cc2ccccc2)c1)[C@H](C)OC(=O)[C@H](C)NC(=O)OC(C)(C)C] | Example 1, step 1; Example 2; Example 3B; Example 4D; Example 5A; Example 9A | Clear Oil |
| 39 | 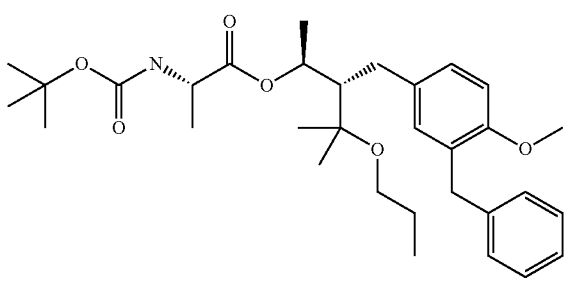 [SMILES: CCCOC(C)(C)[C@@H](Cc1ccc(OC)c(Cc2ccccc2)c1)[C@H](C)OC(=O)[C@H](C)NC(=O)OC(C)(C)C] | Example 1, step 1; Example 2; Example 3C; Example 4D; Example 5A; Example 9A | Colorless Oil |
| 40 | 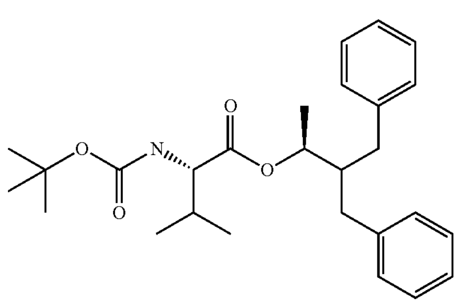 [SMILES: CC(C)[C@H](NC(=O)OC(C)(C)C)C(=O)O[C@@H](C)C(Cc1ccccc1)Cc1ccccc1] | Example 8, steps 1-3; Example 9A | Oil |

TABLE 1-continued

Compound Structure and Appearance

| *Cmpd. No. | Structure | Prepared According to Example | Appearance |
|---|---|---|---|
| 41 | 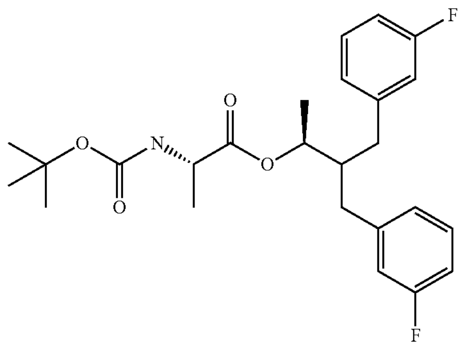 [SMILES: C[C@H](NC(=O)OC(C)(C)C)C(=O)O[C@@H](C)C(Cc1cccc(F)c1)Cc1cccc(F)c1] | Example 8, steps 1-3; Example 9A | Oil |
| 42 | 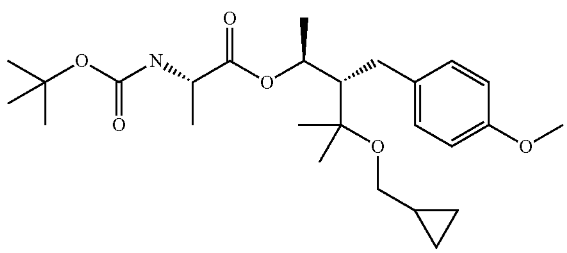 [SMILES: COc1ccc(C[C@@H]([C@H](C)OC(=O)[C@H](C)NC(=O)OC(C)(C)C)C(C)(C)OCC2CC2)cc1] | Example 1, step 1; Example 2; Example 3C; Example 4D; Example 5A; Example 9A | Clear Oil |
| 43 | 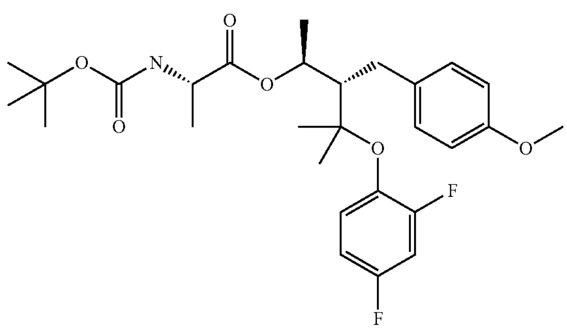 [SMILES: COc1ccc(C[C@@H]([C@H](C)OC(=O)[C@H](C)NC(=O)OC(C)(C)C)C(C)(C)Oc2ccc(F)cc2F)cc1] | Example 1, step 1; Example 2; Example 3C; Example 4E; Example 5A; Example 9A | Clear Oil |
| 44 | 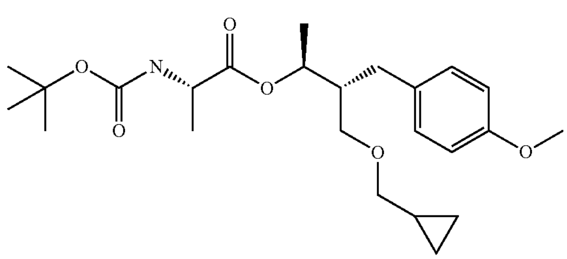 [SMILES: COc1ccc(C[C@H](COCC2CC2)[C@H](C)OC(=O)[C@H](C)NC(=O)OC(C)(C)C)cc1] | Example 1, step 1; Example 2; Example 3B; Example 4D; Example 5A; Example 9A | Clear Oil |
| 45 | 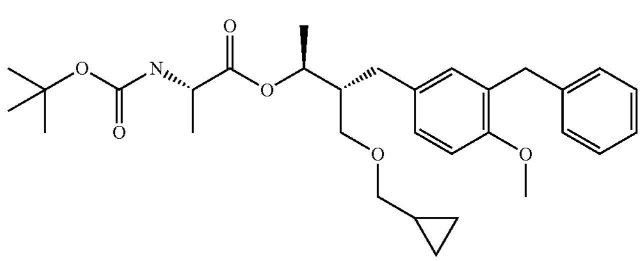 [SMILES: COc1ccc(C[C@H](COCC2CC2)[C@H](C)OC(=O)[C@H](C)NC(=O)OC(C)(C)C)cc1Cc1ccccc1] | Example 1, step 1; Example 2; Example 3B; Example 4D; Example 5A; Example 9A | Clear Oil |

TABLE 1-continued

Compound Structure and Appearance

| *Cmpd. No. | Structure | Prepared According to Example | Appearance |
|---|---|---|---|
| 46 | 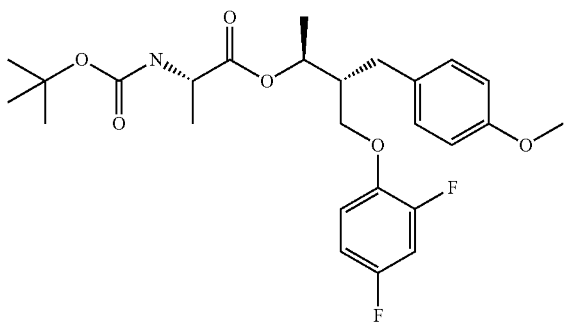 [SMILES: COc1ccc(C[C@H](COc2ccc(F)cc2F)[C@H](C)OC(=O)[C@H](C)NC(=O)OC(C)(C)C)cc1] | Example 1, step 1; Example 2; Example 3B; Example 4E; Example 5A; Example 9A | As A White Semi-Solid |
| 47 | 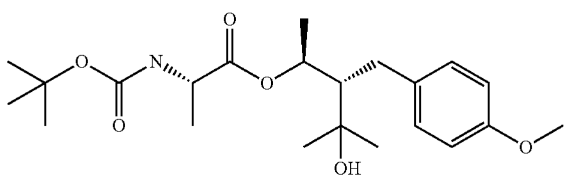 [SMILES: COc1ccc(C[C@@H]([C@H](C)OC(=O)[C@H](C)NC(=O)OC(C)(C)C)C(C)(C)O)cc1] | Example 1, step 1; Example 2; Example 3C; Example 5A; Example 9A | Clear Oil |
| 48 | 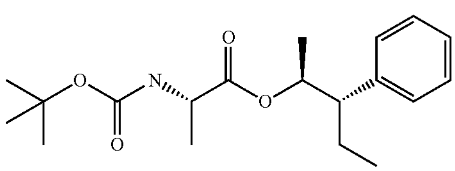 [SMILES: CC[C@@H](c1ccccc1)[C@H](C)OC(=O)[C@H](C)NC(=O)OC(C)(C)C] | Example 7; Example 9B | Colorless Oil |
| 49 | 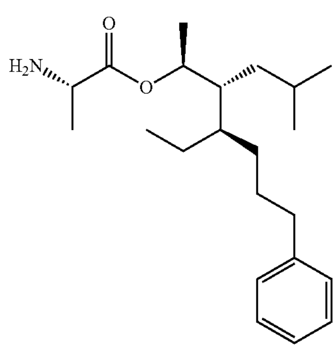 [SMILES: CC[C@H](CCCc1ccccc1)[C@@H](CC(C)C)[C@H](C)OC(=O)[C@H](C)N] | Example 11A, Step 1 | White Solid |
| 50 | 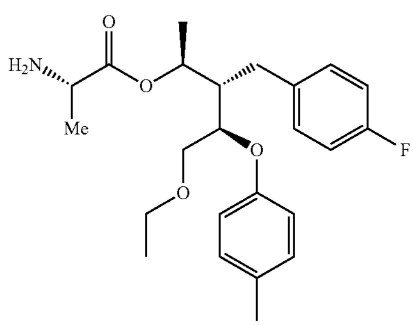 [SMILES: CCOC[C@H](Oc1ccc(C)cc1)[C@@H](Cc1ccc(F)cc1)[C@H](C)OC(=O)[C@H](C)N] | Example 1, Steps 1 and 3; Example 3A, Steps 1-2; Example 4B, Steps 1-3; Example 5D; Example 9A; Example 11A, Step 1 | White Solid |

TABLE 1-continued

Compound Structure and Appearance

| *Cmpd. No. | Structure | Prepared According to Example | Appearance |
|---|---|---|---|
| 51 | 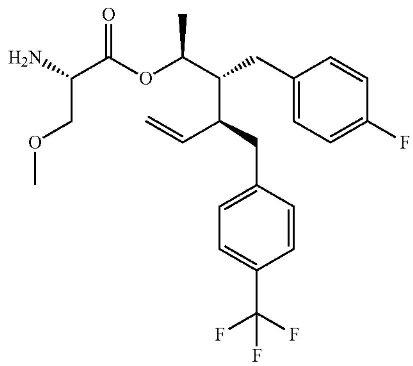 [SMILES: C=C[C@H](Cc1ccc(C(F)(F)F)cc1)[C@@H](Cc1ccc(F)cc1)[C@H](C)OC(=O)[C@@H](N)COC] | Example 11B, Step 1 | Colorless Oil |
| 52 | 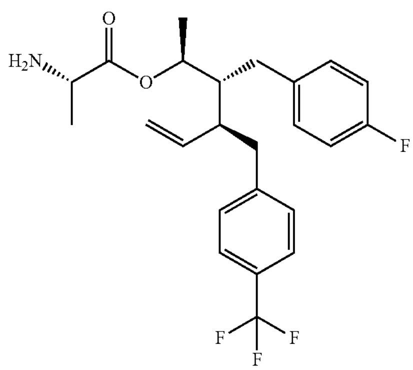 [SMILES: C=C[C@H](Cc1ccc(C(F)(F)F)cc1)[C@@H](Cc1ccc(F)cc1)[C@H](C)OC(=O)[C@H](C)N] | Example 11B, Step 1 | Light Yellow Oil |
| 53 | 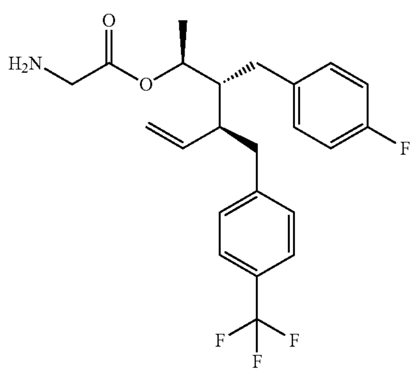 [SMILES: C=C[C@H](Cc1ccc(C(F)(F)F)cc1)[C@@H](Cc1ccc(F)cc1)[C@H](C)OC(=O)CN] | Example 11B, Step 1 | Light Yellow Oil |
| 54 | 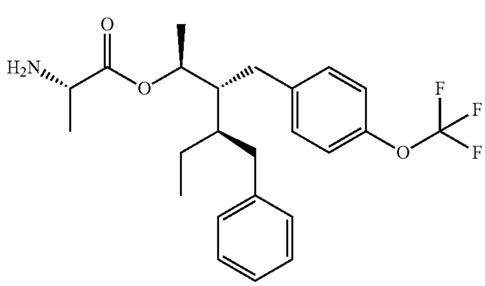 [SMILES: CC[C@H](Cc1ccccc1)[C@@H](Cc1ccc(OC(F)(F)F)cc1)[C@H](C)OC(=O)[C@H](C)N] | Example 11A, step 1 | White Solid |

TABLE 1-continued

Compound Structure and Appearance

| *Cmpd. No. | Structure | Prepared According to Example | Appearance |
|---|---|---|---|
| 55 | 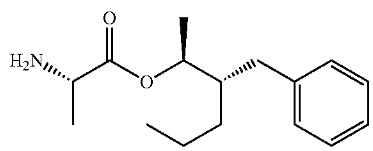 [SMILES: CCC[C@@H](Cc1ccccc1)[C@H](C)OC(=O)[C@H](C)N] | Example 11A, Step 1 | White Solid |
| 56 | 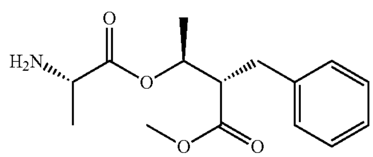 [SMILES: COC(=O)[C@@H](Cc1ccccc1)[C@H](C)OC(=O)[C@H](C)N] | Example 11A, Step 1 | White Solid |
| 57 | 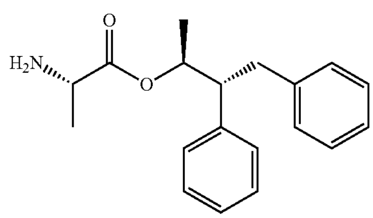 [SMILES: C[C@H](N)C(=O)O[C@@H](C)[C@H](Cc1ccccc1)c1ccccc1] | Example 11A, Step 1 | Colorless Oil |
| 58 | 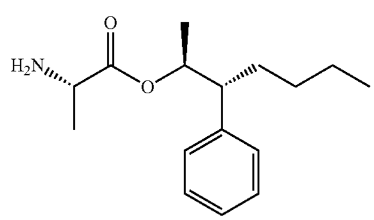 [SMILES: CCCC[C@H](c1ccccc1)[C@H](C)OC(=O)[C@H](C)N] | Example 11A, Step 1 | Colorless Oil |
| 59 | 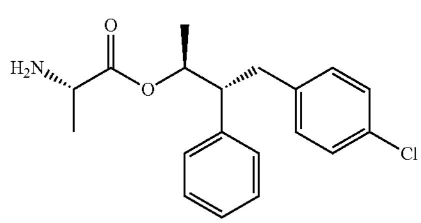 [SMILES: C[C@H](N)C(=O)O[C@@H](C)[C@H](Cc1ccc(Cl)cc1)c1ccccc1] | Example 11A, Step 1 | Colorless Oil |
| 60 | 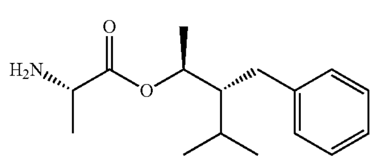 [SMILES: CC(C)[C@@H](Cc1ccccc1)[C@H](C)OC(=O)[C@H](C)N] | Example 11A, Step 1 | Pale Yellow Oil |
| 61 | 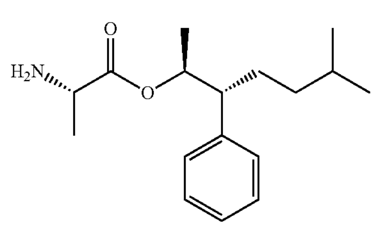 [SMILES: CC(C)CC[C@H](c1ccccc1)[C@H](C)OC(=O)[C@H](C)N] | Example 11A, Step 1 | Colorless Oil |

TABLE 1-continued

Compound Structure and Appearance

| *Cmpd. No. | Structure | Prepared According to Example | Appearance |
|---|---|---|---|
| 62 | 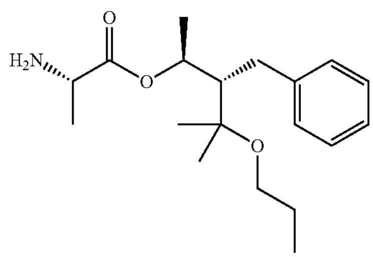 [SMILES: CCCOC(C)(C)[C@@H](Cc1ccccc1)[C@H](C)OC(=O)[C@H](C)N] | Example 11A, step 1 | Clear Glass |
| 63 | 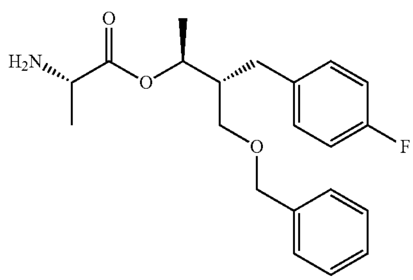 [SMILES: C[C@H](N)C(=O)O[C@@H](C)[C@@H](COCc1ccccc1)Cc1ccc(F)cc1] | Example 11A, Step 1 | Clear, Colorless Oil |
| 64 | 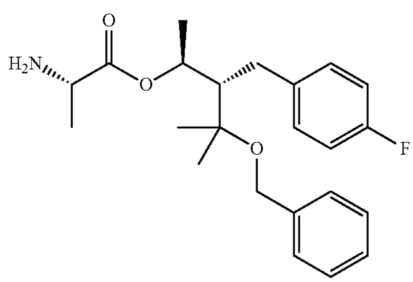 [SMILES: C[C@H](N)C(=O)O[C@@H](C)[C@H](Cc1ccc(F)cc1)C(C)(C)OCc1ccccc1] | Example 11A, Step 1 | Clear, Colorless Oil |
| 65 | 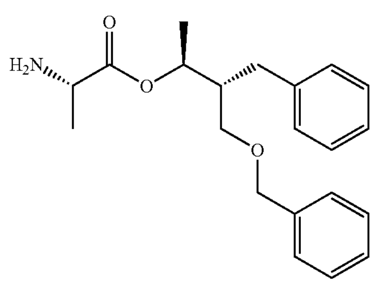 [SMILES: C[C@H](N)C(=O)O[C@@H](C)[C@@H](COCc1ccccc1)Cc1ccccc1] | Example 11A, Step 1 | Clear, Colorless Oil |
| 66 | 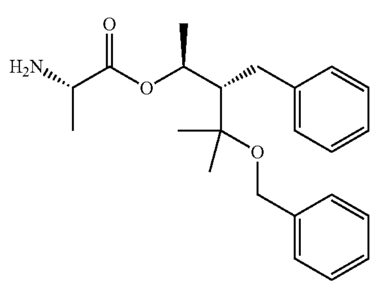 [SMILES: C[C@H](N)C(=O)O[C@@H](C)[C@H](Cc1ccccc1)C(C)(C)OCc1ccccc1] | Example 11A Step 1 | Clear, Colorless Oil |

TABLE 1-continued

Compound Structure and Appearance

| *Cmpd. No. | Structure | Prepared According to Example | Appearance |
|---|---|---|---|
| 67 | 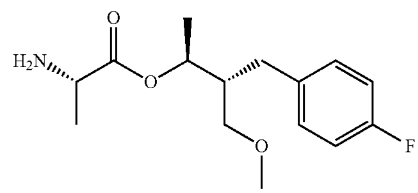 [SMILES: COC[C@@H](Cc1ccc(F)cc1)[C@H](C)OC(=O)[C@H](C)N] | Example 11A, Step 1 | White Solid |
| 68 | 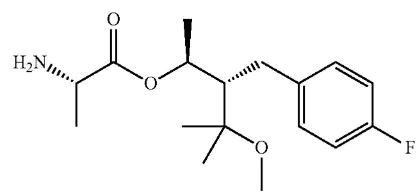 [SMILES: COC(C)(C)[C@@H](Cc1ccc(F)cc1)[C@H](C)OC(=O)[C@H](C)N] | Example 11A, Step 1 | Clear, Colorless Oil |
| 69 | 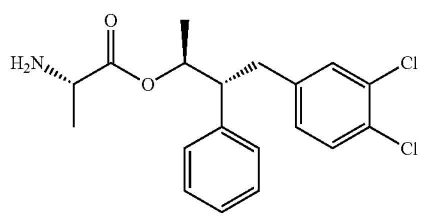 [SMILES: C[C@H](N)C(=O)O[C@@H](C)[C@H](Cc1ccc(Cl)c(Cl)c1)c1ccccc1] | Example 11A, Step 1 | Colorless Oil |
| 70 | 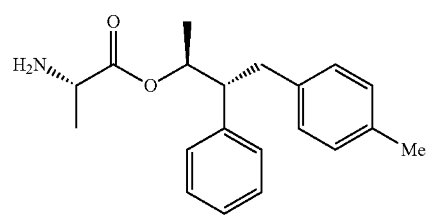 [SMILES: Cc1ccc(C[C@H](c2ccccc2)[C@H](C)OC(=O)[C@H](C)N)cc1] | Example 11A, Step 1 | Colorless Oil |
| 71 | 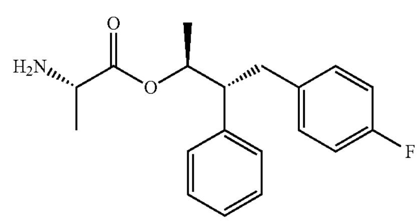 [SMILES: C[C@H](N)C(=O)O[C@@H](C)[C@H](Cc1ccc(F)cc1)c1ccccc1] | Example 11A, Step 1 | Colorless Oil |
| 72 | 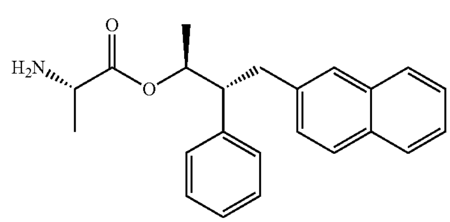 [SMILES: C[C@H](N)C(=O)O[C@@H](C)[C@H](Cc1ccc2ccccc2c1)c1ccccc1] | Example 11A, Step 1 | White Foam |
| 73 | 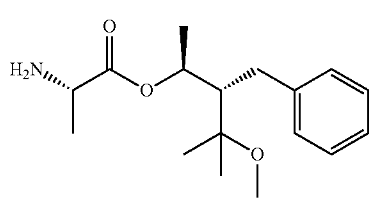 [SMILES: COC(C)(C)[C@@H](Cc1ccccc1)[C@H](C)OC(=O)[C@H](C)N] | Example 11A, Step 1 | Colorless Oil |

TABLE 1-continued

Compound Structure and Appearance

| *Cmpd. No. | Structure | Prepared According to Example | Appearance |
|---|---|---|---|
| 74 | 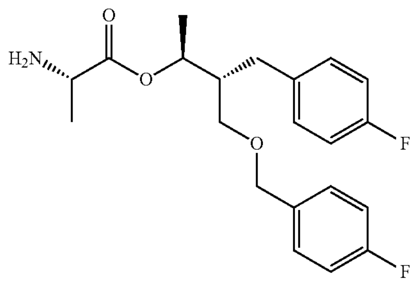 [SMILES: C[C@H](N)C(=O)O[C@@H](C)[C@@H](COCc1ccc(F)cc1)Cc1ccc(F)cc1] | Example 11A, Step 1 | Clear, Colorless Oil |
| 75 | 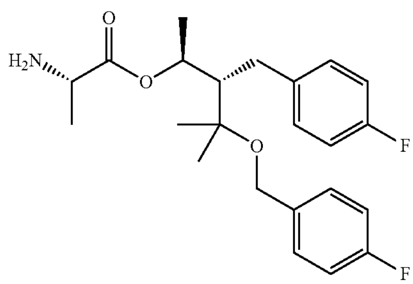 [SMILES: C[C@H](N)C(=O)O[C@@H](C)[C@H](Cc1ccc(F)cc1)C(C)(C)OCc1ccc(F)cc1] | Example 11A, Step 1 | Pale Orange Oil |
| 76 | 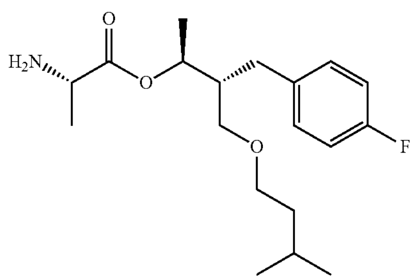 [SMILES: CC(C)CCOC[C@@H](Cc1ccc(F)cc1)[C@H](C)OC(=O)[C@H](C)N] | Example 11A, Step 1 | Clear, Colorless Oil |
| 77 | 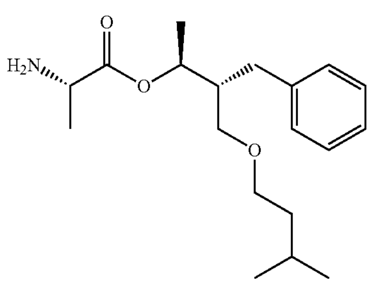 [SMILES: CC(C)CCOC[C@@H](Cc1ccccc1)[C@H](C)OC(=O)[C@H](C)N] | Example 11A, Step 1 | Clear, Colorless Oil |
| 78 | 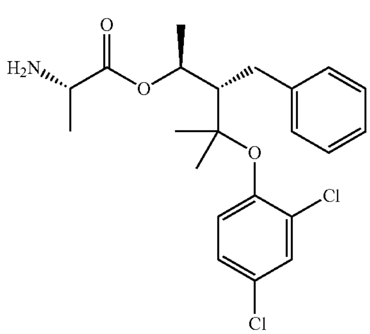 [SMILES: C[C@H](N)C(=O)O[C@@H](C)[C@H](Cc1ccccc1)C(C)(C)Oc1ccc(Cl)cc1Cl] | Example 11A, step 1 | Sticky Wax |

TABLE 1-continued

Compound Structure and Appearance

| *Cmpd. No. | Structure | Prepared According to Example | Appearance |
|---|---|---|---|
| 79 | 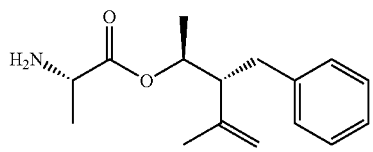 [SMILES: C=C(C)[C@@H](Cc1ccccc1)[C@H](C)OC(=O)[C@H](C)N] | Example 11C, step 1 | Sticky Wax |
| 80 | 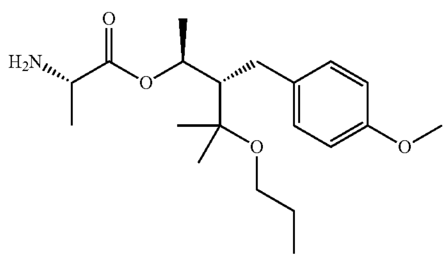 [SMILES: CCCOC(C)(C)[C@@H](Cc1ccc(OC)cc1)[C@H](C)OC(=O)[C@H](C)N] | Example 11A, step 1 | Yellow/Orange Oil |
| 81 | 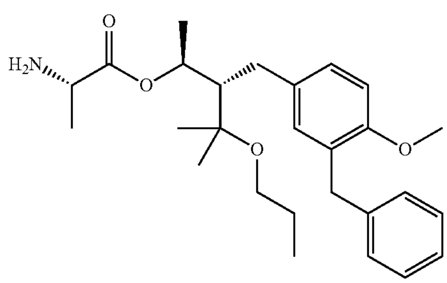 [SMILES: CCCOC(C)(C)[C@@H](Cc1ccc(OC)c(Cc2ccccc2)c1)[C@H](C)OC(=O)[C@H](C)N] | Example 11A, step 1 | Yellow/Orange Oil |
| 82 | 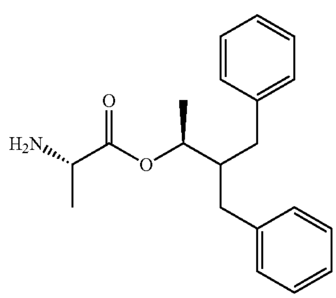 [SMILES: C[C@H](N)C(=O)O[C@@H](C)C(Cc1ccccc1)Cc1ccccc1] | Example 8, steps 1-3; Example 9A; Example 11A, step 1 | Oil |
| 83 | 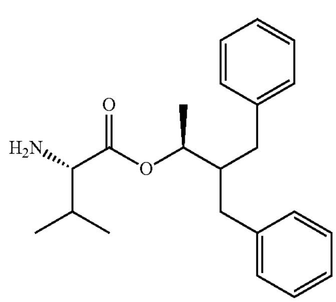 [SMILES: CC(C)[C@H](N)C(=O)O[C@@H](C)C(Cc1ccccc1)Cc1ccccc1] | Example 11A, step 1 | |

TABLE 1-continued

Compound Structure and Appearance

| *Cmpd. No. | Structure | Prepared According to Example | Appearance |
|---|---|---|---|
| 84 | 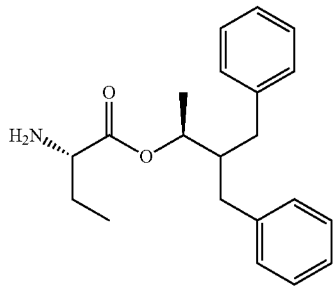 [SMILES: CC[C@H](N)C(=O)O[C@@H](C)C(Cc1ccccc1)Cc1ccccc1] | Example 8, steps 1-3; Example 9A; Example 11A, step 1 | Oil |
| 85 | 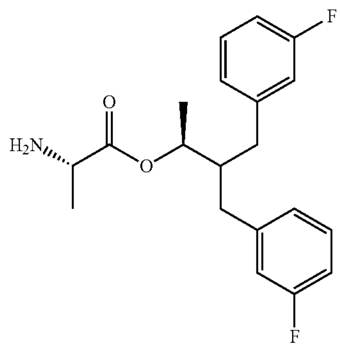 [SMILES: C[C@H](N)C(=O)O[C@@H](C)C(Cc1cccc(F)c1)Cc1cccc(F)c1] | Example 11A, step 1 | Oil |
| 86 | 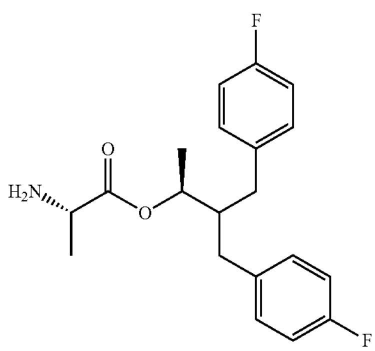 [SMILES: C[C@H](N)C(=O)O[C@@H](C)C(Cc1ccc(F)cc1)Cc1ccc(F)cc1] | Example 8, steps 1-3; Example 9A; Example 11A, step 1 | Oil |
| 87 | 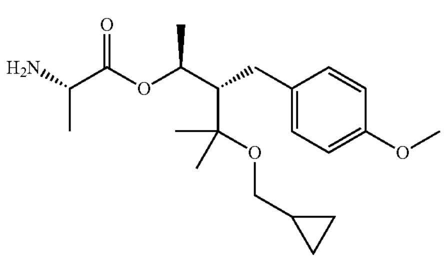 [SMILES: COc1ccc(C[C@@H]([C@H](C)OC(=O)[C@H](C)N)C(C)(C)OCC2CC2)cc1] | Example 11A, step 1 | Sticky Wax |

TABLE 1-continued

Compound Structure and Appearance

| *Cmpd. No. | Structure | Prepared According to Example | Appearance |
|---|---|---|---|
| 88 | 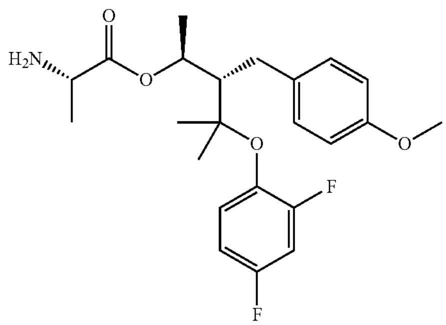 [SMILES: COc1ccc(C[C@@H]([C@H](C)OC(=O)[C@H](C)N)C(C)(C)Oc2ccc(F)cc2F)cc1] | Example 11A, step 1 | Yellow Oil |
| 89 | 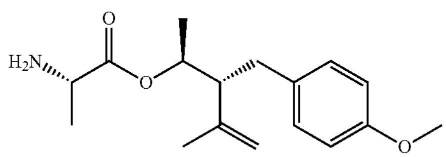 [SMILES: C=C(C)[C@@H](Cc1ccc(OC)cc1)[C@H](C)OC(=O)[C@H](C)N] | Example 11C, step 1 | Sticky Wax |
| 90 | 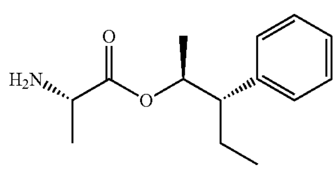 [SMILES: CC[C@@H](c1ccccc1)[C@H](C)OC(=O)[C@H](C)N] | Example 11A, Step 1 | Colorless Oil |
| 91 | 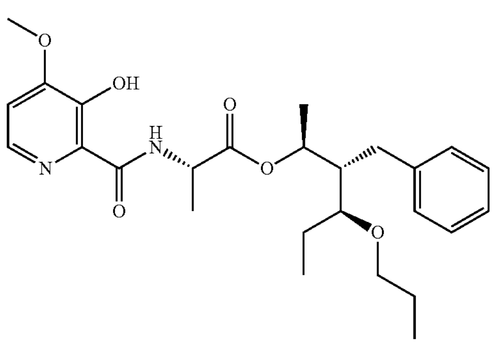 [SMILES: CCCO[C@@H](CC)[C@@H](Cc1ccccc1)[C@H](C)OC(=O)[C@H](C)NC(=O)c1nccc(OC)c1O] | Example 1, steps 1 and 3; Example 3A steps 1-2; Example 4A; Example 5A; Example 9A; Example 11A, steps 1-2 | Colorless Oil |
| 92 | 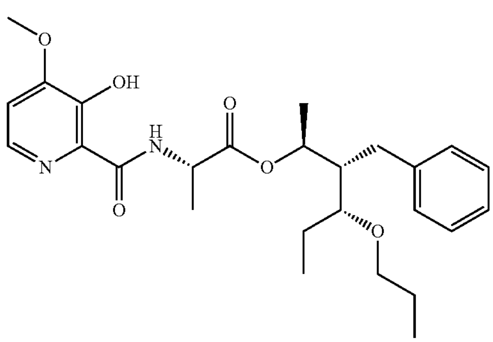 [SMILES: CCCO[C@H](CC)[C@@H](Cc1ccccc1)[C@H](C)OC(=O)[C@H](C)NC(=O)c1nccc(OC)c1O] | Example 1, steps 1 and 3; Example 3A steps 1-2; Example 4A; Example 5A; Example 9A; Example 11A, steps 1-2 | Colorless Oil |

TABLE 1-continued

Compound Structure and Appearance

| *Cmpd. No. | Structure | Prepared According to Example | Appearance |
|---|---|---|---|
| 93 | 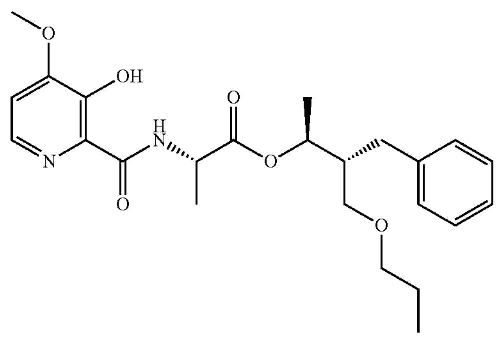 [SMILES: CCCOC[C@@H](Cc1ccccc1)[C@H](C)OC(=O)[C@H](C)NC(=O)c1nccc(OC)c1O] | Example 1, steps 1 and 3; Example 3B; Example 4A; Example 5A; Example 9A; Example 11A, steps 1-2 | Colorless Oil |
| 94 | 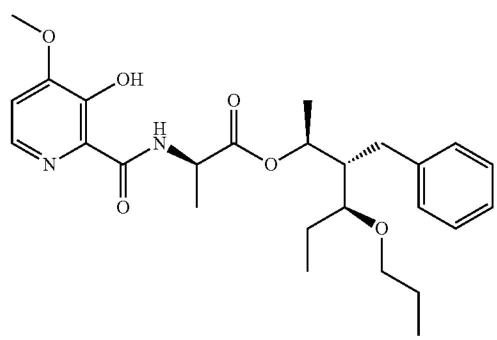 [SMILES: CCCO[C@@H](CC)[C@@H](Cc1ccccc1)[C@H](C)OC(=O)[C@@H](C)NC(=O)c1nccc(OC)c1O] | Example 1, steps 1 and 3; Example 3A steps 1-2; Example 4A; Example 5A; Example 9A; Example 11A, steps 1-2 | Colorless Oil |
| 95 | 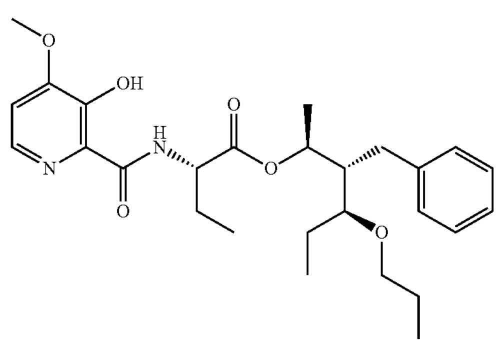 [SMILES: CCCO[C@@H](CC)[C@@H](Cc1ccccc1)[C@H](C)OC(=O)[C@H](CC)NC(=O)c1nccc(OC)c1O] | Example 1, steps 1 and 3; Example 3A steps 1-2; Example 4A; Example 5A; Example 9A; Example 11A, steps 1-2 | Colorless Oil |
| 96 | 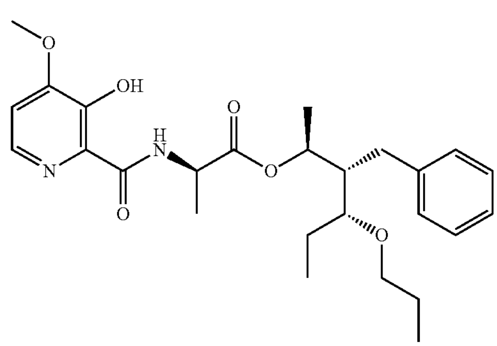 [SMILES: CCCO[C@H](CC)[C@@H](Cc1ccccc1)[C@H](C)OC(=O)[C@@H](C)NC(=O)c1nccc(OC)c1O] | Example 1, steps 1 and 3; Example 3A steps 1-2; Example 4A; Example 5A; Example 9A; Example 11A, steps 1-2 | Colorless Oil |

TABLE 1-continued

Compound Structure and Appearance

| *Cmpd. No. | Structure | Prepared According to Example | Appearance |
|---|---|---|---|
| 97 | 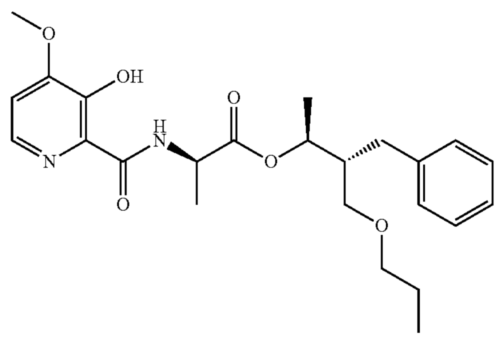 [SMILES: CCCOC[C@@H](Cc1ccccc1)[C@H](C)OC(=O)[C@@H](C)NC(=O)c1nccc(OC)c1O] | Example 1, step 1 and 3; Example 3B; Example 4A; Example 5A; Example 9A; Example 11A, steps 1-2 | Colorless Oil |
| 98 | 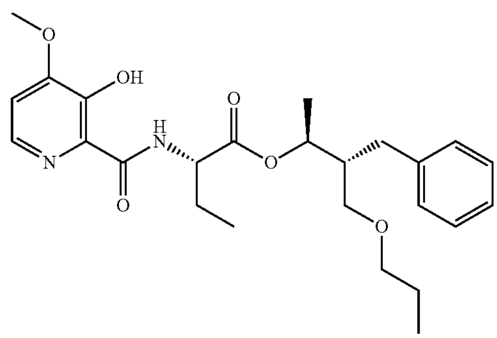 [SMILES: CCCOC[C@@H](Cc1ccccc1)[C@H](C)OC(=O)[C@H](CC)NC(=O)c1nccc(OC)c1O] | Example 1, steps 1 and 3; Example 3B; Example 4A; Example 5A; Example 9A; Example 11A, steps 1-2 | Colorless Oil |
| 99 | 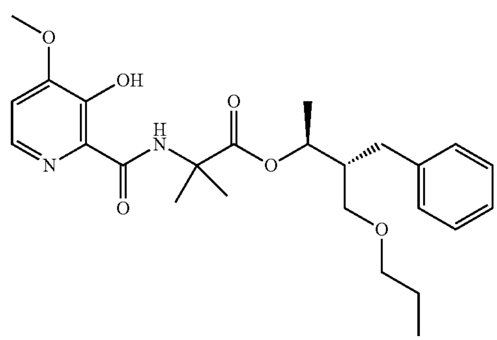 [SMILES: CCCOC[C@@H](Cc1ccccc1)[C@H](C)OC(=O)C(C)(C)NC(=O)c1nccc(OC)c1O] | Example 1, steps 1 and 3; Example 3B; Example 4A; Example 5A; Example 9A; Example 11A, steps 1-2 | Colorless Oil |
| 100 | 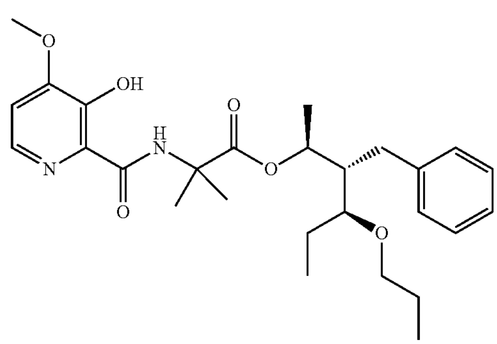 [SMILES: CCCO[C@@H](CC)[C@@H](Cc1ccccc1)[C@H](C)OC(=O)C(C)(C)NC(=O)c1nccc(OC)c1O] | Example 1, steps 1 and 3; Example 3A steps 1-2; Example 4A; Example 5A; Example 9A; Example 11A, steps 1-2 | Colorless Oil |

TABLE 1-continued
Compound Structure and Appearance
| *Cmpd. No. | Structure | Prepared According to Example | Appearance |
|---|---|---|---|
| 101 | 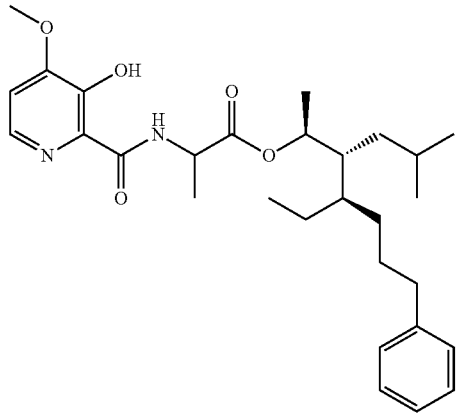 [SMILES: CC[C@H](CCCc1ccccc1)[C@@H](CC(C)C)[C@H](C)OC(=O)C(C)NC(=O)c1nccc(OC)c1O] | Example 11A, Step 2 | Colorless Oil |
| 102 | 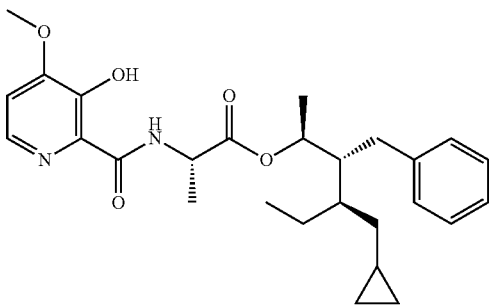 [SMILES: CC[C@H](CC1CC1)[C@@H](Cc1ccccc1)[C@H](C)OC(=O)[C@H](C)NC(=O)c1nccc(OC)c1O] | Example 6, steps 1-6, Example 5A, Example 9A; Example 11A, steps 1-2 | Slightly Red Oil |
| 103 | 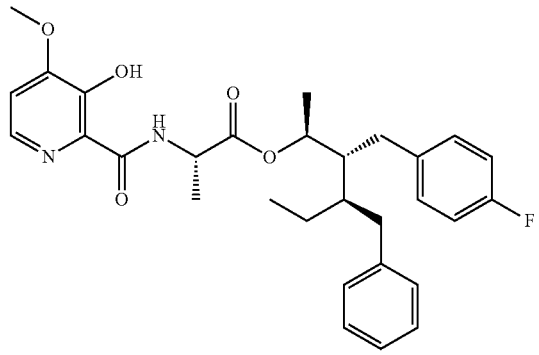 [SMILES: CC[C@H](Cc1ccccc1)[C@@H](Cc1ccc(F)cc1)[C@H](C)OC(=O)[C@H](C)NC(=O)c1nccc(OC)c1O] | Example 6, steps 1-6, Example 5A, Example 9A; Example 11A, steps 1-2 | Colorless Oil |
| 104 | 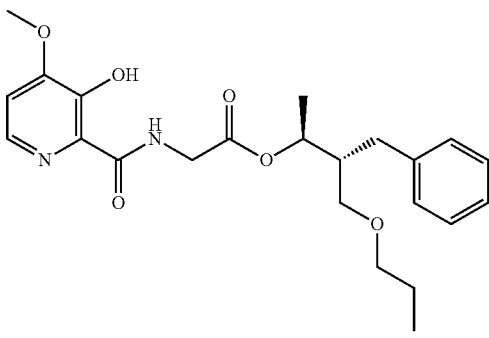 [SMILES: CCCOC[C@@H](Cc1ccccc1)[C@H](C)OC(=O)CNC(=O)c1nccc(OC)c1O] | Example 1, steps 1 and 3; Example 3B; Example 4A; Example 5A; Example 9A; Example 11A, steps 1-2 | Colorless Oil |

TABLE 1-continued

Compound Structure and Appearance

| *Cmpd. No. | Structure | Prepared According to Example | Appearance |
|---|---|---|---|
| 105 | 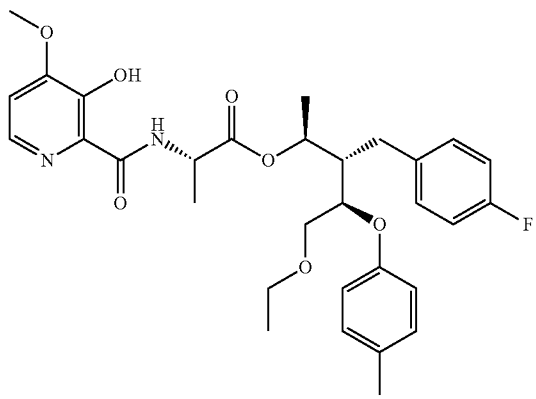 [SMILES: CCOC[C@H](Oc1ccc(C)cc1)[C@@H](Cc1ccc(F)cc1)[C@H](C)OC(=O)[C@H](C)NC(=O)c1nccc(OC)c1O] | Example 11A, Step 2 | Colorless Tacky Oil |
| 106 | 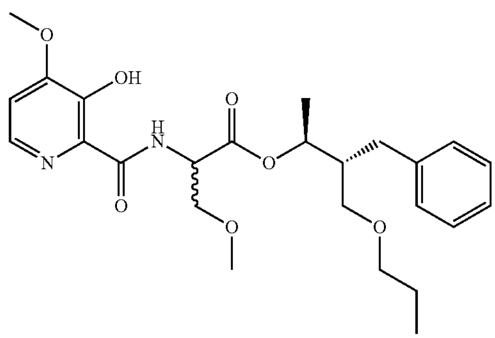 [SMILES: CCCOC[C@@H](Cc1ccccc1)[C@H](C)OC(=O)C(COC)NC(=O)c1nccc(OC)c1O] | Example 1, steps 1 and 3; Example 3B; Example 4A; Example 5A; Example 9A; Example 11A, steps 1-2 | Colorless Oil |
| 107 | 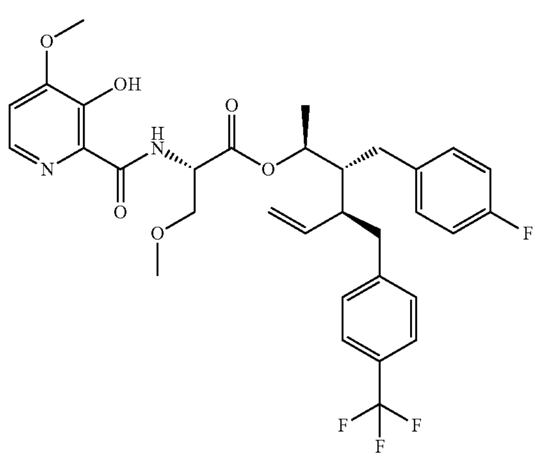 [SMILES: C=C[C@H](Cc1ccc(C(F)(F)F)cc1)[C@@H](Cc1ccc(F)cc1)[C@H](C)OC(=O)[C@H](COC)NC(=O)c1nccc(OC)c1O] | Example 11B, Step 2 | White Foam |

TABLE 1-continued

Compound Structure and Appearance

| *Cmpd. No. | Structure | Prepared According to Example | Appearance |
|---|---|---|---|
| 108 | 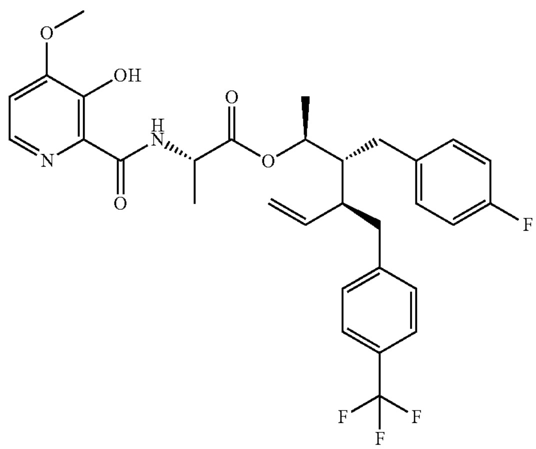 [SMILES: C=C[C@H](Cc1ccc(C(F)(F)F)cc1)[C@@H](Cc1ccc(F)cc1)[C@H](C)OC(=O)[C@H](C)NC(=O)c1nccc(OC)c1O] | Example 11B, Step 2 | Colorless Oil |
| 109 | 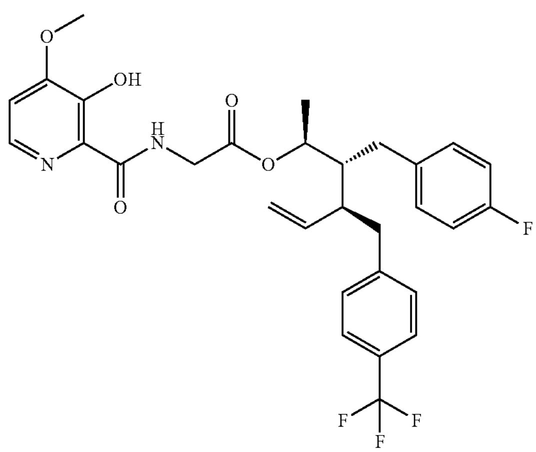 [SMILES: C=C[C@H](Cc1ccc(C(F)(F)F)cc1)[C@@H](Cc1ccc(F)cc1)[C@H](C)OC(=O)CNC(=O)c1nccc(OC)c1O] | Example 11B, Step 2 | White Foam |
| 110 | 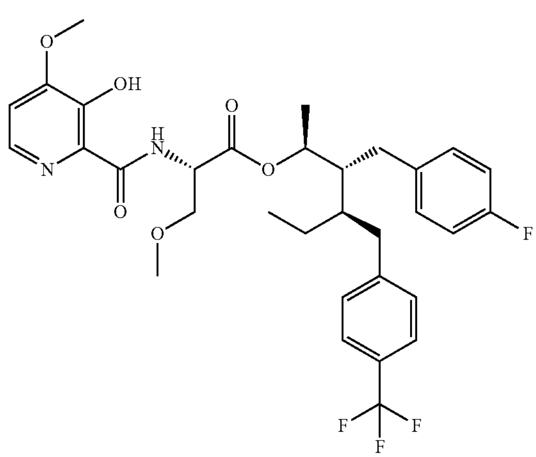 [SMILES: CC[C@H](Cc1ccc(C(F)(F)F)cc1)[C@@H](Cc1ccc(F)cc1)[C@H](C)OC(=O)[C@H](COC)NC(=O)c1nccc(OC)c1O] | Example 10, Step 3 | Sticky White Foam |

TABLE 1-continued

Compound Structure and Appearance

| *Cmpd. No. | Structure | Prepared According to Example | Appearance |
| --- | --- | --- | --- |
| 111 | 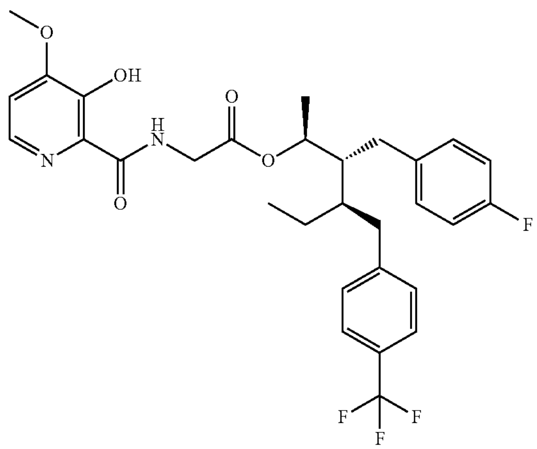 [SMILES: CC[C@H](Cc1ccc(C(F)(F)F)cc1)[C@@H](Cc1ccc(F)cc1)[C@H](C)OC(=O)CNC(=O)c1nccc(OC)c1O] | Example 10, Step 3 | Off White Foam |
| 112 | 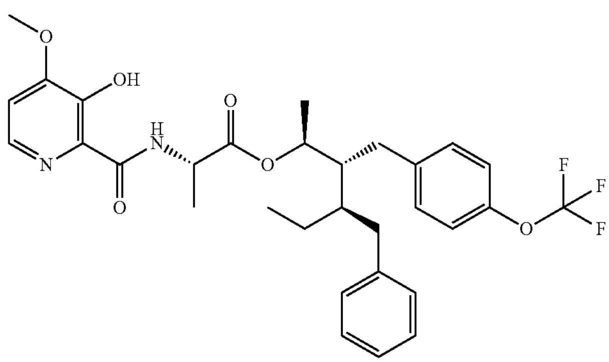 [SMILES: CC[C@H](Cc1ccccc1)[C@@H](Cc1ccc(OC(F)(F)F)cc1)[C@H](C)OC(=O)[C@H](C)NC(=O)c1nccc(OC)c1O] | Example 11A, step 2 | Thick Colorless Oil |
| 113 | 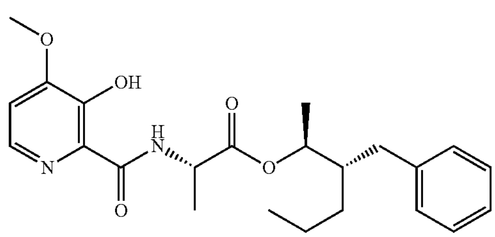 [SMILES: CCC[C@@H](Cc1ccccc1)[C@H](C)OC(=O)[C@H](C)NC(=O)c1nccc(OC)c1O] | Example 11A, Step 2 | White Solid |
| 114 | 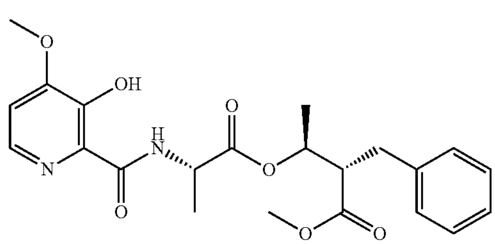 [SMILES: COC(=O)[C@@H](Cc1ccccc1)[C@H](C)OC(=O)[C@H](C)NC(=O)c1nccc(OC)c1O] | Example 11A, Step 2 | White Solid |

TABLE 1-continued

Compound Structure and Appearance

| *Cmpd. No. | Structure | Prepared According to Example | Appearance |
|---|---|---|---|
| 115 | 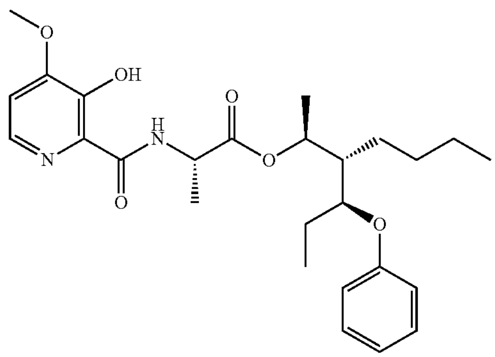 [SMILES: CCCC[C@@H]([C@H](C)OC(=O)[C@H](C)NC(=O)c1nccc(OC)c1O)[C@H](CC)Oc1ccccc1] | Example 11A, steps 1-2 | Colorless Oil |
| 116 | 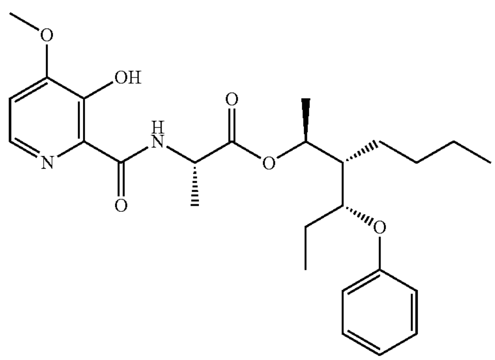 [SMILES: CCCC[C@@H]([C@H](C)OC(=O)[C@H](C)NC(=O)c1nccc(OC)c1O)[C@@H](CC)Oc1ccccc1] | Example 11A, steps 1-2 | Colorless Oil |
| 117 | 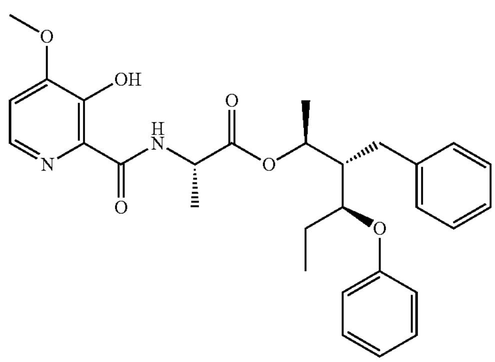 [SMILES: CC[C@H](Oc1ccccc1)[C@@H](Cc1ccccc1)[C@H](C)OC(=O)[C@H](C)NC(=O)c1nccc(OC)c1O] | Example 11A, steps 1-2 | Colorless Oil |
| 118 | 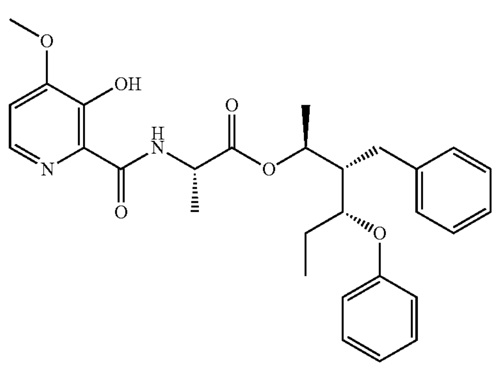 [SMILES: CC[C@@H](Oc1ccccc1)[C@@H](Cc1ccccc1)[C@H](C)OC(=O)[C@H](C)NC(=O)c1nccc(OC)c1O] | Example 11A, steps 1-2 | Colorless Oil |

TABLE 1-continued

Compound Structure and Appearance

| *Cmpd. No. | Structure | Prepared According to Example | Appearance |
|---|---|---|---|
| 119 | 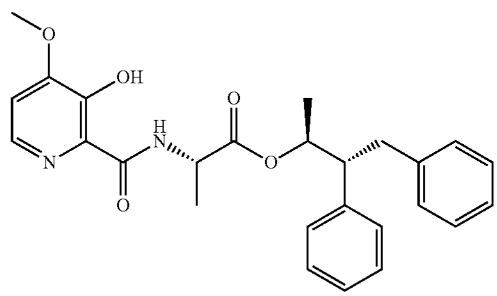 [SMILES: COc1ccnc(C(=O)N[C@@H](C)C(=O)O[C@@H](C)[C@H](Cc2ccccc2)c2ccccc2)c1O] | Example 11A, Step 2 | Colorless Oil |
| 120 | 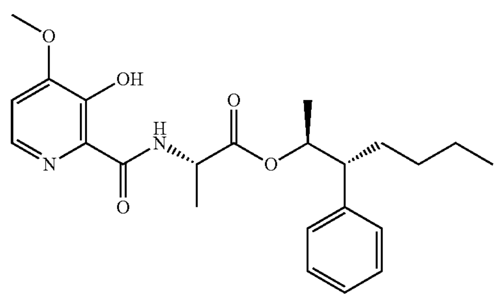 [SMILES: CCCC[C@H](c1ccccc1)[C@H](C)OC(=O)[C@H](C)NC(=O)c1nccc(OC)c1O] | Example 11A, Step 2 | Colorless Foam |
| 121 | 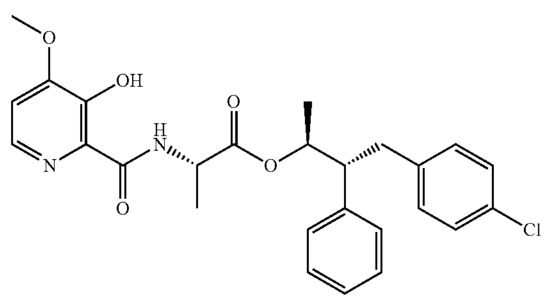 [SMILES: COc1ccnc(C(=O)N[C@@H](C)C(=O)O[C@@H](C)[C@H](Cc2ccc(Cl)cc2)c2ccccc2)c1O] | Example 11A, Step 2 | Colorless Foam |
| 122 | 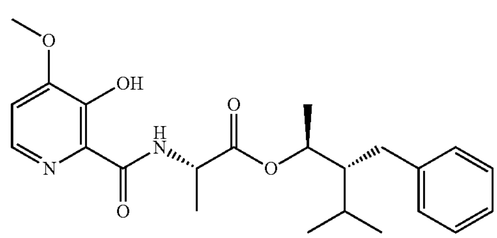 [SMILES: COc1ccnc(C(=O)N[C@@H](C)C(=O)O[C@@H](C)[C@H](Cc2ccccc2)C(C)C)c1O] | Example 11A, Step 2 | Colorless Oil |
| 123 | 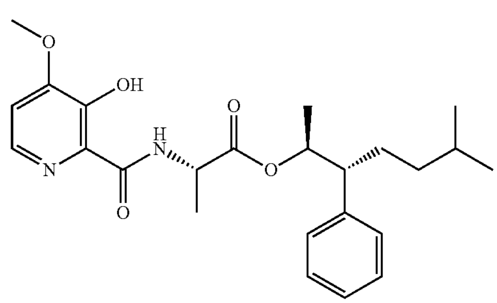 [SMILES: COc1ccnc(C(=O)N[C@@H](C)C(=O)O[C@@H](C)[C@H](CCC(C)C)c2ccccc2)c1O] | Example 11A, Step 2 | Colorless Oil |

TABLE 1-continued

| *Cmpd. No. | Structure | Prepared According to Example | Appearance |
|---|---|---|---|
| 124 | 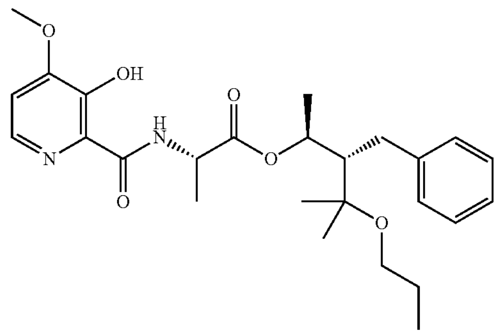 [SMILES: CCCOC(C)(C)[C@@H](Cc1ccccc1)[C@H](C)OC(=O)[C@H](C)NC(=O)c1nccc(OC)c1O] | Example 11A, step 2 | Sticky Wax |
| 125 | 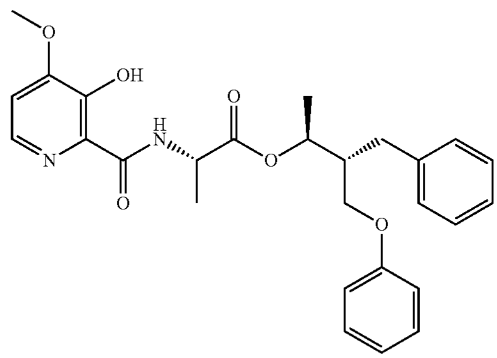 [SMILES: COc1ccnc(C(=O)N[C@@H](C)C(=O)O[C@@H](C)[C@@H](COc2ccccc2)Cc2ccccc2)c1O] | Example 11A, step 2 | White Foam |
| 126 | 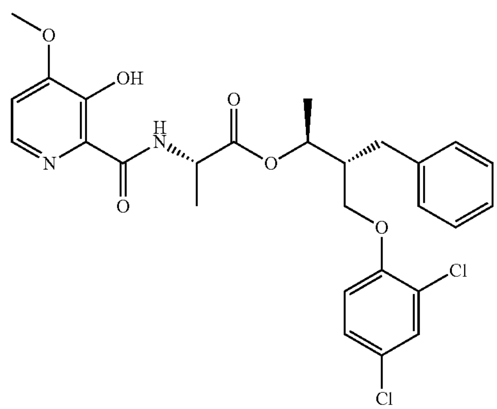 [SMILES: COc1ccnc(C(=O)N[C@@H](C)C(=O)O[C@@H](C)[C@@H](COc2ccc(Cl)cc2Cl)Cc2ccccc2)c1O] | Example 11A, step 2 | White Foam |
| 127 | 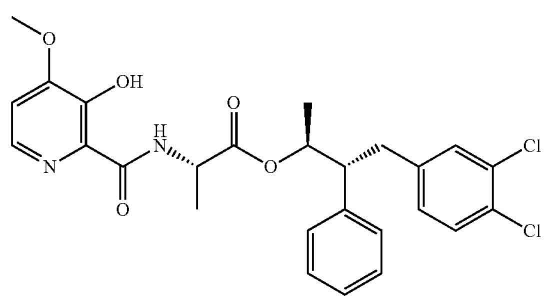 [SMILES: COc1ccnc(C(=O)N[C@@H](C)C(=O)O[C@@H](C)[C@H](Cc2ccc(Cl)c(Cl)c2)c2ccccc2)c1O] | Example 11A, Step 2 | White Foam |

TABLE 1-continued

Compound Structure and Appearance

| *Cmpd. No. | Structure | Prepared According to Example | Appearance |
|---|---|---|---|
| 128 | 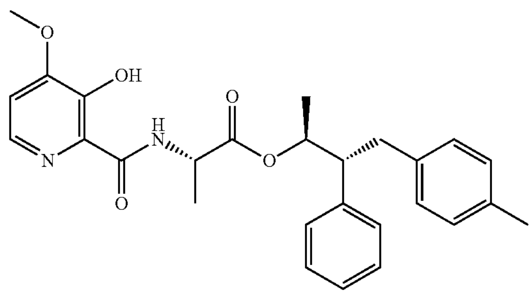 [SMILES: COc1ccnc(C(=O)N[C@@H](C)C(=O)O[C@@H](C)[C@H](Cc2ccc(C)cc2)c2ccccc2)c1O] | Example 11A, Step 2 | White Foam |
| 129 | 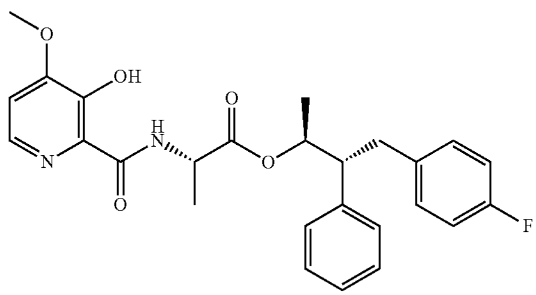 [SMILES: COc1ccnc(C(=O)N[C@@H](C)C(=O)O[C@@H](C)[C@H](Cc2ccc(F)cc2)c2ccccc2)c1O] | Example 11A, Step 2 | White Foam |
| 130 | 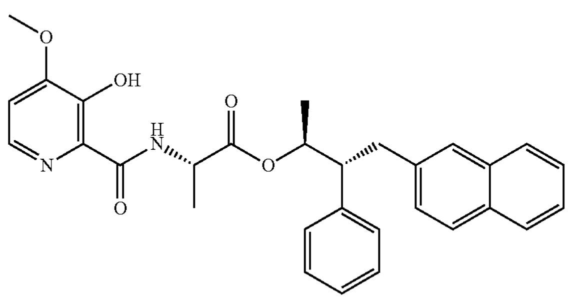 [SMILES: COc1ccnc(C(=O)N[C@@H](C)C(=O)O[C@@H](C)[C@H](Cc2ccc3ccccc3c2)c2ccccc2)c1O] | Example 11A, Step 2 | White Foam |
| 131 | 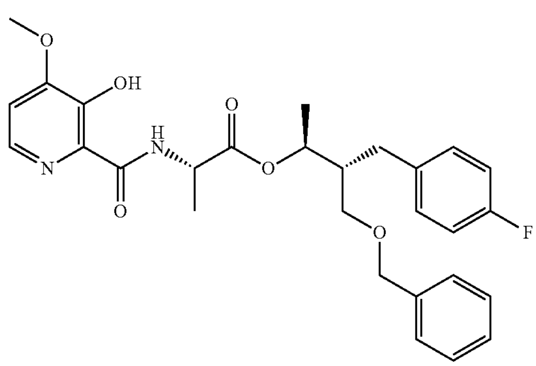 [SMILES: COc1ccnc(C(=O)N[C@@H](C)C(=O)O[C@@H](C)[C@@H](COCc2ccccc2)Cc2ccc(F)cc2)c1O] | Example 11A, Step 2 | Clear, Colorless Oil |

… TABLE 1-continued

Compound Structure and Appearance

| *Cmpd. No. | Structure | Prepared According to Example | Appearance |
|---|---|---|---|
| 132 | 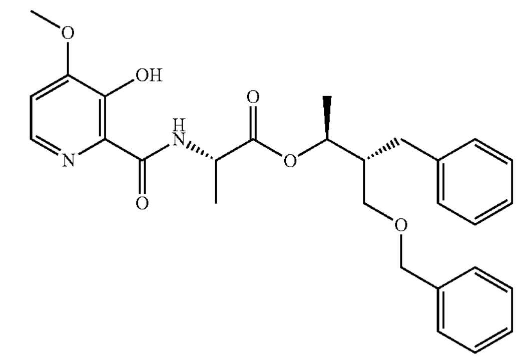 [SMILES: COc1ccnc(C(=O)N[C@@H](C)C(=O)O[C@@H](C)[C@@H](COCc2ccccc2)Cc2ccccc2)c1O] | Example 11A, Step 2 | Clear, Colorless Oil |
| 133 | 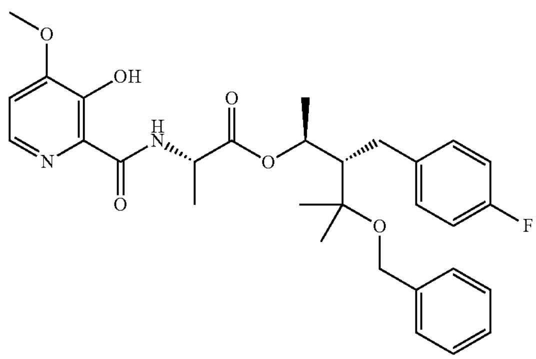 [SMILES: COc1ccnc(C(=O)N[C@@H](C)C(=O)O[C@@H](C)[C@H](Cc2ccc(F)cc2)C(C)(C)OCc2ccccc2)c1O] | Example 11A, Step 2 | Clear, Colorless Oil |
| 134 | 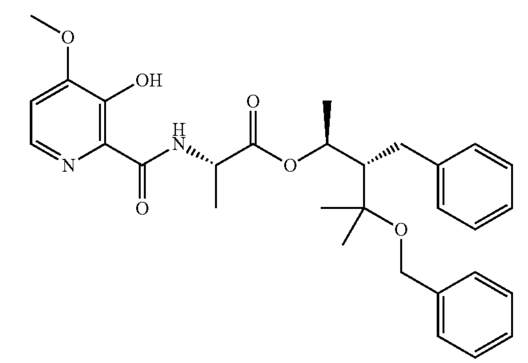 [SMILES: COc1ccnc(C(=O)N[C@@H](C)C(=O)O[C@@H](C)[C@H](Cc2ccccc2)C(C)(C)OCc2ccccc2)c1O] | Example 11A, Step 2 | Clear, Colorless Oil |
| 135 | 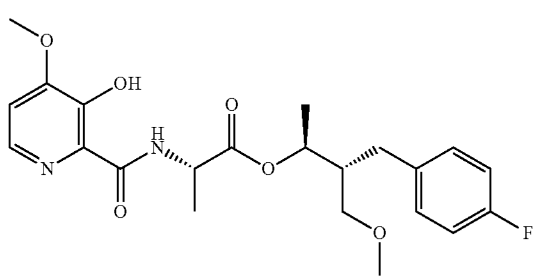 [SMILES: COC[C@@H](Cc1ccc(F)cc1)[C@H](C)OC(=O)[C@H](C)NC(=O)c1nccc(OC)c1O] | Example 11A, Step 2 | Clear, Colorless Oil |

TABLE 1-continued

Compound Structure and Appearance

| *Cmpd. No. | Structure | Prepared According to Example | Appearance |
|---|---|---|---|
| 136 | 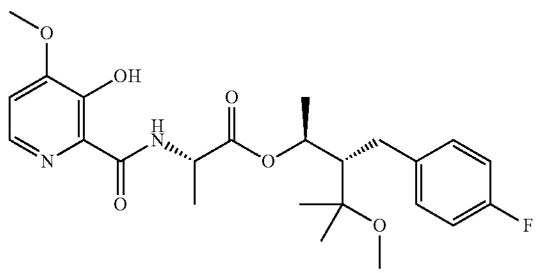 [SMILES: COc1ccnc(C(=O)N[C@@H](C)C(=O)O[C@@H](C)[C@H](Cc2ccc(F)cc2)C(C)(C)OC)c1O] | Example 11A, Step 2 | Clear, Colorless Oil |
| 137 | 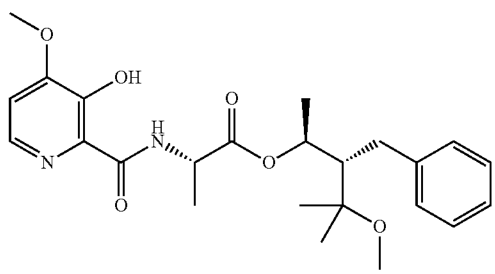 [SMILES: COc1ccnc(C(=O)N[C@@H](C)C(=O)O[C@@H](C)[C@H](Cc2ccccc2)C(C)(C)OC)c1O] | Example 11A, Step 2 | Colorless Oil |
| 138 | 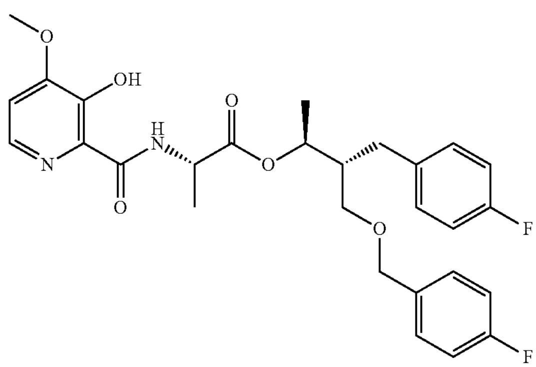 [SMILES: COc1ccnc(C(=O)N[C@@H](C)C(=O)O[C@@H](C)[C@@H](COCc2ccc(F)cc2)Cc2ccc(F)cc2)c1O] | Example 11A, Step 2 | Pale Yellow Oil |
| 139 | 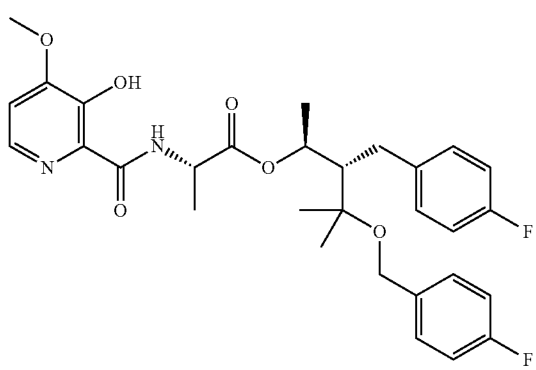 [SMILES: COc1ccnc(C(=O)N[C@@H](C)C(=O)O[C@@H](C)[C@H](Cc2ccc(F)cc2)C(C)(C)OCc2ccc(F)cc2)c1O] | Example 11A, Step 2 | Clear, Colorless Oil |

TABLE 1-continued
Compound Structure and Appearance
| *Cmpd. No. | Structure | Prepared According to Example | Appearance |
|---|---|---|---|
| 140 | 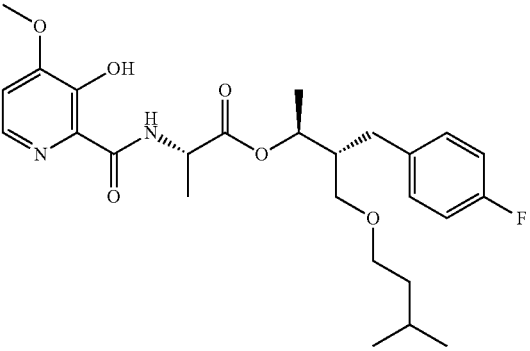 [SMILES: COc1ccnc(C(=O)N[C@@H](C)C(=O)O[C@@H](C)[C@@H](COCCC(C)C)Cc2ccc(F)cc2)c1O] | Example 11A, Step 2 | Clear, Colorless Oil |
| 141 | 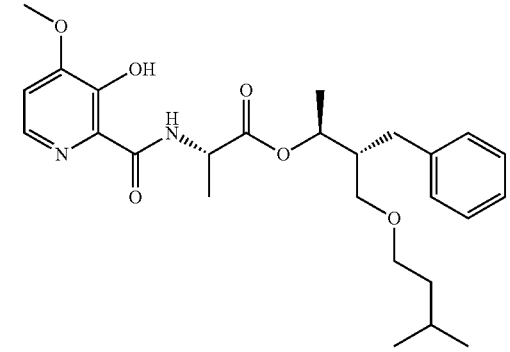 [SMILES: COc1ccnc(C(=O)N[C@@H](C)C(=O)O[C@@H](C)[C@@H](COCCC(C)C)Cc2ccccc2)c1O] | Example 11A, Step 2 | Clear, Colorless Oil |
| 142 | 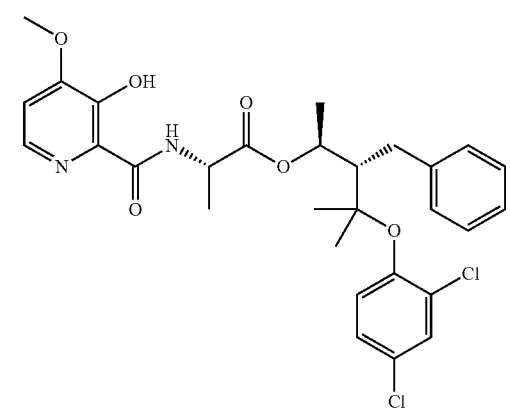 [SMILES: COc1ccnc(C(=O)N[C@@H](C)C(=O)O[C@@H](C)[C@H](Cc2ccccc2)C(C)(C)Oc2ccc(Cl)cc2Cl)c1O] | Example 11A, step 2 | Sticky Wax |
| 143 | 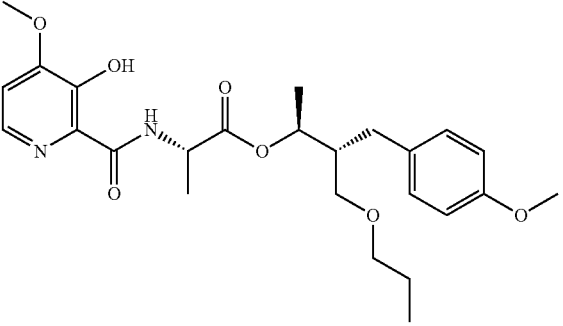 [SMILES: CCCOC[C@@H](Cc1ccc(OC)cc1)[C@H](C)OC(=O)[C@H](C)NC(=O)c1nccc(OC)c1O] | Example 11A, step 2 | Clear Sticky Wax |

TABLE 1-continued

Compound Structure and Appearance

| *Cmpd. No. | Structure | Prepared According to Example | Appearance |
| --- | --- | --- | --- |
| 144 | 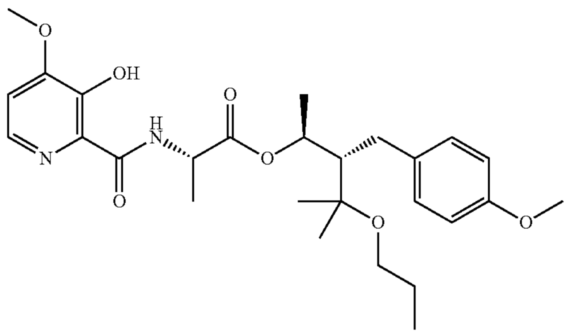 [SMILES: CCCOC(C)(C)[C@@H](Cc1ccc(OC)cc1)[C@H](C)OC(=O)[C@H](C)NC(=O)c1nccc(OC)c1O] | Example 11A, step 2 | Clear Sticky Oil |
| 145 | 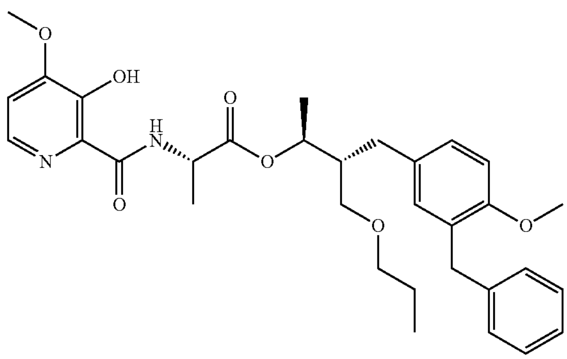 [SMILES: CCCOC[C@@H](Cc1ccc(OC)c(Cc2ccccc2)c1)[C@H](C)OC(=O)[C@H](C)NC(=O)c1nccc(OC)c1O] | Example 11A, step 2 | Clear Sticky Wax |
| 146 | 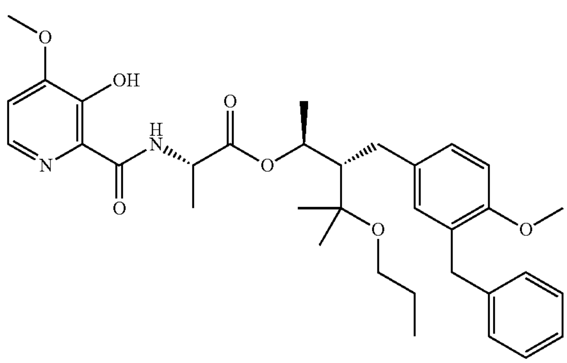 [SMILES: CCCOC(C)(C)[C@@H](Cc1ccc(OC)c(Cc2ccccc2)c1)[C@H](C)OC(=O)[C@H](C)NC(=O)c1nccc(OC)c1O] | Example 11A, step 2 | Clear Sticky Wax |
| 147 | 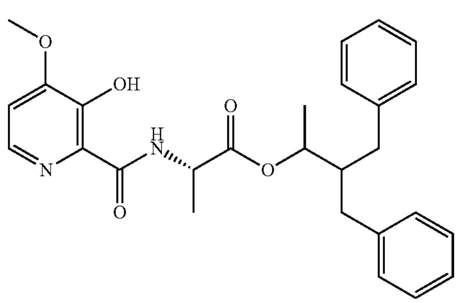 [SMILES: COc1ccnc(C(=O)N[C@@H](C)C(=O)OC(C)C(Cc2ccccc2)Cc2ccccc2)c1O] | Example 11A, step 2 | Oil |

TABLE 1-continued

Compound Structure and Appearance

| *Cmpd. No. | Structure | Prepared According to Example | Appearance |
|---|---|---|---|
| 148 | 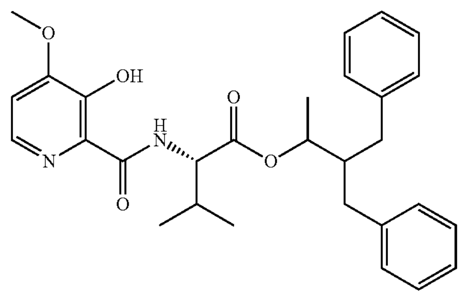 [SMILES: COc1ccnc(C(=O)N[C@H](C(=O)OC(C)C(Cc2ccccc2)Cc2ccccc2)C(C)C)c1O] | Example 11A, step 2 | Oil |
| 149 | 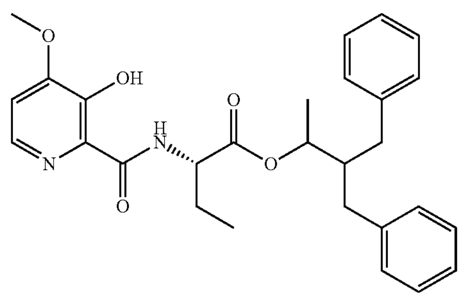 [SMILES: CC[C@H](NC(=O)c1nccc(OC)c1O)C(=O)OC(C)C(Cc1ccccc1)Cc1ccccc1] | Example 11A, step 2 | Oil |
| 150 | 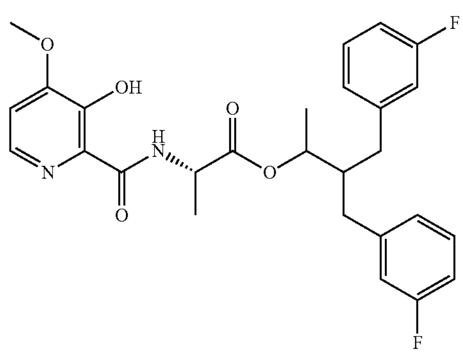 [SMILES: COc1ccnc(C(=O)N[C@@H](C)C(=O)OC(C)C(Cc2cccc(F)c2)Cc2cccc(F)c2)c1O] | Example 11A, step 2 | Oil |
| 151 | 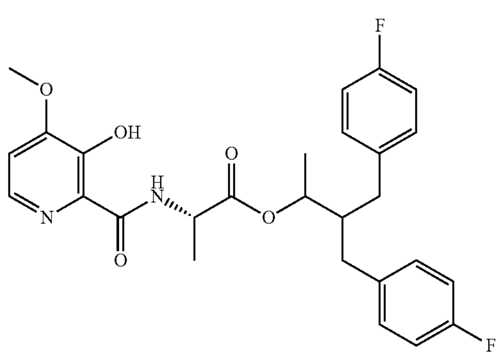 [SMILES: COc1ccnc(C(=O)N[C@@H](C)C(=O)OC(C)C(Cc2ccc(F)cc2)Cc2ccc(F)cc2)c1O] | Example 11A, step 2 | Oil |

TABLE 1-continued

Compound Structure and Appearance

| *Cmpd. No. | Structure | Prepared According to Example | Appearance |
|---|---|---|---|
| 152 | 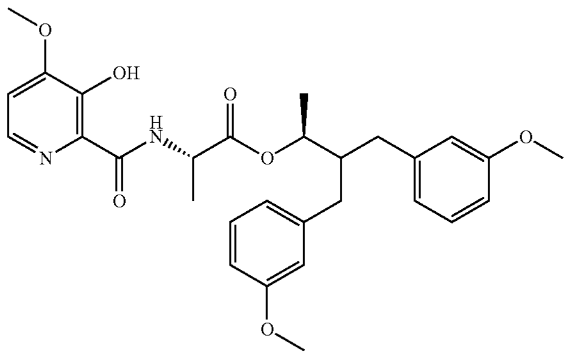 [SMILES: COc1cccc(CC(Cc2cccc(OC)c2)[C@H](C)OC(=O)[C@H](C)NC(=O)c2nccc(OC)c2O)c1] | Example 8, steps 1-3; Example 9A; Example 11A, step 1-2 | Oil |
| 153 | 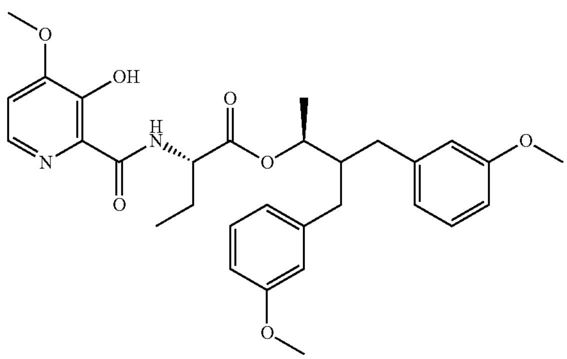 [SMILES: CC[C@H](NC(=O)c1nccc(OC)c1O)C(=O)O[C@@H](C)C(Cc1cccc(OC)c1)Cc1cccc(OC)c1] | Example 8, steps 1-3; Example 9A; Example 11A, step 1-2 | Oil |
| 154 | 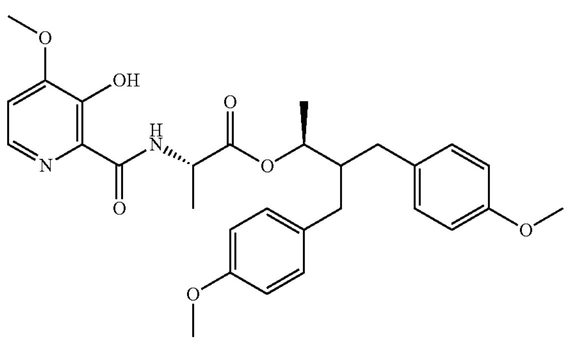 [SMILES: COc1ccc(CC(Cc2ccc(OC)cc2)[C@H](C)OC(=O)[C@H](C)NC(=O)c2nccc(OC)c2O)cc1] | Example 8, steps 1-3; Example 9A; Example 11A, step 1-2 | Oil |
| 155 | 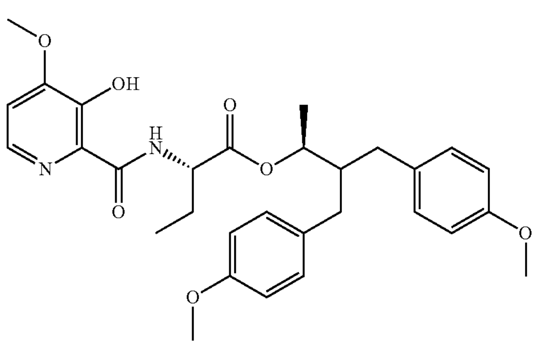 [SMILES: CC[C@H](NC(=O)c1nccc(OC)c1O)C(=O)O[C@@H](C)C(Cc1ccc(OC)cc1)Cc1ccc(OC)cc1] | Example 8, steps 1-3; Example 9A; Example 11A, step 1-2 | Oil |

TABLE 1-continued

Compound Structure and Appearance

| *Cmpd. No. | Structure | Prepared According to Example | Appearance |
|---|---|---|---|
| 156 | 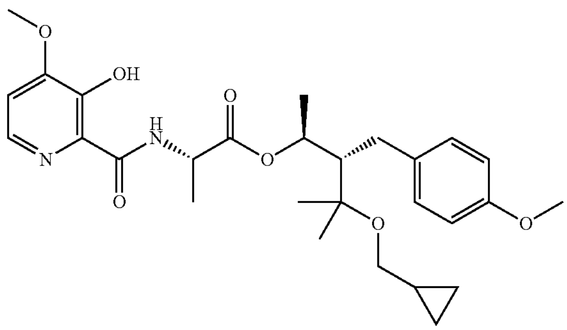 [SMILES: COc1ccc(C[C@@H]([C@H](C)OC(=O)[C@H](C)NC(=O)c2nccc(OC)c2O)C(C)(C)OCC2CC2)cc1] | Example 11A, step 2 | Sticky Wax |
| 157 | 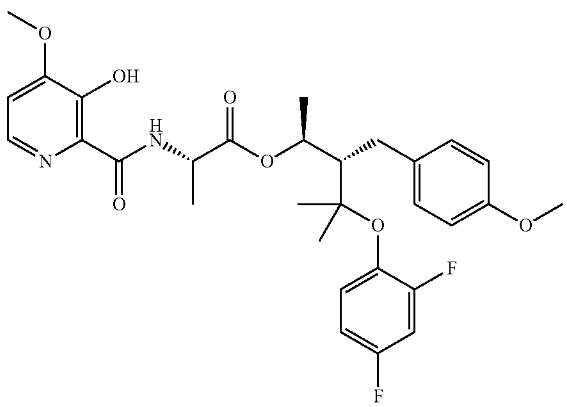 [SMILES: COc1ccc(C[C@@H]([C@H](C)OC(=O)[C@H](C)NC(=O)c2nccc(OC)c2O)C(C)(C)Oc2ccc(F)cc2F)cc1] | Example 11A, step 2 | Sticky Wax |
| 158 | 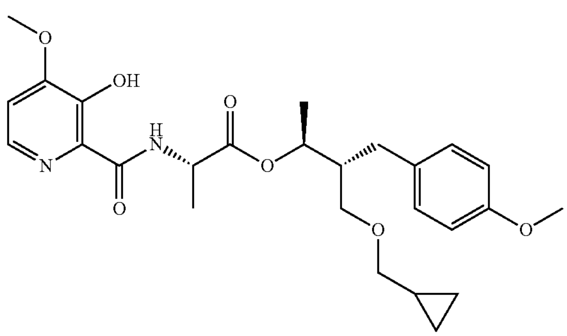 [SMILES: COc1ccc(C[C@H](COCC2CC2)[C@H](C)OC(=O)[C@H](C)NC(=O)c2nccc(OC)c2O)cc1] | Example 11A, step 2 | Sticky Wax |
| 159 | 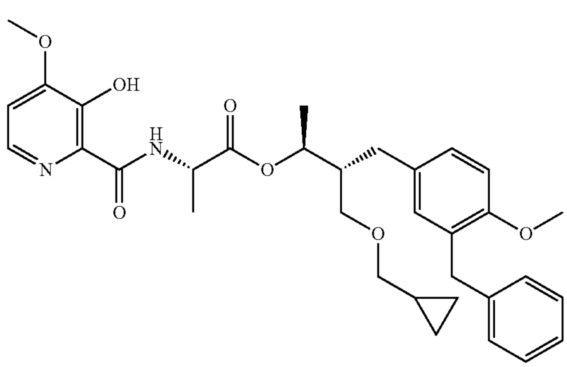 [SMILES: COc1ccc(C[C@H](COCC2CC2)[C@H](C)OC(=O)[C@H](C)NC(=O)c2nccc(OC)c2O)cc1Cc1ccccc1] | Example 11A, step 2 | Sticky Wax |

TABLE 1-continued

Compound Structure and Appearance

| *Cmpd. No. | Structure | Prepared According to Example | Appearance |
|---|---|---|---|
| 160 | 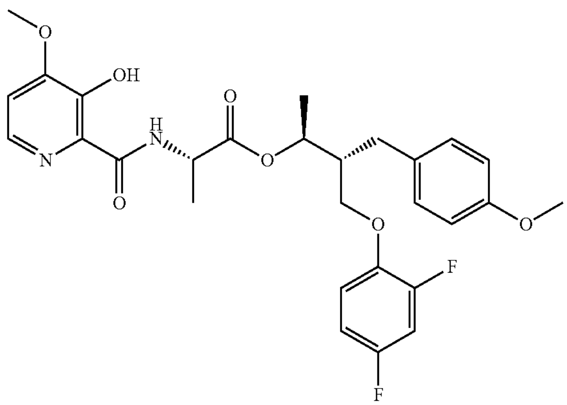 [SMILES: COc1ccc(C[C@H](COc2ccc(F)cc2F)[C@H](C)OC(=O)[C@H](C)NC(=O)c2nccc(OC)c2O)cc1] | Example 11A, step 2 | Sticky Wax |
| 161 | 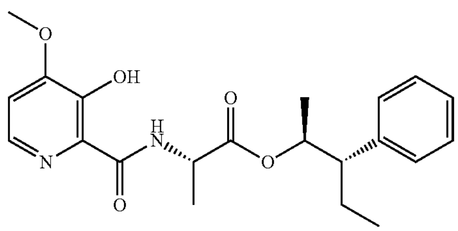 [SMILES: CC[C@@H](c1ccccc1)[C@H](C)OC(=O)[C@H](C)NC(=O)c1nccc(OC)c1O] | Example 11A, step 2 | Colorless Oil |
| 162 | 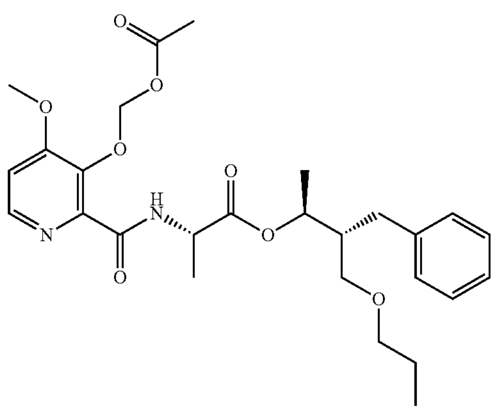 [SMILES: CCCOC[C@@H](Cc1ccccc1)[C@H](C)OC(=O)[C@H](C)NC(=O)c1nccc(OC)c1OCOC(C)=O] | Example 12A | Colorless Oil |
| 163 | 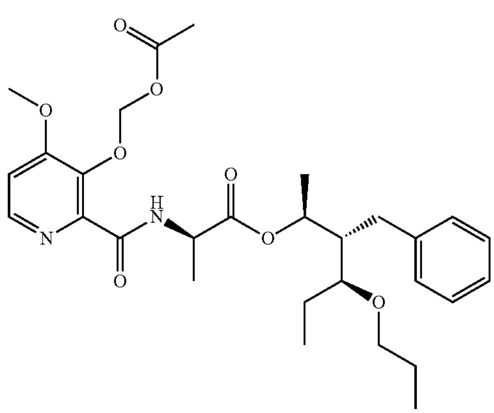 [SMILES: CCCO[C@@H](CC)[C@@H](Cc1ccccc1)[C@H](C)OC(=O)[C@@H](C)NC(=O)c1nccc(OC)c1OCOC(C)=O] | Example 12A | Colorless Oil |

TABLE 1-continued

Compound Structure and Appearance

| *Cmpd. No. | Structure | Prepared According to Example | Appearance |
|---|---|---|---|
| 164 | 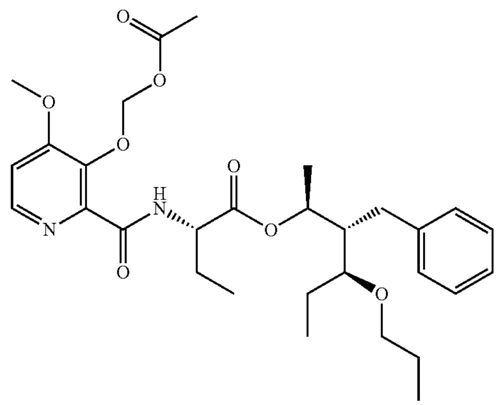 [SMILES: CCCO[C@@H](CC)[C@@H](Cc1ccccc1)[C@H](C)OC(=O)[C@H](CC)NC(=O)c1nccc(OC)c1OCOC(C)=O] | Example 12A | Colorless Oil |
| 165 | 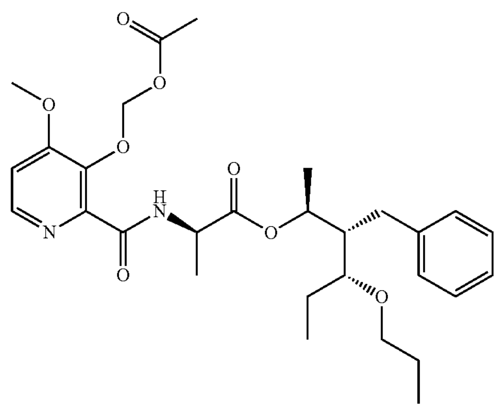 [SMILES: CCCO[C@H](CC)[C@@H](Cc1ccccc1)[C@H](C)OC(=O)[C@@H](C)NC(=O)c1nccc(OC)c1OCOC(C)=O] | Example 12A | Colorless Oil |
| 166 | 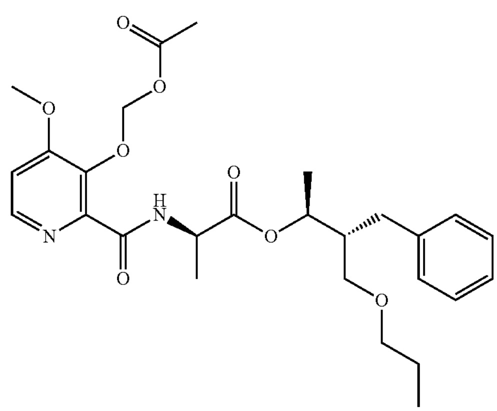 [SMILES: CCCOC[C@@H](Cc1ccccc1)[C@H](C)OC(=O)[C@@H](C)NC(=O)c1nccc(OC)c1OCOC(C)=O] | Example 12A | Colorless Oil |

TABLE 1-continued

Compound Structure and Appearance

| *Cmpd. No. | Structure | Prepared According to Example | Appearance |
|---|---|---|---|
| 167 | 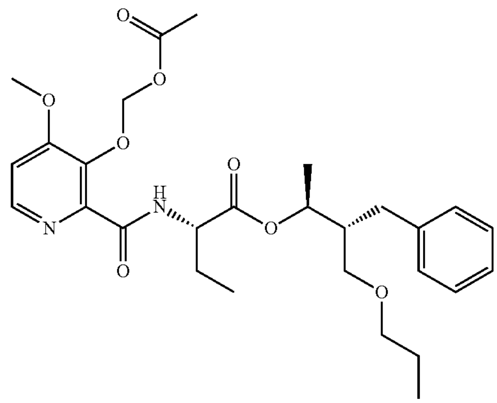 [SMILES: CCCOC[C@@H](Cc1ccccc1)[C@H](C)OC(=O)[C@H](CC)NC(=O)c1nccc(OC)c1OCOC(C)=O] | Example 12A | Colorless Oil |
| 168 | 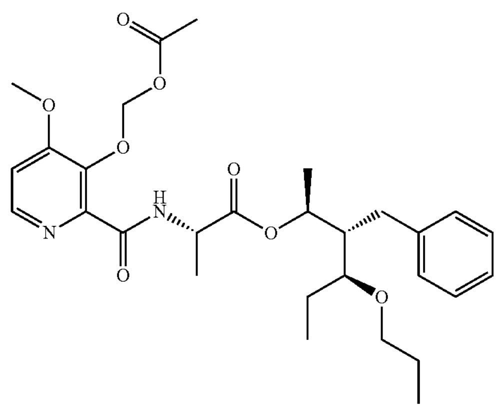 [SMILES: CCCO[C@@H](CC)[C@@H](Cc1ccccc1)[C@H](C)OC(=O)[C@H](C)NC(=O)c1nccc(OC)c1OCOC(C)=O] | Example 12A | Colorless Oil |
| 169 | 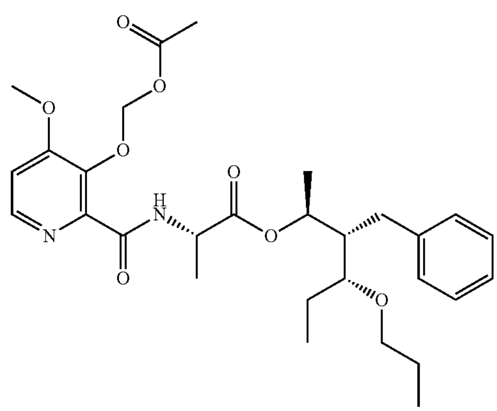 [SMILES: CCCO[C@H](CC)[C@@H](Cc1ccccc1)[C@H](C)OC(=O)[C@H](C)NC(=O)c1nccc(OC)c1OCOC(C)=O] | Example 12A | Colorless Oil |

TABLE 1-continued
Compound Structure and Appearance
| *Cmpd. No. | Structure | Prepared According to Example | Appearance |
|---|---|---|---|
| 170 | 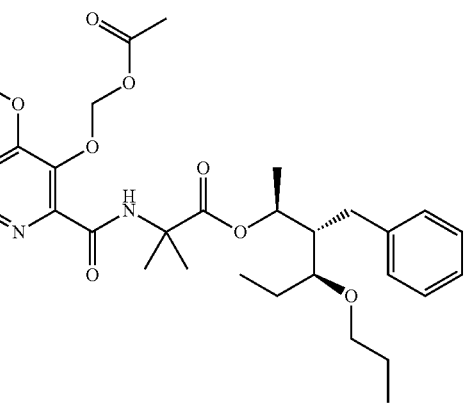 | Example 12A | Colorless Oil |
| 171 | 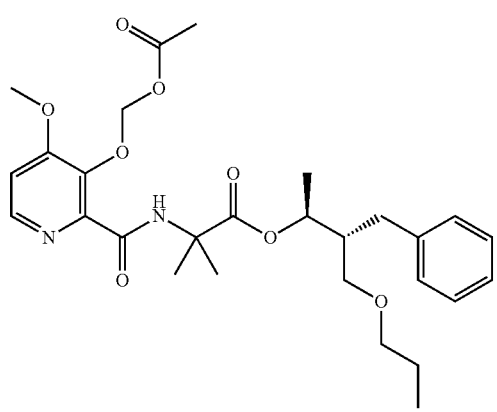 [SMILES: CCCOC[C@@H](Cc1ccccc1)[C@H](C)OC(=O)C(C)(C)NC(=O)c1nccc(OC)c1OCOC(C)=O] | Example 12A | Colorless Oil |
| 172 | 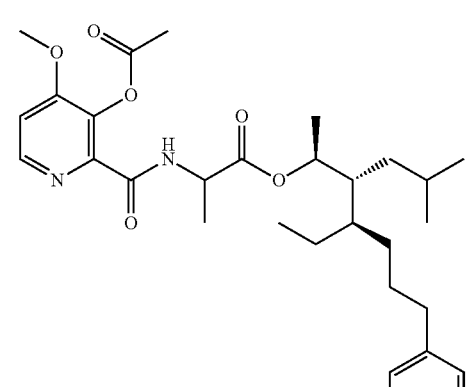 | Example 12C | Colorless Oil |

TABLE 1-continued

| *Cmpd. No. | Structure | Prepared According to Example | Appearance |
|---|---|---|---|
| 173 | 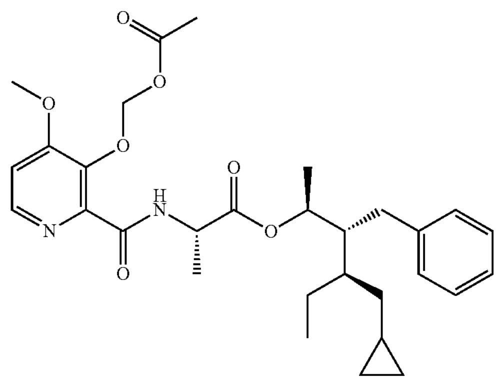 [SMILES: CC[C@H](CC1CC1)[C@@H](Cc1ccccc1)[C@H](C)OC(=O)[C@H](C)NC(=O)c1nccc(OC)c1OCOC(C)=O] | Example 12A | Slight Yellow Oil |
| 174 | 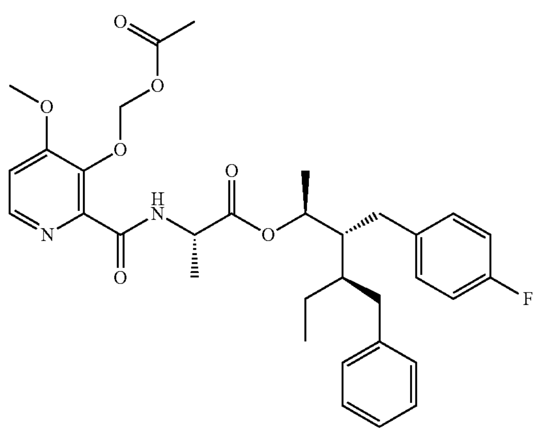 [SMILES: CC[C@H](Cc1ccccc1)[C@@H](Cc1ccc(F)cc1)[C@H](C)OC(=O)[C@H](C)NC(=O)c1nccc(OC)c1OCOC(C)=O] | Example 12A | Colorless Oil |
| 175 | 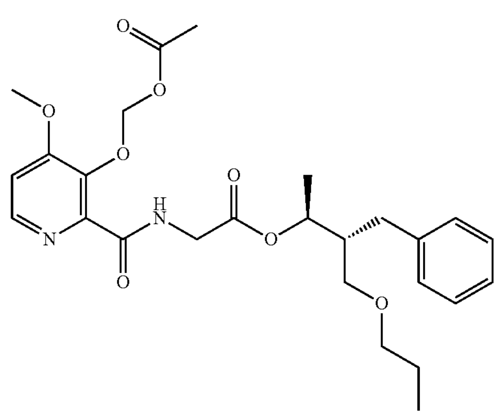 [SMILES: CCCOC[C@@H](Cc1ccccc1)[C@H](C)OC(=O)CNC(=O)c1nccc(OC)c1OCOC(C)=O] | Example 12A | Slight Yellow Oil |

TABLE 1-continued

Compound Structure and Appearance

| *Cmpd. No. | Structure | Prepared According to Example | Appearance |
|---|---|---|---|
| 176 | 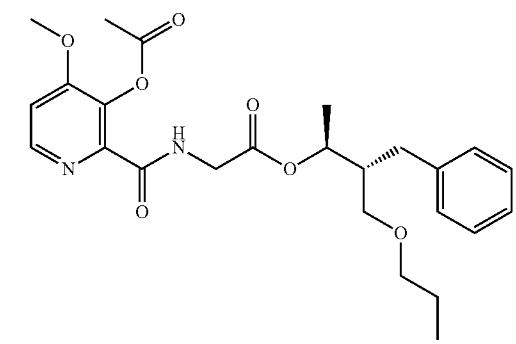 [SMILES: CCCOC[C@@H](Cc1ccccc1)[C@H](C)OC(=O)CNC(=O)c1nccc(OC)c1OC(C)=O] | Example 12C | Slight Yellow Oil |
| 177 | 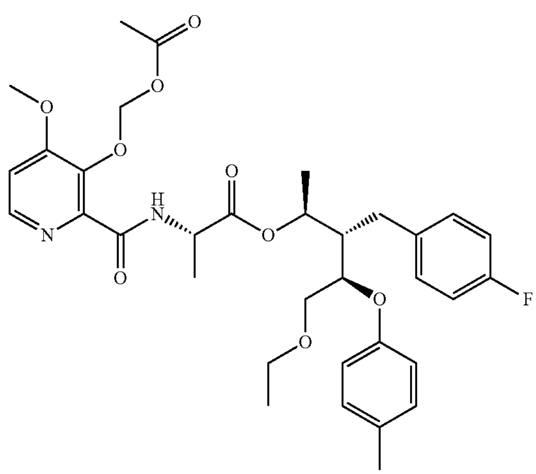 [SMILES: CCOC[C@H](Oc1ccc(C)cc1)[C@@H](Cc1ccc(F)cc1)[C@H](C)OC(=O)[C@H](C)NC(=O)c1nccc(OC)c1OCOC(C)=O] | Example 12A | Clear Tacky Oil |
| 178 | 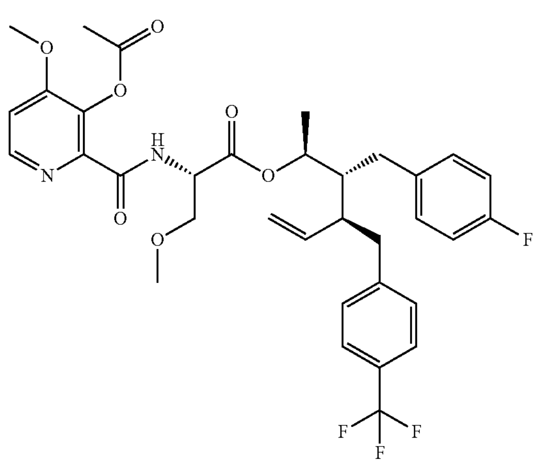 [SMILES: C=C[C@H](Cc1ccc(C(F)(F)F)cc1)[C@@H](Cc1ccc(F)cc1)[C@H](C)OC(=O)[C@H](COC)NC(=O)c1nccc(OC)c1OC(C)=O] | Example 12C | Sticky White Foam |

TABLE 1-continued

Compound Structure and Appearance

| *Cmpd. No. | Structure | Prepared According to Example | Appearance |
|---|---|---|---|
| 179 | 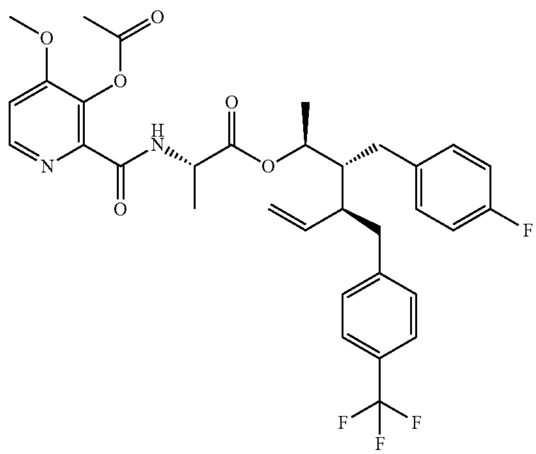 [SMILES: C=C[C@H](Cc1ccc(C(F)(F)F)cc1)[C@@H](Cc1ccc(F)cc1)[C@H](C)OC(=O)[C@H](C)NC(=O)c1nccc(OC)c1OC(C)=O] | Example 12C | Light Yellow Oily Foam |
| 180 | 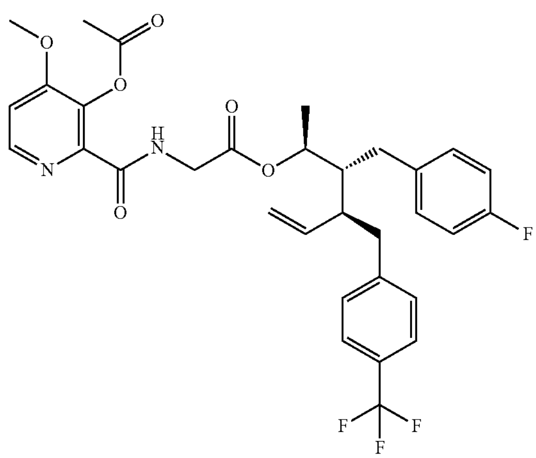 [SMILES: C=C[C@H](Cc1ccc(C(F)(F)F)cc1)[C@@H](Cc1ccc(F)cc1)[C@H](C)OC(=O)CNC(=O)c1nccc(OC)c1OC(C)=O] | Example 12C | Sticky Off White Foam |
| 181 | 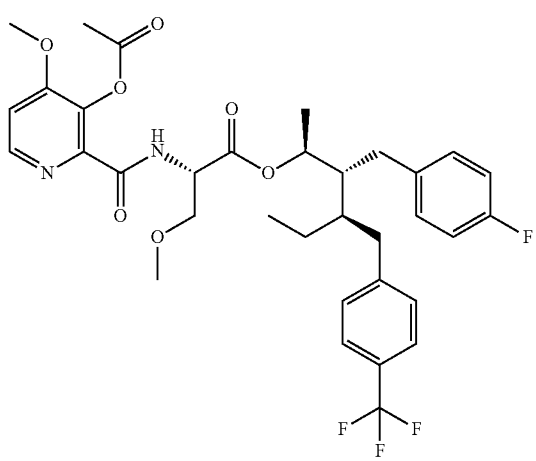 [SMILES: CC[C@H](Cc1ccc(C(F)(F)F)cc1)[C@@H](Cc1ccc(F)cc1)[C@H](C)OC(=O)[C@H](COC)NC(=O)c1nccc(OC)c1OC(C)=O] | Example 12C | Light Orange Foam |

TABLE 1-continued

Compound Structure and Appearance

| *Cmpd. No. | Structure | Prepared According to Example | Appearance |
|---|---|---|---|
| 182 | 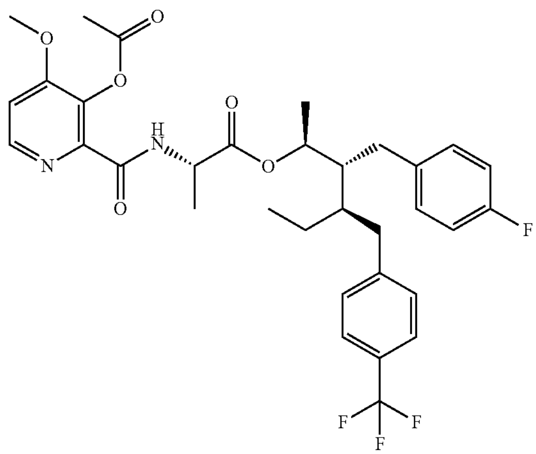 [SMILES: CC[C@H](Cc1ccc(C(F)(F)F)cc1)[C@@H](Cc1ccc(F)cc1)[C@H](C)OC(=O)[C@H](C)NC(=O)c1nccc(OC)c1OC(C)=O] | Example 12C | Light Orange Foam |
| 183 | 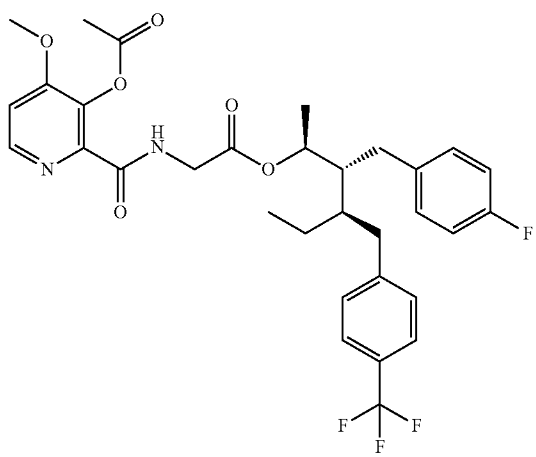 [SMILES: CC[C@H](Cc1ccc(C(F)(F)F)cc1)[C@@H](Cc1ccc(F)cc1)[C@H](C)OC(=O)CNC(=O)c1nccc(OC)c1OC(C)=O] | Example 12C | Off White Foam |
| 184 | 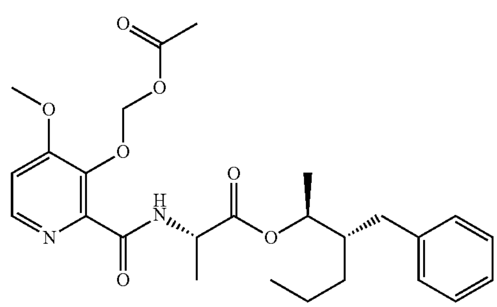 [SMILES: CCC[C@@H](Cc1ccccc1)[C@H](C)OC(=O)[C@H](C)NC(=O)c1nccc(OC)c1OCOC(C)=O] | Example 12A | Light Yellow Oil |
| 185 | 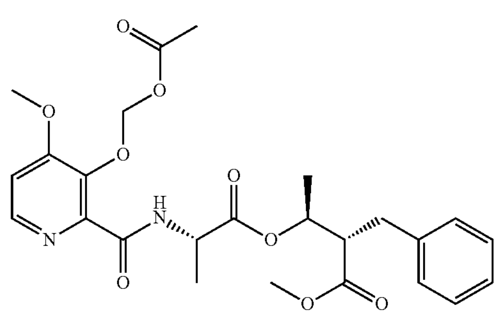 [SMILES: COC(=O)[C@@H](Cc1ccccc1)[C@H](C)OC(=O)[C@H](C)NC(=O)c1nccc(OC)c1OCOC(C)=O] | Example 12A | Light Yellow Oil |

TABLE 1-continued

Compound Structure and Appearance

| *Cmpd. No. | Structure | Prepared According to Example | Appearance |
|---|---|---|---|
| 186 | 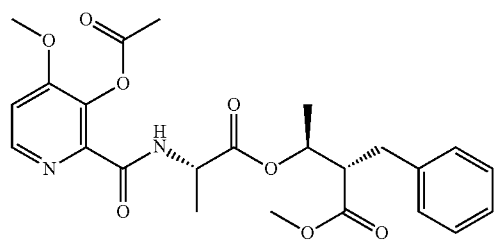 [SMILES: COC(=O)[C@@H](Cc1ccccc1)[C@H](C)OC(=O)[C@H](C)NC(=O)c1nccc(OC)c1OC(C)=O] | Example 12C | Light Yellow Oil |
| 187 | 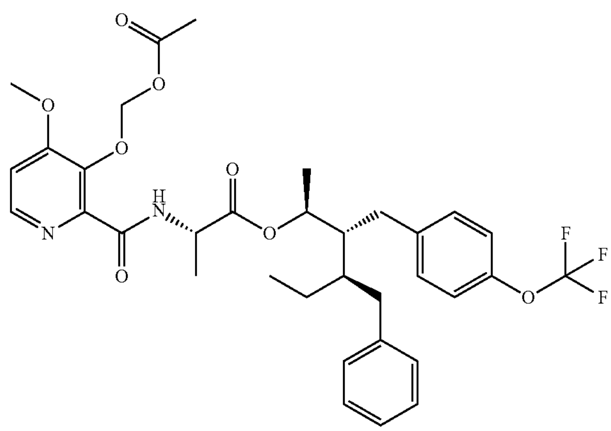 [SMILES: CC[C@H](Cc1ccccc1)[C@@H](Cc1ccc(OC(F)(F)F)cc1)[C@H](C)OC(=O)[C@H](C)NC(=O)c1nccc(OC)c1OCOC(C)=O] | Example 12A | Colorless Oil |
| 188 | 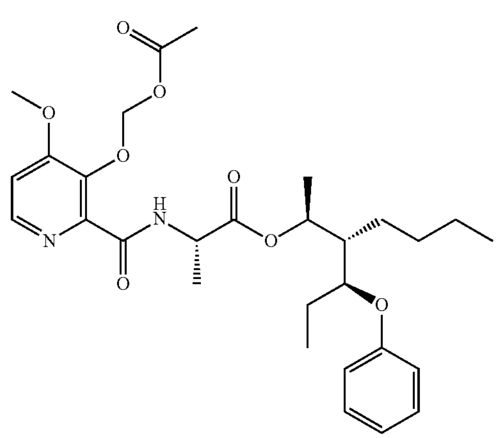 [SMILES: CCCC[C@@H]([C@H](C)OC(=O)[C@H](C)NC(=O)c1nccc(OC)c1OCOC(C)=O)[C@H](CC)Oc1ccccc1] | Example 12A | Colorless Oil |

TABLE 1-continued

Compound Structure and Appearance

| *Cmpd. No. | Structure | Prepared According to Example | Appearance |
|---|---|---|---|
| 189 | 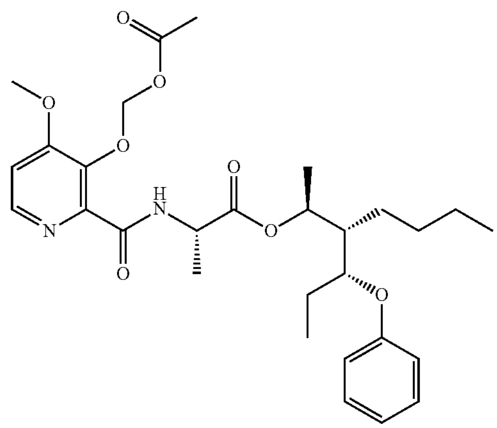 [SMILES: CCCC[C@@H]([C@H](C)OC(=O)[C@H](C)NC(=O)c1nccc(OC)c1OCOC(C)=O)[C@@H](CC)Oc1ccccc1] | Example 12A | Colorless Oil |
| 190 | 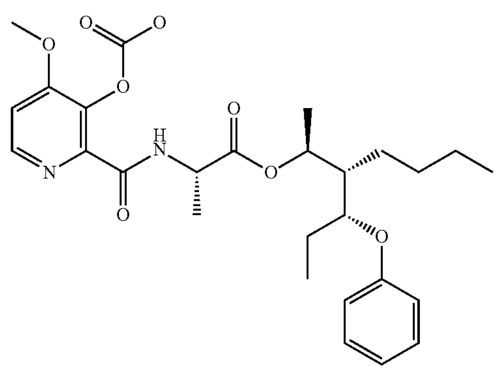 [SMILES: CCCC[C@@H]([C@H](C)OC(=O)[C@H](C)NC(=O)c1nccc(OC)c1OC(=O)O)[C@@H](CC)Oc1ccccc1] | Example 12C | Red-Orange Oil |
| 191 | 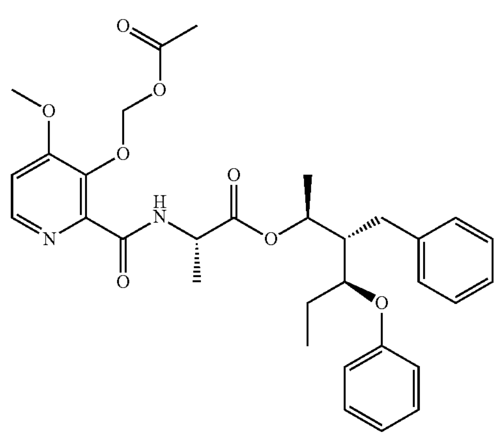 [SMILES: CC[C@H](Oc1ccccc1)[C@@H](Cc1ccccc1)[C@H](C)OC(=O)[C@H](C)NC(=O)c1nccc(OC)c1OCOC(C)=O] | Example 12A | Colorless Oil |

TABLE 1-continued

Compound Structure and Appearance

| *Cmpd. No. | Structure | Prepared According to Example | Appearance |
|---|---|---|---|
| 192 | 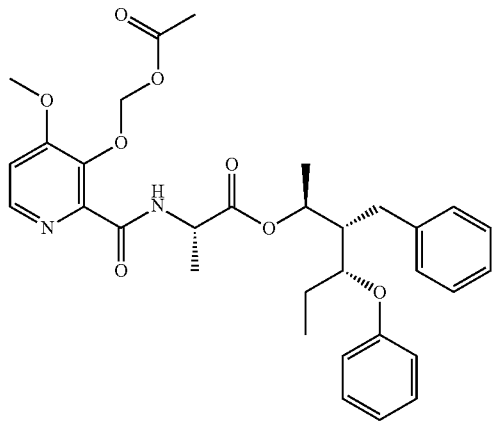 [SMILES: CC[C@@H](Oc1ccccc1)[C@@H](Cc1ccccc1)[C@H](C)OC(=O)[C@H](C)NC(=O)c1nccc(OC)c1OCOC(C)=O] | Example 12A | Colorless Oil |
| 193 | 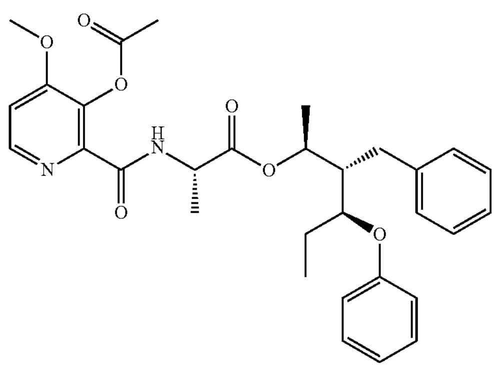 [SMILES: CC[C@H](Oc1ccccc1)[C@@H](Cc1ccccc1)[C@H](C)OC(=O)[C@H](C)NC(=O)c1nccc(OC)c1OC(C)=O] | Example 12C | Yellow Oil |
| 194 | 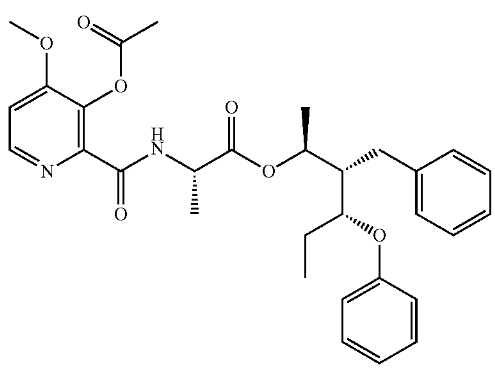 [SMILES: CC[C@@H](Oc1ccccc1)[C@@H](Cc1ccccc1)[C@H](C)OC(=O)[C@H](C)NC(=O)c1nccc(OC)c1OC(C)=O] | Example 12C | Yellow Oil |
| 195 | 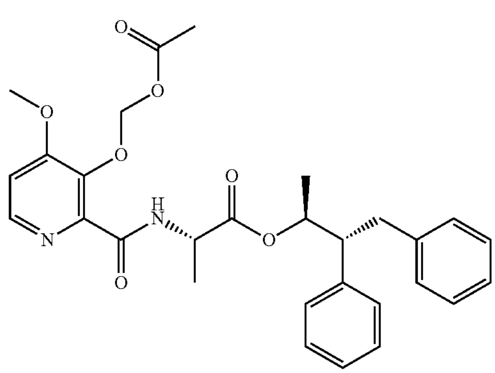 [SMILES: COc1ccnc(C(=O)N[C@@H](C)C(=O)O[C@@H](C)[C@H](Cc2ccccc2)c2ccccc2)c1OCOC(C)=O] | Example 12A | Colorless Oil |

TABLE 1-continued

Compound Structure and Appearance

| *Cmpd. No. | Structure | Prepared According to Example | Appearance |
|---|---|---|---|
| 196 | 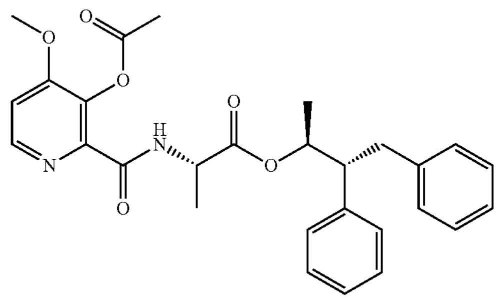 [SMILES: COc1ccnc(C(=O)N[C@@H](C)C(=O)O[C@@H](C)[C@H](Cc2ccccc2)c2ccccc2)c1OC(C)=O] | Example 12C | Colorless Oil |
| 197 | 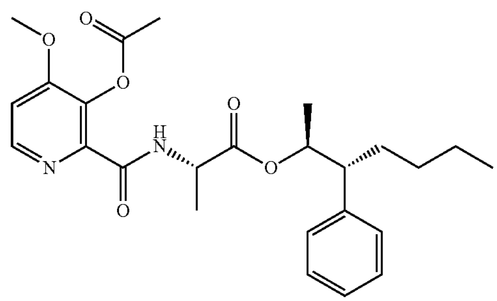 [SMILES: CCCC[C@H](c1ccccc1)[C@H](C)OC(=O)[C@H](C)NC(=O)c1nccc(OC)c1OC(C)=O] | Example 12C | Colorless Oil |
| 198 | 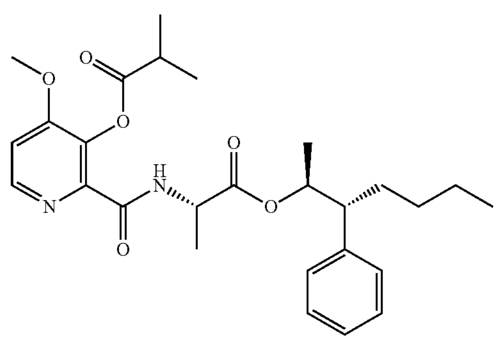 [SMILES: CCCC[C@H](c1ccccc1)[C@H](C)OC(=O)[C@H](C)NC(=O)c1nccc(OC)c1OC(=O)C(C)C] | Example 12C | Colorless Oil |
| 199 | 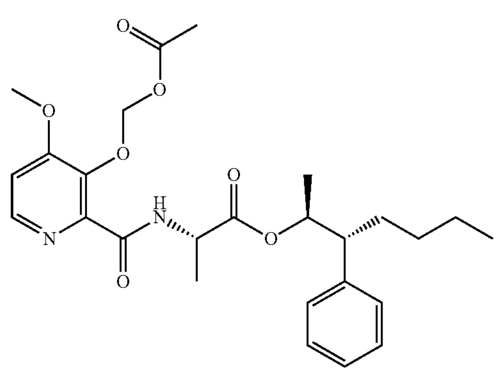 [SMILES: CCCC[C@H](c1ccccc1)[C@H](C)OC(=O)[C@H](C)NC(=O)c1nccc(OC)c1OCOC(C)=O] | Example 12A | Colorless Oil |

TABLE 1-continued

Compound Structure and Appearance

| *Cmpd. No. | Structure | Prepared According to Example | Appearance |
|---|---|---|---|
| 200 | 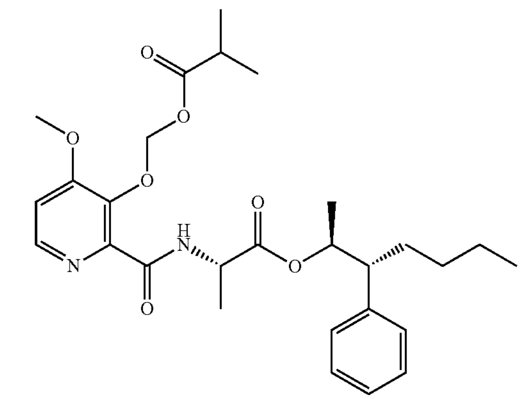 [SMILES: CCCC[C@H](c1ccccc1)[C@H](C)OC(=O)[C@H](C)NC(=O)c1nccc(OC)c1OCOC(=O)C(C)C] | Example 12B | Colorless Oil |
| 201 | 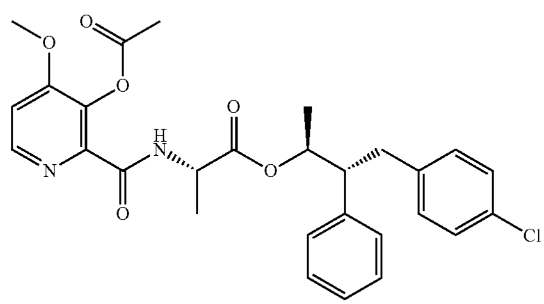 [SMILES: COc1ccnc(C(=O)N[C@@H](C)C(=O)O[C@@H](C)[C@H](Cc2ccc(Cl)cc2)c2ccccc2)c1OC(C)=O] | Example 12C | Colorless Oil |
| 202 | 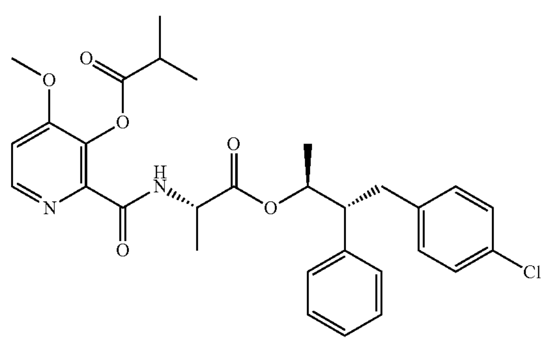 [SMILES: COc1ccnc(C(=O)N[C@@H](C)C(=O)O[C@@H](C)[C@H](Cc2ccc(Cl)cc2)c2ccccc2)c1OC(=O)C(C)C] | Example 12C | Colorless Oil |
| 203 | 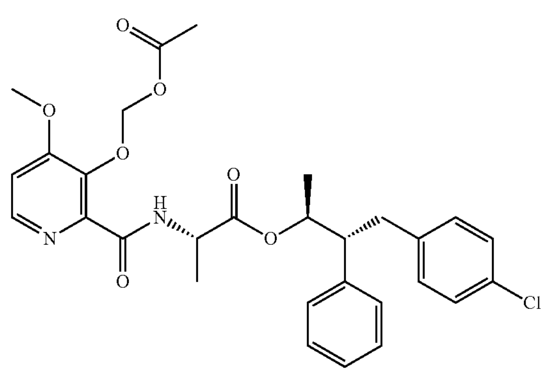 [SMILES: COc1ccnc(C(=O)N[C@@H](C)C(=O)O[C@@H](C)[C@H](Cc2ccc(Cl)cc2)c2ccccc2)c1OCOC(C)=O] | Example 12A | Colorless Oil |

TABLE 1-continued
Compound Structure and Appearance
| *Cmpd. No. | Structure | Prepared According to Example | Appearance |
|---|---|---|---|
| 204 | 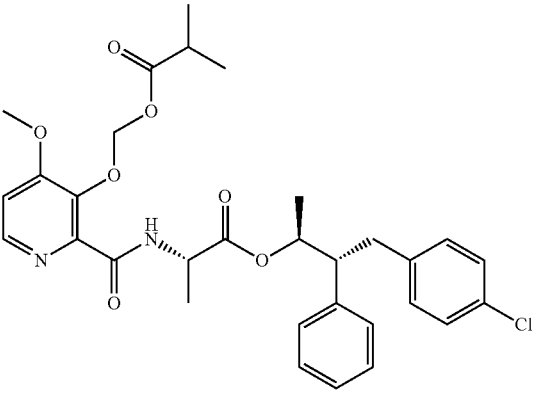 [SMILES: COc1ccnc(C(=O)N[C@@H](C)C(=O)O[C@@H](C)[C@H](Cc2ccc(Cl)cc2)c2ccccc2)c1OCOC(=O)C(C)C] | Example 12B | Colorless Oil |
| 205 | 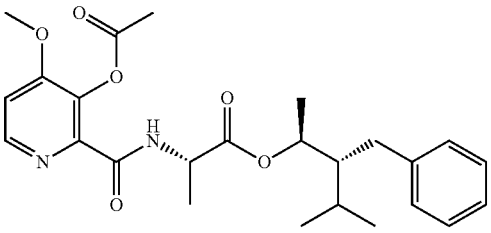 [SMILES: COc1ccnc(C(=O)N[C@@H](C)C(=O)O[C@@H](C)[C@H](Cc2ccccc2)C(C)C)c1OC(C)=O] | Example 12C | Colorless Oil |
| 206 | 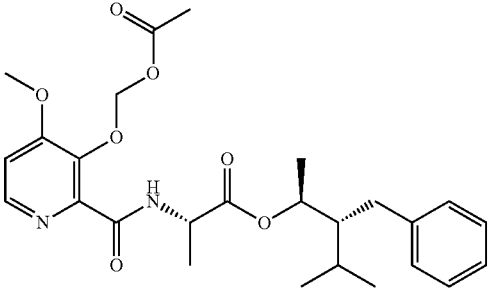 [SMILES: COc1ccnc(C(=O)N[C@@H](C)C(=O)O[C@@H](C)[C@H](Cc2ccccc2)C(C)C)c1OCOC(C)=O] | Example 12A | Colorless Oil |
| 207 | 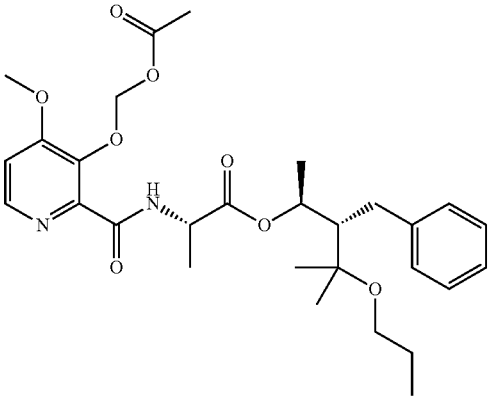 [SMILES: CCCOC(C)(C)[C@@H](Cc1ccccc1)[C@H](C)OC(=O)[C@H](C)NC(=O)c1nccc(OC)c1OCOC(C)=O] | Example 12A | Sticky Wax |

TABLE 1-continued
Compound Structure and Appearance
| *Cmpd. No. | Structure | Prepared According to Example | Appearance |
|---|---|---|---|
| 208 | 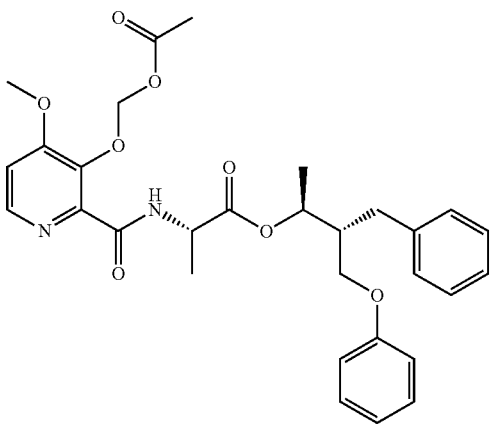 [SMILES: COc1ccnc(C(=O)N[C@@H](C)C(=O)O[C@@H](C)[C@@H](COc2ccccc2)Cc2ccccc2)c1OCOC(C)=O] | Example 12A | Clear Glass |
| 209 | 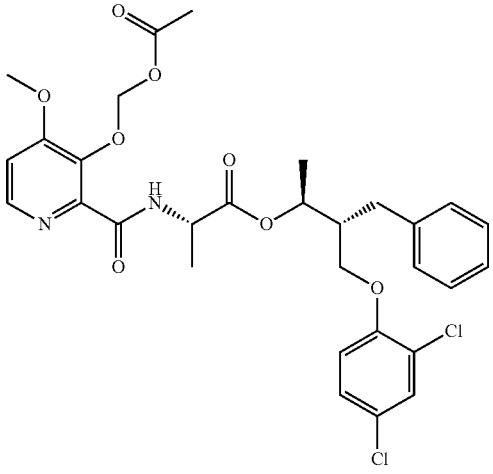 [SMILES: COc1ccnc(C(=O)N[C@@H](C)C(=O)O[C@@H](C)[C@@H](COc2ccc(Cl)cc2Cl)Cc2ccccc2)c1OCOC(C)=O] | Example 12A | White Foam |
| 210 | 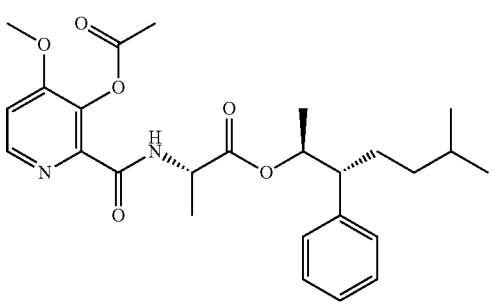 [SMILES: COc1ccnc(C(=O)N[C@@H](C)C(=O)O[C@@H](C)[C@H](CCC(C)C)c2ccccc2)c1OC(C)=O] | Example 12C | Colorless Oil |

TABLE 1-continued

Compound Structure and Appearance

| *Cmpd. No. | Structure | Prepared According to Example | Appearance |
|---|---|---|---|
| 211 | 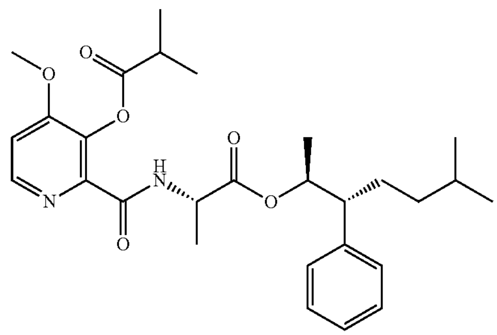 [SMILES: COc1ccnc(C(=O)N[C@@H](C)C(=O)O[C@@H](C)[C@H](CCC(C)C)c2ccccc2)c1OC(=O)C(C)C] | Example 12C | Colorless Oil |
| 212 | 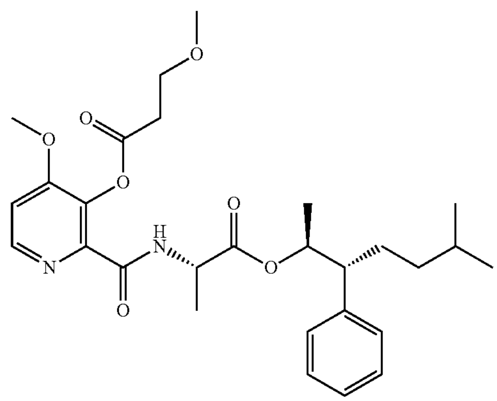 [SMILES: COCCC(=O)Oc1c(OC)ccnc1C(=O)N[C@@H](C)C(=O)O[C@@H](C)[C@H](CCC(C)C)c1ccccc1] | Example 12C | Colorless Oil |
| 213 | 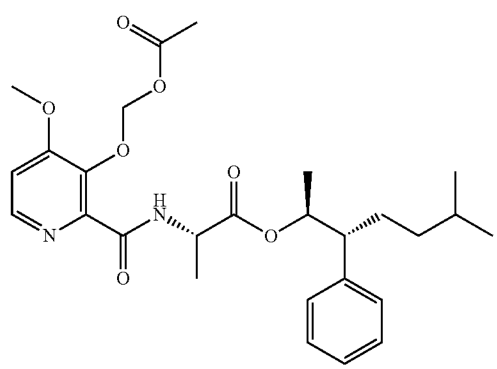 [SMILES: COc1ccnc(C(=O)N[C@@H](C)C(=O)O[C@@H](C)[C@H](CCC(C)C)c2ccccc2)c1OCOC(C)=O] | Example 12A | Colorless Oil |
| 214 | 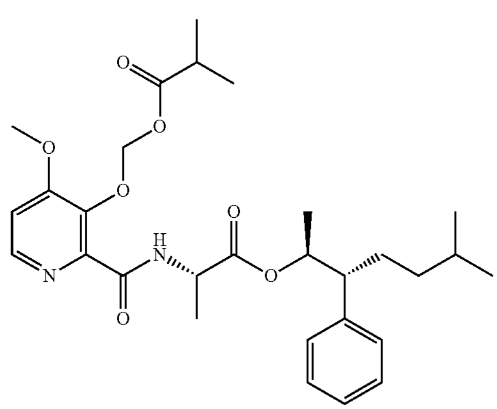 [SMILES: COc1ccnc(C(=O)N[C@@H](C)C(=O)O[C@@H](C)[C@H](CCC(C)C)c2ccccc2)c1OCOC(=O)C(C)C] | Example 12B | Colorless Oil |

| *Cmpd. No. | Structure | Prepared According to Example | Appearance |
|---|---|---|---|
| 215 | 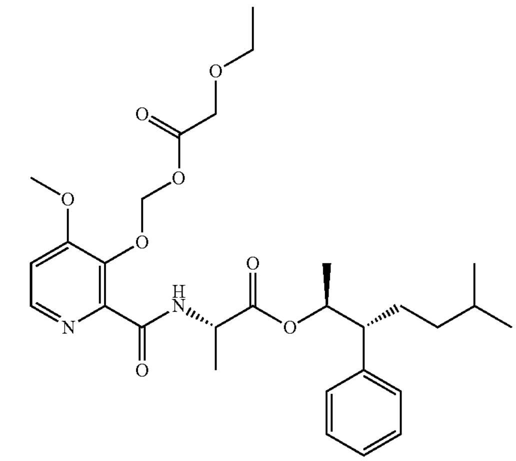 [SMILES: CCOCC(=O)OCOc1c(OC)ccnc1C(=O)N[C@@H](C)C(=O)O[C@@H](C)[C@H](CCC(C)C)c1ccccc1] | Example 12B | Colorless Oil |
| 216 | 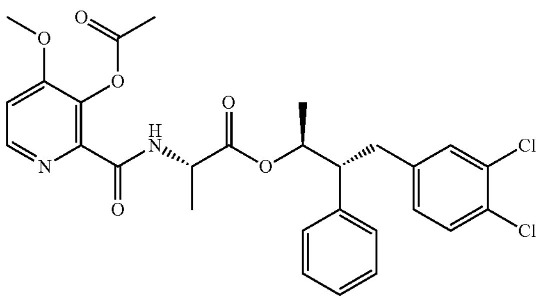 [SMILES: COc1ccnc(C(=O)N[C@@H](C)C(=O)O[C@@H](C)[C@H](Cc2ccc(Cl)c(Cl)c2)c2ccccc2)c1OC(C)=O] | Example 12C | White Foam |
| 217 | 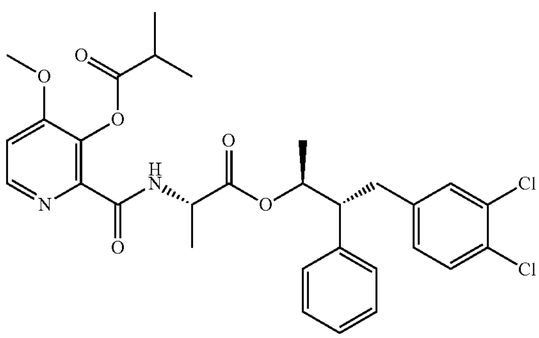 [SMILES: COc1ccnc(C(=O)N[C@@H](C)C(=O)O[C@@H](C)[C@H](Cc2ccc(Cl)c(Cl)c2)c2ccccc2)c1OC(=O)C(C)C] | Example 12C | White Foam |
| 218 | 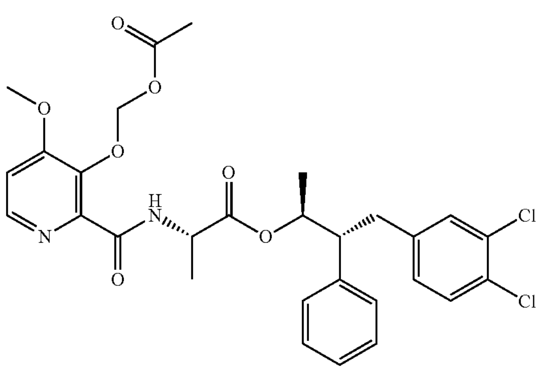 [SMILES: COc1ccnc(C(=O)N[C@@H](C)C(=O)O[C@@H](C)[C@H](Cc2ccc(Cl)c(Cl)c2)c2ccccc2)c1OCOC(C)=O] | Example 12A | White Foam |

TABLE 1-continued

Compound Structure and Appearance

| *Cmpd. No. | Structure | Prepared According to Example | Appearance |
|---|---|---|---|
| 219 | 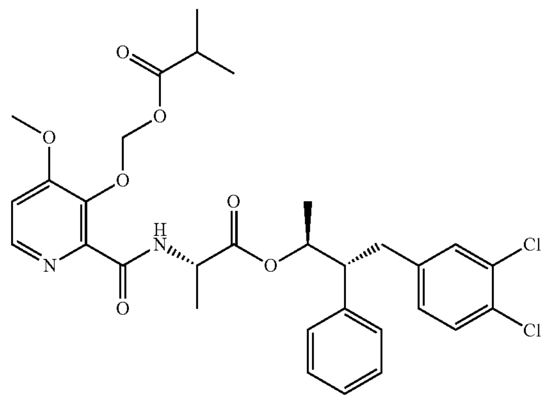 [SMILES: COc1ccnc(C(=O)N[C@@H](C)C(=O)O[C@@H](C)[C@H](Cc2ccc(Cl)c(Cl)c2)c2ccccc2)c1OCOC(=O)C(C)C] | Example 12B | White Foam |
| 220 | 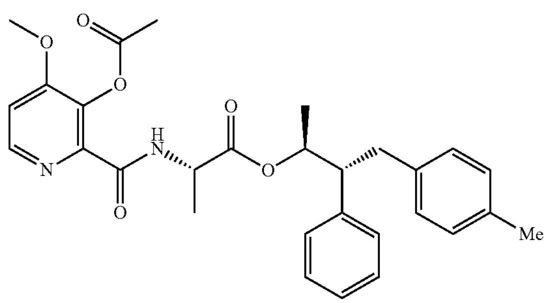 [SMILES: COc1ccnc(C(=O)N[C@@H](C)C(=O)O[C@@H](C)[C@H](Cc2ccc(C)cc2)c2ccccc2)c1OC(C)=O] | Example 12C | White Foam |
| 221 | 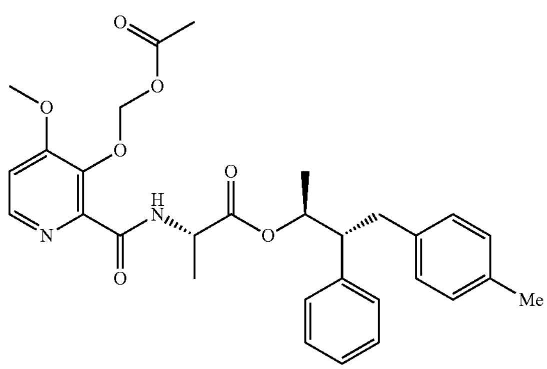 [SMILES: COc1ccnc(C(=O)N[C@@H](C)C(=O)O[C@@H](C)[C@H](Cc2ccc(C)cc2)c2ccccc2)c1OCOC(C)=O] | Example 12A | White Foam |
| 222 | 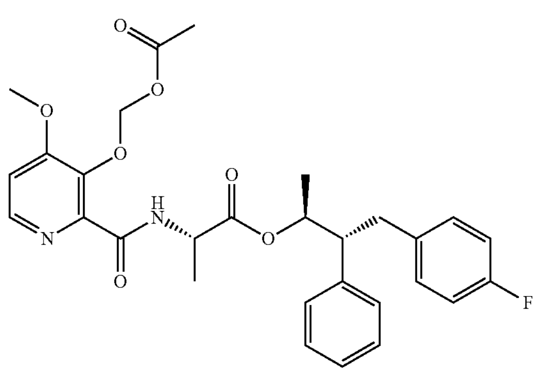 [SMILES: COc1ccnc(C(=O)N[C@@H](C)C(=O)O[C@@H](C)[C@H](Cc2ccc(F)cc2)c2ccccc2)c1OCOC(C)=O] | Example 12A | White Foam |

TABLE 1-continued
Compound Structure and Appearance
| *Cmpd. No. | Structure | Prepared According to Example | Appearance |
|---|---|---|---|
| 223 | 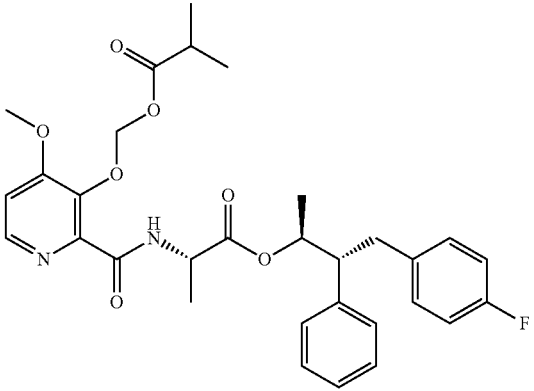 [SMILES: COc1ccnc(C(=O)N[C@@H](C)C(=O)O[C@@H](C)[C@H](Cc2ccc(F)cc2)c2ccccc2)c1OCOC(=O)C(C)C] | Example 12B | White Foam |
| 224 | 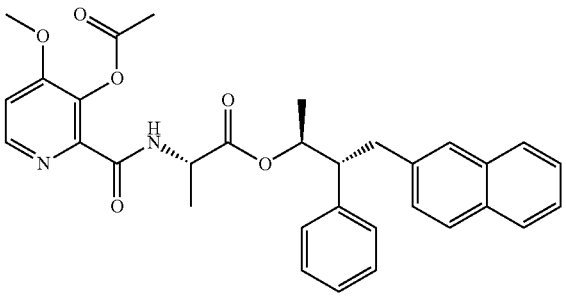 [SMILES: COc1ccnc(C(=O)N[C@@H](C)C(=O)O[C@@H](C)[C@H](Cc2ccc3ccccc3c2)c2ccccc2)c1OC(C)=O] | Example 12C | White Foam |
| 225 | 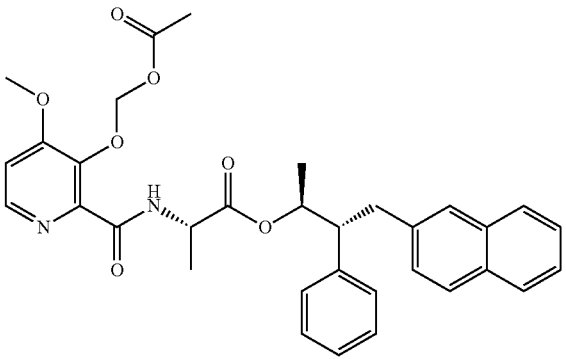 [SMILES: COc1ccnc(C(=O)N[C@@H](C)C(=O)O[C@@H](C)[C@H](Cc2ccc3ccccc3c2)c2ccccc2)c1OCOC(C)=O] | Example 12A | White Foam |
| 226 | 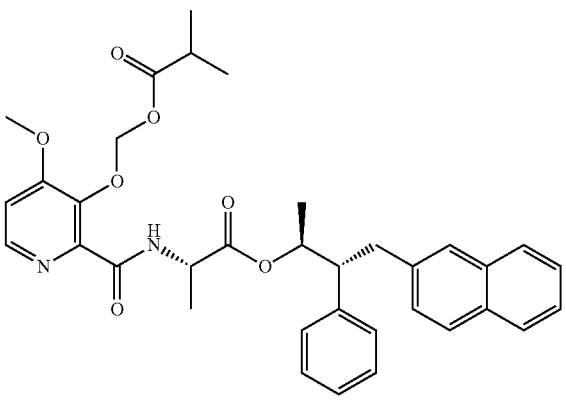 [SMILES: COc1ccnc(C(=O)N[C@@H](C)C(=O)O[C@@H](C)[C@H](Cc2ccc3ccccc3c2)c2ccccc2)c1OCOC(=O)C(C)C] | Example 12B | White Foam |

TABLE 1-continued

| *Cmpd. No. | Structure | Prepared According to Example | Appearance |
|---|---|---|---|
| 227 | 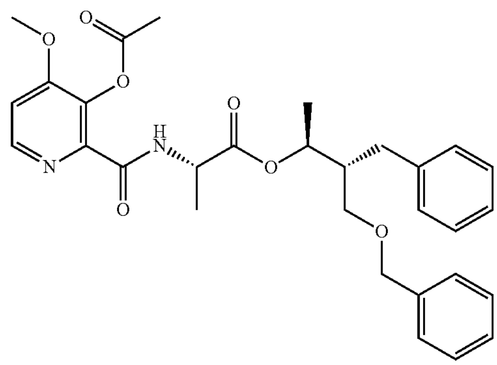 [SMILES: COc1ccnc(C(=O)N[C@@H](C)C(=O)O[C@@H](C)[C@@H](COCc2ccccc2)Cc2ccccc2)c1OC(C)=O] | Example 12C | Yellow Oil |
| 228 | 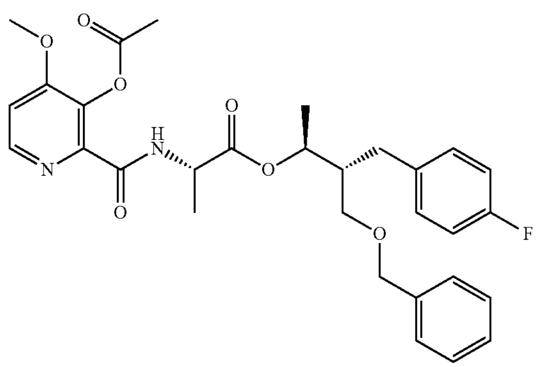 [SMILES: COc1ccnc(C(=O)N[C@@H](C)C(=O)O[C@@H](C)[C@@H](COCc2ccccc2)Cc2ccc(F)cc2)c1OC(C)=O] | Example 12C | Yellow Oil |
| 229 | 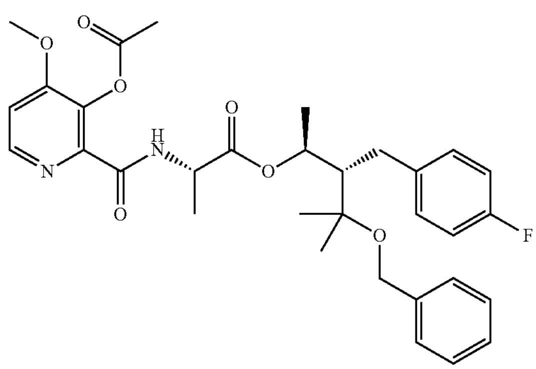 [SMILES: COc1ccnc(C(=O)N[C@@H](C)C(=O)O[C@@H](C)[C@H](Cc2ccc(F)cc2)C(C)(C)OCc2ccccc2)c1OC(C)=O] | Example 12C | Yellow Oil |
| 230 | 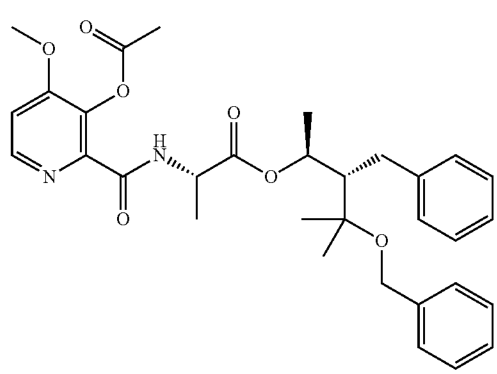 [SMILES: COc1ccnc(C(=O)N[C@@H](C)C(=O)O[C@@H](C)[C@H](Cc2ccccc2)C(C)(C)OCc2ccccc2)c1OC(C)=O] | Example 12C | Yellow Oil |

TABLE 1-continued

Compound Structure and Appearance

| *Cmpd. No. | Structure | Prepared According to Example | Appearance |
|---|---|---|---|
| 231 | 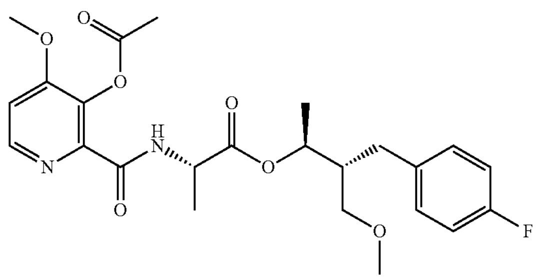 [SMILES: COC[C@@H](Cc1ccc(F)cc1)[C@H](C)OC(=O)[C@H](C)NC(=O)c1nccc(OC)c1OC(C)=O] | Example 12C | Yellow Oil |
| 232 | 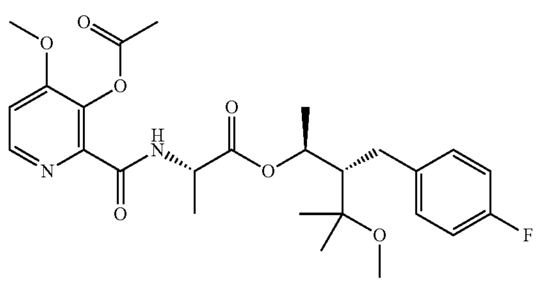 [SMILES: COc1ccnc(C(=O)N[C@@H](C)C(=O)O[C@@H](C)[C@H](Cc2ccc(F)cc2)C(C)(C)OC)c1OC(C)=O] | Example 12C | Yellow Oil |
| 233 | 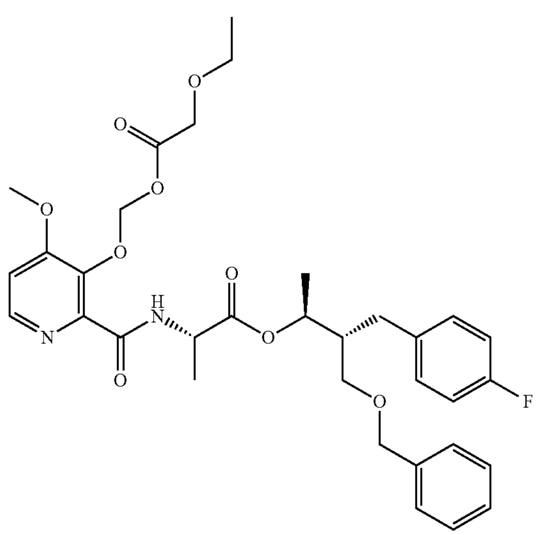 [SMILES: CCOCC(=O)OCOc1c(OC)ccnc1C(=O)N[C@@H](C)C(=O)O[C@@H](C)[C@@H](COCc1ccccc1)Cc1ccc(F)cc1] | Example 12B | Clear, Colorless Oil |

TABLE 1-continued

Compound Structure and Appearance

| *Cmpd. No. | Structure | Prepared According to Example | Appearance |
|---|---|---|---|
| 234 | 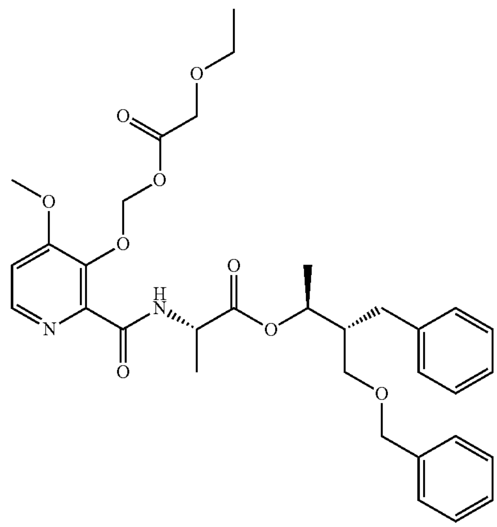 [SMILES: CCOCC(=O)OCOc1c(OC)ccnc1C(=O)N[C@@H](C)C(=O)O[C@@H](C)[C@@H](COCc1ccccc1)Cc1ccccc1] | Example 12B | Clear, Colorless Oil |
| 235 | 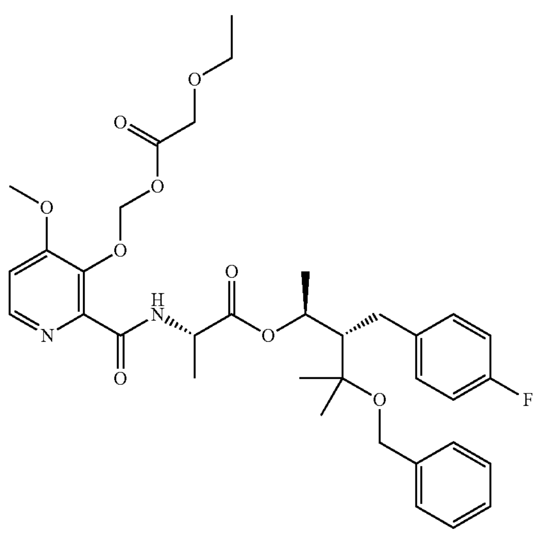 [SMILES: CCOCC(=O)OCOc1c(OC)ccnc1C(=O)N[C@@H](C)C(=O)O[C@@H](C)[C@H](Cc1ccc(F)cc1)C(C)(C)OCc1ccccc1] | Example 12B | Clear, Colorless Oil |

TABLE 1-continued

Compound Structure and Appearance

| *Cmpd. No. | Structure | Prepared According to Example | Appearance |
|---|---|---|---|
| 236 | 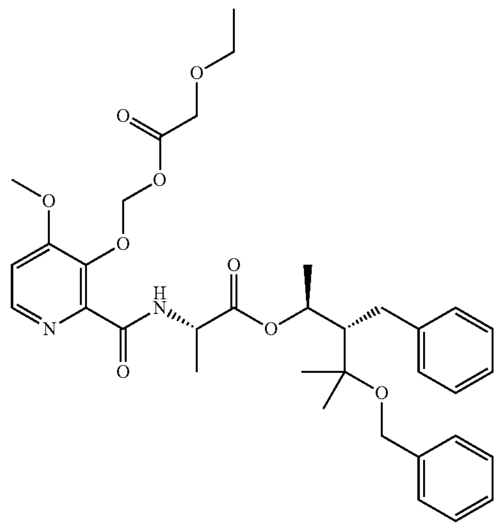 [SMILES: CCOCC(=O)OCOc1c(OC)ccnc1C(=O)N[C@@H](C)C(=O)O[C@@H](C)[C@H](Cc1ccccc1)C(C)(C)OCc1ccccc1] | Example 12B | Clear, Colorless Oil |
| 237 | 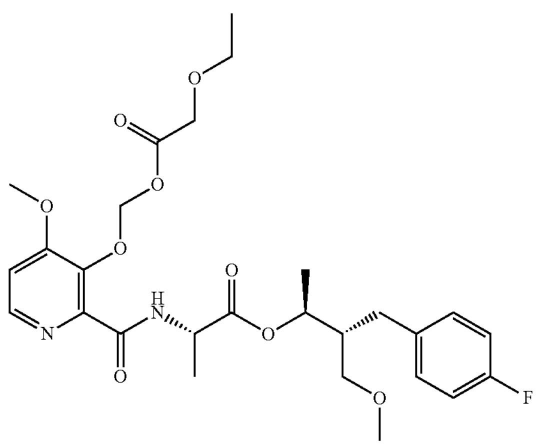 [SMILES: CCOCC(=O)OCOc1c(OC)ccnc1C(=O)N[C@@H](C)C(=O)O[C@@H](C)[C@@H](COC)Cc1ccc(F)cc1] | Example 12B | Clear, Colorless Oil |
| 238 | 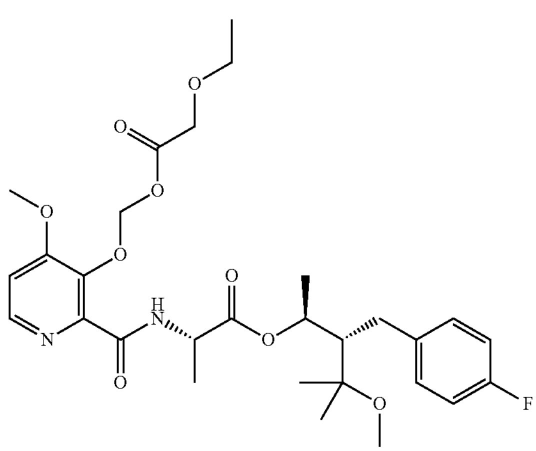 [SMILES: CCOCC(=O)OCOc1c(OC)ccnc1C(=O)N[C@@H](C)C(=O)O[C@@H](C)[C@H](Cc1ccc(F)cc1)C(C)(C)OC] | Example 12B | Clear, Colorless Oil |

TABLE 1-continued

Compound Structure and Appearance

| *Cmpd. No. | Structure | Prepared According to Example | Appearance |
|---|---|---|---|
| 239 | 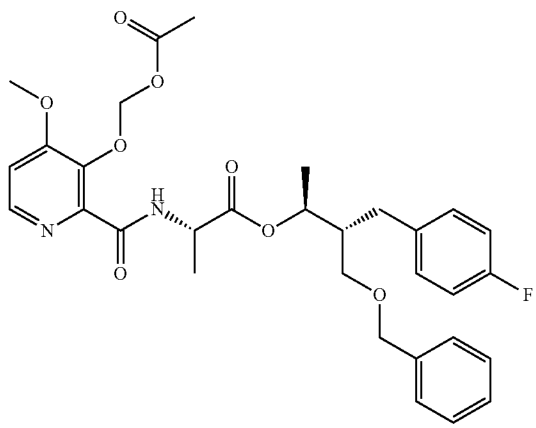 [SMILES: COc1ccnc(C(=O)N[C@@H](C)C(=O)O[C@@H](C)[C@@H](COCc2ccccc2)Cc2ccc(F)cc2)c1OCOC(C)=O] | Example 12A | Clear, Colorless Oil |
| 240 | 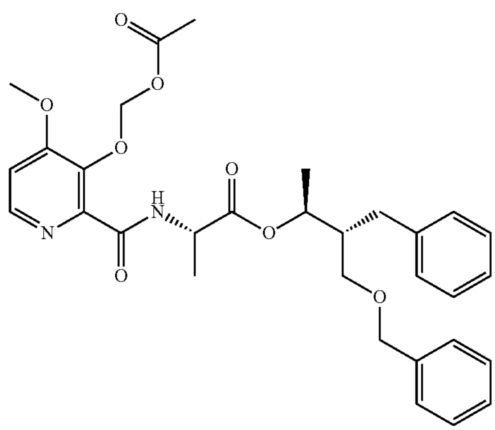 [SMILES: COc1ccnc(C(=O)N[C@@H](C)C(=O)O[C@@H](C)[C@@H](COCc2ccccc2)Cc2ccccc2)c1OCOC(C)=O] | Example 12A | Clear, Colorless Oil |
| 241 | 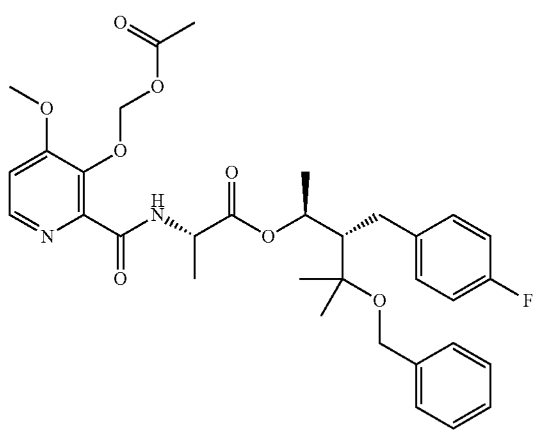 [SMILES: COc1ccnc(C(=O)N[C@@H](C)C(=O)O[C@@H](C)[C@H](Cc2ccc(F)cc2)C(C)(C)OCc2ccccc2)c1OCOC(C)=O] | Example 12A | Clear, Colorless Oil |

TABLE 1-continued

Compound Structure and Appearance

| *Cmpd. No. | Structure | Prepared According to Example | Appearance |
|---|---|---|---|
| 242 | 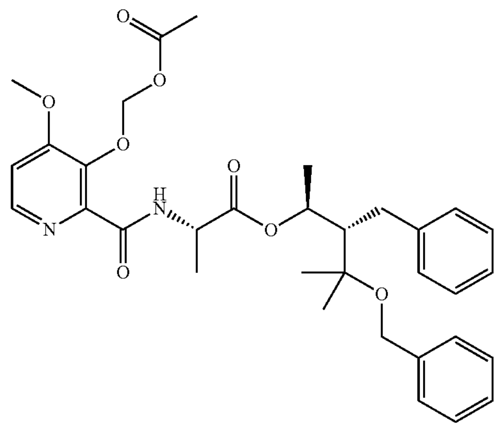 [SMILES: COc1ccnc(C(=O)N[C@@H](C)C(=O)O[C@@H](C)[C@H](Cc2ccccc2)C(C)(C)OCc2ccccc2)c1OCOC(C)=O] | Example 12A | Clear, Colorless Oil |
| 243 | 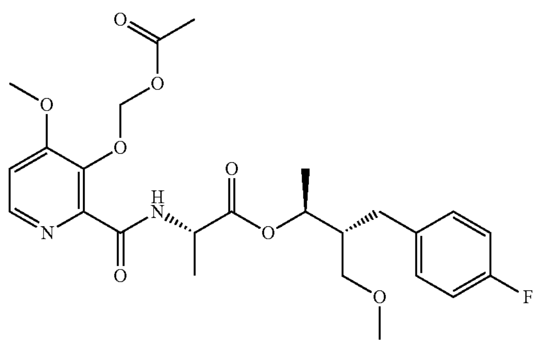 [SMILES: COC[C@@H](Cc1ccc(F)cc1)[C@H](C)OC(=O)[C@H](C)NC(=O)c1nccc(OC)c1OCOC(C)=O] | Example 12A | Clear, Colorless Oil |
| 244 | 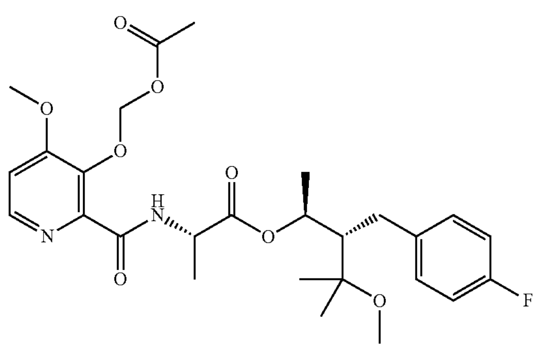 [SMILES: COc1ccnc(C(=O)N[C@@H](C)C(=O)O[C@@H](C)[C@H](Cc2ccc(F)cc2)C(C)(C)OC)c1OCOC(C)=O] | Example 12A | Clear, Colorless Oil |
| 245 | 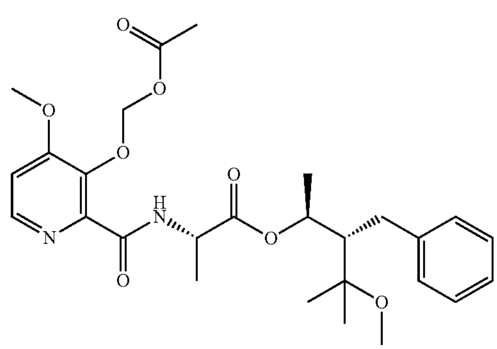 [SMILES: COc1ccnc(C(=O)N[C@@H](C)C(=O)O[C@@H](C)[C@H](Cc2ccccc2)C(C)(C)OC)c1OCOC(C)=O] | Example 12A | Colorless Oil |

TABLE 1-continued

Compound Structure and Appearance

| *Cmpd. No. | Structure | Prepared According to Example | Appearance |
|---|---|---|---|
| 246 | 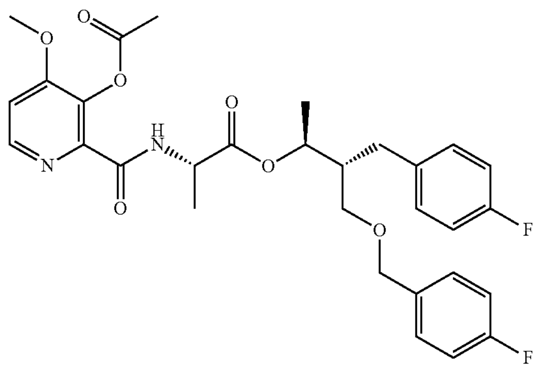 [SMILES: COc1ccnc(C(=O)N[C@@H](C)C(=O)O[C@@H](C)[C@@H](COCc2ccc(F)cc2)Cc2ccc(F)cc2)c1OC(C)=O] | Example 12C | Yellow Oil |
| 247 | 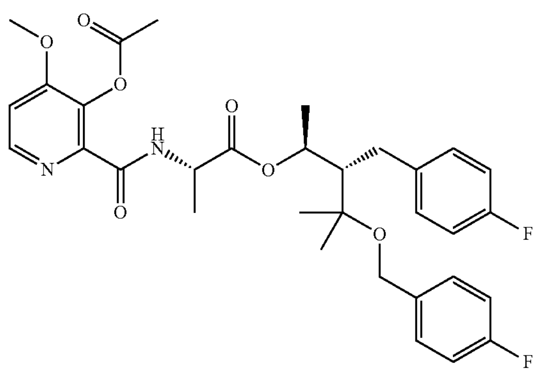 [SMILES: COc1ccnc(C(=O)N[C@@H](C)C(=O)O[C@@H](C)[C@H](Cc2ccc(F)cc2)C(C)(C)OCc2ccc(F)cc2)c1OC(C)=O] | Example 12C | Pale, Yellow Oil |
| 248 | 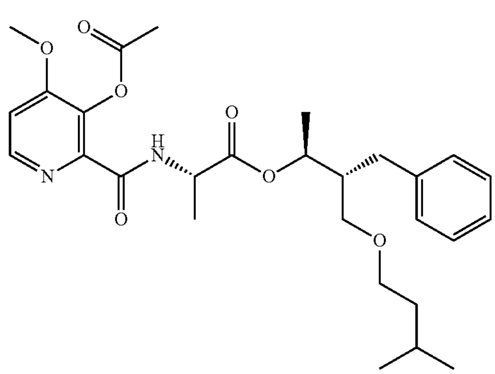 [SMILES: COc1ccnc(C(=O)N[C@@H](C)C(=O)O[C@@H](C)[C@@H](COCCC(C)C)Cc2ccccc2)c1OC(C)=O] | Example 12C | Yellow Oil |

TABLE 1-continued

Compound Structure and Appearance

| *Cmpd. No. | Structure | Prepared According to Example | Appearance |
|---|---|---|---|
| 249 | 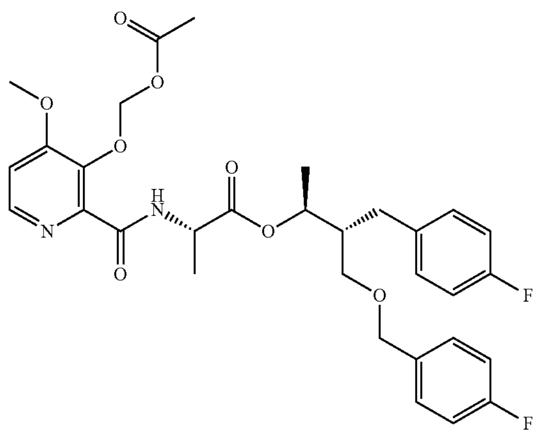 [SMILES: COc1ccnc(C(=O)N[C@@H](C)C(=O)O[C@@H](C)[C@@H](COCc2ccc(F)cc2)Cc2ccc(F)cc2)c1OCOC(C)=O] | Example 12A | Clear, Colorless Oil |
| 250 | 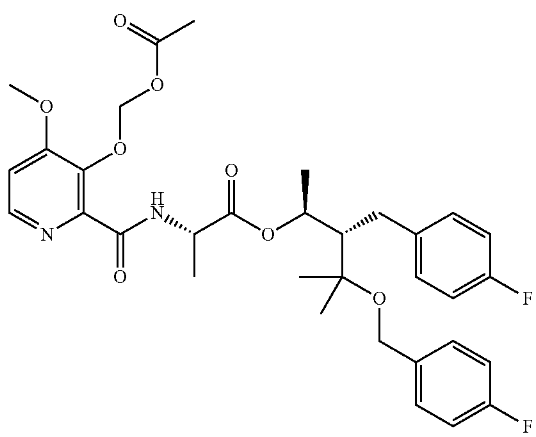 [SMILES: COc1ccnc(C(=O)N[C@@H](C)C(=O)O[C@@H](C)[C@H](Cc2ccc(F)cc2)C(C)(C)OCc2ccc(F)cc2)c1OCOC(C)=O] | Example 12A | Clear, Colorless Oil |
| 251 | 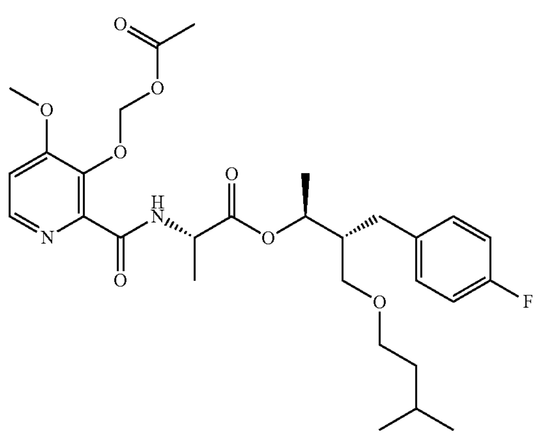 [SMILES: COc1ccnc(C(=O)N[C@@H](C)C(=O)O[C@@H](C)[C@@H](COCCC(C)C)Cc2ccc(F)cc2)c1OCOC(C)=O] | Example 12A | Clear, Colorless Oil |

TABLE 1-continued

Compound Structure and Appearance

| *Cmpd. No. | Structure | Prepared According to Example | Appearance |
|---|---|---|---|
| 252 | 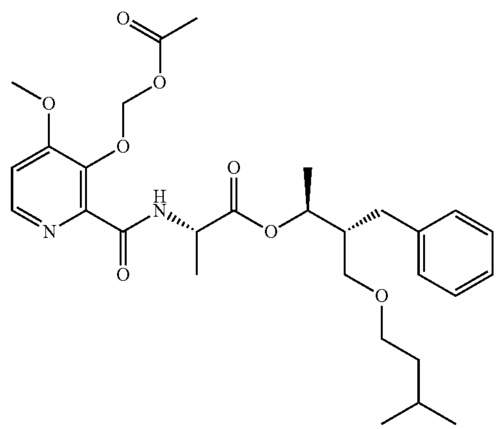 [SMILES: COc1ccnc(C(=O)N[C@@H](C)C(=O)O[C@@H](C)[C@@H](COCCC(C)C)Cc2ccccc2)c1OCOC(C)=O] | Example 12A | Clear, Colorless Oil |
| 253 | 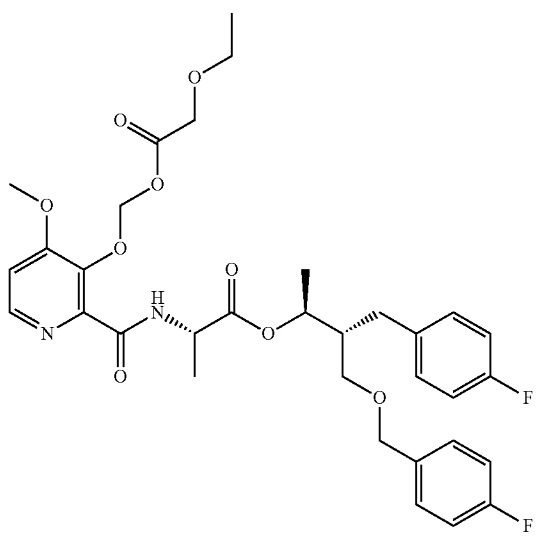 [SMILES: CCOCC(=O)OCOc1c(OC)ccnc1C(=O)N[C@@H](C)C(=O)O[C@@H](C)[C@@H](COCc1ccc(F)cc1)Cc1ccc(F)cc1] | Example 12B | Clear, Colorless Oil |
| 254 | 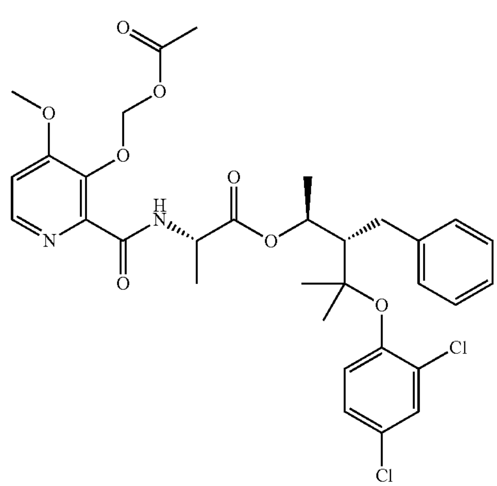 [SMILES: COc1ccnc(C(=O)N[C@@H](C)C(=O)O[C@@H](C)[C@H](Cc2ccccc2)C(C)(C)Oc2ccc(Cl)cc2Cl)c1OCOC(C)=O] | Example 12A | Sticky Wax |

TABLE 1-continued

Compound Structure and Appearance

| *Cmpd. No. | Structure | Prepared According to Example | Appearance |
|---|---|---|---|
| 255 | 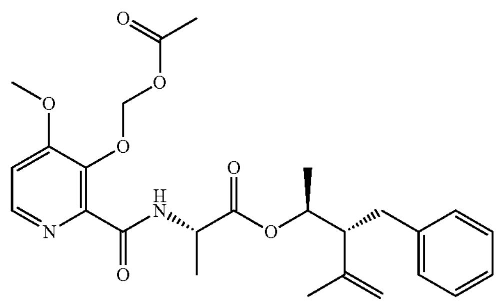 [SMILES: C=C(C)[C@@H](Cc1ccccc1)[C@H](C)OC(=O)[C@H](C)NC(=O)c1nccc(OC)c1OCOC(C)=O] | Example 12A | Sticky Wax |
| 256 | 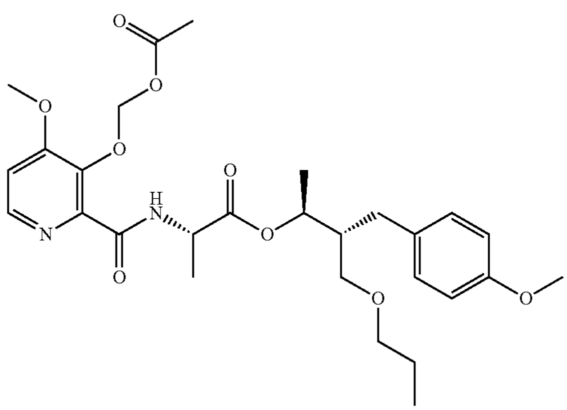 [SMILES: CCCOC[C@@H](Cc1ccc(OC)cc1)[C@H](C)OC(=O)[C@H](C)NC(=O)c1nccc(OC)c1OCOC(C)=O] | Example 12A | Sticky Wax |
| 257 | 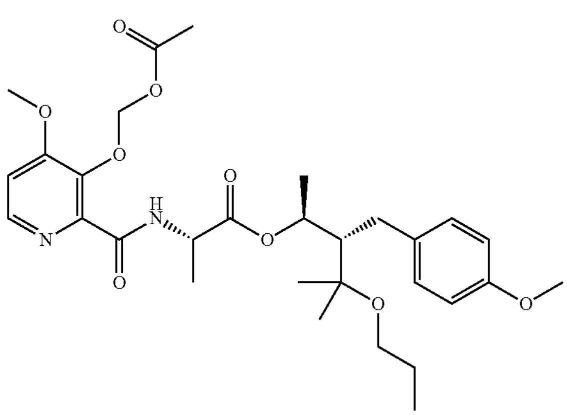 [SMILES: CCCOC(C)(C)[C@@H](Cc1ccc(OC)cc1)[C@H](C)OC(=O)[C@H](C)NC(=O)c1nccc(OC)c1OCOC(C)=O] | Example 12A | Sticky Wax |

TABLE 1-continued

Compound Structure and Appearance

| *Cmpd. No. | Structure | Prepared According to Example | Appearance |
|---|---|---|---|
| 258 | 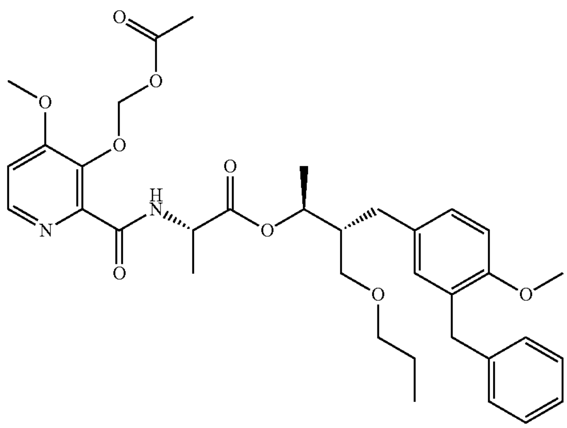 [SMILES: CCCOC[C@@H](Cc1ccc(OC)c(Cc2ccccc2)c1)[C@H](C)OC(=O)[C@H](C)NC(=O)c1nccc(OC)c1OCOC(C)=O] | Example 12A | Sticky Wax |
| 259 | 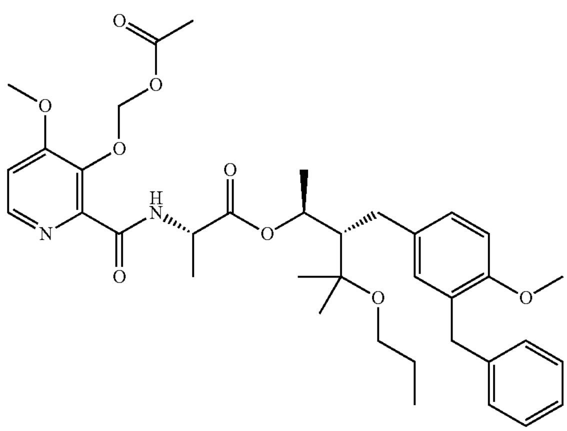 [SMILES: CCCOC(C)(C)[C@@H](Cc1ccc(OC)c(Cc2ccccc2)c1)[C@H](C)OC(=O)[C@H](C)NC(=O)c1nccc(OC)c1OCOC(C)=O] | Example 12A | Sticky Wax |
| 260 | 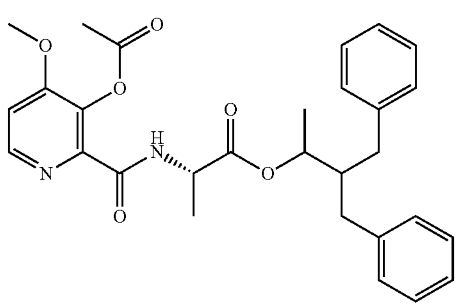 [SMILES: COc1ccnc(C(=O)N[C@@H](C)C(=O)OC(C)C(Cc2ccccc2)Cc2ccccc2)c1OC(C)=O] | Example 12C | Semi-Soild |
| 261 | 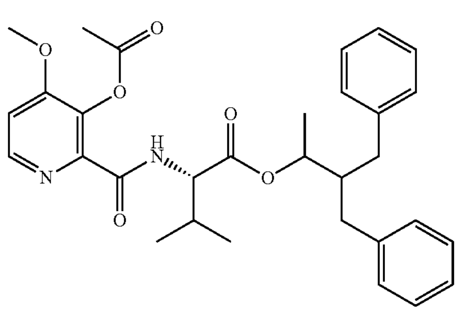 [SMILES: COc1ccnc(C(=O)N[C@H](C(=O)OC(C)C(Cc2ccccc2)Cc2ccccc2)C(C)C)c1OC(C)=O] | Example 12C | Semi-Solid |

TABLE 1-continued
Compound Structure and Appearance
| *Cmpd. No. | Structure | Prepared According to Example | Appearance |
|---|---|---|---|
| 262 | 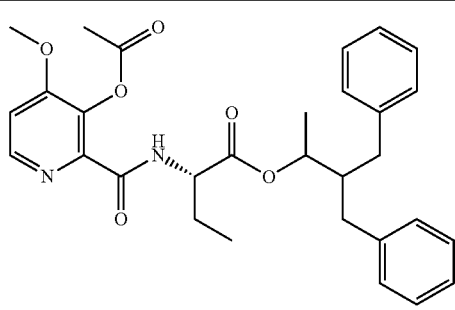 | Example 12C | Oil |
| 263 | 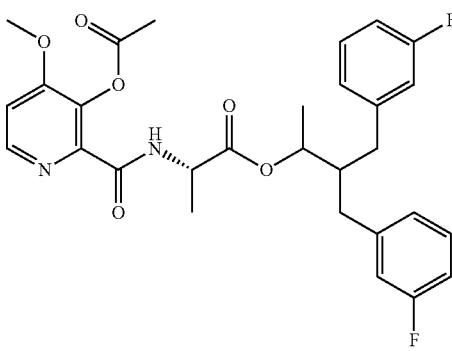 [SMILES: COc1ccnc(C(=O)N[C@@H](C)C(=O)OC(C)C(Cc2cccc(F)c2)Cc2cccc(F)c2)c1OC(C)=O] | Example 12C | Oil |
| 264 | 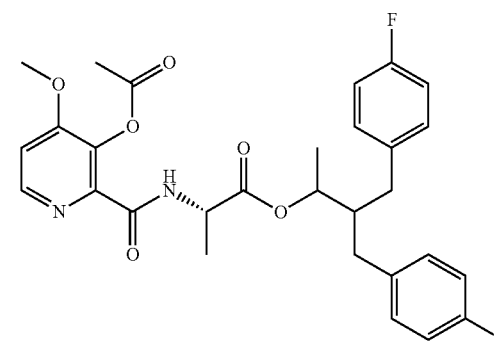 | Example 12C | Oil |
| 265 | 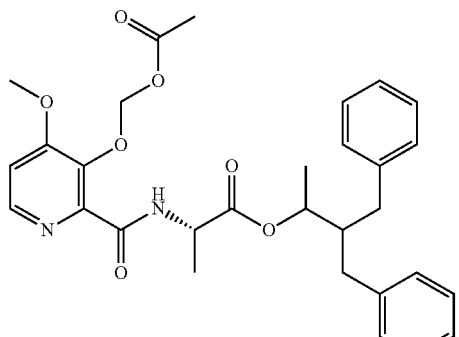 | Example 12A | Oil |

TABLE 1-continued

Compound Structure and Appearance

| *Cmpd. No. | Structure | Prepared According to Example | Appearance |
|---|---|---|---|
| 266 | 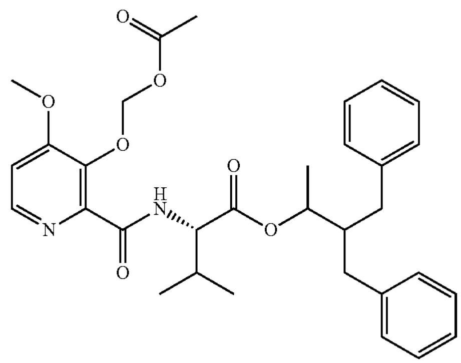 [SMILES: COc1ccnc(C(=O)N[C@H](C(=O)OC(C)C(Cc2ccccc2)Cc2ccccc2)C(C)C)c1OCOC(C)=O] | Example 12A | Oil |
| 267 | 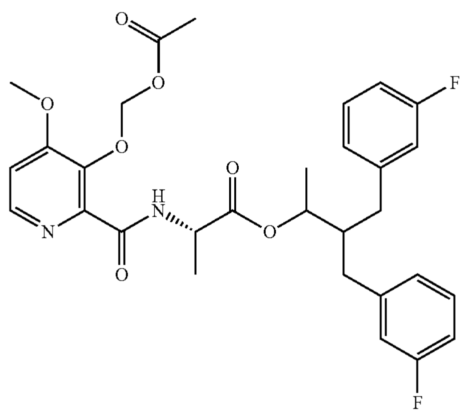 [SMILES: COc1ccnc(C(=O)N[C@@H](C)C(=O)OC(C)C(Cc2cccc(F)c2)Cc2cccc(F)c2)c1OCOC(C)=O] | Example 12A | Oil |
| 268 | 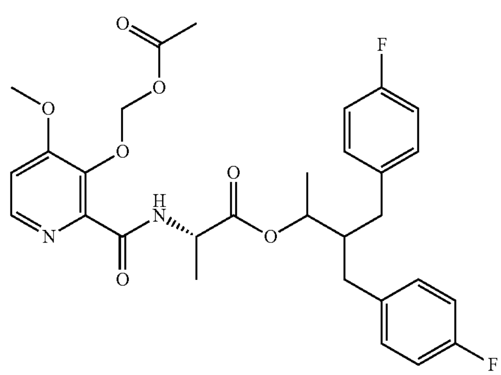 [SMILES: COc1ccnc(C(=O)N[C@@H](C)C(=O)OC(C)C(Cc2ccc(F)cc2)Cc2ccc(F)cc2)c1OCOC(C)=O] | Example 12A | Oil |
| 269 | 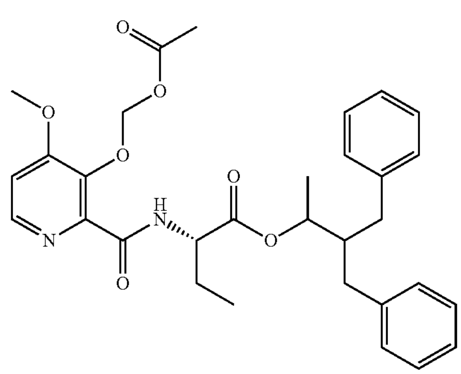 [SMILES: CC[C@H](NC(=O)c1nccc(OC)c1OCOC(C)=O)C(=O)OC(C)C(Cc1ccccc1)Cc1ccccc1] | Example 12A | Oil |

TABLE 1-continued

Compound Structure and Appearance

| *Cmpd. No. | Structure | Prepared According to Example | Appearance |
|---|---|---|---|
| 270 | 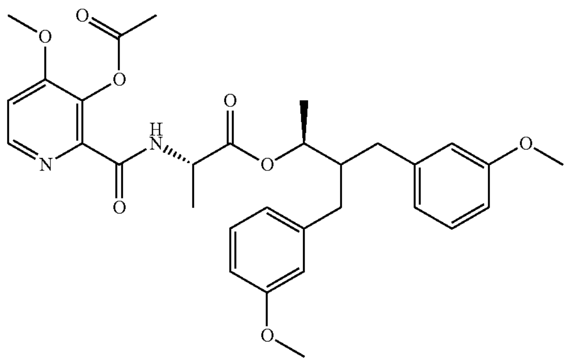 [SMILES: COc1cccc(CC(Cc2cccc(OC)c2)[C@H](C)OC(=O)[C@H](C)NC(=O)c2nccc(OC)c2OC(C)=O)c1] | Example 12C | Oil |
| 271 | 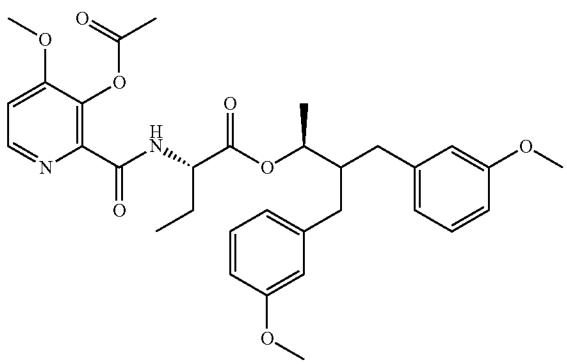 [SMILES: CC[C@H](NC(=O)c1nccc(OC)c1OC(C)=O)C(=O)O[C@@H](C)C(Cc1cccc(OC)c1)Cc1cccc(OC)c1] | Example 12C | Oil |
| 272 | 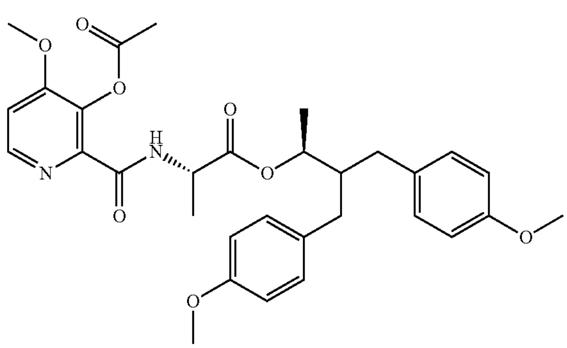 [SMILES: COc1ccc(CC(Cc2ccc(OC)cc2)[C@H](C)OC(=O)[C@H](C)NC(=O)c2nccc(OC)c2OC(C)=O)cc1] | Example 12C | Oil |
| 273 | 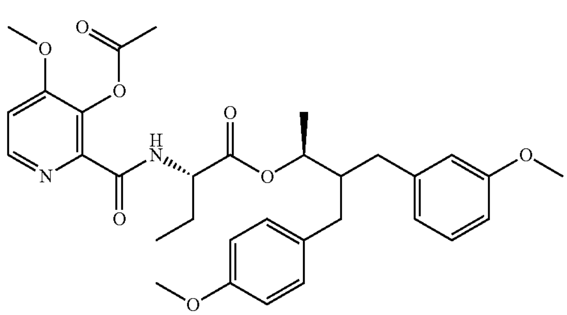 [SMILES: CC[C@H](NC(=O)c1nccc(OC)c1OC(C)=O)C(=O)O[C@@H](C)C(Cc1ccc(OC)cc1)Cc1cccc(OC)c1] | Example 12C | Oil |

TABLE 1-continued

Compound Structure and Appearance

| *Cmpd. No. | Structure | Prepared According to Example | Appearance |
|---|---|---|---|
| 274 | 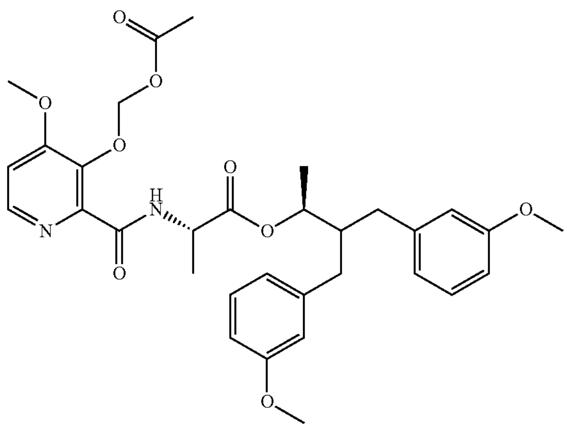 [SMILES: COc1cccc(CC(Cc2cccc(OC)c2)[C@H](C)OC(=O)[C@H](C)NC(=O)c2nccc(OC)c2OCOC(C)=O)c1] | Example 12A | Oil |
| 275 | 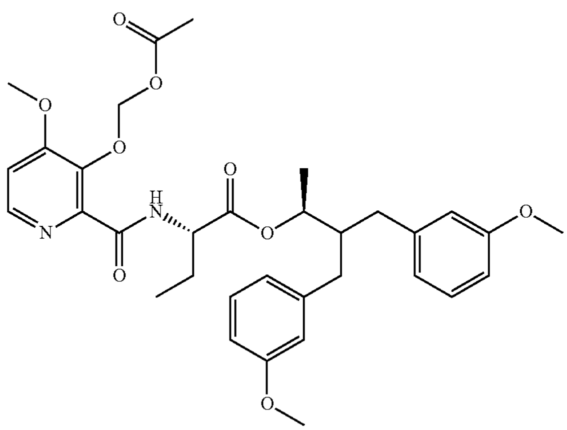 [SMILES: CC[C@H](NC(=O)c1nccc(OC)c1OCOC(C)=O)C(=O)O[C@@H](C)C(Cc1cccc(OC)c1)Cc1cccc(OC)c1] | Example 12A | Oil |
| 276 | 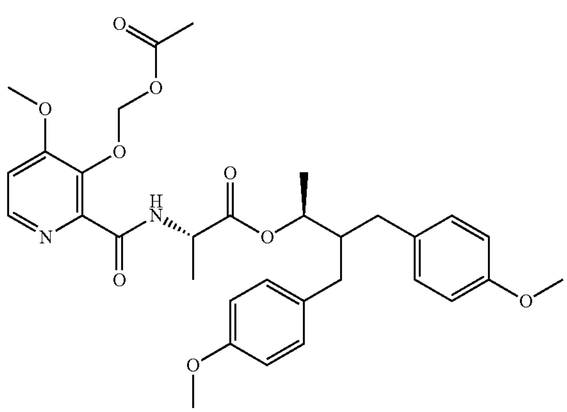 [SMILES: COc1ccc(CC(Cc2ccc(OC)cc2)[C@H](C)OC(=O)[C@H](C)NC(=O)c2nccc(OC)c2OCOC(C)=O)cc1] | Example 12A | Oil |

TABLE 1-continued
Compound Structure and Appearance
| *Cmpd. No. | Structure | Prepared According to Example | Appearance |
|---|---|---|---|
| 277 | 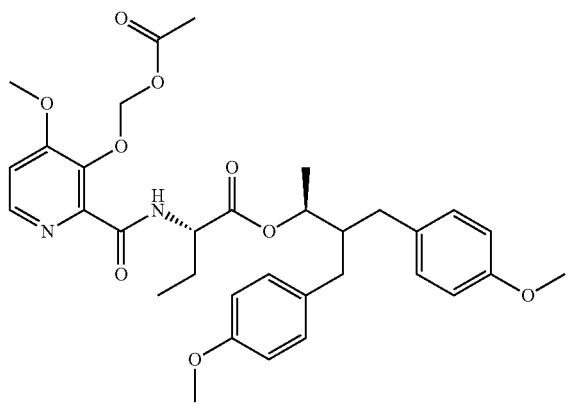 [SMILES: CC[C@H](NC(=O)c1nccc(OC)c1OCOC(C)=O)C(=O)O[C@@H](C)C(Cc1ccc(OC)cc1)Cc1ccc(OC)cc1] | Example 12A | Oil |
| 278 | 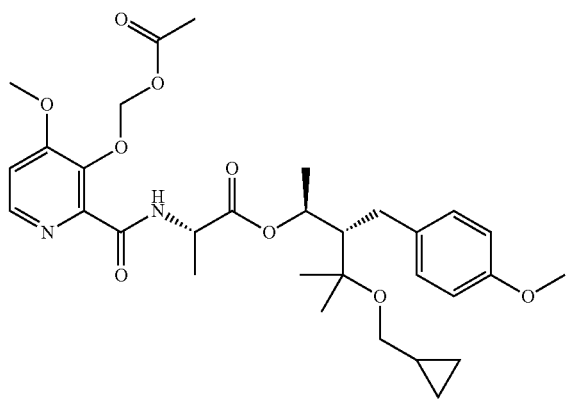 [SMILES: COc1ccc(C[C@@H]([C@H](C)OC(=O)[C@H](C)NC(=O)c2nccc(OC)c2OCOC(C)=O)C(C)(C)OCC2CC2)cc1] | Example 12A | Sticky Wax |
| 279 | 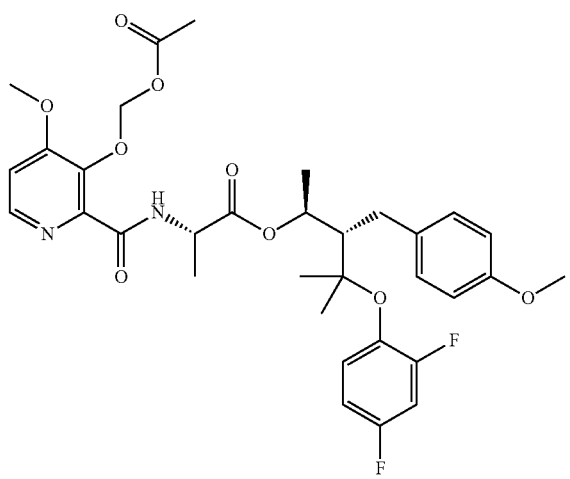 [SMILES: COc1ccc(C[C@@H]([C@H](C)OC(=O)[C@H](C)NC(=O)c2nccc(OC)c2OCOC(C)=O)C(C)(C)Oc2ccc(F)cc2F)cc1] | Example 12A | Sticky Wax |

TABLE 1-continued

Compound Structure and Appearance

| *Cmpd. No. | Structure | Prepared According to Example | Appearance |
|---|---|---|---|
| 280 | 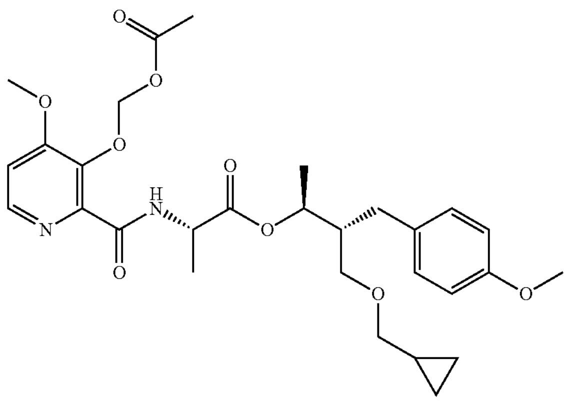 [SMILES: COc1ccc(C[C@H](COCC2CC2)[C@H](C)OC(=O)[C@H](C)NC(=O)c2nccc(OC)c2OCOC(C)=O)cc1] | Example 12A | Sticky Wax |
| 281 | 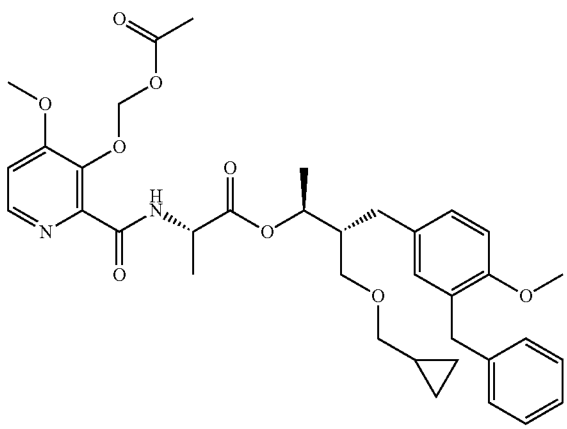 [SMILES: COc1ccc(C[C@H](COCC2CC2)[C@H](C)OC(=O)[C@H](C)NC(=O)c2nccc(OC)c2OCOC(C)=O)cc1Cc1ccccc1] | Example 12A | Sticky Wax |
| 282 | 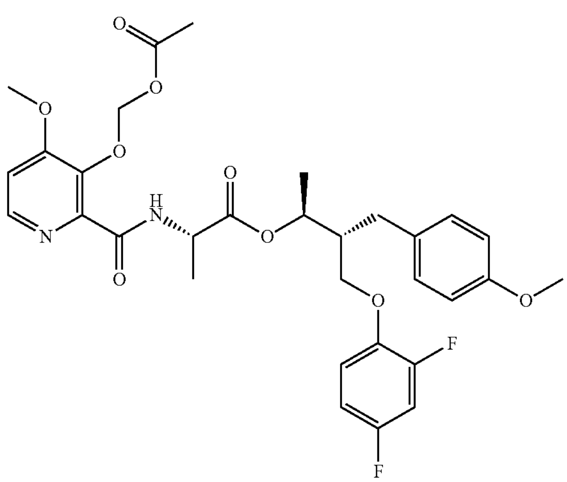 [SMILES: COc1ccc(C[C@H](COc2ccc(F)cc2F)[C@H](C)OC(=O)[C@H](C)NC(=O)c2nccc(OC)c2OCOC(C)=O)cc1] | Example 12A | Sticky White Foam |

TABLE 1-continued

Compound Structure and Appearance

| *Cmpd. No. | Structure | Prepared According to Example | Appearance |
|---|---|---|---|
| 283 | 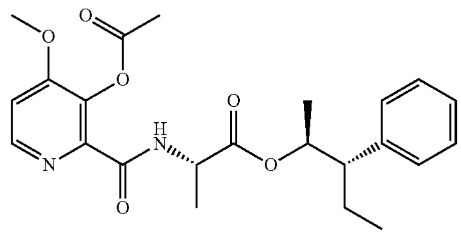 [SMILES: CC[C@@H](c1ccccc1)[C@H](C)OC(=O)[C@H](C)NC(=O)c1nccc(OC)c1OC(C)=O] | Example 12C | Colorless Oil |
| 284 | 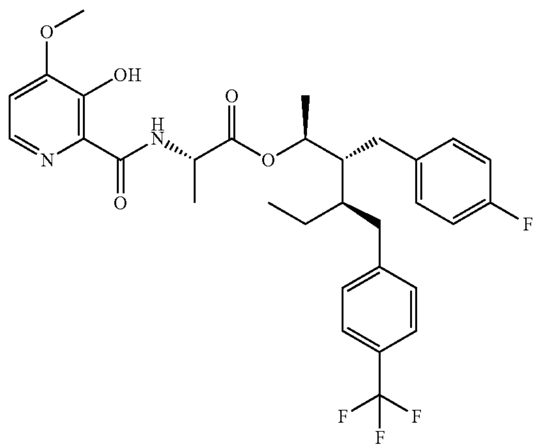 [SMILES: CC[C@H](Cc1ccc(C(F)(F)F)cc1)[C@@H](Cc1ccc(F)cc1)[C@H](C)OC(=O)[C@H](C)NC(=O)c1nccc(OC)c1O] | Example 10, Step 3 | White foam |

*Cmpd. No.—Compound Number

TABLE 2

Analytical Data

| *Cmpd. No. | IR (cm$^{-1}$) | MASS | NMR ($^1$H, $^{13}$C or $^{19}$F) |
|---|---|---|---|
| 1 | | ESIMS m/z 470 ([M + Na]$^+$) | $^1$H NMR (400 MHz, CDCl$_3$) δ 7.31-7.26 (m, 2H), 7.21-7.14 (m, 3H), 5.15-4.94 (m, 2H), 4.35-4.15 (m, 1H), 2.72-2.52 (m, 2H), 1.73-1.49 (m, 4H), 1.45 (s, 9H), 1.38-1.28 (m, 3H), 1.33 (d, J = 7.0 Hz, 3H), 1.20 (d, J = 6.4 Hz, 3H), 1.18-0.97 (m, 2H), 0.95-0.78 (m, 11H). $^{13}$C NMR (101 MHz, CDCl$_3$) δ 172.83, 155.01, 142.66, 128.34, 128.27, 125.64, 80.65, 73.59, 49.46, 41.07, 40.21, 36.38, 35.71, 30.33, 30.16, 28.36, 26.11, 24.12, 23.47, 22.31, 18.94, 17.93, 12.50. |
| 2 | | ESIMS m/z 590 ([M + Na]$^+$) | $^1$H NMR (400 MHz, CDCl$_3$) δ 7.44 (d, J = 8.0 Hz, 2H), 7.09 (d, J = 7.9 Hz, 2H), 7.00 (dd, J = 8.6, 5.5 Hz, 2H), 6.95-6.87 (m, 2H), 5.73 (m, 1H), 5.42 (d, J = 8.6 Hz, 1H), 5.19 (m, 1H), 5.05 (d, J = 11.4 Hz, 1H), 4.86 (d, J = 17.1 Hz, 1H), 4.43 (s, 1H), 3.84 (dd, J = 9.2, 2.9 Hz, 1H), 3.58 (dd, J = 9.2, 3.2 Hz, 1H), 3.29 (s, 3H), 2.99 (dd, J = 13.4, 5.5 Hz, 1H), 2.71 (dd, J = 14.0, 6.1 Hz, 1H), 2.59 (ddd, J = 13.8, 8.6, 4.1 Hz, 2H), 2.45 (m, 1H), 2.00 (m, 1H), |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 1.44 (s, 9H), 1.28 (d, J = 6.4 Hz, 3H). $^{13}$C NMR (101 MHz, CDCl$_3$) δ 170.06, 161.32 (d, J = 243 Hz), 155.43, 144.59, 138.67, 135.97 (d, J = 4 Hz), 130.28 (d, J = 8 Hz), 129.47, 128.13 (q, J = 34 Hz), 124.96 (q, J = 4 Hz), 124.34 (q, J = 271 Hz), 117.06, 115.18, (d, J = 21 Hz), 80.05, 72.76, 72.46, 59.22, 54.24, 47.94, 45.44, 37.96, 32.57, 28.32, 17.66. |
| 3 | | ESIMS m/z 560 ([M + Na]$^+$) | $^1$H NMR (400 MHz, CDCl$_3$) δ 7.44 (d, J = 8.0 Hz, 2H), 7.07 (d, J = 7.9 Hz, 2H), 7.02-6.88 (m, 4H), 5.70 (ddd, J = 17.1, 10.2, 8.9 Hz, 1H), 5.15 (m, 1H), 5.06 (dd, J = 8.0, 2.0 Hz, 1H), 5.03 (d, J = 7.7 Hz, 1H), 4.87 (dd, J = 17.1, 1.0 Hz, 1H), 4.30 (m, 1H), 2.96 (dd, J = 13.6, 5.8 Hz, 1H), 2.73 (dd, J = 14.1, 5.7 Hz, 1H), 2.60 (m, 2H), 2.43 (m, 1H), 1.97 (td, J = 8.4, 5.6 Hz, 1H), 1.44 (s, 9H), 1.37 (d, J = 7.3 Hz, 3H), 1.28 (d, J = 6.4 Hz, 3H). $^{13}$C NMR (101 MHz, CDCl$_3$) δ 172.62, 161.33 (d, J = 243 Hz), 155.01, 144.43, 138.38, 135.94 (d, J = 3 Hz), 130.22 (d, J = 8 Hz), 129.39, 128.23 (q, J = 32 Hz), 124.00 (q, J = 3 Hz), 124.29 (q, J = 270 Hz), 117.06, 115.24, (d, J = 22 Hz), 79.94, 72.25, 49.49, 47.76, 45.56, 38.22, 32.88, 28.33, 18.72, 17.52. |
| 4 | | ESIMS m/z 546 ([M + Na]$^+$) | $^1$H NMR (400 MHz, CDCl$_3$) δ 7.45 (bd, J = 8.0 Hz, 2H), 7.07 (bd, J = 8.0 Hz, 2H), 7.00 (td, J = 5.6, 2.3 Hz, 2H), 6.95 (m, 2H), 5.70 (ddd, J = 17.1, 10.2, 8.8 Hz, 1H), 5.14 (p, J = 6.1 Hz, 1H), 5.06 (dd, J = 10.3, 1.1 Hz, 1H), 4.99 (bs, 1H), 4.87 (dt, J = 17.1, 1.3 Hz, 1H), 3.87 (m, 2H), 2.94 (dd, J = 13.6, 5.9 Hz, 1H), 2.73 (dd, J = 14.2, 5.9 Hz, 1H), 2.60 (m, 2H), 2.41 (m, 1H), 2.01 (m, 1H), 1.46 (s, 9H), 1.28 (d, J = 6.3 Hz, 3H). $^{13}$C NMR (101 MHz, CDCl$_3$) δ 171.13, 161.32 (d, J = 243 Hz), 155.66, 144.43, 138.26, 135.96 (d, J = 4 Hz), 130.26 (d, J = 8 Hz), 129.41, 128.21 (q, J = 32 Hz), 125.01 (q, J = 4 Hz), 124.31 (q, J = 270 Hz), 117.26, 115.22, (d, J = 21 Hz), 80.10, 72.68, 47.56, 45.72, 42.78, 38.48, 33.09, 28.30, 17.57. |
| 5 | | ESIMS m/z 364 ([M + H]$^+$) | $^1$H NMR (400 MHz, CDCl$_3$) δ 7.32-7.22 (m, 2H), 7.21-7.14 (m, 1H), 7.14-7.08 (m, 2H), 5.16-5.05 (m, 1H), 5.00 (qd, J = 6.5, 3.7 Hz, 1H), 4.43-4.21 (m, 1H), 2.65 (dd, J = 13.6, 6.6 Hz, 1H), 2.50 (dd, J = 13.6, 7.6 Hz, 1H), 1.90-1.78 (m, 1H), 1.45 (s, 9H), 1.39 (d, J = 7.2 Hz, 3H), 1.36-1.28 (m, 4H), 1.21 (d, J = 6.5 Hz, 3H), 0.92-0.80 (m, 3H). $^{13}$C NMR (101 MHz, CDCl$_3$) δ 172.78, 155.08, 140.77, 129.10, 128.33, 125.93, 79.68, 72.93, |

TABLE 2-continued

Analytical Data

| *Cmpd. No. | IR (cm$^{-1}$) | MASS | NMR ($^1$H, $^{13}$C or $^{19}$F) |
|---|---|---|---|
| 6 | | ESIMS m/z 380 ([M + H]$^+$) | 49.48, 44.51, 36.23, 31.54, 28.36, 20.30, 18.93, 16.20, 14.25.<br>$^1$H NMR (400 MHz, CDCl$_3$) δ 7.32-7.23 (m, 2H), 7.23-7.17 (m, 1H), 7.17-7.10 (m, 2H), 5.26-5.08 (m, 2H), 4.34-4.20 (m, 1H), 3.54 (s, 3H), 3.10-2.76 (m, 3H), 1.44 (s, 9H), 1.40-1.29 (m, 6H).<br>$^{13}$C NMR (101 MHz, CDCl$_3$) δ 172.46, 172.33, 155.04, 138.24, 128.75, 128.50, 126.60, 79.69, 71.70, 52.93, 51.57, 49.30, 34.23, 28.31, 18.60, 17.83. |
| 7 | IR (neat) 3361, 2932, 1715, 1508, 1260 | HRMS-ESI m/z [M]$^+$ calcd for C$_{29}$H$_{38}$F$_3$NO$_5$, 537.2702; found, 537.2704. | $^1$H NMR (400 MHz, CDCl$_3$) δ 7.25-7.21 (m, 2H), 7.20-7.17 (m, 1H), 7.12-7.03 (m, 6H), 5.15-5.08 (m, 1H), 5.08-5.01 (m, 1H), 4.37-4.24 (m, 1H), 3.00-2.90 (m, 1H), 2.73-2.54 (m, 2H), 2.44-2.34 (m, 1H), 1.98-1.90 (m, 1H), 1.83-1.73 (m, 1H), 1.47-1.32 (m, 5H), 1.43 (s, 9H), 1.26 (d, J = 6.4 Hz, 3H), 0.88 (t, J = 6.9 Hz, 3H) |
| 8 | | ESIMS m/z 444 ([M + Na]$^{+)}$) | $^1$H NMR (400 MHz, CDCl$_3$) δ 7.30-7.19 (m, 2H), 6.93-6.83 (m, 3H), 5.15-5.00 (m, 2H), 4.27 (td, J = 6.5, 3.0 Hz, 1H), 4.20 (t, J = 7.3 Hz, 1H), 1.84 (qd, J = 5.7, 2.9 Hz, 1H), 1.81-1.71 (m, 1H), 1.72-1.61 (m, 1H), 1.59-1.50 (m, 1H), 1.44 (s, 9H), 1.41-1.30 (m, 4H), 1.26 (td, J = 6.9, 3.6 Hz, 7H), 0.97 (t, J = 7.4 Hz, 3H), 0.92 (t, J = 7.1 Hz, 3H).<br>$^{13}$C NMR (101 MHz, CDCl$_3$) δ 172.52, 158.49, 154.99, 129.47, 120.60, 115.81, 79.33, 72.80, 49.44, 44.79, 31.59, 31.05, 28.34, 25.81, 24.43, 23.19, 18.72, 17.76, 13.99, 10.43. |
| 9 | (Thin film) 3363, 2962, 1714, 1493 | ESIMS m/z 444 ([M + Na]$^+$) | $^1$H NMR (400 MHz, CDCl$_3$) δ 7.30-7.23 (m, 2H), 6.96-6.86 (m, 3H), 5.20 (dt, J = 11.6, 6.3 Hz, 1H), 5.11 (d, J = 8.1 Hz, 1H), 4.36-4.26 (m, 2H), 2.02-1.91 (m, 1H), 1.79-1.67 (m, 2H), 1.58-1.47 (m, 1H), 1.45 (s, 9H), 1.38 (d, J = 7.2 Hz, 3H), 1.32 (d, J = 6.4 Hz, 3H), 1.30-1.18 (m, 5H), 0.97 (t, J = 7.4 Hz, 3H), 0.91-0.82 (m, 3H). |
| 10 | (Thin film) 3340, 2975, 1711, 1493 | ESIMS m/z 478 ([M + Na]$^{+)}$) | $^1$H NMR (400 MHz, CDCl$_3$) δ 7.36-7.28 (m, 2H), 7.26-7.17 (m, 5H), 6.92-6.86 (m, 1H), 6.73 (dt, J = 7.9, 1.1 Hz, 2H), 5.06 (td, J = 6.5, 4.9 Hz, 1H), 4.99 (d, J = 8.1 Hz, 1H), 4.30 (td, J = 6.5, 2.5 Hz, 1H), 4.20-4.11 (m, 1H), 2.88 (dd, J = 14.5, 6.6 Hz, 1H), 2.75 (dd, J = 14.3, 7.2 Hz, 1H), 2.25 (tdd, J = 7.0, 4.9, 2.5 Hz, 1H), 1.84-1.63 (m, 2H), 1.44 (s, 9H), 1.28 (d, J = 6.4 Hz, 3H), 1.24 (d, J = 7.1 Hz, 3H), 0.95 (t, J = 7.4 Hz, 3H). |
| 11 | (Thin film) 3340, 2976, 1713, 1493 | ESIMS m/z 478 ([M + Na]$^{+)}$) | $^1$H NMR (400 MHz, CDCl$_3$) δ 7.27 (dd, J = 8.7, 7.4 Hz, 2H), 7.24-7.13 (m, 3H), 7.02-6.92 (m, 3H), 6.88-6.82 (m, 2H), 5.25 (td, J = 5.3, 4.8 Hz, 1H), 5.06 (d, J = 7.9 Hz, 1H), 4.39-4.28 (m, 1H), 4.25 (td, J = 6.5, 3.6 Hz, 1H), 2.88 (dd, J = 13.8, 7.7 |

| *Cmpd. No. | IR (cm$^{-1}$) | MASS | NMR ($^1$H, $^{13}$C or $^{19}$F) |
|---|---|---|---|
| | | | Hz, 1H), 2.70 (dd, J = 13.8, 6.5 Hz, 1H), 2.35-2.25 (m, 1H), 1.83-1.67 (m, 2H), 1.45 (s, 9H), 1.43 (d, J = 7.3 Hz, 3H), 1.36 (d, J = 6.5 Hz, 3H), 0.90 (t, J = 7.4 Hz, 3H). |
| 12 | | ESIMS m/z 398 ([M + H]$^+$) | $^1$H NMR (400 MHz, CDCl$_3$) δ 7.26-7.07 (m, 8H), 7.03-6.91 (m, 2H), 5.25-5.16 (m, 1H), 5.06 (d, J = 7.9 Hz, 1H), 4.24 (p, J = 7.3 Hz, 1H), 3.05 (dd, J = 12.4, 5.8 Hz, 1H), 2.99 (dt, J = 8.4, 5.6 Hz, 1H), 2.90 (dd, J = 12.4, 8.1 Hz, 1H), 1.44 (s, 9H), 1.21 (d, J = 6.3 Hz, 3H), 1.14 (d, J = 7.1 Hz, 3H). $^{13}$C NMR (101 MHz, CDCl$_3$) δ 172.64, 155.06, 140.38, 139.57, 129.03, 128.97, 128.23, 128.16, 126.74, 126.08, 79.72, 73.41, 53.16, 49.47, 38.50, 28.38, 18.48, 18.42. |
| 13 | | ESIMS m/z 364 ([M + H]$^+$) | $^1$H NMR (400 MHz, CDCl$_3$) δ 7.31-7.24 (m, 2H), 7.22-7.12 (m, 3H), 5.06-4.95 (m, 2H), 4.32-4.20 (m, 1H), 2.68 (dd, J = 14.3, 5.2 Hz, 1H), 2.52 (dd, J = 14.2, 8.2 Hz, 1H), 2.03-1.89 (m,1H), 1.83-1.73 (m, 1H), 1.45 (s, 9H), 1.36 (d, J = 7.2 Hz, 3H), 1.19 (d, J = 6.5 Hz, 3H), 1.01 (d, J = 6.9 Hz, 3H), 0.95 (d, J = 6.8 Hz, 3H). |
| 14 | | ESIMS m/z 378.5 ([M + H]$^+$) | $^1$H NMR (400 MHz, CDCl$_3$) δ 7.31-7.24 (m, 2H), 7.24-7.13 (m, 3H), 5.17 (p, J = 6.4 Hz, 1H), 4.96 (d, J = 7.9 Hz, 1H), 4.25-4.08 (m, 1H), 2.66 (ddd, J = 11.0, 7.0, 4.7 Hz, 1H), 1.75-1.57 (m, 2H), 1.53-1.44 (m, 1H), 1.43 (s, 9H), 1.22 (d, J = 6.3 Hz, 3H), 1.12-0.87 (m, 2H), 1.00 (d, J = 7.0 Hz, 3H)., 0.81 (d, J = 4.6 Hz, 3H), 0.80 (d, J = 4.6 Hz, 3H). $^{13}$C NMR (101 MHz, CDCl$_3$) δ 172.70, 154.95, 141.29, 128.62, 128.20, 126.52, 79.63, 74.61, 51.41, 49.29, 36.46, 29.44, 28.33, 27.95, 22.74, 22.20, 18.43, 18.37. |
| 15 | | ESIMS m/z 364 ([M + H]$^+$) | $^1$H NMR (400 MHz, CDCl$_3$) δ 7.50-6.96 (m, 5H), 5.26-5.09 (m, 1H), 5.07-4.95 (m, 1H), 4.16 (p, J = 7.5 Hz, 1H), 2.69 (ddd, J = 10.4, 7.0, 4.7 Hz, 1H), 1.75-1.55 (m, 2H), 1.42 (s, 9H), 1.33-1.24 (m, 2H), 1.24-1.20 (m, 3H), 1.16-1.04 (m, 2H), 0.99 (d, J = 7.2 Hz, 3H), 0.81 (t, J = 7.3 Hz, 3H). $^{13}$C NMR (101 MHz, CDCl$_3$) δ 172.67, 154.95, 141.28, 128.59, 128.18, 126.50, 79.55, 74.58, 51.17, 49.29, 31.42, 29.45, 28.31, 22.60, 18.38, 18.33, 13.88. |
| 16 | | ESIMS m/z 432 ([M + H]$^+$) | $^1$H NMR (400 MHz, CDCl$_3$) δ 7.38-6.84 (m, 9H), 5.26-5.14 (m, 1H), 5.02 (d, J = 8.3 Hz, 1H), 4.31-4.15 (m, 1H), 3.02 (dd, J = 12.6, 5.3 Hz, 1H), 2.94 (dt, J = 8.8, 5.5 Hz, 1H), 2.86 (dd, J = 12.6, 8.8 Hz, 1H), 1.44 (s, 9H), 1.22 (d, J = 5.6 Hz, 3H), 1.12 (d, J = 6.1 Hz, 3H). $^{13}$C NMR (101 MHz, CDCl$_3$) δ 172.62, 155.04, 139.87, 138.00, 131.84, 130.33, 128.90, 128.32, 128.23, 126.87, 79.79, 73.34, |

TABLE 2-continued

| *Cmpd. No. | IR (cm⁻¹) | MASS | NMR ($^1$H, $^{13}$C or $^{19}$F) |
|---|---|---|---|
| 17 | | ESIMS m/z 466.4 ([M + H]⁺) | 53.14, 49.45, 37.83, 28.36, 18.41, 18.41. $^1$H NMR (400 MHz, CDCl$_3$) δ 7.28-7.18 (m, 4H), 7.16-7.04 (m, 3H), 6.77 (dd, J = 8.3, 2.1 Hz, 1H), 5.27-5.15 (m, 1H), 4.98 (d, J = 7.8 Hz, 1H), 4.30-4.17 (m, 1H), 3.08-2.91 (m, 2H), 2.85 (dd, J = 12.6, 8.9 Hz, 1H), 1.44 (s, 9H), 1.22 (d, J = 5.7 Hz, 3H), 1.13 (d, J = 7.2 Hz, 3H). |
| 18 | | ESIMS m/z 412.5 ([M + H]⁺) | $^1$H NMR (400 MHz, CDCl$_3$) δ 7.28-7.20 (m, 2H), 7.22-7.12 (m, 3H), 6.98 (d, J = 8.1 Hz, 2H), 6.88 (d, J = 7.7 Hz, 2H), 5.25-5.12 (m, 1H), 5.05 (d, J = 8.0 Hz, 1H), 4.32-4.16 (m, 1H), 3.04-2.93 (m, 2H), 2.87 (dd, J = 11.8, 7.2 Hz, 1H), 2.24 (s, 3H), 1.44 (s, 9H), 1.19 (d, J = 6.3 Hz, 3H), 1.15 (d, J = 7.2 Hz, 3H). $^{13}$C NMR (101 MHz, CDCl$_3$) δ 172.64, 155.05, 140.51, 136.43, 135.48, 129.00, 128.94, 128.89, 128.14, 126.69, 79.72, 73.39, 53.18, 49.46, 38.04, 28.38, 21.00, 18.53, 18.44. |
| 19 | | ESIMS m/z 416.5 ([M + H]⁺) | $^1$H NMR (400 MHz, CDCl$_3$) δ 7.29-7.09 (m, 5H), 6.98-6.88 (m, 2H), 6.88-6.80 (m, 2H), 5.32-5.13 (m, 1H), 5.05 (d, J = 7.5 Hz, 1H), 4.33-4.15 (m, 1H), 3.03 (dd, J = 12.7, 5.4 Hz, 1H), 2.94 (dt, J = 8.8, 5.5 Hz, 1H), 2.86 (dd, J = 12.7, 8.8 Hz, 1H), 1.44 (s, 9H), 1.22 (d, J = 6.5 Hz, 3H), 1.13 (d, J = 7.2 Hz, 3H). $^{13}$C NMR (101 MHz, CDCl$_3$) δ 172.63, 161.32 (d, J = 244.0 Hz), 155.05, 140.05, 135.17 (d, J = 3.2 Hz), 130.37 (d, J = 7.8 Hz), 128.92, 128.20, 126.81, 114.98 (d, J = 21.1 Hz), 79.76, 73.30, 53.34, 49.46, 37.69, 28.35, 18.43, 18.38. |
| 20 | (Thin film) 3354, 2979, 2934, 1710, 1509, 1158, 1056, 732 | HRMS-ESI m/z ([M + Na]⁺) calcd for C$_{26}$H$_{34}$FNNaO$_5$, 482.2316; found, 483.2313 | $^1$H NMR (400 MHz, CDCl$_3$) δ 7.38-7.23 (m, 5H), 7.12-7.00 (m, 2H), 6.99-6.88 (m, 2H), 5.12 (dt, J = 12.1, 4.2 Hz, 2H), 4.49-4.36 (m, 2H), 4.27 (p, J = 7.6 Hz, 1H), 3.38 (d, J = 5.1 Hz, 2H), 2.73-2.55 (m, 2H), 2.13-1.98 (m, 1H), 1.44 (s, 9H), 1.34 (d, J = 7.2 Hz, 3H), 1.29 (d, J = 6.5 Hz, 3H). $^{13}$C NMR (101 MHz, CDCl$_3$) δ 172.55, 161.38 (d, J = 243.9 Hz), 155.06, 138.20, 135.54 (d, J = 3.3 Hz), 130.47 (d, J = 7.8 Hz), 128.35, 127.61, 127.60, 115.13 (d, J = 21.2 Hz), 79.71, 73.08, 71.93, 68.23, 49.46, 45.64, 32.67, 28.35, 18.76, 17.29. |
| 21 | (Thin film) 3353, 2979, 2933, 1712, 1164, 1063, 698 | HRMS-ESI m/z ([M + Na]⁺) calcd for C$_{26}$H$_{35}$NNaO$_5$, 464.2407; found, 464.2416 | $^1$H NMR (400 MHz, CDCl$_3$) δ 7.37-7.22 (m, 7H), 7.22-7.07 (m, 3H), 5.23-4.99 (m, 2H), 4.48-4.36 (m, 2H), 4.27 (p, J = 7.6 Hz, 1H), 3.39 (d, J = 5.2 Hz, 2H), 2.68 (d, J = 7.4 Hz, 2H), 2.13 (qt, J = 7.5, 5.1 Hz, 1H), 1.44 (s, 9H), 1.33 (d, J = 7.2 Hz, 3H), 1.29 (d, J = 6.5 Hz, 3H). $^{13}$C NMR (101 MHz, CDCl$_3$) δ 172.53, 155.04, 139.96, 138.28, 129.11, 128.36, 128.31, 127.57, |

TABLE 2-continued

Analytical Data

| *Cmpd. No. | IR (cm$^{-1}$) | MASS | NMR ($^1$H, $^{13}$C or $^{19}$F) |
|---|---|---|---|
| 22 | (Thin film) 3357, 2977, 1711, 1509, 1159, 1043, 732 | HRMS-ESI m/z ([M + Na]$^+$) calcd for C$_{28}$H$_{38}$FNNaO$_5$, 510.2626; found, 510.2614 | 127.52, 126.06, 79.64, 73.03, 72.08, 68.45, 49.43, 45.49, 33.45, 28.34, 18.80, 17.18. $^1$H NMR (400 MHz, CDCl$_3$) δ 7.40-7.30 (m, 4H), 7.29-7.21 (m, 1H), 7.19-7.09 (m, 2H), 7.01-6.88 (m, 2H), 5.40 (qd, J = 6.6, 2.9 Hz, 1H), 4.89 (d, J = 7.9 Hz, 1H), 4.55-4.37 (m, 2H), 4.11 (dt, J = 15.1, 5.5 Hz, 1H), 3.01 (dd, J = 14.8, 4.9 Hz, 1H), 2.77 (dd, J = 14.8, 7.4 Hz, 1H), 2.26 (ddd, J = 7.7, 4.9, 2.9 Hz, 1H), 1.43 (s, 9H), 1.38-1.32 (m, 6H), 1.29 (s, 3H), 1.11 (d, J = 7.2 Hz, 3H). $^{13}$C NMR (101 MHz, CDCl$_3$) δ 172.40, 161.06 (d, J = 243.6 Hz), 154.97, 139.46, 138.34 (d, J = 3.3 Hz), 130.16 (d, J = 7.6 Hz), 128.27, 127.12, 127.08, 115.02 (d, J = 21.0 Hz), 79.71, 76.94, 72.78, 63.39, 53.30, 49.45, 30.35, 28.32, 24.87, 24.73, 18.36, 17.14. |
| 23 | (Thin film) 3354, 2976, 1711, 1164, 1043, 732, 697 | HRMS-ESI m/z ([M + Na]$^+$) calcd for C$_{28}$H$_{39}$NNaO$_5$, 492.2720; found, 492.2712 | $^1$H NMR (400 MHz, CDCl$_3$) δ 7.36-7.29 (m, 4H), 7.29-7.18 (m, 5H), 7.18-7.11 (m, 1H), 5.41 (qd, J = 6.5, 2.8 Hz, 1H), 4.85 (d, J = 8.0 Hz, 1H), 4.53-4.37 (m, 2H), 4.12-3.95 (m, 1H), 3.04 (dd, J = 14.7, 4.8 Hz, 1H), 2.81 (dd, J = 14.8, 7.7 Hz, 1H), 2.33 (ddd, J = 7.7, 4.8, 2.8 Hz, 1H), 1.43 (s, 9H), 1.39-1.34 (m, 6H), 1.30 (s, 3H), 1.07 (d, J = 7.2 Hz, 3H). $^{13}$C NMR (101 MHz, CDCl$_3$) δ 172.37, 154.96, 142.73, 139.52, 128.89, 128.29, 128.25, 127.09, 127.08, 125.59, 79.59, 76.97, 72.84, 63.38, 53.01, 49.46, 31.13, 28.33, 24.85, 24.82, 18.33, 17.09. |
| 24 | (Thin film) 3353, 2979, 2932, 1711, 1509, 1159, 1062 | HRMS-ESI m/z ([M + Na]$^+$) calcd for C$_{20}$H$_{30}$FNNaO$_5$, 406.2000; found, 406.2002 | $^1$H NMR (400 MHz, CDCl$_3$) δ 7.19-7.04 (m, 2H), 7.03-6.90 (m, 2H), 5.13 (d, J = 7.5 Hz, 1H), 5.11-5.01 (m, 1H), 4.38-4.20 (m, 1H), 3.36-3.20 (m, 5H), 2.63 (d, J = 7.4 Hz, 2H), 2.03 (ddt, J = 12.7, 7.6, 5.2 Hz, 1H), 1.45 (s, 9H), 1.40 (d, J = 7.2 Hz, 3H), 1.28 (d, J = 6.4 Hz, 3H). $^{13}$C NMR (101 MHz, CDCl$_3$) δ 172.57, 161.41 (d, J = 243.9 Hz), 155.08, 135.57 (d, J = 3.2 Hz), 130.48 (d, J = 7.8 Hz), 115.17 (d, J = 21.1 Hz), 79.73, 71.86, 70.89, 58.76, 49.50, 45.57, 32.70, 28.36, 18.85, 17.21. |
| 25 | (Thin film) 3353, 2977, 2939, 1711, 1509, 1159, 1043 | HRMS-ESI m/z ([M + Na]$^+$) calcd for C$_{22}$H$_{34}$FNNaO$_5$, 434.2313; found, 434.2307 | $^1$H NMR (400 MHz, CDCl$_3$) δ 7.20-7.09 (m, 2H), 7.01-6.88 (m, 2H), 5.31 (qd, J = 6.6, 2.9 Hz, 1H), 4.89 (d, J = 7.8 Hz, 1H), 4.17-4.00 (m, 1H), 3.18 (s, 3H), 2.88 (dd, J = 14.7, 4.8 Hz, 1H), 2.70 (dd, J = 14.8, 7.7 Hz, 1H), 2.18 (ddd, J = 7.7, 4.9, 2.9 Hz, 1H), 1.44 (s, 9H), 1.32 (d, J = 6.6 Hz, 3H), 1.22 (s, 3H), 1.19 (s, 3H), 1.12 (d, J = 7.2 Hz, 3H). $^{13}$C NMR (101 MHz, CDCl$_3$) δ 172.37, 161.07 (d, J = 243.6 Hz), 154.97, 138.25 (d, J = 3.3 Hz), |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 130.14 (d, J = 7.7 Hz), 115.01 (d, J = 21.1 Hz), 79.72, 76.40, 72.67, 52.48, 49.46, 48.86, 30.45, 28.33, 24.19, 24.01, 18.40, 17.14. |
| 26 | (Thin film) 3432, 2974, 1715, 1496, 1366, 1167 | HRMS-ESI m/z ([M + Na]$^+$) calcd for C$_{24}$H$_{39}$NNaO$_5$, 444.272; found, 444.2723 | $^1$H NMR (400 MHz, CDCl$_3$) δ 7.31-7.12 (m, 5H), 5.35 (qd, J = 6.6, 2.8 Hz, 1H), 4.84 (s, 1H), 4.12-3.99 (m, 1H), 3.29 (td, J = 6.5, 1.0 Hz, 2H), 2.96 (dd, J = 14.7, 4.7 Hz, 1H), 2.74 (dd, J = 14.7, 7.8 Hz, 1H), 2.23 (ddd, J = 7.7, 4.8, 2.8 Hz, 1H), 1.61-1.48 (m, 2H), 1.44 (s, 9H), 1.34 (d, J = 6.5 Hz, 3H), 1.23 (s, 3H), 1.18 (s, 3H), 1.07 (d, J = 7.2 Hz, 3H), 0.92 (t, J = 7.4 Hz, 3H). |
| 27 | (Thin film) 3363, 2982, 1729, 1682, 1526, 1236, 1156, 1039 | HRMS-ESI m/z ([M + Na]$^+$) calcd for C$_{25}$H$_{33}$NNaO$_5$, 450.2251; found, 450.2235 | $^1$H NMR (400 MHz, CDCl$_3$) δ 7.32-7.11 (m, 7H), 6.93 (tt, J = 7.4, 1.1 Hz, 1H), 6.87-6.80 (m, 2H), 5.26-5.16 (m, 1H), 5.06 (d, J = 7.9 Hz, 1H), 4.38-4.19 (m, 1H), 3.97-3.83 (m, 2H), 2.88-2.70 (m, 2H), 2.29 (ddq, J = 8.5, 6.4, 5.1 Hz, 1H), 1.44 (s, 9H), 1.37 (d, J = 6.5 Hz, 3H), 1.33 (d, J = 7.1 Hz, 3H). |
| 28 | (Thin film) 3361, 2979, 1708, 1484, 1464, 1246, 1161, 1059 | HRMS-ESI m/z ([M + Na]$^+$) calcd for C$_{25}$H$_{31}$Cl$_2$NNaO$_5$, 518.1471; found, 518.147 | $^1$H NMR (400 MHz, CDCl$_3$) δ 7.36 (d, J = 2.5 Hz, 1H), 7.32-7.22 (m, 2H), 7.23-7.17 (m, 1H), 7.17-7.14 (m, 2H), 7.12 (dd, J = 8.8, 2.6 Hz, 1H), 6.68 (d, J = 8.8 Hz, 1H), 5.27-5.15 (m, 1H), 5.06 (d, J = 7.9 Hz, 1H), 4.42-4.19 (m, 1H), 3.91 (qd, J = 9.4, 4.7 Hz, 2H), 2.88 (dd, J = 13.6, 9.1 Hz, 1H), 2.80 (dd, J = 13.6, 5.9 Hz, 1H), 2.38-2.21 (m, 1H), 1.44 (s, 9H), 1.41 (d, J = 6.5 Hz, 3H), 1.34 (d, J = 7.2 Hz, 3H). |
| 29 | | ESIMS m/z 448.5 ([M + H]$^+$) | $^1$H NMR (400 MHz, CDCl$_3$) δ 7.78-7.71 (m, 1H), 7.67 (dd, J = 7.6, 5.1 Hz, 2H), 7.46-7.34 (m, 3H), 7.25-7.06 (m, 6H), 5.36-5.19 (m, 1H), 5.01 (d, J = 7.8 Hz, 1H), 4.35-4.21 (m, 1H), 3.30-3.16 (m, 1H), 3.15-3.01 (m, 2H), 1.45 (s, 9H), 1.25 (d, J = 6.4 Hz, 3H), 1.16 (d, J = 7.2 Hz, 3H). |
| 30 | | ESIMS m/z 394.5 ([M + H]$^+$) | |
| 31 | (Thin film) 3358, 2979, 2934, 1710, 1509, 1220, 1157, 1063 | HRMS-ESI m/z ([M + Na]$^+$) calcd for C$_{26}$H$_{33}$F$_2$NNaO$_5$, 500.2219; found, 500.2217 | $^1$H NMR (400 MHz, CDCl$_3$) δ 7.30-7.19 (m, 2H), 7.13-6.98 (m, 4H), 6.98-6.88 (m, 2H), 5.23-4.94 (m, 2H), 4.46-4.33 (m, 2H), 4.28 (t, J = 7.3 Hz, 1H), 3.37 (d, J = 5.1 Hz, 2H), 2.65 (d, J = 7.5 Hz, 2H), 2.13-1.96 (m, 1H), 1.45 (s, 9H), 1.35 (d, J = 7.2 Hz, 3H), 1.28 (d, J = 6.5 Hz, 3H). $^{13}$C NMR (101 MHz, CDCl$_3$) δ 172.57, 162.29 (d, J = 245.5 Hz), 161.41 (d, J = 244.1 Hz), 155.06, 135.49 (d, J = 3.3 Hz), 133.97 (d, J = 3.1 Hz), 130.45 (d, J = 7.8 Hz), 129.32 (d, J = 8.1 Hz), 115.20 (d, J = 21.3 Hz), 115.17 (d, J = 21.1 Hz), 79.77, 72.37, 71.88, 68.27, 49.46, 45.59, 32.69, 28.35, 18.79, 17.25. |
| 32 | (Thin film) 3359, 2978, 1710, 1509, 1219, 1157, 1042 | HRMS-ESI m/z ([M + Na]$^+$) calcd for C$_{28}$H$_{37}$F$_2$NNaO$_5$, 528.2532; found, 528.2542 | $^1$H NMR (400 MHz, CDCl$_3$) δ 7.37-7.22 (m, 2H), 7.20-7.09 (m, 2H), 7.09-6.98 (m, 2H), 6.98-6.89 (m, 2H), 5.40 (qd, J = 6.5, 2.8 Hz, 1H), 4.88 (d, J = 7.9 Hz, 1H), 4.49-4.30 (m, 2H), 4.17- |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 4.02 (m, 1H), 2.97 (dd, J = 14.8, 5.0 Hz, 1H), 2.77 (dd, J = 14.8, 7.4 Hz, 1H), 2.26 (ddd, J = 7.7, 5.0, 2.9 Hz, 1H), 1.43 (s, 9H), 1.37-1.31 (m, 6H), 1.28 (s, 3H), 1.12 (d, J = 7.2 Hz, 3H). $^{13}$C NMR (101 MHz, CDCl$_3$) δ 172.42, 162.02 (d, J = 244.9 Hz), 161.09 (d, J = 243.8 Hz), 154.98, 138.22 (d, J = 3.3 Hz), 135.10 (d, J = 3.2 Hz), 130.14 (d, J = 7.7 Hz), 128.78 (d, J = 8.0 Hz), 115.10 (d, J = 21.3 Hz), 115.05 (d, J = 21.0 Hz), 79.76, 77.06, 72.66, 62.77, 53.17, 49.46, 30.39, 28.33, 24.82, 24.78, 18.36, 17.14. |
| 33 | (Thin film) 3357, 2956, 2869, 1714, 1510, 1165, 1063 | HRMS-ESI m/z ([M + Na]$^+$) calcd for C$_{24}$H$_{38}$FNNaO$_5$, 462.2626; found, 462.2635 | $^1$H NMR (400 MHz, CDCl$_3$) δ 7.16-7.04 (m, 2H), 7.02-6.90 (m, 2H), 5.22-4.93 (m, 2H), 4.40-4.23 (m, 1H), 3.44-3.21 (m, 4H), 2.74-2.53 (m, 2H), 2.07-1.96 (m, 1H), 1.68 (dq, J = 13.4, 6.8 Hz, 1H), 1.45 (m, 10H), 1.43-1.37 (m, 4H), 1.28 (d, J = 6.5 Hz, 3H), 0.90 (d, J = 1.6 Hz, 3H), 0.89 (d, J = 1.6 Hz, 3H). $^{13}$C NMR (101 MHz, CDCl$_3$) δ 172.59, 161.39 (d, J = 243.9 Hz), 155.06, 135.71 (d, J = 3.2 Hz), 130.47 (d, J = 7.7 Hz), 115.12 (d, J = 21.2 Hz), 79.75, 72.07, 69.55, 68.88, 49.48, 45.59, 38.54, 32.72, 28.36, 25.09, 22.64, 22.61, 18.91, 17.18. |
| 34 | (Thin film) 3357, 2955, 2931, 1714, 1165, 1054, 700 | HRMS-ESI m/z ([M + Na]$^+$) calcd for C$_{24}$H$_{39}$NNaO$_5$, 444.2720; found, 444.2711 | $^1$H NMR (400 MHz, CDCl$_3$) δ 7.31-7.23 (m, 2H), 7.23-7.09 (m, 3H), 5.10 (qd, J = 6.5, 4.6 Hz, 2H), 4.29 (p, J = 7.6 Hz, 1H), 3.42-3.26 (m, 4H), 2.66 (d, J = 7.4 Hz, 2H), 2.14-2.03 (m, 1H), 1.69 (tt, J = 13.4, 6.6 Hz, 1H), 1.49-1.42 (m, 11H), 1.39 (d, J = 7.2 Hz, 3H), 1.29 (d, J = 6.5 Hz, 3H), 0.90 (d, J = 1.8 Hz, 3H), 0.89 (d, J = 1.7 Hz, 3H). $^{13}$C NMR (101 MHz, CDCl$_3$) δ 172.57, 155.05, 140.14, 129.13, 128.35, 126.03, 79.69, 72.22, 69.50, 69.05, 49.46, 45.44, 38.54, 33.49, 28.36, 25.08, 22.65, 22.61, 18.96, 17.07. |
| 35 | (Thin film) 3357.58, 2977.98, 1710.52, 1472.76, 1163.16, 1046.48 | HRMS-ESI m/z ([M + Na]$^+$) calcd for C$_{27}$H$_{35}$Cl$_2$NNaO$_5$, 546.1784; found, 546.1779 | $^1$H NMR (400 MHz, CDCl$_3$) δ 7.39 (d, J = 2.6 Hz, 1H), 7.31-7.21 (m, 5H), 7.20-7.16 (m, 1H), 7.14 (dd, J = 8.8, 2.6 Hz, 1H), 7.02 (d, J = 8.7 Hz, 1H), 5.54 (qd, J = 6.5, 2.9 Hz, 1H), 4.86 (s, 1H), 3.25 (dd, J = 14.9, 5.0 Hz, 1H), 2.93 (dd, J = 14.9, 7.3 Hz, 1H), 2.47 (ddd, J = 7.7, 5.0, 2.9 Hz, 1H), 1.46 (d, J = 6.5 Hz, 3H), 1.44 (s, 9H), 1.43 (s, 3H), 1.33 (s, 3H), 1.12 (d, J = 7.2 Hz, 3H). |
| 36 | (Thin film) 3361.50, 2975.54, 1712.32, 1511.62, 1244.78, 1163.20 | HRMS-ESI m/z ([M + Na]$^+$) calcd for C$_{23}$H$_{37}$NNaO$_6$, 446.2513; found, 446.2506 | $^1$H NMR (400 MHz, CDCl$_3$) δ 7.13-6.99 (m, 2H), 6.87-6.77 (m, 2H), 5.10 (dtd, J = 11.2, 7.0, 6.5, 3.6 Hz, 2H), 4.40-4.21 (m, 1H), 3.78 (s, 3H), 3.38-3.22 (m, 4H), 2.60 (d, J = 7.4 Hz, 2H), 2.03 (ddt, J = 12.7, 7.6, 5.2 Hz, 1H), 1.56 (dtd, J = 13.9, 7.4, 6.5 Hz, 2H), 1.45 (s, 9H), 1.40 (d, J = 7.2 Hz, 3H), 1.29 (d, J = 6.4 Hz, 3H), 0.91 (t, J = 7.4 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| 37 | (Thin film) 3370.66, 2973.75, 1713.10, 1511.68, 1245.81, 1165.36 | HRMS-ESI m/z ([M + Na]$^+$) calcd for C$_{25}$H$_{41}$NNaO$_6$, 474.2826; found, 474.2822 | $^1$H NMR (400 MHz, CDCl$_3$) δ 7.15-7.06 (m, 2H), 6.86-6.77 (m, 2H), 5.34 (qd, J = 6.6, 2.8 Hz, 1H), 5.00-4.85 (m, 1H), 4.10 (s, 1H), 3.78 (s, 3H), 3.29 (td, J = 6.5, 1.5 Hz, 2H), 2.89 (dd, J = 14.8, 4.9 Hz, 1H), 2.75-2.59 (m, 1H), 2.22-2.13 (m, 1H), 1.60-1.47 (m, 2H), 1.44 (s, 9H), 1.33 (d, J = 6.5 Hz, 3H), 1.22 (s, 3H), 1.17 (s, 3H), 1.15-1.09 (m, 3H), 0.92 (t, J = 7.4 Hz, 3H). |
| 38 | (Thin film) 3360.47, 2975.23, 1712.60, 1501.2, 1247.74, 1162.84 | HRMS-ESI m/z ([M + Na]$^+$) calcd for C$_{30}$H$_{43}$NNaO$_6$, 536.2983; found, 536.2982 | $^1$H NMR (400 MHz, CDCl$_3$) δ 7.30-7.22 (m, 2H), 7.22-7.14 (m, 3H), 6.95 (dd, J = 8.3, 2.3 Hz, 1H), 6.85-6.81 (m, 1H), 6.77 (d, J = 8.3 Hz, 1H), 5.16-4.99 (m, 2H), 4.35-4.19 (m, 1H), 3.93 (d, J = 4.3 Hz, 2H), 3.79 (s, 3H), 3.37-3.15 (m, 4H), 2.54 (d, J = 7.4 Hz, 2H), 2.05-1.91 (m, 1H), 1.61-1.47 (m, 2H), 1.45 (s, 9H), 1.34 (d, J = 7.2 Hz, 3H), 1.26 (d, J = 6.5 Hz, 3H), 0.89 (t, J = 7.4 Hz, 3H). |
| 39 | (Thin film) 3355.80, 2973.95, 1712.81, 1501.20, 1248.78, 1163.47 | HRMS-ESI m/z ([M + H]$^+$) calcd for C$_{32}$H$_{47}$NNaO$_6$, 564.3296; found, 564.3289 | $^1$H NMR (400 MHz, CDCl$_3$) δ 7.30-7.20 (m, 2H), 7.22-7.13 (m, 3H), 6.99 (dd, J = 8.2, 2.3 Hz, 1H), 6.88 (d, J = 2.3 Hz, 1H), 6.77 (d, J = 8.3 Hz, 1H), 5.30 (qd, J = 6.6, 2.9 Hz, 1H), 4.92 (s, 1H), 4.05 (d, J = 7.7 Hz, 1H), 3.93 (s, 2H), 3.78 (s, 3H), 3.33-3.18 (m, 2H), 2.83 (dd, J = 14.8, 5.2 Hz, 1H), 2.61 (dd, J = 14.8, 7.4 Hz, 1H), 2.12 (ddd, J = 7.2, 5.2, 2.9 Hz, 1H), 1.50 (dtd, J = 13.9, 7.3, 6.4 Hz, 2H), 1.44 (s, 9H), 1.29 (d, J = 6.6 Hz, 3H), 1.18 (s, 3H), 1.12 (s, 3H), 1.05 (d, J = 7.2 Hz, 3H), 0.90 (t, J = 7.4 Hz, 3H). |
| 40 | (Thin film) 3369, 2972, 1709, 1494, 1365, 1157, | HRMS-ESI m/z ([M + Na]$^+$) calcd for C$_{27}$H$_{37}$NNaO$_4$, 462.2615; found, 462.2611 | $^1$H NMR (400 MHz, CDCl$_3$) δ 7.32-7.03 (m, 10H), 4.96 (qd, J = 6.5, 3.0 Hz, 2H), 2.83-2.48 (m, 5H), 2.24-2.12 (m, 2H), 1.46 (d, J = 7.7 Hz, 9H), 1.29-1.25 (m, 3H), 1.04-0.87 (m, 6H). |
| 41 | (Thin film) 3359, 2980, 1705, 1587, 1487, 1249, 1162, | HRMS-ESI m/z ([M + Na]$^+$) calcd for C$_{25}$H$_{31}$F$_2$NNaO$_4$, 470.2113; found, 470.2116 | $^1$H NMR (400 MHz, CDCl$_3$) δ 7.25-7.20 (m, 2H), 6.95-6.81 (m, 5H), 6.75 (dd, J = 9.9, 2.2 Hz, 1H), 5.03 (s, 1H), 4.98-4.88 (m, 1H), 4.34-4.23 (m, 1H), 2.76 (d, J = 6.6 Hz, 1H), 2.69-2.47 (m, 4H), 1.45 (s, 9H), 1.42 (d, J = 7.2 Hz, 3H), 1.29-1.24 (m, 3H). |
| 42 | (Thin film) 3366, 2976, 1713, 1512, 1246, 1165, 1039 | HRMS-ESI m/z ([M + Na]$^+$) calcd for C$_{26}$H$_{41}$NNaO$_6$, 486.2826; found, 486.2836 | $^1$H NMR (400 MHz, CDCl$_3$) δ 7.18-7.07 (m, 2H), 6.88-6.77 (m, 2H), 5.32 (qd, J = 6.5, 2.8 Hz, 1H), 5.07-4.86 (m, 1H), 4.20-4.02 (m, 1H), 3.78 (d, J = 2.4 Hz, 3H), 3.28-3.10 (m, 2H), 2.88 (dd, J = 14.7, 4.8 Hz, 1H), 2.67 (dd, J = 14.8, 7.7 Hz, 1H), 2.18 (ddt, J = 7.7, 4.9, 2.7 Hz, 1H), 1.44 (s, 9H), 1.34 (d, J = 6.5 Hz, 3H), 1.21 (s, 3H), 1.17 (s, 3H), 1.14 (d, J = 7.2 Hz, 3H), 1.04-0.91 (m, 1H), 0.57-0.41 (m, 2H), 0.21-0.15 (m, 2H). |
| 43 | | HRMS-ESI m/z ([M + Na]$^+$) calcd for C$_{28}$H$_{37}$F$_2$NNaO$_6$, 544.2481; found, 544.2492 | $^1$H NMR (400 MHz, CDCl$_3$) δ 7.17-7.12 (m, 2H), 7.08-6.99 (m, 1H), 6.87-6.81 (m, 2H), 6.81-6.71 (m, 2H), 5.51 (qd, J = 6.6, 2.9 Hz, 1H), 4.96 (d, J = 7.9 Hz, 1H), 4.25-4.09 (m, 1H), 3.79 (s, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 3H), 3.13 (dd, J = 14.9, 5.5 Hz, 1H), 2.85 (dd, J = 14.9, 6.7 Hz, 1H), 2.36 (ddd, J = 6.7, 5.5, 2.9 Hz, 1H), 1.44 (s, 9H), 1.44 (d, J = 6.6 Hz, 3H), 1.39-1.35 (m, 3H), 1.25 (d, J = 2.1 Hz, 3H), 1.19 (d, J = 7.2 Hz, 3H). $^{13}$C NMR (101 MHz, CDCl$_3$) δ 172.55, 158.04 (dd, J = 243.0, 2.4 Hz), 157.76, 155.03, 153.62 (dd, J = 242.2, 3.5 Hz), 142.69 (dd, J = 13.7, 10.8 Hz), 134.31, 129.69, 116.57 (dd, J = 22.8, 10.1 Hz), 113.86, 113.82 (dd, J = 24.2, 1.0 Hz), 110.86 (dd, J = 23.7, 7.4 Hz), 84.85, 79.72, 72.71, 55.28, 53.98, 49.49, 30.34, 28.34, 25.75, 25.66, 18.48, 17.09. |
| 44 | (Thin film) 3357, 2979, 1712, 1512, 1245, 1163, 1057 | HRMS-ESI m/z ([M + Na]$^+$) calcd for C$_{24}$H$_{37}$NNaO$_6$, 458.2513; found, 458.2513 | $^1$H NMR (400 MHz, CDCl$_3$) δ 7.15-6.99 (m, 2H), 6.86-6.76 (m, 2H), 5.21-5.02 (m, 2H), 4.30 (t, J = 7.4 Hz, 1H), 3.78 (s, 3H), 3.39 (dd, J = 9.7, 5.8 Hz, 1H), 3.33 (dd, J = 9.7, 5.1 Hz, 1H), 3.19 (dd, J = 6.8, 1.3 Hz, 2H), 2.61 (d, J = 7.4 Hz, 2H), 2.05 (ddt, J = 12.7, 7.5, 5.2 Hz, 1H), 1.45 (s, 9H), 1.40 (d, J = 7.2 Hz, 3H), 1.29 (d, J = 6.5 Hz, 3H), 1.08-0.95 (m, 1H), 0.57-0.44 (m, 2H), 0.23-0.12 (m, 2H). |
| 45 | (Thin film) 3357, 2978, 1713, 1501, 1249, 1163 | | $^1$H NMR (400 MHz, CDCl$_3$) δ 7.30-7.20 (m, 2H), 7.22-7.13 (m, 3H), 6.95 (dd, J = 8.3, 2.3 Hz, 1H), 6.86-6.80 (m, 1H), 6.77 (d, J = 8.3 Hz, 1H), 5.18-5.01 (m, 2H), 4.37-4.19 (m, 1H), 3.96 (d, J = 15.1 Hz, 1H), 3.91 (d, J = 15.1 Hz, 1H), 3.78 (s, 3H), 3.34 (dd, J = 9.7, 5.8 Hz, 1H), 3.30 (dd, J = 9.7, 5.1 Hz, 1H), 3.20-3.10 (m, 2H), 2.55 (d, J = 7.4 Hz, 2H), 2.08-1.92 (m, 1H), 1.45 (s, 9H), 1.34 (d, J = 7.1 Hz, 3H), 1.26 (d, J = 6.6 Hz, 3H), 1.07-0.90 (m, 1H), 0.56-0.43 (m, 2H), 0.22-0.10 (m, 2H). $^{13}$C NMR (101 MHz, CDCl$_3$) δ 172.53, 155.75, 155.05, 141.05, 131.73, 131.16, 129.47, 128.90, 128.23, 127.82, 125.74, 110.40, 79.69, 75.45, 72.19, 68.66, 55.45, 49.43, 45.42, 35.83, 32.64, 28.36, 19.00, 17.11, 10.53, 2.95, 2.89. |
| 46 | (Thin film) 3365, 2979, 1738, 1710, 1512, 1242, 1160 | HRMS-ESI m/z ([M + Na]$^+$) calcd for C$_{26}$H$_{33}$F$_2$NNaO$_6$, 516.2168; found, 516.2177 | $^1$H NMR (400 MHz, CDCl$_3$) δ 7.10-7.04 (m, 2H), 7.04-6.96 (m, 1H), 6.85-6.79 (m, 2H), 6.60-6.52 (m, 2H), 5.26-5.14 (m, 1H), 5.08 (d, J = 7.9 Hz, 1H), 4.42-4.21 (m, 1H), 3.92 (d, J = 4.8 Hz, 2H), 3.78 (s, 3H), 2.75 (dd, J = 7.6, 3.8 Hz, 2H), 2.24 (ddq, J = 9.7, 6.6, 4.9 Hz, 1H), 1.44 (s, 9H), 1.38 (d, J = 6.5 Hz, 3H), 1.37 (d, J = 7.3 Hz, 3H). |
| 47 | (Thin film) 3374, 2977, 1697, 1512, 1246, 1164, 1040 | HRMS-ESI m/z ([M + Na]$^+$) calcd for C$_{22}$H$_{35}$NNaO$_6$, 432.2357; found, 432.2364 | $^1$H NMR (400 MHz, CDCl$_3$) δ 7.16-7.06 (m, 2H), 6.91-6.75 (m, 2H), 5.31 (qd, J = 6.6, 3.3 Hz, 1H), 4.96 (d, J = 7.8 Hz, 1H), 4.25-4.07 (m, 1H), 3.78 (s, 3H), 2.81 (dd, J = 14.7, 5.3 Hz, 1H), 2.66 (dd, J = 15.0, 7.7 Hz, 1H), 2.14-2.03 (m, 1H), 1.84 |

TABLE 2-continued

Analytical Data

| *Cmpd. No. | IR (cm$^{-1}$) | MASS | NMR ($^1$H, $^{13}$C or $^{19}$F) |
|---|---|---|---|
| 48 | | ESIMS m/z 336 ([M + H]$^+$) | (s, 1H), 1.44 (s, 9H), 1.33 (d, J = 6.6 Hz, 3H), 1.31 (s, 3H), 1.25 (s, 3H), 1.21 (d, J = 7.2 Hz, 3H). $^1$H NMR (300 MHz, CDCl$_3$) δ 7.34-7.19 (m, 3H), 7.17-7.11 (m, 2H), 5.21-5.01 (m, 2H), 4.42-4.22 (m, 1H), 2.63 (ddd, J = 11.0, 8.6, 3.8 Hz, 1H), 1.84 (dqd, J = 13.4, 7.5, 3.9 Hz, 1H), 1.69-1.51 (m, 1H), 1.45 (s, 9H), 1.41 (d, J = 7.2 Hz 3H) 1.04 (d, J = 6.3 Hz, 3H), 0.72 (t, J = 7.4 Hz, 3H). $^{13}$C NMR (101 MHz, CDCl$_3$) δ 172.91, 155.04, 140.84, 128.60, 128.42, 126.76, 79.72, 75.34, 53.05, 49.54, 28.34, 24.58, 18.83, 18.38, 11.84. |
| 49 | | ESIMS m/z 348 ([M + H]$^+$) | |
| 50 | | ESIMS m/z 418 ([M + H]$^+$) | |
| 51 | | LCMS m/z 468 | $^1$H NMR (400 MHz, DMSO-d$_6$) δ 8.47 (bs, 3H), 7.57 (m, 2H), 7.28 (d, J = 8.2 Hz, 2H), 7.17 (dd, J = 8.6, 5.7 Hz, 2H), 7.08 (t, J = 8.8 Hz, 2H), 5.80 (m, 1H), 5.12 (m, 1H), 5.00 (d, J = 10.2 Hz, 1H), 4.86 (d, J = 16.9 Hz, 1H), 4.39 (bs, 1H), 3.82 (dd, J = 10.5, 3.5 Hz, 1H), 3.62 (dd, J = 10.6, 2.8 Hz, 1H), 3.28 (s, 3H), 3.02-2.89 (m, 1H), 2.80-2.61 (m, 3H), 2.50 (m, 1H, signal obscured by DMSO), 2.04 (m, 1H), 1.27 (d, J = 6.4 Hz, 3H). |
| 52 | | LCMS m/z 438 | $^1$H NMR (400 MHz, d6-DMSO) δ 8.30 (bs, 3H), 7.55 (d, J = 7.9 Hz, 2H), 7.24 (d, J = 7.9 Hz, 2H), 7.17 (dd, J = 8.7, 5.6 Hz, 2H), 7.08 (t, J = 8.9 Hz, 2H), 5.75 (m, 1H), 5.10 (m, 1H), 4.98 (dd, J = 10.3, 1.6 Hz, 1H), 4.83 (d, J = 17.2 Hz, 1H), 4.10 (m, 1H), 2.94 (dd, J = 13.6, 4.4 Hz, 1H), 2.73 (m, 2H), 2.65 (m, 1H), 2.46 (m, 1H), 2.05 (m, 1H), 1.36 (d, J = 7.3 Hz, 3H), 1.25 (d, J = 6.4 Hz, 3H). |
| 53 | | LCMS m/z 424 | $^1$H NMR (400 MHz, CDCl$_3$) δ 8.23 (bs, 3H), 7.55 (d, J = 8.0 Hz, 2H), 7.24 (d, J = 7.9 Hz, 2H), 7.18 (dd, J = 8.7, 5.6 Hz, 2H), 7.07 (t, J = 8.8 Hz, 2H), 5.74 (m, 1H), 5.04 (p, J = 6.3 Hz, 1H), 4.98 (dd, J = 10.4, 1.7 Hz, 1H), 4.85 (d, J = 17.1 Hz, 1H), 3.83 (bd, J = 5.5 Hz, 2H), 2.93 (dd, J = 13.5, 4.5 Hz, 1H), 2.74 (dd, J = 14.2, 6.3 Hz, 1H), 2.70-2.60 (m, 2H), 2.46 (m, 1H), 2.03 (m, 1H), 1.25 (d, J = 6.4 Hz, 3H). |
| 54 | | ESIMS m/z 438.4 ([M + H]$^+$) | $^1$H NMR (400 MHz, CDCl$_3$) δ 8.93 (bs, 3H), 7.26-7.20 (m, 2H), 7.16-7.11 (m, 1H), 7.10-7.04 (m, 2H), 7.04-6.98 (m, 4H), 5.23-5.13 (m, 1H), 4.15-4.04 (m, 1H), 2.83-2.75 (m, 1H), 2.70-2.52 (m, 2H), 2.45-2.34 (m, 1H), 1.99-1.91 (m, 1H), 1.77-1.63 (m, 1H), 1.70 (d, J = 7.0 Hz, 3H), 1.39-1.21 (m, 2H), 1.25 (d, J = 6.3 Hz, 3H), 0.85 (t, J = 7.3 Hz, 3H) |
| 55 | | ESIMS m/z 264 ([M + H]$^+$) | |
| 56 | | ESIMS m/z 280 ([M + H]$^+$) | |

TABLE 2-continued

Analytical Data

| *Cmpd. No. | IR (cm⁻¹) | MASS | NMR ($^1$H, $^{13}$C or $^{19}$F) |
|---|---|---|---|
| 57 | | ESIMS m/z 298 ([M + H]⁺) | |
| 58 | | ESIMS m/z 264 ([M + H]⁺) | |
| 59 | | ESIMS m/z 333 ([M + H]⁺) | |
| 60 | | ESIMS m/z 264.4 ([M + H]⁺) | |
| 61 | | ESIMS m/z 278.4 ([M + H]⁺) | |
| 62 | | ESIMS m/z 322.4 ([M + H]⁺) | |
| 63 | (Thin film) 3395, 2863, 1740, 1508, 1218, 1116, 698 | HRMS-ESI m/z ([M + H]⁺) calcd for $C_{21}H_{27}FNO_3$, 360.1969; found, 360.1970 | $^1$H NMR (400 MHz, CDCl$_3$) δ 8.82 (s, 3H), 7.40-7.17 (m, 5H), 7.12-6.99 (m, 2H), 6.99-6.83 (m, 2H), 5.24-5.04 (m, 1H), 4.51-4.28 (m, 2H), 4.31-4.11 (m, 1H), 3.33 (d, J = 5.0 Hz, 2H), 2.71-2.51 (m, 2H), 2.17-1.98 (m, 1H), 1.67 (d, J = 7.0 Hz, 3H), 1.27 (d, J = 6.4 Hz, 3H). |
| 64 | (Thin film) 3403, 2976, 1737, 1509, 1218, 732 | HRMS-ESI m/z ([M + H]⁺) calcd for $C_{23}H_{31}FNO_3$, 388.2282; found, 388.2281 | $^1$H NMR (400 MHz, CDCl$_3$) δ 8.66 (d, J = 5.4 Hz, 3H), 7.43-7.19 (m, 5H), 7.19-7.06 (m, 2H), 6.99-6.85 (m, 2H), 5.44 (qd, J = 5.9, 5.4, 2.4 Hz, 1H), 4.41 (s, 2H), 4.02-3.88 (m, 1H), 3.00 (dd, J = 15.0, 5.2 Hz, 1H), 2.76 (dd, J = 15.0, 6.8 Hz, 1H), 2.28-2.19 (m, 1H), 1.36 (dd, J = 11.7, 6.9 Hz, 5H), 1.30 (s, 3H), 1.22 (s, 3H). |
| 65 | (Thin film) 3399, 2860, 1739, 1116, 735, 698 | HRMS-ESI m/z ([M + H]⁺) calcd for $C_{21}H_{28}NO_3$, 342.2064; found, 342.2063 | $^1$H NMR (400 MHz, CDCl$_3$) δ 8.96-8.63 (m, 3H), 7.36-7.18 (m, 7H), 7.18-7.03 (m, 3H), 5.26-5.10 (m, 1H), 4.50-4.29 (m, 2H), 4.20 (q, J = 6.6, 6.2 Hz, 1H), 3.35 (d, J = 5.2 Hz, 2H), 2.78-2.55 (m, 2H), 2.13 (dt, J = 8.7, 5.6 Hz, 1H), 1.65 (d, J = 7.1 Hz, 3H), 1.28 (d, J = 6.4 Hz, 3H). |
| 66 | (Thin film) 3400, 2975, 1736, 1207, 1042, 734, 697 | HRMS-ESI m/z ([M + H]⁺) calcd for $C_{23}H_{32}NO_3$, 370.2377; found, 370.2378 | $^1$H NMR (400 MHz, CDCl$_3$) δ 8.58 (d, J = 5.5 Hz, 3H), 7.39-7.14 (m, 9H), 7.14-7.05 (m, 1H), 5.46 (qd, J = 6.3, 2.8 Hz, 1H), 4.43 (s, 2H), 3.92-3.71 (m, 1H), 3.04 (dd, J = 14.9, 4.7 Hz, 1H), 2.80 (dd, J = 14.9, 7.3 Hz, 1H), 2.31 (ddd, J = 7.6, 4.7, 2.8 Hz, 1H), 1.37 (d, J = 6.5 Hz, 3H), 1.32 (s, 3H), 1.28 (d, J = 7.2 Hz, 3H), 1.25 (s, 3H). |
| 67 | (Thin film) 3384, 2896, 1737, 1508, 1218, 1120 | HRMS-ESI m/z ([M + H]⁺) calcd for $C_{15}H_{23}FNO_3$, 284.1656; found, 284.1659 | |
| 68 | (Thin film) 3400, 2976, 2941, 1737, 1509, 1219 | HRMS-ESI m/z ([M + Na]⁺) calcd for $C_{17}H_{26}FNNaO_3$, 334.1789; found, 334.1795 | $^1$H NMR (400 MHz, CDCl$_3$) δ 8.63 (d, J = 5.4 Hz, 3H), 7.26-7.06 (m, 2H), 7.04-6.82 (m, 2H), 5.53-5.27 (m, 1H), 3.99 (t, J = 6.6 Hz, 1H), 3.15 (s, 3H), 2.86 (dd, J = 14.9, 5.1 Hz, 1H), 2.70 (dd, J = 14.9, 7.0 Hz, 1H), 2.19 (ddt, J = 6.9, 5.0, 2.8 Hz, 1H), 1.39 (d, J = 7.2 Hz, 3H), 1.32 (d, J = 6.5 Hz, 3H), 1.18 (s, 3H), 1.14 (s, 3H). |
| 69 | | ESIMS m/z 366.3 ([M + H]⁺) | |
| 70 | | ESIMS m/z 312.4 ([M + H]⁺) | |
| 71 | | ESIMS m/z 316.4 ([M + H]⁺) | |
| 72 | | ESIMS m/z 348.4 ([M + H]⁺) | |

TABLE 2-continued

Analytical Data

| *Cmpd. No. | IR (cm$^{-1}$) | MASS | NMR ($^1$H, $^{13}$C or $^{19}$F) |
|---|---|---|---|
| 73 | | ESIMS m/z 295.4 ([M + H]$^+$) | |
| 74 | (Thin film) 2868, 1740, 1509, 1220, 1115, 824 | HRMS-ESI m/z ([M + H]$^+$) calcd for C$_{21}$H$_{26}$F$_2$NO$_3$, 378.1875; found, 378.1872 | $^1$H NMR (400 MHz, CDCl$_3$) δ 8.83 (s, 3H), 7.27-7.14 (m, 2H), 7.11-7.03 (m, 2H), 7.03-6.96 (m, 2H), 6.96-6.88 (m, 2H), 5.23-5.08 (m, 1H), 4.48-4.27 (m, 2H), 4.22 (t, J = 6.5 Hz, 1H), 3.32 (d, J = 5.1 Hz, 2H), 2.72-2.51 (m, 2H), 2.16-1.99 (m, 1H), 1.69 (d, J = 7.1 Hz, 3H), 1.26 (d, J = 6.4 Hz, 3H). |
| 75 | (Thin film) 3488, 3091, 2981, 1742, 1238, 1158, 1027 | HRMS-ESI m/z ([M + H]$^+$) calcd for C$_{23}$H$_{30}$F$_2$NO$_3$, 406.2188; found, 406.2196 | |
| 76 | (Thin film) 2954, 2868, 1742, 1509, 1221, 1110 | HRMS-ESI m/z ([M + H]$^+$) calcd for C$_{19}$H$_{31}$FNO$_3$, 340.2282; found, 340.2294 | $^1$H NMR (400 MHz, CDCl$_3$) δ 8.83 (s, 3H), 7.20-7.03 (m, 2H), 7.03-6.84 (m, 2H), 5.11 (dt, J = 10.8, 5.4 Hz, 1H), 4.16 (s, 1H), 3.42-3.19 (m, 4H), 2.63 (d, J = 7.5 Hz, 2H), 2.07 (ddd, J = 14.1, 11.2, 6.3 Hz, 1H), 1.72 (d, J = 7.0 Hz, 3H), 1.65 (dt, J = 13.4, 6.7 Hz, 1H), 1.48-1.33 (m, 2H), 1.28 (d, J = 6.4 Hz, 3H), 0.89 (d, J = 0.8 Hz, 3H), 0.87 (d, J = 0.7 Hz, 3H). |
| 77 | (Thin film) 2953, 2867, 1741, 1238, 1110, 700 | HRMS-ESI m/z ([M + H]$^+$) calcd for C$_{19}$H$_{32}$NO$_3$, 322.2377; found, 322.2379 | $^1$H NMR (400 MHz, CDCl$_3$) δ 8.95-8.64 (m, 3H), 7.35-7.22 (m, 2H), 7.22-7.07 (m, 3H), 5.14 (qd, J = 6.4, 4.4 Hz, 1H), 4.17 (d, J = 6.7 Hz, 1H), 3.42-3.19 (m, 4H), 2.75-2.52 (m, 2H), 2.18-2.05 (m, 1H), 1.79-1.57 (m, 4H), 1.41 (qd, J = 6.7, 1.4 Hz, 2H), 1.29 (d, J = 6.5 Hz, 3H), 0.89 (d, J = 0.9 Hz, 3H), 0.87 (d, J = 0.9 Hz, 3H). |
| 78 | | ESIMS m/z 424.4 ([M + H]$^+$) | |
| 79 | | ESIMS m/z 262.4 ([M + H]$^+$) | |
| 80 | | ESIMS m/z 352.5 ([M + H]$^+$) | |
| 81 | | ESIMS m/z 442.7 ([M + H]$^+$) | |
| 82 | | ESIMS m/z 312.5 ([M + H]$^+$) | |
| 83 | | ESIMS m/z 340.5 ([M + H]$^+$) | |
| 84 | | ESIMS m/z 326.5 ([M + H]$^+$) | |
| 85 | | ESIMS m/z 348.5 ([M + H]$^+$) | |
| 86 | | ESIMS m/z 348.5 ([M + H]$^+$) | |
| 87 | | ESIMS m/z 364.6 ([M + H]$^+$) | |
| 88 | | ESIMS m/z 422.6 ([M + H]$^+$) | |
| 89 | | ESIMS m/z 293.5 ([M + H]$^+$) | |
| 90 | | ESIMS m/z 236 ([M + H]$^+$) | |
| 91 | (Thin film) 3370, 2963, 2935, 1733, 1649, 1528 | ESIMS m/z 473 ([M + H]$^+$) | $^1$H NMR (400 MHz, CDCl$_3$) δ 12.17 (d, J = 0.6 Hz, 1H), 8.49 (d, J = 7.9 Hz, 1H), 7.99 (dd, J = 5.2, 0.7 Hz, 1H), 7.31-7.22 (m, 2H), 7.23-7.12 (m, 3H), 6.87 (dd, J = 5.3, 1.6 Hz, 1H), 5.18-5.06 (m, 1H), 4.69-4.57 (m, 1H), 3.94 (s, 3H), 3.37-3.27 (m, 2H), 3.19 (ddd, J = 6.9, 5.8, 3.1 Hz, 1H), |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 2.82 (dd, J = 14.6, 5.9 Hz, 1H), 2.61 (dd, J = 14.6, 7.2 Hz, 1H), 2.22-2.11 (m, 1H), 1.62-1.51 (m, 4H), 1.48 (d, J = 7.1 Hz, 3H), 1.26 (d, J = 6.3 Hz, 3H), 0.91 (t, J = 7.2 Hz, 3H), 0.85 (t, J = 7.4 Hz, 3H). $^{13}$C NMR (101 MHz, CDCl$_3$) δ 171.44, 168.69, 155.37, 148.76, 141.50, 140.47, 130.50, 128.89, 128.33, 125.82, 109.44, 80.79, 73.50, 71.67, 56.07, 48.19, 47.00, 32.06, 24.68, 23.42, 18.30, 17.90, 10.82, 10.56. |
| 92 | (Thin film) 3368, 2963, 2936, 1735, 1650, 1530 | ESIMS m/z 473 ([M + H]$^+$) | $^1$H NMR (400 MHz, CDCl$_3$) δ 12.16 (d, J = 0.6 Hz, 1H), 8.51 (d, J = 7.9 Hz, 1H), 7.98 (d, J = 5.2 Hz, 1H), 7.31-7.23 (m, 2H), 7.22-7.07 (m, 3H), 6.86 (dd, J = 5.3, 0.6 Hz, 1H), 5.22 (qd, J = 6.5, 4.1 Hz, 1H), 4.77-4.63 (m, 1H), 3.93 (s, 3H), 3.40 (dt, J = 8.8, 6.4 Hz, 1H), 3.30 (dt, J = 8.8, 6.5 Hz, 1H), 3.17 (td, J = 6.5, 3.8 Hz, 1H), 2.83 (dd, J = 13.8, 7.4 Hz, 1H), 2.64 (dd, J = 13.7, 6.6 Hz, 1H), 2.20-2.12 (m, 1H), 1.64-1.49 (m, 4H), 1.56 (d, J = 7.2 Hz, 3H), 1.30 (d, J = 6.5 Hz, 3H), 0.96 (t, J = 7.4 Hz, 3H), 0.82 (t, J = 7.4 Hz, 3H). $^{13}$C NMR (101 MHz, CDCl$_3$) δ 171.42, 168.75, 155.38, 148.77, 141.13, 140.48, 130.46, 129.01, 128.35, 125.87, 109.45, 79.84, 72.33, 71.47, 56.07, 48.17, 46.78, 31.65, 23.89, 23.53, 18.40, 17.41, 11.01, 10.18. |
| 93 | (Thin film) 3370, 2963, 2936, 1735, 1649, 1528 | ESIMS m/z 445 ([M + H]$^+$) | $^1$H NMR (400 MHz, CDCl$_3$) δ 12.17 (d, J = 0.6 Hz, 1H), 8.52 (d, J = 7.9 Hz, 1H), 7.99 (d, J = 5.2 Hz, 1H), 7.32-7.22 (m, 2H), 7.22-7.16 (m, 1H), 7.16-7.12 (m, 2H), 6.90-6.84 (m, 1H), 5.16 (qd, J = 6.4, 4.7 Hz, 1H), 4.78-4.64 (m, 1H), 3.94 (s, 3H), 3.32 (dd, J = 5.4, 2.2 Hz, 2H), 3.27 (td, J = 6.6, 2.1 Hz, 2H), 2.71-2.62 (m, 2H), 2.11 (ddt, J = 12.5, 7.0, 5.3 Hz, 1H), 1.56 (d, J = 7.2 Hz, 3H), 1.55-1.50 (m, 2H), 1.32 (d, J = 6.5 Hz, 3H), 0.91 (t, J = 7.4 Hz, 3H). |
| 94 | (Thin film) 3372, 2964, 2937, 1736, 1651 | ESIMS m/z 473 ([M + H]$^+$) | $^1$H NMR (400 MHz, CDCl$_3$) δ 12.21 (s, 1H), 8.42 (d, J = 7.8 Hz, 1H), 8.00 (d, J = 5.2 Hz, 1H), 7.26 (s, 2H), 7.22-7.14 (m, 3H), 6.87 (d, J = 5.3 Hz, 1H), 5.18-5.07 (m, 1H), 4.57-4.46 (m, 1H), 3.95 (s, 3H) 3.41-3.26 (m, 2H), 3.20 (td, J = 6.3, 3.5 Hz, 1H), 2.84 (dd, J = 14.6, 5.7 Hz, 1H), 2.63 (dd, J = 14.6, 7.5 Hz, 1H), 2.27-2.18 (m, 1H), 1.63-1.45 (m, 4H), 1.43 (d, J = 7.2 Hz, 3H), 1.25 (d, J = 6.5 Hz, 3H), 0.94-0.85 (m, 6H). |
| 95 | (Thin film) 2965, 2936, 1733, 1650, 1527 | ESIMS m/z 487 ([M + H]$^+$) | $^1$H NMR (400 MHz, CDCl$_3$) δ 12.19 (d, J = 0.6 Hz, 1H), 8.47 (d, J = 8.6 Hz, 1H), 7.99 (d, J = 5.2 Hz, 1H), 7.28-7.20 (m, 2H), 7.21-7.13 (m, 3H), 6.87 (d, J = 5.2 Hz, 1H), 5.19-5.09 (m, 1H), 4.59 (ddd, J = 8.5, 7.3, 5.0 Hz, 1H), 3.95 (d, J = 1.1 Hz, 3H), 3.40- |

TABLE 2-continued

| *Cmpd. No. | IR (cm$^{-1}$) | MASS | NMR ($^1$H, $^{13}$C or $^{19}$F) |
|---|---|---|---|
| | | | 3.28 (m, 2H), 3.19 (dtd, J = 9.9, 6.4, 3.3 Hz, 1H), 2.81 (dd, J = 14.2, 6.1 Hz, 1H), 2.61 (dd, J = 14.5, 7.1 Hz, 1H), 2.18-2.10 (m, 1H), 2.02-1.87 (m, 1H), 1.85-1.70 (m, 1H), 1.59-1.44 (m, 4H), 1.26 (d, J = 6.5 Hz, 3H), 0.99 (t, J = 7.4 Hz, 3H), 0.91 (t, J = 7.5 Hz, 3H), 0.84 (t, J = 7.4 Hz, 3H). |
| 96 | (Thin film) 3369, 2962, 2936, 1735, 1650, 1528 | ESIMS m/z 473 ([M + H]$^+$) | $^1$H NMR (400 MHz, CDCl$_3$) δ 12.19 (d, J = 0.7 Hz, 1H), 8.47 (d, J = 7.8 Hz, 1H), 7.99 (d, J = 5.2 Hz, 1H), 7.30-7.23 (m, 2H), 7.20-7.13 (m, 3H), 6.87 (d, J = 5.2 Hz, 1H), 5.26-5.18 (m, 1H), 4.66-4.57 (m, 1H), 3.95 (s, 3H), 3.42 (dt, J = 8.8, 6.4 Hz, 1H), 3.30 (dt, J = 8.8, 6.5 Hz, 1H), 3.21-3.14 (m, 1H), 2.81 (dd, J = 13.8, 7.3 Hz, 1H), 2.68 (dd, J = 13.8, 6.9 Hz, 1H), 2.20 (ddd, J = 10.8, 7.0, 3.8 Hz, 1H), 1.65-1.55 (m, 4H), 1.51 (d, J = 7.2 Hz, 3H), 1.29 (d, J = 6.5 Hz, 3H), 0.96 (t, J = 7.4 Hz, 3H), 0.82 (t, J = 7.4 Hz, 3H). |
| 97 | (Thin film) 3370, 2963, 2937, 1736, 1649, 1528 | ESIMS m/z 445 ([M + H]$^+$) | $^1$H NMR (400 MHz, CDCl$_3$) δ 12.19 (d, J = 0.6 Hz, 1H), 8.48 (d, J = 7.9 Hz, 1H), 7.99 (d, J = 5.2 Hz, 1H), 7.29-7.24 (m, 2H), 7.22-7.13 (m, 3H), 6.87 (d, J = 5.2 Hz, 1H), 5.20-5.12 (m, 1H), 4.70-4.61 (m, 1H), 3.95 (s, 3H), 3.37-3.31 (m, 2H), 3.31-3.23 (m, 2H), 2.68 (dd, J = 11.4, 7.3 Hz, 2H), 2.15 (dq, J = 14.1, 5.7 Hz, 1H), 1.59-1.54 (m, 2H), 1.53 (d, J = 7.2 Hz, 3H), 1.31 (d, J = 6.4 Hz, 3H), 0.89 (t, J = 7.4 Hz, 3H). |
| 98 | (Thin film) 3370, 2968, 2936, 1734, 1650, 1527 | ESIMS m/z 459 ([M + H]$^+$) | $^1$H NMR (400 MHz, CDCl$_3$) δ 12.18 (d, J = 0.6 Hz, 1H), 8.52 (d, J = 8.6 Hz, 1H), 7.99 (d, J = 5.2 Hz, 1H), 7.31-7.23 (m, 2H), 7.23-7.16 (m, 1H), 7.16-7.11 (m, 2H), 6.87 (dd, J = 5.3, 0.6 Hz, 1H), 5.23-5.13 (m, 1H), 4.72-4.63 (m, 1H), 3.95 (s, 3H), 3.34-3.29 (m, 2H), 3.26 (tt, J = 6.6, 3.1 Hz, 2H), 2.67 (dd, J = 7.4, 2.8 Hz, 2H), 2.16-1.98 (m, 2H), 1.88 (dp, J = 14.6, 7.4 Hz, 1H), 1.60-1.48 (m, 2H), 1.32 (d, J = 6.5 Hz, 3H), 1.04 (t, J = 7.5 Hz, 3H), 0.90 (t, J = 7.4 Hz, 3H). |
| 99 | (Thin film) 3365, 2969, 2937, 1734, 1651, 1527 | ESIMS m/z 459 ([M + H]$^+$) | $^1$H NMR (400 MHz, CDCl$_3$) δ 12.28 (d, J = 0.6 Hz, 1H), 8.56 (s, 1H), 7.97 (d, J = 5.2 Hz, 1H), 7.30-7.20 (m, 2H), 7.20-7.16 (m, 1H), 7.16-7.11 (m, 2H), 6.86 (d, J = 5.2 Hz, 1H), 5.21-5.09 (m, 1H), 3.94 (s, 3H), 3.36-3.17 (m, 4H), 2.70-2.61 (m, 2H), 2.10 (q, J = 6.5 Hz, 1H), 1.69 (d, J = 3.8 Hz, 6H), 1.60-1.46 (m, 2H), 1.29 (d, J = 6.5 Hz, 3H), 0.89 (t, J = 7.4 Hz, 3H). |
| 100 | (Thin film) 3365, 2962, 2936, 1734, 1652, 1527 | ESIMS m/z 487 ([M + H]$^+$) | $^1$H NMR (400 MHz, CDCl$_3$) δ 12.29 (d, J = 0.6 Hz, 1H), 8.48 (s, 1H), 7.98 (d, J = 5.2 Hz, 1H), 7.22 (s, 2H), 7.17-7.12 (m, 3H), 6.87 (d, J = 5.2 Hz, 1H), 5.19-5.08 (m, 1H), 3.94 (s, 3H), 3.31 (td, J = 6.6, 3.7 Hz, 2H), 3.17 (td, J = 6.4, 3.3 Hz, 1H), 2.79 (dd, J = 14.5, 5.9 Hz, 1H), 2.59 (dd, J = 14.5, 7.3 Hz, 1H), 2.20-2.10 (m, |

TABLE 2-continued

Analytical Data

| *Cmpd. No. | IR (cm⁻¹) | MASS | NMR (¹H, ¹³C or ¹⁹F) |
|---|---|---|---|
| 101 | | HRMS-ESI m/z ([M + H]⁺) calcd for $C_{29}H_{43}N_2O_5$, 499.3172; found, 499.3173. | 1H), 1.61 (d, J = 6.7 Hz, 6H), 1.23 (d, J = 6.4 Hz, 3H), 0.89 (t, J = 7.4 Hz, 3H), 0.82 (t, J = 7.4 Hz, 3H), 1.60-1.35 (m, 4H). ¹H NMR (400 MHz, CDCl₃) δ 12.19 (s, 1H), 8.50 (d, J = 7.8 Hz, 1H), 7.98 (d, J = 5.2 Hz, 1H), 7.34-7.22 (m, 2H), 7.22-7.09 (m, 3H), 6.85 (d, J = 5.1 Hz, 1H), 5.18-5.03 (m, 1H), 4.74-4.58 (m, 1H), 3.93 (s, 3H), 2.65-2.49 (m, 2H), 1.72-1.43 (m, 8H), 1.41-1.23 (m, 3H), 1.23 (d, J = 6.4 Hz, 3H), 1.18-0.99 (m, 3H), 0.90-0.78 (m, 9H). ¹³C NMR (101 MHz, CDCl₃) δ 171.69, 168.67, 155.36, 148.76, 142.64, 140.47, 130.51, 128.34, 128.27, 125.67, 125.66, 109.45, 74.04, 56.06, 48.20, 41.06, 40.19, 36.31, 35.70, 30.31, 30.10, 26.08, 24.04, 23.46, 22.31, 18.40, 17.92, 12.49. |
| 102 | (Thin film) 3373, 2957, 2934, 1734, 1650, 1528 | ESIMS m/z 469 ([M + H]⁺) | ¹H NMR (400 MHz, CDCl₃) δ 12.16 (d, J = 0.6 Hz, 1H), 8.50 (d, J = 7.8 Hz, 1H), 7.99 (d, J = 5.3 Hz, 1H), 7.32-7.22 (m, 2H), 7.21-7.10 (m, 3H), 6.87 (d, J = 5.2 Hz, 1H), 5.10-5.00 (m, 1H), 4.72-4.60 (m, 1H), 3.94 (s, 3H), 2.63 (dd, J = 14.2, 5.5 Hz, 1H), 2.49 (dd, J = 14.2, 8.3 Hz, 1H), 2.13-2.03 (m, 1H), 1.68-1.59 (m, 1H), 1.56 (d, J = 7.2 Hz, 3H), 1.54-1.47 (m, 1H), 1.46-1.24 (m, 2H), 1.20 (d, J = 6.4 Hz, 3H), 1.18-1.11 (m, 1H), 0.93 (t, J = 7.4 Hz, 2H), 0.89-0.77 (m, 2H), 0.69-0.55 (m, 1H), 0.45-0.30 (m, 2H), −0.01−−0.12 (m, 1H). |
| 103 | (Thin film) 3370, 2935, 1733, 1649, 1529 | ESIMS m/z 523 ([M + H]⁺) | ¹H NMR (400 MHz, CDCl₃) δ 12.11 (d, J = 0.6 Hz, 1H), 8.46 (d, J = 7.9 Hz, 1H), 7.81 (d, J = 5.2 Hz, 1H), 7.25-7.17 (m, 2H), 7.17-7.10 (m, 1H), 7.06-6.90 (m, 6H), 6.75 (d, J = 5.2 Hz, 1H), 5.12 (qd, J = 6.4, 4.4 Hz, 1H), 4.80-4.69 (m, 1H), 3.95-3.92 (m, 1H), 3.91 (s, 3H), 2.88 (dd, J = 13.5, 4.9 Hz, 1H), 2.66 (dd, J = 14.1, 5.7 Hz, 1H), 2.55 (dd, J = 14.1, 8.8 Hz, 1H), 2.24 (dd, J = 13.5, 9.8 Hz, 1H), 2.01-1.87 (m, 2H), 1.85-1.74 (m, 1H), 1.58 (d, J = 7.2 Hz, 3H), 1.27 (d, J = 6.4 Hz, 3H), 0.83 (t, J = 7.4 Hz, 3H). |
| 104 | (Thin film) 3372, 2936, 1739, 1650, 1533 | ESIMS m/z 431 ([M + H]⁺) | ¹H NMR (400 MHz, CDCl₃) δ 12.08 (s, 1H), 8.47 (s, 1H), 7.99 (d, J = 5.3 Hz, 1H), 7.30-7.24 (m, 2H), 7.22-7.18 (m, 1H), 7.18-7.13 (m, 2H), 6.87 (d, J = 5.2 Hz, 1H) 5.19 (qd, J = 6.5, 4.6 Hz 1H), 4.23-4.05 (m, 2H), 3.94 (s, 3H), 3.39-3.21 (m, 4H), 2.67 (dd, J = 11.6, 7.3 Hz, 2H), 2.22-2.11 (m, 1H), 1.55 (dtd, J = 13.9, 7.4, 6.5 Hz, 2H), 1.32 (d, J = 6.4 Hz, 3H), 0.90 (t, J = 7.4 Hz, 3H). |
| 105 | | HRMS-ESI m/z ([M + H]⁺) calcd for $C_{31}H_{38}FN_2O_7$, 569.2658; found, 569.2662 | ¹H NMR (400 MHz, CDCl₃) δ 12.15 (s, 1H), 8.43 (d, J = 7.8 Hz, 1H), 7.97 (d, J = 5.2 Hz, 1H), 7.18 (dd, J = 8.5, 5.5 Hz, 2H), 7.06-7.02 (m, 2H), 6.97 (t, J = 8.7 Hz, 2H), 6.86 (d, J = 5.2 Hz, 1H), 6.77 (d, J = 8.6 Hz, 2H), |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 5.13 (qd, J = 6.4, 4.5 Hz, 1H), 4.60-4.47 (m, 2H), 3.93 (s, 3H), 3.56 (dd, J = 10.0, 5.3 Hz, 1H), 3.47-3.36 (m, 2H), 3.32 (dt, J = 9.4, 7.0 Hz, 1H), 2.98 (dd, J = 14.5, 6.3 Hz, 1H), 2.70 (dd, J = 14.5, 7.1 Hz, 1H), 2.44-2.34 (m, 1H), 2.27 (s, 3H), 1.42 (d, J = 7.2 Hz, 3H), 1.30 (d, J = 6.4 Hz, 3H), 1.13 (t, J = 7.0 Hz, 3H). |
| 106 | (Thin film) 3383, 2935, 1739, 1650, 1527 | HRMS-ESI m/z ([M + H]$^+$) calcd for C$_{25}$H$_{34}$N$_2$O$_7$, 475.2439; found, 475.2441. | $^1$H NMR (400 MHz, CDCl$_3$) δ 12.13 (d, J = 0.6 Hz, 1H), 8.77 (d, J = 8.5 Hz, 1H), 8.01 (d, J = 5.2 Hz, 1H), 7.30-7.24 (m, 2H), 7.22-7.13 (m, 3H), 6.87 (d, J = 5.2 Hz, 1H), 5.22-5.13 (m, 1H), 4.85 (dt, J = 8.6, 3.3 Hz, 1H), 3.96 (dd, J = 9.5, 3.4 Hz, 1H), 3.93 (s, 3H), 3.74 (dd, J = 9.5, 3.3 Hz, 1H), 3.40 (d, J = 1.0 Hz, 3H), 3.39-3.22 (m, 4H), 2.73-2.59 (m, 2H), 2.15-2.07 (m, 1H), 1.61-1.47 (m, 2H), 1.31 (d, J = 6.6 Hz, 3H), 0.91 (t, J = 7.4 Hz, 3H). |
| 107 | | ESIMS m/z 619 ([M + H]$^+$) | $^1$H NMR (400 MHz, CDCl$_3$) δ 12.07 (s, 1H), 8.76 (d, J = 8.7 Hz, 1H), 7.88 (d, J = 5.1 Hz, 1H), 7.39 (d, J = 8.0 Hz, 2H), 7.00 (dd, J = 8.4, 5.0 Hz, 4H), 6.91 (t, J = 8.7 Hz, 2H), 6.74 (d, J = 5.1 Hz, 1H), 5.71 (ddd, J = 17.6, 10.1, 8.0 Hz, 1H), 5.18 (m, 1H), 5.01 (dd, J = 10.3, 1.4 Hz, 1H), 4.92-4.79 (m, 2H), 4.01 (dd, J = 9.4, 3.3 Hz, 1H), 3.89 (s, 3H), 3.72 (dd, J = 9.4, 3.4 Hz, 1H), 3.38 (s, 3H), 2.91 (q, J = 9.9 Hz, 1H), 2.75-2.56 (m, 2H), 2.47 (m, 2H), 1.98 (m, 1H), 1.31 (d, J = 6.4 Hz, 3H). $^{13}$C NMR (101 MHz, CDCl$_3$) δ 169.14, 169.04, 161.33 (d, J = 243 Hz), 155.27, 148.74, 144.6, 140.62, 138.73, 135.87 (d, J = 3 Hz), 130.29 (d, J = 7 Hz), 129.39, 127.93 (q, J = 32 Hz), 124.81 (q, J = 4 Hz), 124.36 (q, J = 270 Hz), 116.99, 115.18, (d, J = 21 Hz), 109.38, 72.90, 72.09, 59.38, 55.98, 52.57, 48.35, 45.16, 37.64, 32.39, 17.74. |
| 108 | | ESIMS m/z 589 ([M + H]$^+$) | $^1$H NMR (400 MHz, CDCl$_3$) δ 12.09 (s, 1H), 8.43 (d, J = 7.9 Hz, 1H), 7.87 (d, J = 5.1 Hz, 1H), 7.39 (d, J = 7.9 Hz, 2H), 7.04-6.96 (m, 4H), 6.91 (t, J = 8.7 Hz, 2H), 6.77 (d, J = 5.1 Hz, 1H), 5.69 (ddd, J = 17.2, 10.3, 8.5 Hz, 1H), 5.17 (m, 1H), 5.03 (dd, J = 10.3, 1.3 Hz, 1H), 4.84 (d, J = 20 Hz, 1H), 4.73 (m, 1H), 3.91 (s, 3H), 2.90 (dd, J = 13.1, 5.1 Hz, 1H), 2.72 (dd, J = 14.1, 6.3 Hz, 1H), 2.60 (dd, J = 14.1, 7.8 Hz, 1H), 2.56-2.48 (m, 1H), 2.46 (m, 1H), 1.97 (m, 1H), 1.56 (d, J = 7.3 Hz, 3H), 1.31 (d, J = 6.4 Hz, 3H). $^{13}$C NMR (101 MHz, CDCl$_3$) δ 171.33, 168.83, 161.34 (d, J = 243 Hz), 155.36, 148.76, 144.44, 140.49, 138.45, 135.83 (d, J = 3 Hz), 130.23, 130.22 (d, J = 7 Hz), 129.32, 127.93 (q, J = 32 Hz), 124.81 (q, J = 4 Hz), 124.36 (q, J = 270 Hz), 116.99, 115.18, (d, J = 21 Hz), 109.40, 72.63, 56.02, |

TABLE 2-continued

Analytical Data

| *Cmpd. No. | IR (cm⁻¹) | MASS | NMR ($^1$H, $^{13}$C or $^{19}$F) |
|---|---|---|---|
| 109 | | ESIMS m/z 575 ([M + H]⁺) | 48.13, 45.33, 37.96, 32.69, 18.10, 17.63.<br>$^1$H NMR (400 MHz, CDCl$_3$) δ 12.02 (bs, 1H), 8.48 (t, J = 5.7 Hz, 1H), 7.91 (d, J = 5.3 Hz, 1H), 7.41 (d, J = 8.0 Hz, 2H), 7.00 (bdd, J = 8.0, 6.4 Hz, 4H), 6.92 (m, 2H), 6.81 (d, J = 5.1 Hz, 1H), 5.69 (ddd, J = 17.1, 10.2, 8.7 Hz, 1H), 5.17 (m, 1H), 5.04 (dd, J = 10.3, 1.3 Hz, 1H), 4.85 (dd, J = 17.1, 0.9 Hz, 1H), 4.24 (dd, J = 18.1, 6.1 Hz, 1H), 4.13 (dd, J = 18.1, 5.8 Hz, 1H), 3.92 (s, 3H), 2.93 (dd, J = 13.4, 5.5 Hz, 1H), 2.73 (dd, J = 14.1, 6.3 Hz, 1H), 2.65-2.52 (m, 2H), 2.43 (m, 1H), 2.02 (m, 1H), 1.31 (d, J = 6.4 Hz, 3H).<br>$^{13}$C NMR (101 MHz, CDCl$_3$) δ 169.47, 168.34, 161.33 (d, J = 244.3 Hz), 155.37, 148.71, 144.40, 140.61, 138.31, 135.87 (d, J = 3.3 Hz), 130.25 (d, J = 8.0 Hz), 130.23, 129.36, 128.09 (q, J = 32.3 Hz), 124.91 (q, J = 3.8 Hz), 124.32 (q, J = 270 Hz), 117.25, 115.24 (d, J = 21.1 Hz), 109.50, 73.07, 56.05, 47.81, 45.56, 41.22, 38.27, 32.92, 17.58. |
| 110 | | ESIMS m/z 621 ([M + H]⁺) | $^1$H NMR (400 MHz, CDCl$_3$) δ 12.06 (s, 1H), 8.74 (d, J = 8.7 Hz, 1H), 7.77 (d, J = 5.1 Hz, 1H), 7.41 (d, J = 8.0 Hz, 2H), 7.10-7.01 (m, 4H), 6.99-6.90 (m, 2H), 6.65 (d, J = 5.1 Hz, 1H), 5.16-5.09 (m, 1H), 4.86 (dt, J = 8.7, 3.1 Hz, 1H), 4.05 (dd, J = 9.4, 3.0 Hz, 1H), 3.87 (s, 3H), 3.73 (dd, J = 9.4, 3.1 Hz, 1H), 3.39 (s, 3H), 2.94 (dd, J = 13.4, 4.1 Hz, 1H), 2.64 (dd, J = 13.9, 5.0 Hz, 1H), 2.54 (dd, J = 13.9, 9.5 Hz, 1H), 2.19 (dd, J = 13.3, 10.3 Hz, 1H), 1.93-1.74 (m, 2H), 1.28 (d, J = 6.4 Hz, 3H), 1.28-1.23 (m, 2H), 0.81 (t, J = 7.3 Hz, 3H).<br>$^{13}$C NMR (101 MHz, CDCl$_3$) δ 168.92, 168.1, 161.38 (d, J = 242 Hz), 156.68, 149.25, 145.8, 139.52, 136.14 (d, J = 3 Hz), 130.49, 130.39 (d, J = 8 Hz), 129.42, 127.83 (q, J = 31 Hz), 124.87 (q, J = 3 Hz), 124.39 (q, J = 270 Hz), 115.25, (d, J = 21 Hz), 109.24, 73.10, 71.75, 59.38, 56.63, 53.04, 45.51, 40.76, 37.32, 31.41, 23.25, 18.44, 12.38. |
| 111 | | ESIMS m/z 577 ([M + H]⁺) | $^1$H NMR (400 MHz, CDCl$_3$) δ 11.99 (d, J = 0.6 Hz, 1H), 8.49 (t, J = 5.9 Hz, 1H), 7.82 (d, J = 5.3 Hz, 1H), 7.41 (d, J = 7.9 Hz, 2H), 7.08-6.98 (m, 4H), 6.97-6.91 (m, 2H), 6.73 (d, J = 5.3 Hz, 1H), 5.18-5.10 (m, 1H), 4.30 (dd, J = 18.0, 6.3 Hz, 1H), 4.17 (dd, J = 18.0, 5.8 Hz, 1H), 3.90 (s, 3H), 2.92 (dd, J = 13.4, 5.0 Hz, 1H), 2.64 (dd, J = 13.9, 5.8 Hz, 1H), 2.56 (dd, J = 14.0, 8.7 Hz, 1H), 2.33 (dd, J = 13.4, 9.7 Hz, 1H), 1.90 (m, 1H), 1.79 (m, 1H), 1.37-1.22 (m, 2H), 1.29 (d, J = 6.4 Hz, 3H), 0.85 (t, J = 7.3 Hz, 3H).<br>$^{13}$C NMR (101 MHz, CDCl$_3$) δ |

TABLE 2-continued

| | | | Analytical Data |
|---|---|---|---|
| *Cmpd. No. | IR (cm$^{-1}$) | MASS | NMR ($^1$H, $^{13}$C or $^{19}$F) |
| | | | 169.51, 168.40, 161.37 (d, J = 243 Hz), 155.28, 148.64, 145.67, 140.54, 136.05 (d, J = 3 Hz), 130.29 (d, J = 8.0 Hz), 130.13, 129.26, 127.93 (q, J = 32 Hz), 124.93 (q, J = 4 Hz), 124.36 (q, J = 270 Hz), 115.27 (d, J = 21 Hz), 109.40, 73.08, 55.99, 45.36, 41.27, 41.00, 37.50, 31.99, 23.17, 18.51, 12.35. |
| 112 | IR (neat) 3371, 2936, 1734, 1650, 1529, 1259 | HRMS-ESI m/z [M]+ calcd for C$_{31}$H$_{35}$F$_3$N$_2$O$_6$, 588.2447; found, 588.2454. | $^1$H NMR (400 MHz, CDCl$_3$) δ 12.10 (s, 1H), 8.44 (d, J = 7.8 Hz, 1H), 7.82 (d, J = 5.2 Hz, 1H), 7.22-7.14 (m, 3H), 7.11-7.04 (m, 4H), 6.99-6.95 (m, 2H), 6.75 (d, J = 5.1 Hz, 1H), 5.17-5.09 (m, 1H), 4.78-4.67 (m, 1H), 3.92 (s, 3H), 2.85 (dd, J = 13.5, 5.2 Hz, 1H), 2.71-2.55 (m, 2H), 2.26 (dd, J = 13.5, 9.5 Hz, 1H), 1.98-1.90 (m, 1H), 1.83-1.72 (m, 1H), 1.57 (d, J = 7.2 Hz, 3H), 1.36-1.27 (m, 2H), 1.29 (d, J = 6.3 Hz, 3H), 0.84 (t, J = 7.4 Hz, 3H) |
| 113 | | HRMS-ESI m/z ([M + H]$^+$) calcd for C$_{23}$H$_{31}$N$_2$O$_5$, 415.2233; found, 415.2233. | $^1$H NMR (400 MHz, CDCl$_3$) δ 12.17 (s, 1H), 8.53 (d, J = 7.9 Hz, 1H), 7.99 (d, J = 5.2 Hz, 1H), 7.33-7.23 (m, 2H), 7.23-7.15 (m, 1H), 7.15-7.04 (m, 2H), 6.87 (d, J = 5.2 Hz, 1H), 5.06 (qd, J = 6.4, 3.7 Hz, 1H), 4.83-4.60 (m, 1H), 3.94 (s, 3H), 2.67 (dd, J = 13.6, 6.5 Hz, 1H), 2.50 (dd, J = 13.6, 7.8 Hz, 1H), 1.94-1.79 (m, 1H), 1.57 (d, J = 7.2 Hz, 3H), 1.38-1.28 (m, 4H), 1.24 (d, J = 6.5 Hz, 3H), 0.90-0.80 (m, 3H). $^{13}$C NMR (101 MHz, CDCl$_3$) δ 171.59, 168.75, 155.38, 148.77, 140.67, 140.49, 130.51, 129.08, 128.34, 125.94, 109.44, 73.46, 56.08, 48.19, 44.50, 36.24, 31.50, 20.27, 18.50, 16.19, 14.25. |
| 114 | | HRMS-ESI m/z ([M + H]$^+$) calcd for C$_{22}$H$_{27}$N$_2$O$_7$, 431.1818; found, 431.1814. | $^1$H NMR (400 MHz, CDCl$_3$) δ 12.12 (d, J = 0.6 Hz, 1H), 8.48 (d, J = 7.9 Hz, 1H), 7.99 (d, J = 5.2 Hz, 1H), 7.30-7.23 (m, 2H), 7.23-7.18 (m, 1H), 7.16-7.11 (m, 2H), 6.87 (dd, J = 5.2, 0.7 Hz, 1H), 5.43-5.11 (m, 1H), 4.85-4.55 (m, 1H), 3.94 (s, 3H), 3.54 (s, 3H), 2.97-2.81 (m, 3H), 1.52 (d, J = 7.2 Hz, 3H), 1.38 (d, J = 6.4 Hz, 3H). $^{13}$C NMR (101 MHz, CDCl$_3$) δ 172.43, 171.25, 168.76, 155.37, 148.76, 140.51, 138.17, 130.44, 128.76, 128.54, 126.65, 109.48, 72.19, 56.08, 52.97, 51.65, 47.96, 34.29, 18.25, 17.85. |
| 115 | (Thin film) 3372, 2958, 1734, 1650, 1528 | ESIMS m/z 473 ([M + H]$^+$) | $^1$H NMR (400 MHz, CDCl$_3$) δ 12.17 (d, J = 0.6 Hz, 1H), 8.44 (d, J = 8.0 Hz, 1H), 7.98 (d, J = 5.3 Hz, 1H), 7.28-7.20 (m, 2H), 6.94-6.81 (m, 4H), 5.17-5.08 (m, 1H), 4.65-4.54 (m, 1H), 4.29 (td, J = 6.5, 3.1 Hz, 1H), 3.94 (s, 3H), 1.91-1.84 (m, 1H), 1.77 (ddd, J = 14.1, 7.5, 6.5 Hz, 1H), 1.71-1.61 (m, 1H), 1.60-1.50 (m, 1H), 1.43 (d, J = 7.2 Hz, 3H), 1.42-1.36 (m, 1H), 1.36-1.32 (m, 1H), 1.31 (d, J = 6.4 Hz, 6H), 0.94 (t, J = 7.4 Hz, 3H), 0.90 (t, J = 7.1 Hz, 3H). |

TABLE 2-continued

| *Cmpd. No. | IR (cm$^{-1}$) | MASS | NMR ($^1$H, $^{13}$C or $^{19}$F) |
|---|---|---|---|
| 116 | (Thin film) 3371, 2936, 1734, 1650, 1528 | ESIMS m/z 473 ([M + H]$^+$) | $^1$H NMR (400 MHz, CDCl$_3$) δ 12.14 (d, J = 0.6 Hz, 1H), 8.49 (d, J = 7.8 Hz, 1H), 7.99 (d, J = 5.2 Hz, 1H), 7.29-7.20 (m, 2H), 6.95-6.84 (m, 4H), 5.32-5.20 (m, 1H), 4.79-4.64 (m, 1H), 4.36-4.27 (m, 1H), 3.95 (s, 3H), 2.02-1.95 (m, 1H), 1.76-1.65 (m, 2H), 1.56 (d, J = 7.1 Hz, 3H), 1.53-1.45 (m, 1H), 1.34 (d, J = 6.5 Hz, 3H), 1.34-1.16 (m, 5H), 0.95 (t, J = 7.4 Hz, 3H), 0.83 (t, J = 7.1 Hz, 3H). |
| 117 | (Thin film) 3371, 2936, 1734, 1649, 1529 | ESIMS m/z 507 ([M + H]$^+$) | $^1$H NMR (400 MHz, CDCl$_3$) δ 12.17 (d, J = 0.6 Hz, 1H), 8.45 (d, J = 7.9 Hz, 1H), 7.97 (d, J = 5.2 Hz, 1H), 7.34-7.26 (m, 2H), 7.24-7.16 (m, 5H), 6.93-6.84 (m, 2H), 6.76-6.68 (m, 2H), 5.12 (qd, J = 6.4, 4.9 Hz, 1H), 4.62-4.51 (m, 1H), 4.29 (td, J = 7.0, 2.6 Hz, 1H), 3.93 (s, 3H), 2.89 (dd, J = 14.4, 6.7 Hz, 1H), 2.75 (dd, J = 14.4, 6.9 Hz, 1H), 2.30 (tdd, J = 7.0, 4.9, 2.6 Hz, 1H), 1.83-1.59 (m, 2H), 1.42 (d, J = 7.2 Hz, 3H), 1.31 (d, J = 6.5 Hz, 3H), 0.90 (t, J = 7.3 Hz, 3H). |
| 118 | (Thin film) 3371, 2938, 1734, 1649, 1529 | ESIMS m/z 507 ([M + H]$^+$) | $^1$H NMR (400 MHz, CDCl$_3$) δ 12.14 (d, J = 0.6 Hz, 1H), 8.51 (d, J = 7.9 Hz, 1H), 7.99 (d, J = 5.1 Hz, 1H), 7.28-7.23 (m, 2H), 7.23-7.11 (m, 3H), 7.01-6.90 (m, 3H), 6.90-6.79 (m, 3H), 5.29 (qd J = 6.5, 4.1 Hz, 1H), 4.80-4.68 (m, 1H), 4.25 (td, J = 6.6, 3.5 Hz, 1H), 3.94 (s, 3H), 2.88 (dd, J = 13.8, 7.7 Hz, 1H), 2.70 (dd, J = 13.8, 6.6 Hz, 1H), 2.36-2.25 (m, 1H), 1.77-1.66 (m, 2H), 1.60 (d, J = 7.2 Hz, 3H), 1.38 (d, J = 6.5 Hz, 3H), 0.86 (t, J = 7.5 Hz, 3H). |
| 119 | | HRMS-ESI m/z ([M + H]$^+$) calcd for C$_{26}$H$_{29}$N$_2$O$_5$, 449.2076; found, 449.2070 | $^1$H NMR (400 MHz, CDCl$_3$) δ 12.16 (s, 1H), 8.45 (d, J = 8.0 Hz, 1H), 7.99 (d, J = 5.2 Hz, 1H), 7.23-6.93 (m, 10H), 6.86 (d, J = 5.3 Hz, 1H), 5.31-5.20 (m, 1H), 4.71-4.55 (m, 1H), 3.92 (s, 3H), 3.10-2.97 (m, 2H), 2.94-2.84 (m, 1H), 1.31 (d, J = 7.2 Hz, 3H), 1.24 (d, J = 6.3 Hz, 3H). $^{13}$C NMR (101 MHz, CDCl$_3$) δ 171.47, 168.71, 155.41, 148.81, 140.50, 140.19, 139.49, 130.47, 129.00, 128.91, 128.23, 128.13, 126.72, 126.08, 109.50, 73.90, 56.08, 53.09, 48.07, 38.45, 18.43, 18.04. |
| 120 | | HRMS-ESI m/z ([M + H]$^+$) calcd for C$_{23}$H$_{31}$N$_2$O$_5$, 415.2233; found, 415.2231. | $^1$H NMR (400 MHz, CDCl$_3$) δ 12.14 (s, 1H), 8.39 (d, J = 8.1 Hz, 1H), 7.98 (d, J = 5.2 Hz, 1H), 7.26-7.13 (m, 5H), 6.86 (d, J = 5.2 Hz, 1H), 5.32-5.10 (m, 1H), 4.63-4.45 (m, 1H), 3.93 (s, 3H), 2.71 (ddd, J = 10.3, 7.1, 4.7 Hz, 1H), 1.74-1.55 (m, 2H), 1.34-1.26 (m, 2H), 1.24 (d, J = 6.3 Hz, 3H), 1.17 (d, J = 7.2 Hz, 3H), 1.14-1.03 (m, 2H), 0.80 (t, J = 7.2 Hz, 3H). $^{13}$C NMR (101 MHz, CDCl$_3$) δ 171.56, 168.57, 155.36, 148.74, 141.19, 140.42, 130.50, 128.58, 128.19, 126.53, 109.40, 75.09, |

TABLE 2-continued

Analytical Data

| *Cmpd. No. | IR (cm$^{-1}$) | MASS | NMR ($^1$H, $^{13}$C or $^{19}$F) |
|---|---|---|---|
| 121 | | HRMS-ESI m/z ([M + H]$^+$) calcd for C$_{26}$H$_{28}$ClN$_2$O$_5$, 483.1686; found, 483.1691. | 56.06, 51.17, 47.97, 31.44, 29.46, 22.62, 18.38, 17.91, 13.89.<br>$^1$H NMR (400 MHz, CDCl$_3$) δ 12.13 (s, 1H), 8.42 (d, J = 8.0 Hz, 1H), 8.01 (d, J = 5.2 Hz, 1H), 7.20-7.04 (m, 7H), 6.95-6.81 (m, 3H), 5.34-5.17 (m, 1H), 4.71-4.59 (m, 1H), 3.94 (s, 3H), 3.06-2.92 (m, 2H), 2.86 (dd, J = 12.4, 8.6 Hz, 1H), 1.30 (d, J = 7.2 Hz, 3H), 1.25 (d, J = 6.3 Hz, 3H). $^{13}$C NMR (101 MHz, CDCl$_3$) δ 171.44, 168.72, 155.42, 148.81, 140.50, 139.66, 137.92, 131.83, 130.44, 130.30, 128.85, 128.32, 128.20, 126.86, 109.49, 73.85, 56.10, 53.07, 48.06, 37.78, 18.41, 17.97. |
| 122 | | HRMS-ESI m/z ([M + H]$^+$) calcd for C$_{23}$H$_{31}$N$_2$O$_5$, 415.2233; found, 415.2232 | $^1$H NMR (400 MHz, CDCl$_3$) δ 12.17 (s, 1H), 8.52 (d, J = 7.8 Hz, 1H), 7.97 (d, J = 5.2 Hz, 1H), 7.34-7.21 (m, 2H), 7.21-7.06 (m, 3H), 6.86 (d, J = 5.3 Hz, 1H), 5.05 (qd, J = 6.4, 4.4 Hz, 1H), 4.74-4.57 (m, 1H), 3.93 (s, 3H), 2.67 (dd, J = 14.2, 5.4 Hz, 1H), 2.53 (dd, J = 14.2, 8.1 Hz, 1H), 2.03-1.90 (m, 1H), 1.85-1.75 (m, 1H), 1.53 (d, J = 7.2 Hz, 3H), 1.22 (d, J = 6.4 Hz, 3H), 1.00 (d, J = 6.9 Hz, 3H), 0.92 (d, J = 6.9 Hz, 3H). $^{13}$C NMR (101 MHz, CDCl$_3$) δ 171.52, 168.74, 155.37, 148.76, 141.49, 140.47, 130.47, 128.91, 128.35, 125.83, 109.45, 73.32, 56.05, 50.32, 48.20, 32.31, 27.41, 21.41, 19.12, 18.32, 17.58. |
| 123 | | | $^1$H NMR (400 MHz, CDCl$_3$) δ 12.14 (s, 1H), 8.40 (d, J = 8.0 Hz, 1H), 7.99 (d, J = 5.2 Hz, 1H), 7.26-7.14 (m, 5H), 6.86 (d, J = 5.2 Hz, 1H), 5.35-5.10 (m, 1H), 4.57 (dq, J = 8.0, 7.2 Hz, 1H), 3.94 (s, 3H), 2.68 (ddd, J = 10.4, 7.0, 4.6 Hz, 1H), 1.75-1.54 (m, 2H), 1.46 (dp, J = 13.3, 6.7 Hz, 1H), 1.24 (d, J = 6.3 Hz, 3H), 1.19 (d, J = 7.2 Hz, 3H), 1.12-0.87 (m, 2H), 0.80 (dd, J = 6.6, 5.4 Hz, 6H). $^{13}$C NMR (101 MHz, CDCl$_3$) δ 171.56, 168.57, 155.36, 148.75, 141.17, 140.42, 130.50, 128.60, 128.20, 126.54, 109.41, 75.06, 56.06, 51.39, 47.96, 36.46, 29.45, 27.95, 22.72, 22.18, 18.35, 17.93. |
| 124 | (Thin film) 3369, 2972, 1730, 1649, 1527, 1263, 1140 | HRMS-ESI m/z ([M + H]$^+$) calcd for C$_{26}$H$_{37}$N$_2$O$_6$, 473.2649; found, 473.2646 | $^1$H NMR (400 MHz, CDCl$_3$) δ 12.17 (s, 1H), 8.40 (d, J = 7.9 Hz, 1H), 7.97 (d, J = 5.2 Hz, 1H), 7.26-7.06 (m, 5H), 6.85 (d, J = 5.2 Hz, 1H), 5.41 (qd, J = 6.6, 2.9 Hz, 1H), 4.53-4.38 (m, 1H), 3.93 (s, 3H), 3.29 (td, J = 6.5, 2.5 Hz, 2H), 2.96 (dd, J = 14.8, 5.0 Hz, 1H), 2.76 (dd, J = 14.8, 7.4 Hz, 1H), 2.26 (ddd, J = 7.6, 5.1, 2.9 Hz, 1H), 1.60-1.47 (m, 2H), 1.38 (d, J = 6.6 Hz, 3H), 1.24 (d, J = 7.2 Hz, 3H), 1.23 (s, 3H), 1.17 (s, 3H), 0.92 (t, J = 7.4 Hz, 3H). |
| 125 | (Thin film) 3368, 2937, 1735, 1648, | HRMS-ESI m/z ([M + H]$^+$) calcd for C$_{27}$H$_{31}$N$_2$O$_6$, | $^1$H NMR (400 MHz, CDCl$_3$) δ 12.13 (s, 1H), 8.49 (d, J = 8.0 Hz, 1H), 7.97 (d, J = 5.2 Hz, |

TABLE 2-continued

| | | Analytical Data | |
|---|---|---|---|
| *Cmpd. No. | IR (cm$^{-1}$) | MASS | NMR ($^1$H, $^{13}$C or $^{19}$F) |
| | 1528, 1240, 1148 | 480.2209; found, 480.221 | 1H), 7.30-7.17 (m, 5H), 7.17-7.12 (m, 2H) 6.92 (tt, J = 7.4, 1.1 Hz, 1H), 6.85 (d, J = 4.7 Hz, 1H), 6.83-6.79 (m, 2H), 5.26 (qd, J = 6.4, 5.0 Hz, 1H), 4.78-4.61 (m, 1H), 3.93 (s, 3H), 3.91-3.86 (m, 2H), 2.84-2.75 (m, 2H), 2.36-2.25 (m, 1H), 1.50 (d, J = 7.2 Hz, 3H), 1.40 (d, J = 6.5 Hz, 3H). |
| 126 | (Thin film) 3369, 2939, 1737, 1649, 1529, 14823, 1465, 1264, 1061 | HRMS-ESI m/z ([M + H]$^+$) calcd for C$_{27}$H$_{29}$Cl$_2$N$_2$O$_6$, 547.1397; found, 547.1407 | $^1$H NMR (400 MHz, CDCl$_3$) δ 12.11 (s, 1H), 8.46 (d, J = 7.9 Hz, 1H), 7.96 (d, J = 5.2 Hz, 1H), 7.35 (d, J = 2.6 Hz, 1H), 7.29-7.23 (m, 2H), 7.23-7.17 (m, 1H), 7.16-7.12 (m, 2H), 7.08 (dd, J = 8.8, 2.6 Hz, 1H), 6.86 (d, J = 5.3 Hz, 1H), 6.62 (d, J = 8.8 Hz, 1H), 5.26 (qd, J = 6.4, 5.1 Hz, 1H), 4.77-4.64 (m, 1H), 3.94 (s, 3H), 3.93-3.81 (m, 2H), 2.87 (dd, J = 13.6, 9.0 Hz, 1H), 2.80 (dd, J = 13.6, 6.0 Hz, 1H), 2.40-2.23 (m, 1H), 1.53 (d, J = 7.2 Hz, 3H), 1.44 (d, J = 6.4 Hz, 3H). |
| 127 | | HRMS-ESI m/z ([M + H]$^+$) calcd for C$_{26}$H$_{27}$Cl$_2$N$_2$O$_5$ 517.1297; found, 517.1286 | $^1$H NMR (400 MHz, CDCl$_3$) δ 12.11 (d, J = 0.6 Hz, 1H), 8.41 (d, J = 7.9 Hz, 1H), 8.01 (d, J = 5.2 Hz, 1H), 7.20 (d, J = 8.2 Hz, 1H), 7.19-7.14 (m, 3H), 7.11-7.06 (m, 2H), 7.05 (d, J = 2.1 Hz, 1H), 6.89 (dd, J = 5.2, 0.7 Hz, 1H), 6.76 (dd, J = 8.2, 2.1 Hz, 1H), 5.29-5.20 (m, 1H), 4.70-4.53 (m, 1H), 3.95 (s, 3H), 3.07-2.91 (m, 2H), 2.90-2.77 (m, 1H), 1.31 (d, J = 7.2 Hz, 3H), 1.25 (d, J = 6.3 Hz, 3H). $^{13}$C NMR (101 MHz, CDCl$_3$) δ 171.41, 168.76, 155.44, 148.83, 140.52, 139.73, 139.19, 132.06, 130.84, 130.41, 130.08, 128.81, 128.44, 128.31, 127.04, 109.52, 73.77, 56.10, 52.80, 48.08, 37.54, 18.36, 17.93. |
| 128 | | HRMS-ESI m/z ([M + H]$^+$) calcd for C$_{27}$H$_{31}$N$_2$O$_5$, 463.2233; found, 463.2214 | $^1$H NMR (400 MHz, CDCl$_3$) δ 12.15 (d, J = 0.6 Hz, 1H), 8.44 (d, J = 8.0 Hz, 1H), 8.01 (d, J = 5.2 Hz, 1H), 7.22-7.11 (m, 5H), 7.02-6.96 (m, 2H), 6.90-6.83 (m, 3H), 5.28-5.18 (m, 1H), 4.71-4.57 (m, 1H), 3.94 (s, 3H), 3.06-2.93 (m, 2H), 2.93-2.81 (m, 1H), 2.26 (s, 3H), 1.32 (d, J = 7.2 Hz, 3H), 1.23 (d, J = 6.3 Hz, 3H). $^{13}$C NMR (101 MHz, CDCl$_3$) δ 171.48, 168.67, 155.41, 148.80, 140.47, 140.33, 136.34, 135.51, 130.50, 128.94, 128.85, 128.11, 126.67, 109.46, 73.89, 56.08, 53.11, 48.05, 37.99, 20.98, 18.43, 18.10. |
| 129 | | HRMS-ESI m/z ([M + H]$^+$) calcd for C$_{26}$H$_{28}$FN$_2$O$_5$, 467.1982; found, 467.1976 | $^1$H NMR (400 MHz, CDCl$_3$) δ 12.13 (d, J = 0.6 Hz, 1H), 8.42 (d, J = 8.0 Hz, 1H), 8.01 (d, J = 5.2 Hz, 1H), 7.20-7.13 (m, 3H), 7.12-7.06 (m, 2H), 6.93-6.82 (m, 5H), 5.36-5.18 (m, 1H), 4.73-4.52 (m, 1H), 3.94 (s, 3H), 3.02 (dd, J = 12.7, 5.5 Hz, 1H), 2.95 (dt, J = 8.8, 5.6 Hz, 1H), 2.85 (dd, |

TABLE 2-continued

Analytical Data

| *Cmpd. No. | IR (cm⁻¹) | MASS | NMR ($^1$H, $^{13}$C or $^{19}$F) |
|---|---|---|---|
| | | | J = 12.6, 8.7 Hz, 1H), 1.30 (d, J = 7.2 Hz, 3H), 1.25 (d, J = 6.3 Hz, 3H).<br>$^{13}$C NMR (101 MHz, CDCl$_3$) δ 171.46, 168.71, 161.33 (d, J = 244.0 Hz), 155.43, 148.81, 140.49, 139.84, 135.08 (d, J = 3.2 Hz), 130.46, 130.34 (d, J = 7.8 Hz), 128.87, 128.17, 126.80, 114.99 (d, J = 21.1 Hz), 109.49, 73.81, 56.09, 53.29, 48.06, 37.66, 18.44, 17.98. |
| 130 | | HRMS-ESI m/z ([M + H]$^+$) calcd for C$_{30}$H$_{31}$FN$_2$O$_5$ 499.2233; found, 499.2220 | $^1$H NMR (400 MHz, CDCl$_3$) δ 12.16 (d, J = 0.6 Hz, 1H), 8.45 (d, J = 8.0 Hz, 1H), 8.01 (d, J = 5.2Hz, 1H), 7.79-7.71 (m, 1H), 7.71-7.62 (m, 2H), 7.45-7.34 (m, 3H), 7.21-7.08 (m, 6H), 6.87 (dd, J = 5.3, 0.7 Hz, 1H), 5.37-5.23 (m, 1H), 4.76-4.56 (m, 1H), 3.93 (s, 3H), 3.22 (dd, J = 12.1, 4.8 Hz, 1H), 3.16-3.01 (m, 2H), 1.32 (d, J = 7.2 Hz, 3H), 1.27 (d, J = 6.3 Hz, 3H).<br>$^{13}$C NMR (101 MHz, CDCl$_3$) δ 171.48, 168.71, 155.42, 148.82, 140.49, 140.09, 137.01, 133.42, 132.01, 130.50, 128.92, 128.17, 127.77, 127.52, 127.47, 127.47, 127.45, 126.76, 125.84, 125.25, 109.48, 74.05, 56.08, 53.02, 48.09, 38.61, 18.46, 18.08. |
| 131 | (Thin film) 3369, 2938, 1509, 1242, 1218, 730 | HRMS-ESI m/z ([M + H]$^+$) calcd for C$_{28}$H$_{32}$FN$_2$O$_6$, 511.2239; found, 511.2217 | $^1$H NMR (400 MHz, CDCl$_3$) δ 12.16 (d, J = 0.6 Hz, 1H), 8.49 (d, J = 7.9 Hz, 1H), 7.99 (dd, J = 12.1, 5.2 Hz, 1H), 7.41-7.17 (m, 4H), 7.16-7.00 (m, 2H), 7.00-6.88 (m, 2H), 6.86 (d, J = 5.2 Hz, 1H), 5.18 (qd, J = 6.5, 5.0 Hz, 1H), 4.78-4.62 (m, 1H), 4.40 (d, J = 2.9 Hz, 2H), 3.93 (d, J = 2.0 Hz, 3H), 3.36 (d, J = 5.1 Hz, 2H), 2.64 (t, J = 7.2 Hz, 2H), 2.14-2.02 (m, 1H), 1.93 (dddd, J = 31.1, 13.0, 6.7, 5.3 Hz, 1H), 1.50 (d, J = 7.2 Hz, 3H), 1.31 (d, J = 6.5 Hz, 3H). |
| 132 | (Thin film) 3367, 2937, 1527, 1452, 1262, 699 | HRMS-ESI m/z ([M + H]$^+$) calcd for C$_{28}$H$_{33}$N$_2$O$_6$, 493.2333; found, 493.2310 | $^1$H NMR (400 MHz, CDCl$_3$) δ 12.17 (d, J = 0.6 Hz, 1H), 8.51 (d, J = 7.9 Hz, 1H), 7.99 (dd, J = 11.6, 5.2 Hz, 1H), 7.43-7.22 (m, 6H), 7.22-7.05 (m, 3H), 6.92-6.77 (m, 1H), 5.20 (qd, J = 6.4, 4.9 Hz, 1H), 4.75-4.62 (m, 1H), 4.49-4.33 (m, 2H), 3.92 (d, J = 1.5 Hz, 3H), 3.39 (d, J = 5.2 Hz, 2H), 2.76-2.65 (m, 2H), 2.29-2.08 (m, 1H), 2.03-1.82 (m, 1H), 1.50 (d, J = 7.2 Hz, 3H), 1.32 (d, J = 6.5 Hz, 3H). |
| 133 | (Thin film) 3368, 2976, 1732, 1528, 1262, 1218, 730 | HRMS-ESI m/z ([M + H]$^+$) calcd for C$_{30}$H$_{36}$FN$_2$O$_6$, 539.2552; found, 539.2542 | $^1$H NMR (400 MHz, CDCl$_3$) δ 12.14 (d, J = 0.6 Hz, 1H), 8.39 (d, J = 7.9 Hz, 1H), 7.98 (dd, J = 21.4, 5.2 Hz, 1H), 7.40-7.21 (m, 4H), 7.18-7.06 (m, 2H), 7.00-6.79 (m, 3H), 5.46 (qd, J = 6.6, 2.8 Hz, 1H), 4.58-4.36 (m, 3H), 3.93 (d, J = 1.5 Hz, 3H), 3.01 (dd, J = 14.9, 5.3 Hz, 1H), 2.78 (dd, J = 14.9, 7.0 Hz, 1H), 2.29 (ddd, J = 7.0, 5.3, 2.9 Hz, 1H), 2.04-1.80 (m, 1H), 1.38 (d, J = 6.6 Hz, 3H), 1.35 (s, 3H), 1.30 (d, J = 7.2 Hz, 3H), 1.26 (s, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| 134 | (Thin film) 3368, 2975, 1731, 1528, 1263, 1040, 730 | HRMS-ESI m/z ([M + H]$^+$) calcd for C$_{30}$H$_{37}$N$_2$O$_6$, 521.2646; found, 521.2619 | $^1$H NMR (400 MHz, CDCl$_3$) δ 12.16 (d, J = 0.6 Hz, 1H), 8.40 (d, J = 7.9 Hz, 1H), 7.96 (d, J = 5.2 Hz, 1H), 7.33 (d, J = 4.4 Hz, 4H), 7.30-7.03 (m, 6H), 6.90-6.77 (m, 1H), 5.47 (qd, J = 6.6, 2.9 Hz, 1H), 4.52-4.39 (m, 3H), 3.92 (s, 2H), 3.04 (dd, J = 14.8, 5.0 Hz, 1H), 2.82 (dd, J = 14.8, 7.4 Hz, 1H), 2.37 (ddd, J = 7.7, 5.1, 2.9 Hz, 1H), 2.03-1.82 (m, 1H), 1.40 (d, J = 6.6 Hz, 3H), 1.36 (s, 3H), 1.29 (s, 3H), 1.23 (d, J = 7.2 Hz, 3H). |
| 135 | (Thin film) 3368, 2936, 1734, 1648, 1241, 1217, 728 | HRMS-ESI m/z ([M + H]$^+$) calcd for C$_{22}$H$_{28}$FN$_2$O$_6$, 435.1926; found, 435.1928 | $^1$H NMR (400 MHz, CDCl$_3$) δ 12.15 (d, J = 0.6 Hz, 1H), 8.51 (d, J = 7.9 Hz, 1H), 7.98 (d, J = 5.2 Hz, 1H), 7.17-7.03 (m, 2H), 7.03-6.91 (m, 2H), 6.91-6.79 (m, 1H), 5.13 (qd, J = 6.5, 4.7 Hz, 1H), 4.78-4.64 (m, 1H), 3.94 (d, J = 3.8 Hz, 3H), 3.26 (d, J = 8.6 Hz, 4H), 2.63 (d, J = 7.3 Hz, 2H), 2.11-1.85 (m, 2H), 1.57 (d, J = 7.2 Hz, 3H), 1.31 (d, J = 6.5 Hz, 3H). |
| 136 | (Thin film) 3369, 2976, 2941, 1731, 1509, 1218, 728 | HRMS-ESI m/z ([M + H]$^+$) calcd for C$_{24}$H$_{32}$FN$_2$O$_6$, 463.2239; found, 463.2237 | $^1$H NMR (400 MHz, CDCl$_3$) δ 12.13 (d, J = 0.6 Hz, 1H), 8.39 (d, J = 7.9 Hz, 1H), 8.05-7.92 (m, 1H), 7.19-7.06 (m, 2H), 6.99-6.77 (m, 2H), 5.37 (qd, J = 6.6, 2.8 Hz, 1H), 4.57-4.45 (m, 1H), 3.94 (s, 3H), 3.17 (s, 3H), 2.87 (dd, J = 14.8, 5.1 Hz, 1H), 2.71 (dd, J = 14.8, 7.3 Hz, 1H), 2.29-2.14 (m, 1H), 2.03-1.84 (m, 1H), 1.35 (d, J = 6.6 Hz, 3H), 1.31 (d, J = 7.2 Hz, 3H), 1.21 (s, 3H), 1.17 (s, 3H). |
| 137 | | HRMS-ESI m/z ([M + H]$^+$) calcd for C$_{24}$H$_{33}$N$_2$O$_6$, 445.2338; found, 445.2335 | $^1$H NMR (400 MHz, CDCl$_3$) δ 12.16 (d, J = 0.7 Hz, 1H), 8.40 (d, J = 7.9 Hz, 1H), 7.96 (d, J = 5.2 Hz, 1H), 7.31-7.07 (m, 5H), 6.85 (dd, J = 5.3, 0.7 Hz, 1H), 5.38 (qd, J = 6.5, 2.9 Hz, 1H), 4.53-4.39 (m, 1H), 3.93 (s, 3H), 3.19 (s, 3H), 2.90 (dd, J = 14.7, 4.9 Hz, 1H), 2.74 (dd, J = 14.7, 7.6 Hz, 1H), 2.29 (ddd, J = 7.7, 4.9, 2.8 Hz, 1H), 1.36 (d, J = 6.6 Hz, 3H), 1.24 (d, J = 7.2 Hz, 3H), 1.22 (s, 3H), 1.19 (s, 3H). $^{13}$C NMR (101 MHz, CDCl$_3$) δ 171.35, 168.62, 155.33, 148.71, 142.50, 140.43, 130.49, 128.80, 128.27, 125.62, 109.42, 76.47, 73.30, 56.05, 52.06, 48.89, 48.07, 31.20, 24.35, 23.98, 17.86, 17.12. |
| 138 | (Thin film) 3373, 2939, 2872, 1736, 1529, 1219, 824 | HRMS-ESI m/z ([M + H]$^+$) calcd for C$_{28}$H$_{31}$F$_2$N$_2$O$_6$, 529.2145; found, 529.2152 | $^1$H NMR (400 MHz, CDCl$_3$) δ 12.15 (d, J = 0.6 Hz, 1H), 8.49 (d, J = 7.9 Hz, 1H), 7.99 (dd, J = 13.4, 5.2 Hz, 1H), 7.27-7.19 (m, 2H), 7.10-6.97 (m, 3H), 6.97-6.89 (m, 2H), 6.89-6.81 (m, 1H), 5.18 (qd, J = 6.5, 5.0 Hz, 1H), 4.76-4.62 (m, 1H), 4.42-4.29 (m, 2H), 3.92 (s, 3H), 3.35 (d, J = 5.1 Hz, 2H), 2.75-2.53 (m, 2H), 2.09 (ddq, J = 8.3, 6.7, 5.2 Hz, 1H), 2.04-1.81 (m, 1H), 1.52 (d, J = 7.2 Hz, 3H), 1.31 (d, J = 6.4 Hz, 3H). |
| 139 | (Thin film) 3369, 2976, 1732, 1528, | HRMS-ESI m/z ([M + H]$^+$) calcd for C$_{30}$H$_{35}$F$_2$N$_2$O$_6$, | $^1$H NMR (400 MHz, CDCl$_3$) δ 12.13 (s, 1H), 8.38 (d, J = 7.9 Hz, 1H), 7.96 (d, J = 5.2 Hz, |

TABLE 2-continued

| *Cmpd. No. | IR (cm⁻¹) | MASS | NMR ($^1$H, $^{13}$C or $^{19}$F) |
|---|---|---|---|
| | 1218, 729 | 557.2458; found, 557.2471 | 1H), 7.36-7.20 (m, 2H), 7.20-7.06 (m, 2H), 7.06-6.95 (m, 2H), 6.94-6.87 (m, 2H), 5.45 (qd, J = 6.5, 2.8 Hz, 1H), 4.59-4.46 (m, 1H), 4.45-4.32 (m, 2H), 3.93 (d, J = 2.0 Hz, 3H), 2.96 (dd, J = 14.8, 5.3 Hz, 1H), 2.78 (dd, J = 14.9, 7.0 Hz, 1H), 2.29 (ddd, J = 7.0, 5.4, 2.8 Hz, 1H), 1.93 (dddd, J = 31.2, 13.0, 7.3, 5.9 Hz, 1H), 1.36 (d, J = 6.6 Hz, 3H), 1.33 (s, 3H), 1.30 (d, J = 7.2 Hz, 3H), 1.26 (s, 3H). |
| 140 | (Thin film) 3373, 2954, 2868, 1736, 1509, 1263, 1219 | HRMS-ESI m/z ([M + H]⁺) calcd for C₂₆H₃₆FN₂O₆, 491.2552; found, 491.2558 | $^1$H NMR (400 MHz, CDCl₃) δ 12.15 (d, J = 0.6 Hz, 1H), 8.51 (d, J = 7.9 Hz, 1H), 7.99 (d, J = 5.2 Hz, 1H), 7.16-7.02 (m, 2H), 7.03-6.90 (m, 2H), 6.87 (dd, J = 5.2, 0.6 Hz, 1H), 5.13 (qd, J = 6.5, 4.7 Hz, 1H), 4.80-4.62 (m, 1H), 3.94 (s, 3H), 3.45-3.19 (m, 4H), 2.63 (d, J = 7.4 Hz, 2H), 2.13-1.94 (m, 1H), 1.76-1.61 (m, 1H), 1.57 (d, J = 7.2 Hz, 3H), 1.47-1.36 (m, 2H), 1.31 (d, J = 6.5 Hz, 3H), 0.90 (d, J = 1.7 Hz, 3H), 0.88 (d, J = 1.6 Hz, 3H). $^{13}$C NMR (101 MHz, CDCl₃) δ 171.38, 168.77, 161.39 (d, J = 243.8 Hz), 155.40, 148.79, 140.51, 135.64 (d, J = 3.2 Hz), 130.46, 130.45 (d, J = 7.8 Hz), 115.12 (d, J = 21.2 Hz), 109.47, 72.58, 69.55, 68.82, 56.08, 48.18, 45.58, 38.51, 32.68, 25.08, 22.64, 22.60, 18.43, 17.11. |
| 141 | (Thin film) 3370, 2954, 2868, 1736, 1528, 1263 | HRMS-ESI m/z ([M + H]⁺) calcd for C₂₆H₃₇N₂O₆, 473.2646; found, 473.2649 | $^1$H NMR (400 MHz, CDCl₃) δ 12.17 (d, J = 0.6 Hz, 1H), 8.53 (d, J = 7.9 Hz, 1H), 7.98 (d, J = 5.2 Hz, 1H), 7.27 (tt, J = 7.1, 1.0 Hz, 2H), 7.23-7.16 (m, 1H), 7.16-7.09 (m, 2H), 6.86 (dd, J = 5.2, 0.6 Hz, 1H), 5.16 (qd, J = 6.5, 4.7 Hz, 1H), 4.80-4.62 (m, 1H), 3.94 (s, 3H), 3.45-3.20 (m, 4H), 2.76-2.56 (m, 2H) 2.16-2.05 (m, 1H), 1.69 (dp, J = 13.4, 6.6 Hz, 1H), 1.56 (d, J = 7.2 Hz, 3H), 1.47-1.36 (m, 2H), 1.32 (d, J = 6.5 Hz, 3H), 0.90 (d, J = 1.8 Hz, 3H), 0.88 (d, J = 1.8 Hz, 3H). $^{13}$C NMR (101 MHz, CDCl₃) δ 171.39, 168.73, 155.37, 148.77, 140.49, 140.05, 130.48, 129.11, 128.35, 126.05, 109.45, 72.73, 69.50, 68.98, 56.06, 48.15, 45.43, 38.52, 33.47, 25.07, 22.65, 22.60, 18.47, 17.03. |
| 142 | (Thin film) 3366, 2978, 1732, 1648, 1473, 1261 | HRMS-ESI m/z ([M + H]⁺) calcd for C₂₉H₃₃Cl₂N₂O₆, 575.171; found, 575.171 | $^1$H NMR (400 MHz, CDCl₃) δ 12.14 (s, 1H), 8.40 (d, J = 7.9 Hz, 1H), 7.97 (d, J = 5.2 Hz, 1H), 7.39 (d, J = 2.6 Hz, 1H), 7.30-7.18 (m, 4H), 7.18-7.11 (m, 2H), 7.01 (d, J = 8.8 Hz, 1H), 6.86 (d, J = 5.2 Hz, 1H), 5.60 (qd, J = 6.5, 2.9 Hz, 1H), 4.56-4.44 (m, 1H), 3.94 (s, 3H), 3.24 (dd, J = 14.9, 5.2 Hz, 1H), 2.93 (dd, J = 14.9, 7.0 Hz, 1H), 2.51 (ddd, J = 7.0, 5.2, 3.0 Hz, 1H), 1.49 (d, J = 6.5 Hz, 3H), 1.43 (s, 3H), 1.31 (s, 3H), 1.29 (d, J = 7.2 Hz, 3H). |
| 143 | (Thin film) 3372, 2936, | HRMS-ESI m/z ([M + H]⁺) calcd | $^1$H NMR (400 MHz, CDCl₃) δ 12.17 (s, 1H), 8.53 (d, J = 7.9 |

TABLE 2-continued

Analytical Data

| *Cmpd. No. | IR (cm$^{-1}$) | MASS | NMR ($^1$H, $^{13}$C or $^{19}$F) |
|---|---|---|---|
| | 1734, 1512, 1242 | for C$_{25}$H$_{35}$N$_2$O$_7$, 475.2439; found, 475.2429 | Hz, 1H), 7.99 (d, J = 5.2 Hz, 1H), 7.04 (d, J = 8.6 Hz, 2H), 6.87 (d, J = 5.2 Hz 1H) 6.81 (d, J = 8.6 Hz, 2H), 5.15 (qd, J = 6.5, 4.7 Hz, 1H), 4.71 (p, J = 7.3 Hz, 1H), 3.94 (s, 3H), 3.79 (s, 3H), 3.38-3.16 (m, 4H), 2.60 (d, J = 7.4 Hz, 2H), 2.09-2.01 (m, 1H), 2.01-1.85 (m, 1H), 1.57 (d, J = 7.2 Hz, 4H), 1.31 (d, J = 6.4 Hz, 3H), 0.91 (t, J = 7.4 Hz, 3H). |
| 144 | (Thin film) 3371, 2971, 1731, 1649, 1511, 1243 | HRMS-ESI m/z ([M + H]$^+$) calcd for C$_{27}$H$_{39}$N$_2$O$_7$, 503.2752; found, 503.2736 | $^1$H NMR (400 MHz, CDCl$_3$) δ 12.17 (s, 1H), 8.43 (d, J = 7.9 Hz, 1H), 7.97 (d, J = 5.2 Hz, 1H), 7.08 (d, J = 8.6 Hz, 1H), 6.85 (d, J = 5.3 Hz, 1H), 6.78 (d, J = 8.6 Hz, 1H), 5.40 (qd, J = 6.6, 2.9 Hz, 1H), 4.50 (p, J = 7.3 Hz, 1H), 3.94 (s, 3H), 3.77 (s, 3H), 3.36-3.15 (m, 2H), 2.89 (dd, J = 14.8, 5.1 Hz, 1H), 2.69 (dd, J = 14.8, 7.2 Hz, 1H), 2.24-2.14 (m, 1H), 2.05-1.84 (m, 2H), 1.61-1.44 (m, 2H), 1.36 (d, J = 6.6 Hz, 3H), 1.30 (d, J = 7.2 Hz, 3H), 1.22 (s, 3H), 1.16 (s, 3H), 0.92 (t, J = 7.4 Hz, 3H). |
| 145 | (Thin film) 3371, 2935, 1733, 1649, 1528, 1244 | HRMS-ESI m/z ([M + H]$^+$) calcd for C$_{32}$H$_{41}$N$_2$O$_7$, 565.2908; found, 565.2913 | $^1$H NMR (400 MHz, CDCl$_3$) δ 12.17 (s, 1H), 8.52 (d, J = 7.9 Hz, 1H), 7.99 (d, J = 5.2 Hz, 1H), 7.29-7.22 (m, 2H), 7.22-7.12(m, 3H), 6.94 (dd, J = 8.3, 2.3 Hz, 1H), 6.85 (d, J = 5.2 Hz, 1H), 6.82 (d, J = 2.5 Hz, 1H), 6.77 (d, J = 8.3 Hz, 1H), 5.19-5.05 (m, 1H), 4.76-4.54 (m, 1H), 3.93 (s, 5H), 3.79 (s, 3H), 3.35-3.16 (m, 4H), 2.55 (d, J = 7.4 Hz, 2H), 2.06-1.83 (m, 3H), 1.50 (d, J = 7.2 Hz, 3H), 1.29 (d, J = 6.5 Hz, 3H), 0.89 (t, J = 7.4 Hz, 3H). |
| 146 | (Thin film) 3371, 2971, 1732, 1650, 1528, 1245 | HRMS-ESI m/z ([M + H]$^+$) calcd for C$_{34}$H$_{45}$N$_2$O$_7$, 593.3221; found, 593.3227 | $^1$H NMR (400 MHz, CDCl$_3$) δ 12.19 (s, 1H), 8.42 (d, J = 8.0 Hz, 1H), 7.96 (d, J = 5.2 Hz, 1H), 7.30-7.22 (m, 2H), 7.21-7.13 (m, 3H), 6.97 (dd, J = 8.4, 2.3 Hz, 1H), 6.87 (d, J = 2.3 Hz, 1H), 6.83 (d, J = 5.2 Hz 1H) 6.74 (d, J = 8.4 Hz, 1H), 5.36 (qd, J = 6.5, 2.7 Hz, 1H), 4.46 (p, J = 7.3 Hz, 1H), 3.97-3.88 (m, 5H), 3.77 (s, 3H), 3.33-3.19 (m, 2H), 2.83 (dd, J = 14.8, 5.4 Hz, 1H), 2.64 (dd, J = 8.2, 7.6 Hz, 1H), 2.02-1.85 (m, 1H), 1.57-1.44 (m, 2H), 1.33 (d, J = 6.6 Hz, 3H), 1.21 (d, J = 7.1 Hz, 3H), 1.18 (s, 3H), 1.12 (s, 3H), 0.90 (t, J = 7.4 Hz, 3H). |
| 147 | (Thin film) 3371, 2937, 1734.22, 1648.72, 1527, 1452, 1262 | HRMS-ESI m/z ([M + H]$^+$) calcd for C$_{27}$H$_{31}$N$_2$O$_5$, 464.226; found, 464.2262 | $^1$H NMR (400 MHz, CDCl$_3$) δ 12.16 (d, J = 0.6 Hz, 1H), 8.51 (d, J = 7.9 Hz, 1H), 8.01-7.98 (m, 1H), 7.25-7.00 (m, 10H), 6.87 (d, J = 5.2 Hz, 1H), 4.97 (td, J = 6.6, 3.1 Hz, 1H), 4.72 (p, J = 7.2 Hz, 1H), 3.94 (d, J = 4.4 Hz, 3H), 2.83-2.46 (m, 5H), 1.58 (d, J = 7.2 Hz, 3H), 1.29 (d, 3H). |
| 148 | (Thin film) 3373, 2963, 1729, 1651, 1526, 1262 | HRMS-ESI m/z ([M + Na]$^+$) calcd for C$_{29}$H$_{34}$N$_2$NaO$_5$, 513.236; found, 513.2364 | $^1$H NMR (400 MHz, CDCl$_3$) δ 12.19 (d, J = 0.6 Hz, 1H), 8.55 (d, J = 9.8 Hz, 1H), 8.00 (d, J = 5.2 Hz, 1H), 7.30-7.01 (m, 10H), 6.88 (d, J = 5.1 Hz, 1H), 5.03-4.95 (m, 1H), 4.66 (dd, J = 9.3, 4.6 Hz, 1H), 3.95 (s, 3H), 2.80- |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 2.68 (m, 2H), 2.67-2.47 (m, 4H), 1.28 (d, J = 6.5 Hz, 3H), 1.08 (d, J = 6.9 Hz, 3H), 1.06 (d, J = 6.9 Hz, 3H). |
| 149 | (Thin film) 3372.52, 2935, 1730, 1649, 1527, 1452, 1260 | HRMS-ESI m/z ([M + H]$^+$) calcd for C$_{28}$H$_{33}$N$_2$O$_5$, 478.2416; found, 478.2423 | $^1$H NMR (400 MHz, CDCl$_3$) δ 12.18 (s, 1H), 8.50 (t, J = 10.2 Hz, 1H), 8.09-7.94 (m, 1H), 7.37-6.97 (m, 10H), 6.87 (d, J = 5.3 Hz, 1H), 4.97 (ddtt, J = 16.4, 9.9, 6.6, 3.3 Hz, 1H), 4.68 (ddd, J = 8.6, 7.3, 5.2 Hz, 1H), 3.95 (s, 3H), 3.71 (t, J = 6.9 Hz, 1H), 3.34 (dd, J = 7.2, 5.3 Hz, 1H), 2.79-2.47 (m, 4H), 2.23 (dtd, J = 17.3, 7.1, 3.1 Hz, 1H), 1.28 (d, J = 6.5 Hz, 3H), 1.26 (d, J = 6.5 Hz, 3H). |
| 150 | | HRMS-ESI m/z ([M + H]$^+$) calcd for C$_{27}$H$_{29}$F$_2$N$_2$O$_5$, 499.2039; found, 499.2043 | $^1$H NMR (400 MHz, CDCl$_3$) δ 12.13 (d, J = 0.6 Hz, 1H), 8.48 (d, J = 8.0 Hz, 1H), 8.01 (dd, J = 5.2, 0.6 Hz, 1H), 7.25-7.16 (m, 2H), 6.92-6.70 (m, 7H), 4.95 (dt, J = 6.9, 3.5 Hz, 1H), 4.78-4.65 (m, 1H), 3.95 (d, J = 1.1 Hz, 3H), 2.83-2.43 (m, 5H), 1.59 (d, J = 7.2 Hz, 3H), 1.28 (d, J = 6.5 Hz, 3H). |
| 151 | (Thin film) 3369, 2939, 1733, 1648, 1508, 1453, 1218 | HRMS-ESI m/z ([M + H]$^+$) calcd for C$_{27}$H$_{29}$F$_2$N$_2$O$_5$ 499.2039; found, 499.2046 | $^1$H NMR (400 MHz, CDCl$_3$) δ 12.13 (s, 1H), 8.48 (d, J = 7.7 Hz, 1H), 7.99 (d, J = 5.2 Hz, 1H), 7.11-6.85 (m, 9H), 4.95 (qd, J = 6.7, 3.0 Hz, 1H), 4.72 (p, J = 7.2 Hz, 1H), 3.95 (s, 3H), 2.71 (dd, J = 14.2, 6.7 Hz, 1H), 2.58 (dd, J = 13.8, 7.4 Hz, 1H), 2.55-2.40 (m, 2H), 2.13-2.04 (m, 1H), 1.59 (d, J = 7.0 Hz, 3H), 1.27 (d, J = 6.5 Hz, 3H). |
| 152 | | ESIMS m/z 523.7 ([M + H]$^+$) | $^1$H NMR (400 MHz, CDCl$_3$) δ 12.16 (s, 1H), 8.51 (d, J = 7.9 Hz, 1H), 8.00 (d, J = 5.2 Hz, 1H), 7.17 (ddd, J = 11.9, 8.2, 7.5 Hz, 2H), 6.87 (d, J = 5.2 Hz, 1H), 6.76-6.57 (m, 7H), 4.99 (dd, J = 6.5, 3.0 Hz, 1H), 3.94 (s, 3H), 3.78 (s, 3H), 3.77 (s, 3H), 2.78-2.46 (m, 5H), 1.59 (d, J = 7.2 Hz, 3H), 1.28 (d, J = 6.5 Hz, 3H). |
| 153 | | HRMS-ESI m/z ([M + H]$^+$) calcd for C$_{30}$H$_{37}$N$_2$O$_7$, 537.2595; found, 537.259 | $^1$H NMR (400 MHz, CDCl$_3$) δ 12.38-11.99 (m, 1H), 8.51 (d, J = 8.4 Hz, 1H), 8.00 (d, J = 5.2 Hz, 1H), 7.17 (dt, J = 12.7, 7.9 Hz, 2H), 6.87 (d, J = 5.2 Hz, 1H), 6.72 (tdd, J = 8.4, 2.6, 1.2 Hz, 3H), 6.64 (dt, J = 3.8, 1.9 Hz, 2H), 6.59 (t, J = 2.0 Hz, 1H), 5.00 (qd, J = 6.4, 3.0 Hz, 1H), 4.68 (ddd, J = 8.6, 7.3, 5.2 Hz, 1H), 3.95 (s, 3H), 3.78 (d, J = 1.0 Hz, 3H), 3.76 (s, 3H), 2.78-2.43 (m, 5H), 2.06 (ddd, J = 14.1, 7.4, 5.2 Hz, 1H), 1.90 (dt, J = 14.2, 7.3 Hz, 1H), 1.28 (dd, J = 6.4, 1.8 Hz, 3H), 1.06 (t, J = 7.4 Hz, 3H). $^{13}$C NMR (126 MHz, CDCl$_3$) δ 170.72, 169.02, 159.66, 159.59, 155.41, 148.77, 141.80, 141.67, 140.54, 130.49, 129.40, 129.33, 121.46, 121.27, 114.93, 114.91, 111.27, 111.19, 109.47, 72.60, 56.07, 55.14, 55.11, 53.46, 46.59, 35.95, 35.58, 25.78, 16.56, 9.89. |

TABLE 2-continued

Analytical Data

| *Cmpd. No. | IR (cm$^{-1}$) | MASS | NMR ($^1$H, $^{13}$C or $^{19}$F) |
|---|---|---|---|
| 154 | | HRMS-ESI m/z ([M + H]$^+$) calcd for C$_{29}$H$_{35}$N$_2$O$_7$, 523.2439; found, 523.2419 | $^1$H NMR (400 MHz, CDCl$_3$) δ 12.17 (d, J = 0.6 Hz, 1H), 8.52 (d, J = 7.9 Hz, 1H), 7.99 (d, J = 5.2 Hz, 1H), 7.07-6.91 (m, 4H), 6.89-6.75 (m, 4H), 5.04-4.91 (m, 1H), 4.79-4.66 (m, 1H), 3.95 (s, 4H), 3.78 (s, 3H), 3.77 (s, 3H), 2.70-2.42 (m, 4H), 2.08 (td, J = 7.1, 2.8 Hz, 1H), 1.59 (d, J = 7.2 Hz, 3H), 1.26 (d, 3H). $^{13}$C NMR (126 MHz, CDCl$_3$) δ 171.43, 168.78, 157.93, 157.90, 155.40, 148.79, 140.51, 132.24, 132.04, 130.48, 130.00, 129.95, 129.79, 113.86, 113.81, 109.47, 72.67, 56.08, 55.23, 48.20, 47.10, 34.87, 34.57, 18.52, 16.41. |
| 155 | | HRMS-ESI m/z ([M + H]$^+$) calcd for C$_{30}$H$_{37}$N$_2$O$_7$, 537.2595; found, 537.2585 | $^1$H NMR (400 MHz, CDCl$_3$) δ 12.20 (s, 1H), 8.52 (d, J = 8.8 Hz, 1H), 8.06-7.93 (m, 1H), 7.10-6.71 (m, 8H), 5.03-4.91 (m, 1H), 4.68 (ddd, J = 8.5, 7.2, 5.2 Hz, 1H), 3.95 (s, 3H), 3.78 (s, 3H), 3.77 (s, 3H), 2.72-2.41 (m, 5H), 2.10-1.97 (m, 1H), 1.95-1.82 (m, 1H), 1.26 (d, J = 6.5, 1.9 Hz, 3H), 1.06 (t, J = 7.4 Hz, 3H). $^{13}$C NMR (126 MHz, CDCl$_3$) δ 171.43, 168.78, 157.93, 157.90, 155.40, 148.79, 140.51, 132.24, 132.04, 130.48, 129.95, 129.79, 113.86, 113.81, 109.47, 72.67, 56.08, 55.23 (2C), 48.20, 47.10, 34.87, 34.57, 18.52, 16.41. |
| 156 | (Thin film) 3371, 2975, 1731, 1528, 1244, 1038 | HRMS-ESI m/z ([M + H]$^+$) calcd for C$_{28}$H$_{39}$N$_2$O$_7$, 515.2752; found, 515.2732 | $^1$H NMR (400 MHz, CDCl$_3$) δ 12.17 (s, 1H), 8.42 (d, J = 7.9 Hz, 1H), 7.97 (d, J = 5.1 Hz, 1H), 7.17-7.01 (m, 2H), 6.86 (d, J = 5.2 Hz, 1H), 6.81-6.74 (m, 2H), 5.38 (qd, J = 6.4, 2.6 Hz, 1H), 4.56-4.45 (m, 1H), 3.94 (s, 3H), 3.77 (s, 3H), 3.25-3.13 (m, 2H), 2.88 (dd, J = 14.8, 5.1 Hz, 1H), 2.69 (dd, J = 14.8, 7.5 Hz, 1H), 2.21 (ddd, J = 7.7, 5.2, 2.8 Hz, 1H), 1.38 (d, J = 6.5 Hz, 3H), 1.31 (d, J = 7.2 Hz, 3H), 1.20 (s, 3H), 1.16 (s, 3H), 1.03-0.92 (m, 1H), 0.55-0.43 (m, 2H), 0.22-0.14 (m, 2H). |
| 157 | (Thin film) 3368, 2979, 1732, 1649, 1501, 1243 | HRMS-ESI m/z ([M + H]$^+$) calcd for C$_{30}$H$_{35}$F$_2$N$_2$O$_7$, 573.2402; found, 573.2407 | $^1$H NMR (400 MHz, CDCl$_3$) δ 12.15 (s, 1H), 8.45 (d, J = 7.9 Hz, 1H), 7.96 (d, J = 5.2 Hz, 1H), 7.18-7.10 (m, 2H), 7.07-6.98 (m, 1H), 6.85 (d, J = 5.3 Hz, 1H), 6.80 (d, J = 8.6 Hz, 2H), 6.79-6.69 (m, 2H), 5.57 (qd, J = 6.6, 2.9 Hz, 1H), 4.68-4.49 (m, 1H), 3.94 (s, 3H), 3.78 (s, 3H), 3.12 (dd, J = 14.9, 5.7 Hz, 1H), 2.87 (dd, J = 14.9, 6.5 Hz, 1H), 2.40 (td, J = 6.1, 2.9 Hz, 1H), 1.48 (d, J = 6.6 Hz, 3H), 1.37 (s, 3H), 1.37 (d, J = 7.1 Hz, 3H), 1.23 (s, 3H). |
| 158 | (Thin film) 3370, 2936, 1734, 1649, 1512, 1243 | HRMS-ESI m/z ([M + H]$^+$) calcd for C$_{26}$H$_{35}$N$_2$O$_7$, 487.2400; found, 487.2439 | $^1$H NMR (400 MHz, CDCl$_3$) δ 12.17 (s, 1H), 8.52 (d, J = 7.9 Hz, 1H), 7.98 (d, J = 5.2 Hz, 1H), 7.16-7.00 (m, 2H), 6.87 (d, J = 5.2 Hz, 1H), 6.85-6.75 (m, 2H), 5.16 (qd, J = 6.4, 4.6 Hz, 1H), 4.83-4.62 (m, 1H), 3.94 (s, 3H), 3.78 (s, 3H), 3.38 (dd, J = 9.8, 5.9 Hz, 1H), 3.32 (dd, J = |

TABLE 2-continued

| *Cmpd. No. | IR (cm⁻¹) | MASS | NMR ($^1$H, $^{13}$C or $^{19}$F) |
|---|---|---|---|
| | | | 9.7, 5.1 Hz, 1H), 3.19 (dd, J = 9.3, 5.7 Hz, 1H), 3.15 (dd, J = 9.3, 5.7 Hz, 1H), 2.74-2.46 (m, 2H), 2.15-2.00 (m, 1H), 1.57 (d, J = 7.2 Hz, 3H), 1.32 (d, J = 6.5 Hz, 3H), 1.08-0.91 (m, 1H), 0.58-0.38 (m, 2H), 0.28-0.09 (m, 2H). |
| 159 | (Thin film) 3367, 2936, 1734, 1649, 1528, 1452, 1244 | HRMS-ESI m/z ([M + H]⁺) calcd for $C_{33}H_{41}N_2O_7$, 577.2905; found, 577.2905 | $^1$H NMR (400 MHz, CDCl$_3$) δ 12.17 (s, 1H), 8.52 (d, J = 7.7 Hz, 1H), 7.98 (d, J = 5.2 Hz, 1H), 7.29-7.23 (m, 2H), 7.22-7.16 (m, 2H), 7.08 (dd, J = 21.8, 7.6 Hz, 1H), 6.95 (dd, J = 8.3, 2.2 Hz, 1H) 6.89-6.82 (m, 1H), 6.86-6.80 (m, 2H), 6.77 (d, J = 8.3 Hz, 1H), 5.17-5.06 (m, 1H), 4.76-4.62 (m, 1H), 4.09-3.86 (m, 5H), 3.79 (s, 3H), 3.39-3.25 (m, 2H), 3.17-3.07 (m, 2H), 2.55 (d, J = 7.4 Hz, 1H), 2.08-1.93 (m, 1H), 1.50 (d, J = 7.2 Hz, 3H), 1.29 (d, J = 6.5 Hz, 3H), 1.00-0.91 (m, 1H), 0.51-0.42 (m, 2H), 0.22-0.09 (m, 2H). |
| 160 | (Thin film) 3373, 2938, 1736, 1649, 1512, 1244, 1154 | HRMS-ESI m/z ([M + H]⁺) calcd for $C_{28}H_{31}F_2N_2O_7$, 545.2092; found, 545.2094 | $^1$H NMR (400 MHz, CDCl$_3$) δ 12.11 (s, 1H), 8.47 (d, J = 8.0 Hz, 1H), 7.97 (d, J = 5.2 Hz, 1H), 7.12-7.01 (m, 2H), 6.99 (ddd, J = 10.6, 8.9, 5.3 Hz, 1H), 6.86 (d, J = 5.2 Hz, 1H), 6.84-6.78 (m, 2H), 6.55 (ddt, J = 8.9, 7.8, 3.1 Hz, 1H), 6.47 (ddd, J = 9.7, 6.7, 3.0 Hz, 1H), 5.23 (qd, J = 6.5, 4.8 Hz, 1H), 4.82-4.65 (m, 1H), 3.94 (s, 3H), 3.93-3.84 (m, 2H), 3.78 (s, 3H), 2.82-2.65 (m, 2H), 2.31-2.21 (m, 1H), 1.55 (d, J = 7.2 Hz, 3H), 1.41 (d, J = 6.5 Hz, 3H). |
| 161 | | HRMS-ESI m/z ([M + H]⁺) calcd for $C_{21}H_{27}N_2O_5$, 387.1920; found, 387.1919 | $^1$H NMR (400 MHz, CDCl$_3$) δ 12.15 (s, 1H), 8.51 (d, J = 7.9 Hz, 1H), 8.00 (d, J = 5.2 Hz, 1H), 7.37-7.09 (m, 5H), 6.87 (d, J = 5.2 Hz, 1H), 5.14 (dq, J = 8.3, 6.3 Hz, 1H), 4.72 (p, J = 7.3 Hz, 1H), 3.94 (s, 3H), 2.66 (ddd, J = 10.8, 8.3, 3.9 Hz, 1H), 1.92-1.77 (m, 1H), 1.69-1.51 (m, 1H), 1.57 (d, J = 7.2 Hz, 3H), 1.08 (d, J = 6.3 Hz, 3H), 0.72 (t, J = 7.4 Hz, 3H). $^{13}$C NMR (101 MHz, CDCl$_3$) δ 171.74, 168.72, 155.40, 148.81, 140.73, 140.46, 130.56, 128.62, 128.41, 126.77, 109.46, 75.79, 56.06, 52.94, 48.20, 24.50, 18.40, 18.22, 11.82. |
| 162 | (Thin film) 3380, 2936, 1736, 1676, 1503 | ESIMS m/z 517 ([M + H]⁺) | $^1$H NMR (400 MHz, CDCl$_3$) δ 8.39 (d, J = 7.8 Hz, 1H), 8.28 (d, J = 5.4 Hz, 1H), 7.32-7.22 (m, 2H), 7.21-7.16 (m, 1H), 7.16-7.12 (m, 2H), 6.94 (d, J = 5.4 Hz, 1H), 5.76 (d, J = 2.3 Hz, 2H), 5.20-5.09 (m, 1H), 4.79-4.68 (m, 1H), 3.91 (s, 3H), 3.34 (dd, J = 5.4, 2.8 Hz, 2H), 3.31-3.24 (m, 2H), 2.72-2.63 (m, 2H), 2.07 (s, 3H), 1.61-1.55 (m, 3H), 1.55-1.52 (m, 3H), 1.31 (d, J = 6.5 Hz, 3H), 0.91 (t, J = 7.4 Hz, 3H). |
| 163 | (Thin film) 3383, 2930, 1736, 1677, 1503 | ESIMS m/z 545 ([M + H]⁺) | $^1$H NMR (400 MHz, CDCl$_3$) δ 8.32-8.25 (m, 2H), 7.30-7.21 (m, 2H), 7.22-7.12 (m, 3H), 6.95 (d, J = 5.4 Hz, 1H), 5.76 (d, J = |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 3.9 Hz, 2H), 5.16-5.05 (m, 1H), 4.64-4.54 (m, 1H), 3.91 (s, 3H), Hz 3.33 (td, J = 6.6, 2.8, 2H), 3.21 (td, J = 6.8, 6.4, 3.4 Hz, 1H), 2.83 (dd, J = 14.6, 5.9 Hz, 1H), 2.63 (dd, J = 14.5, 7.4 Hz, 1H), 2.26-2.17 (m, 1H), 2.08 (s, 3H), 1.63-1.43 (m, 4H), 1.42 (d, J = 7.1 Hz, 3H), 1.24 (d, J = 6.4 Hz, 3H), 0.89 (t, J = 7.4 Hz, 6H). |
| 164 | (Thin film) 3380, 2956, 1733, 1678, 1502 | ESIMS m/z 559 ([M + H]$^+$) | $^1$H NMR (400 MHz, CDCl$_3$) δ 8.36 (d, J = 8.4 Hz, 1H), 8.27 (d, J = 5.3 Hz, 1H), 7.29-7.22 (m, 2H), 7.22-7.13 (m, 3H), 6.94 (d, J = 5.4 Hz, 1H), 5.75 (d, J = 4.5 Hz, 2H), 5.16-5.08 (m, 1H), 4.70-4.61 (m, 1H), 3.91 (s, 3H), 3.32 (t, J = 6.6 Hz, 2H), 3.19 (td, J = 6.4, 3.1 Hz, 1H), 2.81 (dd, J = 14.5, 6.1 Hz, 1H), 2.63 (dd, J = 14.5, 7.2 Hz, 1H), 2.23-2.08 (m, 1H), 2.07 (s, 3H), 2.02-1.87 (m, 1H), 1.82-1.70 (m, 1H), 1.63-1.41 (m, 4H), 1.25 (d, J = 6.5 Hz, 3H), 0.97 (t, J = 7.4 Hz, 3H), 0.90 (t, J = 7.5 Hz, 3H), 0.86 (t, J = 7.4 Hz, 3H). |
| 165 | (Thin film) 3382, 2936, 1736, 1677, 1503 | ESIMS m/z 545 ([M + H]$^+$) | $^1$H NMR (400 MHz, CDCl$_3$) δ 8.36 (d, J = 7.6 Hz, 1H), 8.27 (d, J = 5.4 Hz, 1H), 7.28-7.23 (m, 2H), 7.22-7.13 (m, 3H), 6.95 (d, J = 5.4 Hz, 1H), 5.76 (d, J = 3.9 Hz, 2H), 5.24-5.16 (m, 1H), 4.72-4.63 (m, 1H), 3.91 (s, 3H), 3.41 (dt, J = 8.8, 6.4 Hz, 1H), 3.31 (dt, J = 8.8, 6.5 Hz, 1H), 3.18 (td, J = 6.4, 3.9 Hz, 1H), 2.81 (dd, J = 13.8, 7.3 Hz, 1H), 2.69 (dd, J = 13.7, 6.7 Hz, 1H), 2.24-2.15 (m, 1H), 2.08 (s, 3H), 1.65-1.51 (m, 4H), 1.49 (d, J = 7.2 Hz, 3H), 1.28 (d, J = 6.5 Hz, 3H), 0.96 (t, J = 7.4 Hz, 3H), 0.82 (t, J = 7.4 Hz, 3H). |
| 166 | (Thin film) 3381, 2937, 1737, 1676, 1503 | ESIMS m/z 517 ([M + H]$^+$) | $^1$H NMR (400 MHz, CDCl$_3$) δ 8.36 (d, J = 7.7 Hz, 1H), 8.28 (d, J = 5.3 Hz, 1H), 7.31-7.22 (m, 2H), 7.22-7.13 (m, 3H), 6.95 (d, J = 5.4 Hz, 1H), 5.76 (d, J = 3.9 Hz, 2H) 5.20-5.10 (m, 1H), 4.77-4.65 (m, 1H), 3.91 (s, 3H), 3.41-3.21 (m, 4H), 2.68 (qd, J = 13.5, 7.3 Hz, 2H), 2.20-2.09 (m, 1H), 2.07 (s, 3H), 1.54 (s, 2H), 1.50 (d, J = 7.2 Hz, 3H), 1.30 (d, J = 6.5 Hz, 3H), 0.90 (t, J = 7.4 Hz, 3H). |
| 167 | (Thin film) 3379, 2936, 1734, 1678, 1502 | ESIMS m/z 531 ([M + H]$^+$) | $^1$H NMR (400 MHz, CDCl$_3$) δ 8.40 (d, J = 8.2 Hz, 1H), 8.28 (d, J = 5.4 Hz, 1H), 7.32-7.23 (m, 2H), 7.22-7.10 (m, 3H), 6.94 (d, J = 5.4 Hz, 1H), 5.76 (d, J = 5.0 Hz, 2H), 5.21-5.11 (m, 1H), 4.72 (ddd, J = 8.3, 6.8, 5.3 Hz, 1H), 3.91 (s, 3H), 3.37-3.31 (m, 2H), 3.31-3.21 (m, 2H), 2.68 (dd, J = 7.4, 4.8 Hz, 2H), 2.15-2.08 (m, 1H), 2.07 (s, 3H), 2.06-1.97 (m, 1H), 1.92-1.81 (m, 1H), 1.62-1.48 (m, 2H), 1.31 (d, J = 6.5 Hz, 3H), 1.02 (t, J = 7.5 Hz, 3H), 0.91 (t, J = 7.4 Hz, 3H). |

TABLE 2-continued

| *Cmpd. No. | IR (cm$^{-1}$) | MASS | NMR ($^1$H, $^{13}$C or $^{19}$F) |
|---|---|---|---|
| 168 | (Thin film) 3381, 2936, 1734, 1676, 1502 | ESIMS m/z 545 ([M + H]$^+$) | $^1$H NMR (400 MHz, CDCl$_3$) δ 8.36 (d, J = 7.7 Hz, 1H), 8.27 (d, J = 5.4 Hz, 1H), 7.31-7.22 (m, 2H), 7.22-7.13 (m, 3H), 6.94 (d, J = 5.4 Hz, 1H), 5.75 (d, J = 1.7 Hz, 2H), 5.16-5.05 (m, 1H), 4.71-4.62 (m, 1H), 3.91 (s, 3H), 3.33 (td, J = 6.6, 0.8 Hz, 2H), 3.21 (td, J = 6.4, 3.0 Hz, 2H), 2.82 (dd, J = 14.5, 6.2 Hz, 1H), 2.62 (dd, J = 14.5, 7.2 Hz, 1H), 2.19-2.11 (m, 1H), 2.07 (s, 3H), 1.64-1.46 (m, 3H), 1.46 (d, J = 7.1 Hz, 3H), 1.25 (d, J = 6.5 Hz, 3H), 0.93-0.84 (m, 6H). |
| 169 | (Thin film) 3382, 2936, 1736, 1676, 1503 | ESIMS m/z 545 ([M + H]$^+$) | $^1$H NMR (400 MHz, CDCl$_3$) δ 8.40 (d, J = 7.8 Hz, 1H), 8.27 (d, J = 5.4 Hz, 1H), 7.31-7.22 (m, 2H), 7.21-7.08 (m, 4H), 6.94 (d, J = 5.4 Hz, 1H), 5.75 (d, J = 4.2 Hz, 2H), 5.25-5.14 (m, 1H), 4.78-4.67 (m, 1H), 3.91 (s, 3H), 3.40 (dt, J = 8.8, 6.4 Hz, 1H), 3.31 (dt, J = 8.9, 6.5 Hz, 1H), 3.18 (td, J = 6.5, 3.8 Hz, 1H), 2.83 (dd, J = 13.8, 7.4 Hz, 1H), 2.65 (dd, J = 13.8, 6.6 Hz, 1H), 2.07 (s, 3H), 1.65-1.53 (m, 4H), 1.54 (d, J = 7.1 Hz, 3H), 1.29 (d, J = 6.5 Hz, 3H), 0.97 (t, J = 7.4 Hz, 3H), 0.83 (t, J = 7.4 Hz, 3H). |
| 170 | (Thin film) 3378, 2936, 1735, 1679, 1505 | ESIMS m/z 559 ([M + H]$^+$) | $^1$H NMR (400 MHz, CDCl$_3$) δ 8.37 (s, 1H), 8.26 (d, J = 5.4 Hz, 1H), 7.24-7.20 (m, 2H), 7.19-7.12 (m, 3H), 6.93 (d, J = 5.4 Hz, 1H), 5.73 (d, J = 0.8 Hz, 2H), 5.18-5.07 (m, 1H), 3.90 (s, 3H), 3.38-3.26 (m, 2H), 3.25-3.15 (m, 1H), 2.79 (dd, J = 14.4, 6.0 Hz, 1H), 2.62 (dd, J = 14.4, 7.3 Hz, 1H), 2.18-2.11 (m, 2H), 2.06 (s, 3H), 1.60 (d, J = 12.4 Hz, 6H), 1.54-1.44 (m, 3H), 1.24 (d, J = 6.4 Hz, 3H), 0.89 (t, J = 7.4 Hz, 3H), 0.84 (t, J = 7.4 Hz, 3H). |
| 171 | (Thin film) 3378, 2936, 1734, 1678, 1504 | ESIMS m/z 531 ([M + H]$^+$) | $^1$H NMR (400 MHz, CDCl$_3$) δ 8.43 (s, 1H), 8.25 (d, J = 5.4 Hz, 1H), 7.29-7.22 (m, 2H), 7.20-7.13 (m, 4H), 6.93 (d, J = 5.4 Hz, 1H), 5.74 (s, 2H), 5.19-5.08 (m, 1H), 3.90 (s, 3H), 3.39-3.20 (m, 4H), 2.67 (t, J = 7.3 Hz, 2H), 2.16-2.08 (m, 1H), 2.06 (s, 3H), 1.68 (d, J = 6.9 Hz, 6H), 1.54 (dt, J = 7.7, 6.8 Hz, 1H), 1.29 (d, J = 6.4 Hz, 3H), 0.90 (t, J = 7.4 Hz, 3H). |
| 172 | | HRMS-ESI m/z ([M + H]$^+$) calcd for C$_{31}$H$_{45}$N$_2$O$_6$, 541.3277; found, 541.3282. | $^1$H NMR (400 MHz, CDCl$_3$) δ 8.57 (d, J = 7.9 Hz, 1H), 8.32 (d, J = 5.4 Hz, 1H), 7.32-7.24 (m, 2H), 7.23-7.11 (m, 3H), 6.98 (d, J = 5.5 Hz, 1H), 5.14-5.01 (m, 1H), 4.74-4.58 (m, 1H), 3.89 (s, 3H), 2.65-2.48 (m, 2H), 2.40 (s, 3H), 1.71-1.51 (m, 5H), 1.47 (d, J = 7.1 Hz, 3H), 1.40-1.23 (m, 3H), 1.21 (d, J = 6.5 Hz, 3H), 1.18-1.08 (m, 2H), 1.02 (ddd, J = 13.9, 8.5, 4.7 Hz, 1H), 0.93-0.78 (m, 9H). $^{13}$C NMR (101 MHz, CDCl$_3$) δ 172.27, 168.91, 162.32, 159.45, 146.66, 142.70, 141.58, 137.50, 128.35, 128.27, 125.63, 109.74, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 73.76, 56.27, 48.20, 41.04, 40.18, 36.37, 35.70, 30.35, 30.18, 26.08, 24.05, 23.50, 22.30, 20.77, 18.81, 17.91, 12.49. |
| 173 | (Thin film) 3381, 2934 1735, 1678, 1503 | ESIMS m/z 541 ([M + H]$^+$) | $^1$H NMR (400 MHz, CDCl$_3$) δ 8.39 (d, J = 7.6 Hz, 1H), 8.28 (d, J = 5.4 Hz, 1H), 7.31-7.23 (m, 2H), 7.20-7.09 (m, 3H), 6.95 (d, J = 5.5 Hz, 1H), 5.75 (d, J = 4.4 Hz, 2H), 5.03 (qd, J = 6.4, 5.1 Hz, 1H), 4.76-4.63 (m, 1H), 3.91 (s, 3H), 2.63 (dd, J = 14.1, 5.6 Hz, 1H), 2.50 (dd, J = 14.2, 8.5 Hz,1H), 2.07 (s, 3H), 2.03-1.91 (m, 1H), 1.71-1.59 (m, 2H), 1.54 (d, J = 7.1 Hz, 3H), 1.48-1.24 (m, 2H), 1.19 (d, J = 6.4 Hz, 3H), 0.94 (t, J = 7.3 Hz, 3H), 0.91-0.78 (m, 1H), 0.63 (dtt, J = 10.6, 6.3, 2.7 Hz, 1H), 0.43-0.32 (m, 2H), −0.02-−0.09 (m, 2H). |
| 174 | (Thin film) 3382, 2935, 1733, 1676, 1508 | ESIMS m/z 595 ([M + H]$^+$) | $^1$H NMR (400 MHz, CDCl$_3$) δ 8.38 (d, J = 7.7 Hz, 1H), 8.11 (d, J = 5.3 Hz, 1H), 7.26-7.18 (m, 2H), 7.19-7.12 (m, 1H), 7.08-6.99 (m, 4H), 6.98-6.89 (m, 2H), 6.86 (d, J = 5.4 Hz, 1H), 5.74 (d, J = 1.5 Hz, 2H), 5.11 (qd, J = 6.4, 4.3 Hz, 1H), 4.80-4.69 (m, 1H), 3.89 (s, 3H), 2.94 (dd, J = 13.5, 4.8 Hz, 1H), 2.66 (dd, J = 14.1, 5.6 Hz, 1H), 2.57 (dd, J = 14.1, 8.7 Hz, 1H), 2.26 (dd, J = 13.4, 9.8 Hz, 1H), 2.07 (s, 3H), 1.97-1.88 (m, 1H), 1.86-1.75 (m, 1H), 1.55 (d, J = 7.2 Hz, 3H), 1.37-1.29 (m, 2H), 1.27 (d, J = 6.4 Hz, 3H), 0.84 (t, J = 7.3 Hz, 3H). |
| 175 | (Thin film) 3384, 2937, 1753, 1678, 1510 | ESIMS m/z 503 ([M + H]$^+$) | $^1$H NMR (400 MHz, CDCl$_3$) δ 8.31-8.26 (m, 2H), 7.30-7.25 (m, 2H), 7.22-7.14 (m, 3H), 6.96 (d, J = 5.4 Hz, 1H), 5.76 (s, 2H), 5.17 (qd, J = 6.5, 4.7 Hz, 1H), 4.15 (dd, J = 6.7, 5.5 Hz, 2H), 3.91 (s, 3H), 3.39-3.22 (m, 4H), 2.68 (dd, J = 12.9, 7.3 Hz, 2H), 2.21-2.10 (m, 1H), 2.08 (s, 3H), 1.61-1.50 (m, 2H), 1.31 (d, J = 6.6 Hz, 3H), 0.90 (t, J = 7.4 Hz, 3H). |
| 176 | (Thin film) 3386, 2937, 1770, 1677, 1511 | ESIMS m/z 473 ([M + H]$^+$) | $^1$H NMR (400 MHz, CDCl$_3$) δ 8.48 (t, J = 5.4 Hz, 1H), 8.33 (d, J = 5.5 Hz, 1H), 7.30-7.24 (m, 2H), 7.22-7.13 (m, 3H), 7.01 (d, J = 5.5 Hz, 1H), 5.17 (qd, J = 6.5, 4.6 Hz, 1H) 4.12 (t, J = 5.8 Hz, 2H), 3.91 (s, 3H), 3.41-3.20 (m, 4H), 2.67 (dd, J = 11.8, 7.3 Hz, 2H), 2.40 (s, 3H), 2.20-2.09 (m, 1H), 1.60-1.49 (m, 2H), 1.31 (d, J = 6.5 Hz, 3H), 0.90 (t, J = 7.4 Hz, 3H). |
| 177 | | HRMS-ESI m/z ([M + H]$^+$) calcd for C$_{34}$H$_{42}$FN$_2$O$_9$, 641.2869; found, 641.2867 | $^1$H NMR (400 MHz, CDCl$_3$) δ 8.29 (d, J = 7.9 Hz, 1H), 8.26 (d, J = 5.3 Hz, 1H), 7.23-7.13 (m, 2H), 7.05-7.01 (m, 2H), 7.02-6.91 (m, 3H), 6.76 (d, J = 8.6 Hz, 2H), 5.77-5.70 (m, 2H), 5.11 (qd, J = 6.4, 4.4 Hz, 1H), 4.58 (p, J = 7.2 Hz, 1H), 4.54-4.51 (m, 1H), 3.90 (s, 3H), 3.56 (dd, J = 10.0, 5.3 Hz, 1H), 3.46-3.39 (m, 2H), 3.39-3.29 (m, 1H), 2.98 |

TABLE 2-continued

| *Cmpd. No. | IR (cm⁻¹) | MASS | NMR ($^1$H, $^{13}$C or $^{19}$F) |
|---|---|---|---|
| | | | (dd, J = 14.5, 6.4 Hz, 1H), 2.72 (dd, J = 14.5, 7.1 Hz, 1H), 2.37 (tdd, J = 6.9, 4.5, 2.6 Hz, 1H), 2.27 (s, 3H), 2.06 (s, 3H), 1.40 (d, J = 7.1 Hz, 3H), 1.29 (d, J = 6.4 Hz, 3H), 1.13 (t, J = 7.0 Hz, 3H). |
| 178 | | ESIMS m/z 661 ([M + H]⁺) | $^1$H NMR (400 MHz, CDCl$_3$) δ 8.82 (d, J = 8.4 Hz, 1H), 8.22-8.13 (m, 1H), 7.40 (d, J = 8.0 Hz, 2H), 7.02 (m, 4H), 6.94-6.85 (m, 3H), 5.71 (m, 1H), 5.13 (m, 1H), 5.00 (dd, J = 10.2, 1.6 Hz, 1H), 4.89-4.77 (m, 2H), 3.97 (dd, J = 9.4, 3.1 Hz, 1H), 3.88 (s, 3H), 3.68 (dd, J = 9.4, 3.4 Hz, 1H), 3.35 (s, 3H), 2.94 (q, J = 9.3 Hz, 1H), 2.71 (dd, J = 13.9, 6.9 Hz, 1H), 2.59 (dd, J = 14.0, 7.5 Hz, 1H), 2.52-2.44 (m, 2H), 2.37 (s, 3H), 1.97 (m, 1H), 1.29 (d, J = 6.4 Hz, 3H). $^{13}$C NMR (101 MHz, CDCl$_3$) δ 169.58, 168.88, 162.8, 161.30 (d, J = 242 Hz), 159.4, 146.66, 144.87, 141.17, 138.96, 137.61, 136.07 (d, J = 3 Hz), 130.35 (d, J = 8 Hz), 129.46, 127.89 (q, J = 31 Hz), 124.78 (q, J = 3 Hz), 124.39 (q, J = 270 Hz), 116.86, 115.14, (d, J = 21 Hz), 109.71, 72.58, 72.49, 59.35, 56.25, 52.80, 48.49, 45.14, 37.54, 32.27, 20.71, 17.71. |
| 179 | | ESIMS m/z 631 ([M + H]⁺) | $^1$H NMR (400 MHz, CDCl$_3$) δ 8.50 (d, J = 7.4 Hz, 1H), 8.17 (d, J = 5.4 Hz, 1H), 7.40 (d, J = 7.9 Hz, 2H), 7.05-6.96 (m, 4H), 6.96-6.85 (m, 3H), 5.69 (ddd, J = 17.2, 10.2, 8.3 Hz, 1H), 5.12 (m, 1H), 5.01 (dd, J = 10.4, 1.4 Hz, 1H), 4.83 (d, J = 16.3 Hz, 1H), 4.72 (m, 1H), 3.89 (s, 3H), 2.92 (dd, J = 12.5, 4.2 Hz, 1H), 2.72 (dd, J = 14.1, 6.5 Hz, 1H), 2.63-2.42 (m, 3H), 2.38 (s, 3H), 1.95 (m, 1H), 1.52 (d, J = 7.3 Hz, 3H), $^{13}$C NMR (101 MHz, CDCl$_3$) δ 171.89, 168.91, 162.48, 161.31 (d, J = 242 Hz), 159.49, 146.54, 144.69, 141.22, 138.68, 137.60, 136.00 (d, J = 3 Hz), 130.30 (d, J = 7 Hz), 129.38, 127.99 (q, J = 31 Hz), 124.83 (q, J = 4 Hz), 124.35 (q, J = 270 Hz), 117.04, 115.19, (d, J = 21 Hz), 109.73, 72.28, 56.27, 48.29, 48.24, 45.24, 37.81, 32.57, 20.73, 18.38, 17.65. |
| 180 | | ESIMS m/z 617 ([M + H]⁺) | $^1$H NMR (400 MHz, CDCl$_3$) δ 8.53 (t, J = 5.6 Hz, 1H), 8.22 (d, J = 5.5 Hz, 1H), 7.41 (d, J = 8.0 Hz, 2H), 7.05-6.97 (m, 4H), 6.97-6.88 (m, 3H), 5.70 (ddd, J = 17.1, 10.2, 8.7 Hz, 1H), 5.13 (m, 1H), 5.03 (dd, J = 10.3, 1.3 Hz, 1H), 4.85 (d, J = 17.1 Hz, 1H), 4.27-4.05 (m, 2H), 3.89 (s, 3H), 2.94 (dd, J = 13.4, 5.5 Hz, 1H), 2.72 (dd, J = 14.1, 6.4 Hz, 1H), 2.65-2.51 (m, 2H), 2.50-2.41 (m, 1H), 2.39 (s, 3H), 1.99 (m, 1H), 1.30 (d. J = 6.4 Hz, 3H). $^{13}$C NMR (101 MHz, CDCl$_3$) δ 168.91, 168.87, 163.15, 161.32 |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | (d, J = 243 Hz), 159.50, 146.63, 144.59, 141.14, 138.48, 137.60, 135.94 (d, J = 3 Hz), 130.0 (d, J = 8 Hz), 129.41, 128.02 (q, J = 32 Hz), 124.89 (q, J = 4 Hz), 124.35 (q, J = 270 Hz), 117.12, 115.21, (d, J = 21 Hz), 109.85, 72.76, 56.27, 47.93, 45.41, 41.56, 38.18, 32.88, 20.72, 17.73. |
| 181 | | ESIMS m/z 663 ([M + H]$^+$) | $^1$H NMR (400 MHz, CDCl$_3$) δ 8.81 (d, J = 8.0 Hz, 1H), 8.06 (d, J = 4.8 Hz, 1H), 7.44 (d, J = 8.0 Hz, 2H), 7.15-7.02 (m, 4H), 6.99-6.89 (m, 2H), 6.82 (d, J = 5.5 Hz, 1H), 5.10-5.06 (m, 1H), 4.85 (dt, J = 8.5, 3.1 Hz, 1H), 3.99 (dd, J = 9.3, 3.1 Hz, 1H), 3.87 (s, 3H), 3.69 (dd, J = 9.4, 3.3 Hz, 1H), 3.37 (s, 3H), 2.99 (dd, J = 13.4, 3.8 Hz, 1H), 2.63 (dd, J = 13.9, 5.0 Hz, 1H), 2.54 (dd, J = 13.6, 9.7 Hz, 1H), 2.37 (s, 3H), 2.21 (dd, J = 13.4, 10.4 Hz, 1H), 1.85 (dd, J = 9.3, 5.0 Hz, 2H), 1.36-1.20 (m, 2H), 1.27 (d, J = 6.0 Hz, 3H) 0.82 (t, J = 7.3 Hz, 3H). $^{13}$C NMR (101 MHz, CDCl$_3$) δ 169.75, 168.86, 162.80, 161.34 (d, J = 243.8 Hz), 159.32, 146.58, 146.17, 141.05, 137.55, 136.38 (d, J = 3.2 Hz), 130.45 (d, J = 7.7 Hz), 129.48, 127.79 (q, J = 32.2 Hz), 124.84 (q, J = 3.7 Hz) 124.44 (q, J = 270 Hz), 115.18 (d, J = 21.1 Hz), 109.60, 72.78, 72.45, 59.30, 56.21, 52.87, 45.58, 40.74, 37.29, 31.25, 23.32, 20.70, 18.35, 12.38. |
| 182 | | ESIMS m/z 633 ([M + H]$^+$) | $^1$H NMR (400 MHz, CDCl$_3$) δ 8.47 (d, J = 6.4 Hz, 1H), 8.05 (d, J = 5.2 Hz, 1H), 7.43 (d, J = 8.0 Hz, 2H), 7.08-7.02 (m, 4H), 6.99-6.88 (m, 2H), 6.84 (d, J = 5.4 Hz, 1H), 5.07 (m, 1H), 4.72 (p, J = 7.2 Hz, 1H), 3.87 (s, 3H), 2.95 (dd, J = 13.5, 4.6 Hz, 1H), 2.62 (dd, J = 13.8, 5.5 Hz, 1H), 2.55 (dd, J = 13.9, 9.0 Hz, 1H), 2.36 (s, 3H), 2.26 (dd, J = 13.2, 10.2 Hz, 1H), 1.94-1.75 (m, 2H), 1.55 (d, J = 7.3 Hz, 3H), 1.37-1.21 (m, 2H), 1.26 (d, J = 6.4 Hz, 3H), 0.83 (t, J = 7.3 Hz, 3H). $^{13}$C NMR (101 MHz, CDCl$_3$) δ 172.00, 168.88, 162.49, 161.34 (d, J = 242 Hz), 159.43, 146.45, 146.00, 141.07, 137.56, 136.30 (d, J = 3 Hz), 130.37 (d, J = 8.0 Hz), 129.37, 127.85 (q, J = 32.0 Hz), 124.88 (q, J = 4.0 Hz), 124.41 (q, J = 270.0 Hz), 115.21 (d, J = 21.0 Hz), 109.63, 72.40, 56.23, 48.32, 45.52, 40.84, 37.33, 31.59, 23.26, 20.71, 18.38, 18.32, 12.40. |
| 183 | | ESIMS m/z 619 ([M + H]$^+$) | $^1$H NMR (400 MHz, CDCl$_3$) δ 8.53 (t, J = 5.7 Hz, 1H), 8.11 (d, J = 5.4 Hz, 1H), 7.42 (d, J = 7.9 Hz, 2H), 7.08 (d, J = 7.9 Hz, 2H), 7.05-6.99 (m, 2H), 6.97-6.91 (m, 2H), 6.88 (d, J = 5.4 Hz, 1H), 5.14-5.06 (m, 1H), 4.21 (qd, J = 19.7, 18.9, 6.5 Hz, 2H), 3.88 (s, |

| *Cmpd. No. | IR (cm⁻¹) | MASS | NMR ($^1$H, $^{13}$C or $^{19}$F) |
|---|---|---|---|
| | | | 3H), 2.95 (dd, J = 13.4, 4.9 Hz, 1H), 2.59 (qd, J = 14.0, 7.3 Hz, 2H), 2.38 (s, 3H), 2.33 (dd, J = 13.3, 9.5 Hz, 1H), 1.93-1.84 (m, 1H), 1.84-1.75 (m, 1H), 1.37-1.22 (m, 2H), 1.27 (d, J = 6.4 Hz, 3H), 0.84 (t, J = 7.3 Hz, 3H). $^{13}$C NMR (101 MHz, CDCl$_3$) δ 168.97, 168.91, 163.16, 161.35 (d, J = 244.1 Hz), 159.44, 146.53, 145.89, 141.00, 137.58, 136.17 (d, J = 3.1 Hz), 130.34 (d, J = 7.8 Hz, 129.36, 127.86 (q, J = 32.2 Hz), 124.93 (q, J = 3.8 Hz), 124.4 (q, J = 270.0 Hz), 115.24 (d, J = 21.1 Hz), 109.77, 72.79, 56.24, 45.41, 41.62, 40.96, 37.53, 31.96, 23.21, 20.71, 18.54, 12.40. |
| 184 | | HRMS-ESI m/z ([M + H]⁺) calcd for C$_{26}$H$_{35}$N$_2$O$_7$, 487.2444; found, 487.2441. | $^1$H NMR (400 MHz, CDCl$_3$) δ 8.41 (d, J = 7.8 Hz, 1H), 8.27 (d, J = 5.4 Hz, 1H), 7.31-7.21 (m, 2H), 7.21-7.15 (m, 1H), 7.15-7.08 (m, 2H), 6.94 (d, J = 5.4 Hz, 1H), 5.81-5.71 (m, 2H), 5.04 (qd, J = 6.5, 3.7 Hz, 1H), 4.79-4.68 (m, 1H), 3.91 (s, 3H), 2.69 (dd, J = 13.6, 6.4 Hz, 1H), 2.50 (dd, J = 13.6, 7.8 Hz, 1H), 2.07 (s, 3H), 1.91-1.79 (m, 1H), 1.54 (d, J = 7.1 Hz, 3H), 1.41-1.25 (m, 4H), 1.23 (d, J = 6.5 Hz, 3H), 0.91-0.80 (m, 3H). $^{13}$C NMR (101 MHz, CDCl$_3$) δ 172.27, 170.28, 163.01, 160.31, 145.70, 144.04, 142.54, 140.77, 129.10, 128.31, 125.90, 109.56, 89.61, 73.09, 56.18, 48.40, 44.52, 36.23, 31.49, 20.89, 20.28, 18.73, 16.18, 14.26. |
| 185 | | HRMS-ESI m/z ([M + H]⁺) calcd for C$_{25}$H$_{31}$N$_2$O$_9$, 503.2029; found, 503.2026. | $^1$H NMR (400 MHz, CDCl$_3$) δ 8.36 (d, J = 7.8 Hz, 1H), 8.28 (d, J = 5.4 Hz, 1H), 7.32-7.23 (m, 2H), 7.23-7.17 (m, 1H), 7.17-7.07 (m, 2H), 6.95 (d, J = 5.4 Hz, 1H), 5.75 (d, J = 0.8 Hz, 2H), 5.27-5.17 (m, 1H), 4.84-4.62 (m, 1H), 3.91 (s, 3H), 3.54 (s, 3H), 3.02-2.80 (m, 3H), 2.07 (s, 3H), 1.49 (d, J = 7.2 Hz, 3H), 1.37 (d, J = 6.3 Hz, 3H). $^{13}$C NMR (101 MHz, CDCl$_3$) δ 172.50, 171.89, 170.28, 163.02, 160.28, 145.72, 144.01, 142.42, 138.27, 128.77, 128.50, 126.60, 109.60, 89.54, 71.91, 56.19, 52.97, 51.63, 48.18, 34.23, 20.87, 18.41, 17.83. |
| 186 | | HRMS-ESI m/z ([M + H]⁺) calcd for C$_{24}$H$_{29}$N$_2$O$_8$, 473.1924; found, 473.1925. | $^1$H NMR (400 MHz, CDCl$_3$) δ 8.53 (d, J = 6.3 Hz, 1H), 8.33 (d, J = 5.5 Hz, 1H), 7.30-7.23 (m, 2H), 7.23-7.18 (m, 1H), 7.17-7.12 (m, 2H), 7.00 (d, J = 5.5 Hz, 1H), 5.33-5.15 (m, 1H), 4.79-4.61 (m, 1H), 3.89 (s, 3H), 3.53 (s, 3H), 2.99-2.81 (m, 3H), 2.39 (s, 3H), 1.47 (d, J = 7.2 Hz, 3H), 1.36 (d, J = 6.4 Hz, 3H). $^{13}$C NMR (101 MHz, CDCl$_3$) δ 172.47, 171.77, 168.89, 162.44, 159.46, 146.69, 141.47, 138.30, 137.51, 128.79, 128.50, 126.59, 109.81, 71.91, 56.29, 52.96, 51.62, 47.97, 34.17, 20.74, 18.55, 17.77. |

TABLE 2-continued

Analytical Data

| *Cmpd. No. | IR (cm$^{-1}$) | MASS | NMR ($^1$H, $^{13}$C or $^{19}$F) |
|---|---|---|---|
| 187 | IR (neat) 3376, 2934, 1735, 1678, 1507, 1260 | HRMS-ESI m/z [M]+ calcd for C$_{34}$H$_{39}$F$_3$N$_2$O$_8$, 660.2659; found, 660.2658. | $^1$H NMR (400 MHz, CDCl$_3$) δ 8.37 (d, J = 7.6 Hz, 1H), 8.11 (d, J = 5.4 Hz, 1H), 7.24-7.14 (m, 3H), 7.12-7.05 (m, 4H), 7.02-6.97 (m, 2H), 6.86 (d, J = 5.4 Hz, 1H), 5.78-5.71 (m, 2H), 5.17-5.08 (m, 1H), 4.79-4.68 (m, 1H), 3.89 (s, 3H), 2.91 (dd, J = 13.5, 5.1 Hz, 1H), 2.72-2.56 (m, 2H), 2.27 (dd, J = 13.4, 9.5 Hz, 1H), 2.07 (s, 3H), 1.97-1.90 (m, 1H), 1.84-1.74 (m, 1H), 1.54 (d, J = 7.3 Hz, 3H), 1.37-1.28 (m, 2H), 1.28 (d, J = 6.4 Hz, 3H), 0.85 (t, J = 7.3 Hz, 3H) |
| 188 | (Thin film) 3384, 2936, 1736, 1677, 1493 | ESIMS m/z 545 ([M + H]$^+$) | $^1$H NMR (400 MHz, CDCl$_3$) δ 8.32 (d, J = 7.8 Hz, 1H), 8.27 (d, J = 5.3 Hz, 1H), 7.26-7.21 (m, 2H), 6.94 (d, J = 5.4 Hz, 1H), 6.90 (tt, J = 7.4, 1.1 Hz, 1H), 6.87-6.82 (m, 2H), 5.74 (d, J = 1.6 Hz, 2H), 5.17-5.05 (m, 1H), 4.67-4.57 (m, 1H), 4.28 (td, J = 6.4, 3.1 Hz, 1H), 3.91 (s, 3H), 2.07 (s, 3H), 1.88 (qd, J = 6.5, 5.7, 2.3 Hz, 1H), 1.83-1.71 (m, 1H), 1.71-1.61 (m, 1H), 1.46 (td, J = 6.3, 3.5 Hz, 1H), 1.41 (d, J = 7.2 Hz, 3H), 1.39-1.31 (m, 4H), 1.30 (d, J = 6.4 Hz, 3H), 0.95 (t, J = 7.4 Hz, 3H), 0.90 (t, J = 7.2 Hz, 3H). |
| 189 | (Thin film) 3382, 2935, 1735, 1677, 1494 | ESIMS m/z 545 ([M + H]$^+$) | $^1$H NMR (400 MHz, CDCl$_3$) δ 8.39 (d, J = 7.8 Hz, 1H), 8.28 (d, J = 5.3 Hz, 1H), 7.32-7.21 (m, 2H), 6.99-6.85 (m, 4H), 5.75 (d, J = 3.2 Hz, 2H), 5.23 (qd, J = 6.5, 5.2 Hz, 1H), 4.80-4.67 (m, 1H), 4.33 (td, J = 6.2, 3.9 Hz, 1H), 3.91 (s, 3H), 2.08 (s, 3H), 2.03-1.95 (m, 1H), 1.78-1.67 (m, 2H), 1.58-1.45 (m, 1H), 1.53 (d, J = 7.1 Hz, 3H), 1.43-1.35 (m, 1H), 1.34 (d, J = 6.4 Hz, 3H), 1.32-1.18 (m, 4H), 0.96 (t, J = 7.4 Hz, 3H), 0.84 (t, J = 7.1 Hz, 3H) |
| 190 | (Thin film) 3384, 2936, 1771, 1677, 1507 | ESIMS m/z 515 ([M + H]$^+$) | $^1$H NMR (400 MHz, CDCl$_3$) δ 8.57 (d, J = 7.7 Hz, 1H), 8.33 (d, J = 5.5 Hz, 1H), 7.31-7.20 (m, 2H), 7.01 (d, J = 5.4 Hz, 1H), 6.95-6.84 (m, 3H), 5.22 (qd, J = 6.4, 5.2 Hz, 1H), 4.76-4.65 (m, 1H), 4.33 (td, J = 6.2, 4.0 Hz, 1H), 3.91 (s, 3H), 2.40 (s, 3H), 2.02-1.94 (m, 1H), 1.79-1.65 (m, 2H), 1.51 (d, J = 7.1 Hz, 3H), 1.58-1.44 (m, 1H), 1.42-1.35 (m, 1H), 1.32 (d, J = 6.4 Hz, 3H), 1.31-1.17 (m, 4H), 0.95 (t, J = 7.4 Hz, 3H), 0.84 (t, J = 7.0 Hz, 3H). |
| 191 | (Thin film) 3383, 2975, 1735, 1676, 1494 | ESIMS m/z 579 ([M + H]$^+$) | $^1$H NMR (400 MHz, CDCl$_3$) δ 8.30 (d, J = 8.6 Hz, 1H), 8.28 (d, J = 5.4 Hz, 1H), 7.34-7.25 (m, 2H), 7.25-7.16 (m, 5H), 6.95 (d, J = 5.4 Hz, 1H), 6.93-6.85 (m, 1H), 6.75-6.70 (m, 2H), 5.75 (d, J = 1.1 Hz, 2H), 5.11 (qd, J = 6.4, 4.8 Hz, 1H), 4.67-4.54 (m, 1H), 4.29 (ddd, J = 7.0, 5.9, 2.6 Hz, 1H), 3.91 (s, 3H), 2.89 (dd, J = 14.4, 6.8 Hz, 1H), 2.77 (dd, J = 14.4, 6.9 Hz, 1H), 2.35-2.25 (m, 1H), 2.06 (s, 3H), 1.83-1.62 (m, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 2H), 1.41 (d, J = 7.1 Hz, 3H), 1.30 (d, J = 6.5 Hz, 3H), 0.91 (t, J = 7.4 Hz, 3H). |
| 192 | (Thin film) 3383, 2939, 1735, 1676, 1493 | ESIMS m/z 579 ([M + H]$^+$) | $^1$H NMR (400 MHz, CDCl$_3$) δ 8.41 (d, J = 7.7 Hz, 1H), 8.27 (d, J = 5.3 Hz, 1H), 7.29-7.24 (m, 2H), 7.23-7.12 (m, 3H), 7.02-6.90 (m, 4H), 6.87-6.81 (m, 2H), 5.76 (d, J = 3.6 Hz, 2H), 5.27 (qd, J = 6.5, 4.2 Hz, 1H), 4.82-4.69 (m, 1H), 4.27 (td, J = 6.6, 3.5 Hz, 1H), 3.91 (s, 3H), 2.88 (dd, J = 13.7, 7.6 Hz, 1H), 2.71 (dd, J = 13.7, 6.6 Hz, 1H), 2.36-2.25 (m, 1H), 2.08 (s, 3H), 1.80-1.67 (m, 2H), 1.58 (d, J = 7.2 Hz, 3H), 1.37 (d, J = 6.5 Hz, 3H), 0.88 (t, J = 7.4 Hz, 3H). |
| 193 | (Thin film) 3383, 2938, 1771, 1734, 1676 | ESIMS m/z 549 ([M + H]$^+$) | $^1$H NMR (400 MHz, CDCl$_3$) δ 8.49 (d, J = 7.2 Hz, 1H), 8.32 (d, J = 5.4 Hz, 1H), 7.32-7.27 (m, 2H), 7.25-7.16 (m, 5H), 6.99 (d, J = 5.5 Hz, 1H), 6.88 (tt, J = 7.3, 1.1 Hz, 1H), 6.74-6.68 (m, 2H), 5.10 (qd, J = 6.5, 4.9 Hz, 1H), 4.66-4.53 (m, 1H), 4.28 (ddd, J = 7.1, 5.8, 2.7 Hz, 1H), 3.90 (s, 3H), 2.88 (dd, J = 14.4, 6.9 Hz, 1H), 2.75 (dd, J = 14.4, 6.8 Hz, 1H), 2.39 (s, 3H), 2.34-2.25 (m, 1H), 1.84-1.58 (m, 2H), 1.40 (d, J = 7.1 Hz, 3H), 1.29 (d, J = 6.5 Hz, 3H), 0.89 (t, J = 7.4 Hz, 3H). |
| 194 | (Thin film) 3384, 2978, 1771, 1734, 1677 | ESIMS m/z 549 ([M + H]$^+$) | $^1$H NMR (400 MHz, CDCl$_3$j) δ 8.57 (d, J = 7.3 Hz, 1H), 8.32 (d, J = 5.4 Hz, 1H), 7.29-7.23 (m, 2H), 7.23-7.12 (m, 3H), 7.02-6.96 (m, 3H), 6.94 (tt, J = 7.4, 1.1 Hz, 1H), 6.86-6.78 (m, 2H), 5.24 (qd, J = 6.5, 4.1 Hz, 1H), 4.81-4.66 (m, 1H), 4.26 (td, J = 6.6, 3.5 Hz, 1H), 3.91 (s, 3H), 2.88 (dd, J = 13.7, 7.5 Hz, 1H), 2.70 (dd, J = 13.7, 7.4 Hz, 1H), 2.39 (s, 3H), 2.33-2.25 (m, 1H), 1.78-1.66 (m, 2H), 1.56 (d, J = 7.2 Hz, 3H), 1.35 (d, J = 6.5 Hz, 3H), 0.87 (t, J = 7.4 Hz, 3H). |
| 195 | | HRMS-ESI m/z ([M + H]$^+$) calcd for C$_{29}$H$_{33}$N$_2$O$_7$, 521.2288; found, 521.2283. | $^1$H NMR (400 MHz, CDCl$_3$) δ 8.33 (d, J = 7.8 Hz, 1H), 8.28 (d, J = 5.4 Hz, 1H), 7.22-6.98 (m, 10H), 6.95 (d, J = 5.4 Hz, 1H), 5.82-5.70 (m, 2H), 5.24 (qd, J = 6.3, 5.1 Hz, 1H), 4.74-4.61 (m, 1H), 3.90 (s, 3H), 3.11-2.98 (m, 2H), 2.91 (dd, J = 12.4, 8.0 Hz, 1H), 2.05 (s, 3H), 1.29 (d, J = 7.2 Hz, 3H), 1.23 (d, J = 6.3 Hz, 3H). $^{13}$C NMR (101 MHz, CDCl$_3$) δ 172.12, 170.22, 162.95, 160.32, 145.68, 144.04, 142.50, 140.26, 139.57, 128.99, 128.95, 128.18, 128.09, 126.66, 126.01, 109.59, 89.54, 73.60, 56.17, 53.09, 48.29, 38.41, 20.83, 18.36, 18.27. |
| 196 | | HRMS-ESI m/z ([M + H]$^+$) calcd for C$_{28}$H$_{31}$N$_2$O$_6$, 491.2182; found, 491.2182. | $^1$H NMR (400 MHz, CDCl$_3$) δ 8.51 (d, J = 7.8 Hz, 1H), 8.34 (d, J = 5.4 Hz, 1H), 7.22-6.98 (m, 11H), 5.21 (qd, J = 6.3, 5.0 Hz, 1H), 4.72-4.57 (m, 1H), 3.89 (s, 3H), 3.14-2.96 (m, 2H), 2.91 (dd, J = 12.4, 8.0 Hz, 1H), 2.37 (s, 3H), 1.30 (d, J = 7.2 Hz, 3H), 1.20 (d, J = 6.3 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | $^{13}$C NMR (101 MHz, CDCl$_3$) δ 171.99, 168.83, 162.39, 159.50, 146.65, 141.49, 140.21, 139.62, 137.54, 129.01, 128.99, 128.17, 128.05, 126.65, 126.00, 109.81, 73.51, 56.26, 53.03, 48.12, 38.34, 20.69, 18.36, 18.31. |
| 197 | | HRMS-ESI m/z ([M + H]$^+$) calcd for C$_{25}$H$_{33}$N$_2$O$_6$, 457.2338; found, 457.2345 | $^1$H NMR (400 MHz, CDCl$_3$) δ 8.46 (d, J = 8.3 Hz, 1H), 8.32 (d, J = 5.4 Hz, 1H), 7.33-7.14 (m, 5H), 6.99 (d, J = 5.5 Hz, 1H), 5.20 (p, J = 6.4 Hz, 1H), 4.58 (dq, J = 8.2, 7.2 Hz, 1H), 3.89 (s, 3H), 2.70 (ddd, J = 10.3, 6.9, 4.9 Hz, 1H), 2.38 (s, 3H), 1.75-1.56 (m, 2H), 1.33-1.23 (m, 2H), 1.22 (d, J = 6.3 Hz, 3H), 1.13 (d, J = 7.2 Hz, 3H), 1.12-0.99 (m, 2H), 0.81 (t, J = 7.2 Hz, 3H). $^{13}$C NMR (101 MHz, CDCl$_3$) δ 172.13, 168.87, 162.28, 159.44, 146.64, 141.56, 141.22, 137.47, 128.65, 128.17, 126.50, 109.73, 74.81, 56.27, 51.11, 47.97, 31.39, 29.48, 22.61, 20.73, 18.32, 18.30, 13.90. |
| 198 | | HRMS-ESI m/z ([M + H]$^+$) calcd for C$_{27}$H$_{37}$N$_2$O$_6$, 485.2651; found, 485.2647 | $^1$H NMR (400 MHz, CDCl$_3$) δ 8.41 (d, J = 7.8 Hz, 1H), 8.31 (d, J = 5.4 Hz, 1H), 7.29-7.12 (m, 5H), 6.97 (d, J = 5.5 Hz, 1H), 5.19 (p, J = 6.4 Hz, 1H), 4.59 (dq, J = 8.2, 7.2 Hz, 1H), 3.86 (s, 3H), 2.93 (hept, J = 7.0 Hz, 1H), 2.70 (ddd, J = 10.2, 6.9, 4.9 Hz, 1H), 1.76-1.58 (m, 2H), 1.35 (d, J = 7.0 Hz, 6H), 1.29-1.23 (m, 2H), 1.21 (d, J = 6.3 Hz, 3H), 1.13 (d, J = 7.2 Hz, 3H), 1.12-1.04 (m, 2H), 0.81 (t, J = 7.2 Hz, 3H). $^{13}$C NMR (101 MHz, CDCl$_3$) δ 174.65, 172.22, 162.27, 159.41, 146.55, 141.95, 141.23, 137.63, 128.67, 128.16, 126.50, 109.58, 74.73, 56.27, 51.10, 47.94, 33.93, 31.40, 29.48, 22.60, 18.80, 18.35, 18.32, 13.89. |
| 199 | | HRMS-ESI m/z ([M + H]$^+$) calcd for C$_{26}$H$_{35}$N$_2$O$_7$, 487.2444; found, 487.2437 | $^1$H NMR (400 MHz, CDCl$_3$) δ 8.43-8.14 (m, 2H), 7.31-7.21 (m, 2H), 7.22-7.11 (m, 3H), 6.94 (d, J = 5.4 Hz, 1H), 5.86-5.60 (m, 2H), 5.31-5.14 (m, 1H), 4.75-4.49 (m, 1H), 3.90 (s, 3H), 2.71 (ddd, J = 10.3, 7.0, 4.6 Hz, 1H), 2.06 (s, 3H), 1.73-1.58 (m, 2H), 1.37-1.19 (m, 2H), 1.24 (d, J = 6.3 Hz, 3H), 1.17-1.04 (m, 2H), 1.14 (d, J = 7.1 Hz, 3H). 0.81 (t, J = 7.2 Hz, 3H). $^{13}$C NMR (101 MHz, CDCl$_3$) δ 172.23, 170.23, 162.87, 160.26, 145.68, 143.96, 142.56, 141.28, 128.62, 128.18, 126.49, 109.54, 89.55, 74.79, 56.17, 51.14, 48.18, 31.40, 29.46, 22.60, 20.85, 18.35, 18.12, 13.89. |
| 200 | | HRMS-ESI m/z ([M + H]$^+$) calcd for C$_{28}$H$_{39}$N$_2$O$_7$, 515.2764; found, 515.2759 | $^1$H NMR (400 MHz, CDCl$_3$) δ 8.34 (d, J = 7.8 Hz, 1H), 8.26 (d, J = 5.4 Hz, 1H), 7.27-7.15 (m, 5H), 6.94 (d, J = 5.4 Hz, 1H), 5.76 (q, J = 6.4 Hz, 2H), 5.33-5.10 (m, 1H), 4.65-4.51 (m, 1H), 3.88 (s, 3H), 2.72 (ddd, J = 10.3, 7.0, 4.7 Hz, 1H), 2.54 (hept, J = |

TABLE 2-continued

Analytical Data

| *Cmpd. No. | IR (cm⁻¹) | MASS | NMR ($^1$H, $^{13}$C or $^{19}$F) |
|---|---|---|---|
| | | | 7.0 Hz, 1H), 1.76-1.55 (m, 2H), 1.32-1.21 (m, 2H), 1.24 (d, J = 6.3 Hz, 3H), 1.20-1.02 (m, 2H), 1.14 (d, J = 7.2 Hz, 3H), 1.14 (d, J = 7.0 Hz, 6H), 0.81 (t, J = 7.2 Hz, 3H). $^{13}$C NMR (101 MHz, CDCl$_3$) δ 176.19, 172.23, 162.84, 160.25, 145.53, 144.19, 142.19, 141.27, 128.62, 128.17, 126.48, 109.48, 89.91, 74.77, 56.12, 51.13, 48.17, 33.84, 31.39, 29.46, 22.60, 18.66, 18.34, 18.12, 13.88. |
| 201 | | HRMS-ESI m/z ([M + H]⁺) calcd for C$_{28}$H$_{30}$ClN$_2$O$_6$, 525.1792; found, 525.1785 | $^1$H NMR (400 MHz, CDCl$_3$) δ 8.49 (d, J = 7.9 Hz, 1H), 8.34 (d, J = 5.4 Hz, 1H), 7.19-7.07 (m, 7H), 7.01 (d, J = 5.5 Hz, 1H), 6.94-6.85 (m, 2H), 5.21 (qd, J = 6.3, 5.1 Hz, 1H), 4.73-4.60 (m, 1H), 3.90 (s, 3H), 3.02 (dd, J = 12.5, 5.4 Hz, 1H), 2.94 (dt, J = 8.7, 5.3 Hz, 1H), 2.86 (dd, J = 12.5, 8.7 Hz, 1H), 2.37 (s, 3H), 1.28 (d, J = 7.2 Hz, 3H), 1.23-1.17 (m, 3H). $^{13}$C NMR (101 MHz, CDCl$_3$) δ 172.01, 168.88, 162.45, 159.54, 146.66, 141.47, 139.73, 138.13, 137.60, 131.77, 130.37, 128.99, 128.30, 128.16, 126.82, 109.83, 73.45, 56.30, 53.01, 48.16, 37.67, 20.74, 18.32, 18.32. |
| 202 | | HRMS-ESI m/z ([M + H]⁺) calcd for C$_{30}$H$_{34}$ClN$_2$O$_6$, 553.2105; found, 553.2106 | $^1$H NMR (400 MHz, CDCl$_3$) δ 8.44 (d, J = 7.7 Hz, 1H), 8.33 (d, J = 5.4 Hz, 1H), 7.17-7.08 (m, 7H), 6.99 (d, J = 5.4 Hz, 1H), 6.92 (d, J = 8.4 Hz, 2H), 5.19 (qd, J = 6.3, 5.0 Hz, 1H), 4.73-4.61 (m, 1H), 3.87 (s, 3H), 3.02 (dd, J = 12.3, 5.3 Hz, 1H), 2.97-2.83 (m, 3H), 1.34 (d, J = 4.7 Hz, 3H), 1.32 (d, J = 4.7 Hz, 3H), 1.29 (d, J = 7.2 Hz, 3H), 1.18 (d, J = 6.3 Hz, 3H). $^{13}$C NMR (101 MHz, CDCl$_3$) δ 174.66, 172.10, 162.43, 159.52, 146.56, 141.82, 139.73, 138.16, 137.79, 131.75, 130.39, 129.02, 128.28, 128.14, 126.80, 109.68, 73.34, 56.31, 53.00, 48.13, 37.69, 33.95, 18.80, 18.78, 18.34. |
| 203 | | HRMS-ESI m/z ([M + H]⁺) calcd for C$_{29}$H$_{32}$ClN$_2$O$_7$, 555.1898; found, 555.1895 | $^1$H NMR (400 MHz, CDCl$_3$) δ 8.45-8.14 (m, 2H), 7.24-7.14 (m, 3H), 7.14-7.09 (m, 4H), 6.99-6.94 (m, 1H), 6.93-6.84 (m, 2H), 5.85-5.63 (m, 2H), 5.28-5.09 (m, 1H), 4.66 (p, J = 7.3 Hz, 1H), 3.90 (s, 3H), 3.03 (dd, J = 12.6, 5.4 Hz, 1H), 2.96 (dt, J =8.9, 5.4 Hz, 1H), 2.87 (dd, J = 12.6, 8.8 Hz, 1H), 2.06 (s, 3H), 1.28 (d, J = 7.1 Hz, 3H), 1.23 (d, J = 6.3 Hz, 3H). $^{13}$C NMR (101 MHz, CDCl$_3$) δ 172.12, 170.25, 163.00, 160.33, 145.68, 142.46, 139.76, 138.06, 131.77, 130.34, 130.34, 128.93, 128.29, 128.19, 126.82, 109.63, 89.58, 73.54, 56.20, 53.06, 48.32, 37.72, 22.65, 20.86, 18.35, 18.20. |
| 204 | | HRMS-ESI m/z ([M + H]⁺) calcd | $^1$H NMR (400 MHz, CDCl$_3$) δ 8.37 (d, J = 7.8 Hz, 1H), 8.28 |

TABLE 2-continued

| Analytical Data | | | |
|---|---|---|---|
| *Cmpd. No. | IR (cm$^{-1}$) | MASS | NMR ($^1$H, $^{13}$C or $^{19}$F) |
| | | for C$_{31}$H$_{36}$ClN$_2$O$_7$, 583.2211; found, 583.2206 | (d, J = 5.3 Hz, 1H), 7.23-7.08 (m, 7H), 6.95 (d, J = 5.4 Hz, 1H), 6.93-6.85 (m, 2H), 5.83-5.70 (m, 2H), 5.28-5.15 (m, 1H), 4.72-4.59 (m, 1H), 3.88 (s, 3H), 3.03 (dd, J = 12.6, 5.4 Hz, 1H), 2.96 (dt, J = 8.9, 5.4 Hz, 1H), 2.87 (dd, J = 12.6, 8.8 Hz, 1H), 2.54 (hept, J = 7.0 Hz, 1H), 1.28 (d, J = 7.2 Hz, 3H), 1.23 (d, J = 6.3 Hz, 3H), 1.13 (d, J = 7.0 Hz, 6H). $^{13}$C NMR (101 MHz, CDCl$_3$) δ 176.22, 172.12, 162.96, 160.32, 145.55, 144.33, 142.09, 139.76, 138.06, 131.77, 130.34, 128.93, 128.29, 128.18, 126.81, 109.55, 89.96, 73.53, 56.14, 53.06, 48.32, 37.72, 33.85, 18.68, 18.34, 18.21. |
| 205 | | HRMS-ESI m/z ([M + H]$^+$) calcd for C$_{25}$H$_{33}$N$_2$O$_6$, 457.2339; found, 457.2329 | $^1$H NMR (400 MHz, CDCl$_3$) δ 8.56 (s, 1H), 8.31 (d, J = 5.4 Hz, 1H), 7.32-7.23 (m, 2H), 7.20-7.09 (m, 3H), 6.99 (d, J = 5.5 Hz, 1H), 5.02 (qd, J = 6.4, 4.4 Hz, 1H), 4.68 (dq, J = 8.1, 7.2 Hz, 1H), 3.90 (s, 3H), 2.66 (dd, J = 13.9, 5.5 Hz, 1H), 2.54 (dd, J = 14.2, 8.1 Hz, 1H), 2.39 (s, 3H), 1.97 (ddq, J = 10.7, 6.9, 3.5 Hz, 1H), 1.82-1.73 (m, 1H), 1.50 (d, J = 7.1 Hz, 3H), 1.20 (d, J = 6.4 Hz, 3H), 1.00 (d, J = 6.9 Hz, 3H), 0.92 (d, J = 6.8 Hz, 3H). $^{13}$C NMR (101 MHz, CDCl$_3$) δ 172.09, 168.90, 162.40, 159.46, 146.64, 141.57, 141.53, 137.52, 128.96, 128.34, 125.79, 109.75, 72.98, 56.28, 50.38, 48.26, 32.26, 27.32, 21.51, 20.75, 19.07, 18.71, 17.64. |
| 206 | | HRMS-ESI m/z ([M + H]$^+$) calcd for C$_{26}$H$_{35}$N$_2$O$_7$, 487.2444; found, 487.2419 | $^1$H NMR (400 MHz, CDCl$_3$) δ 8.39 (d, J = 7.8 Hz, 1H), 8.27 (d, J = 5.3 Hz, 1H), 7.35-7.22 (m, 2H), 7.22-7.07 (m, 3H), 6.94 (d, J = 5.3 Hz, 1H), 5.85-5.64 (m, 2H), 5.04 (qd, J = 6.4, 4.5 Hz, 1H), 4.83-4.58 (m, 1H), 3.90 (s, 3H), 2.67 (dd, J = 14.2, 5.4 Hz, 1H), 2.55 (dd, J = 14.2, 8.0 Hz, 1H), 2.07 (s, 3H), 2.04-1.91 (m, 1H), 1.84-1.74 (m, 1H), 1.51 (d, J = 7.1 Hz, 3H), 1.21 (d, J = 6.4 Hz, 3H), 1.00 (d, J = 6.9 Hz, 3H), 0.94 (d, J = 6.9 Hz, 3H). $^{13}$C NMR (101 MHz, CDCl$_3$) δ 172.21, 170.27, 162.98, 160.30, 145.68, 144.05, 142.51, 141.58, 128.93, 128.34, 125.80, 109.56, 89.62, 73.00, 56.18, 50.36, 48.42, 32.33, 27.38, 21.46, 20.87, 19.12, 18.60, 17.64. |
| 207 | (Thin film) 3380, 2973, 1756, 1731, 1676, 1501, 1201 | HRMS-ESI m/z ([M + H]$^+$) calcd for C$_{29}$H$_{41}$N$_2$O$_8$, 545.2857; found, 545.2857 | $^1$H NMR (400 MHz, CDCl$_3$) δ 8.27 (d, J = 5.4 Hz, 1H), 8.25 (d, J = 5.4 Hz, 1H), 7.25-7.16 (m, 4H), 7.16-7.09 (m, 1H), 6.93 (d, J = 5.4 Hz, 1H), 5.74 (s, 1H), 5.74 (s, 1H), 5.39 (qd, J = 6.7, 2.9 Hz, 1H), 4.59-4.44 (m, 1H), 3.90 (s, 3H), 3.36-3.20 (m, 2H), 2.96 (dd, J = 14.7, 5.2 Hz, 1H), 2.77 (dd, J = 14.7, 7.2 Hz, 1H), 2.26 (ddd, J = 7.2, 5.2, 2.8 Hz, 1H), 2.07 (s, 3H), 1.53 (h, J = 7.4 Hz, 2H), 1.36 (d, J = |

TABLE 2-continued

Analytical Data

| *Cmpd. No. | IR (cm$^{-1}$) | MASS | NMR ($^1$H, $^{13}$C or $^{19}$F) |
|---|---|---|---|
| 208 | (Thin film) 3382, 2937, 1739, 1676, 1497, 1201 | HRMS-ESI m/z ([M + H]$^+$) calcd for C$_{30}$H$_{35}$N$_2$O$_8$, 551.2388; found, 551.2389 | 6.6 Hz, 3H), 1.23 (d, J = 7.0 Hz, 3H), 1.23 (s, 3H), 1.16 (s, 3H), 0.92 (t, J = 7.4 Hz, 3H). $^1$H NMR (400 MHz, CDCl$_3$) δ 8.36 (d, J = 7.8 Hz, 1H), 8.25 (d, J = 5.4 Hz, 1H), 7.31-7.11 (m, 7H), 6.96-6.90 (m, 2H), 6.86-6.80 (m, 2H), 5.75 (d, J = 6.4 Hz, 1H), 5.73 (d, J = 6.4 Hz, 1H), 5.24 (qd, J = 6.5, 5.0 Hz, 1H), 4.81-4.65 (m, 1H), 3.96-3.85 (m, 2H), 3.90 (s, 3H), 2.83-2.78 (m, 2H), 2.38-2.25 (m, 1H), 2.06 (s, 3H), 1.48 (d, J = 7.1 Hz, 3H), 1.39 (d, J = 6.5 Hz, 3H). |
| 209 | (Thin film) 3384, 2939, 1739, 1677, 1506, 1465, 1202 | HRMS-ESI m/z ([M + H]$^+$) calcd for C$_{30}$H$_{33}$Cl$_2$N$_2$O$_8$, 619.1608; found, 619.1617 | $^1$H NMR (400 MHz, CDCl$_3$) δ 8.33 (d, J = 7.7 Hz, 1H), 8.24 (d, J = 5.4 Hz, 1H), 7.35 (d, J = 2.5 Hz, 1H), 7.31-7.22 (m, 2H), 7.23-7.13 (m, 3H), 7.09 (dd, J = 8.8, 2.6 Hz, 1H), 6.93 (d, J = 5.4 Hz, 1H), 6.66 (d, J = 8.8 Hz, 1H), 5.74 (s, 2H), 5.23 (qd, J = 6.4, 5.1 Hz, 1H), 4.72 (p, J = 7.3 Hz, 1H), 3.98-3.84 (m, 2H), 3.91 (s, 3H), 2.88 (dd, J = 13.6, 8.9 Hz, 1H), 2.81 (dd, J = 13.6, 6.0 Hz, 1H), 2.33 (ddd, J = 10.7, 9.3, 5.2 Hz, 1H), 2.07 (s, 3H), 1.49 (d, J = 7.2 Hz, 3H), 1.43 (d, J = 6.5 Hz, 3H). |
| 210 | | HRMS-ESI m/z ([M + H]$^+$) calcd for C$_{26}$H$_{35}$N$_2$O$_6$, 471.2495; found, 471.2475 | $^1$H NMR (400 MHz, CDCl$_3$) δ 8.47 (d, J = 8.1 Hz, 1H), 8.32 (d, J = 5.4 Hz, 1H), 7.27-7.21 (m, 2H), 7.23-7.13 (m, 3H), 6.99 (d, J = 5.5 Hz, 1H), 5.26-5.11 (m, 1H), 4.59 (dq, J = 8.2, 7.2 Hz, 1H), 3.89 (s, 3H), 2.67 (ddd, J = 10.3, 6.7, 4.7 Hz, 1H), 2.38 (s, 3H), 1.74-1.59 (m, 2H), 1.51-1.41 (m, 1H), 1.21 (d, J = 6.3 Hz, 3H), 1.15 (d, J = 7.1 Hz, 3H), 1.12-0.99 (m, 1H), 0.99-0.94 (m, 1H), 0.81 (d, J = 4.8 Hz, 3H), 0.79 (d, J = 4.8 Hz, 3H). $^{13}$C NMR (101 MHz, CDCl$_3$) δ 172.13, 168.87, 162.28, 159.44, 146.64, 141.56, 141.21, 137.47, 128.67, 128.17, 126.51, 109.73, 74.78, 56.27, 51.34, 47.97, 36.49, 29.41, 27.94, 22.73, 22.21, 20.74, 18.33, 18.30. |
| 211 | | HRMS-ESI m/z ([M + H]$^+$) calcd for C$_{28}$H$_{39}$N$_2$O$_6$, 499.2808; found, 499.2791 | $^1$H NMR (400 MHz, CDCl$_3$) δ 8.41 (d, J = 8.1 Hz, 1H), 8.31 (d, J = 5.4 Hz, 1H), 7.27-7.21 (m, 2H), 7.21-7.12 (m, 3H), 6.97 (d, J = 5.4 Hz, 1H), 5.20 (p, J = 6.4 Hz, 1H), 4.60 (dq, J = 8.2, 7.1 Hz, 1H), 3.87 (s, 3H), 2.93 (hept, J = 7.0 Hz, 1H), 2.67 (ddd, J = 10.2, 6.8, 4.8 Hz, 1H), 1.76-1.59 (m, 2H), 1.53-1.42 (m, 1H), 1.35 (d, J = 7.0 Hz, 6H), 1.21 (d, J = 6.3 Hz, 3H), 1.15 (d, J = 7.1 Hz, 3H), 1.11-1.03 (m, 1H), 1.00-0.94 (m, 1H), 0.81 (d, J = 4.7 Hz, 3H), 0.79 (d, J = 4.7 Hz, 3H). $^{13}$C NMR (101 MHz, CDCl$_3$) δ 174.66, 172.23, 162.27, 159.41, 146.55, 141.95, 141.22, 137.63, 128.68, 128.17, 126.50, 109.57, |

TABLE 2-continued

Analytical Data

| *Cmpd. No. | IR (cm⁻¹) | MASS | NMR ($^1$H, $^{13}$C or $^{19}$F) |
|---|---|---|---|
| | | | 74.71, 56.27, 51.33, 47.94, 36.49, 33.94, 29.42, 27.94, 22.73, 22.21, 18.80, 18.39, 18.30. |
| 212 | | HRMS-ESI m/z ([M + H]⁺) calcd for C$_{28}$H$_{39}$N$_2$O$_7$, 515.2757; found, 515.2750 | $^1$H NMR (400 MHz, CDCl$_3$) δ 8.45 (d, J = 8.6 Hz, 1H), 8.32 (d, J = 5.4 Hz, 1H), 7.27-7.21 (m, 2H), 7.21-7.15 (m, 3H), 6.99 (d, J = 5.5 Hz, 1H), 5.20 (p, J = 6.4 Hz, 1H), 4.58 (dq, J = 8.2, 7.2 Hz, 1H), 3.88 (s, 3H), 3.80 (t, J = 6.6 Hz, 2H), 3.39 (s, 3H), 2.97 (t, J = 6.6 Hz, 2H), 2.67 (ddd, J = 10.3, 6.7, 4.7 Hz, 1H), 1.75-1.55 (m, 2H), 1.55-1.39 (m, 1H), 1.21 (d, J = 6.3 Hz, 3H), 1.14 (d, J = 7.2 Hz, 3H), 1.10-1.01 (m, 1H), 1.00-0.92 (m, 1H), 0.81 (d, J = 4.8 Hz, 3H), 0.79 (d, J = 4.8 Hz, 3H). $^{13}$C NMR (101 MHz, CDCl$_3$) δ 172.15, 169.40, 162.24, 159.45, 146.70, 141.59, 141.21, 137.32, 128.67, 128.18, 126.51, 109.73, 74.76, 67.58, 58.75, 56.30, 51.34, 47.96, 36.49, 34.63, 29.42, 27.94, 22.73, 22.21, 18.33, 18.30. |
| 213 | | HRMS-ESI m/z ([M + H]⁺) calcd for C$_{27}$H$_{37}$N$_2$O$_7$, 501.2601; found, 501.2584 | $^1$H NMR (400 MHz, CDCl$_3$) δ 8.28 (d, J = 7.9 Hz, 1H), 8.27 (d, J = 5.3 Hz, 1H), 7.28-7.22 (m, 2H), 7.23-7.14 (m, 3H), 6.94 (d, J = 5.4 Hz, 1H), 5.84-5.67 (m, 2H), 5.26-5.14 (m, 1H), 4.71-4.52 (m, 1H), 3.90 (s, 3H), 2.68 (ddd, J = 10.3, 6.9, 4.6 Hz, 1H), 2.06 (s, 3H), 1.77-1.55 (m, 2H), 1.53-1.41 (m, 1H), 1.23 (d, J = 6.3 Hz, 3H), 1.15 (d, J = 7.1 Hz, 3H), 1.07 (ddt, J = 13.4, 10.8, 6.0 Hz, 1H), 1.01-0.90 (m, 1H), 0.81 (d, J = 5.2 Hz, 3H), 0.79 (d, J = 5.1 Hz, 3H). $^{13}$C NMR (101 MHz, CDCl$_3$) δ 172.23, 170.23, 162.86, 160.26, 145.68, 143.96, 142.55, 141.26, 128.63, 128.18, 126.49, 109.53, 89.55, 74.77, 56.17, 51.37, 48.18, 36.47, 29.42, 27.94, 22.72, 22.19, 20.86, 18.32, 18.16. |
| 214 | | HRMS-ESI m/z ([M + H]⁺) calcd for C$_{29}$H$_{41}$N$_2$O$_7$, 529.2914; found, 529.2880 | $^1$H NMR (400 MHz, CDCl$_3$) δ 8.34 (d, J = 7.8 Hz, 1H), 8.26 (d, J = 5.3 Hz, 1H), 7.28-7.22 (m, 2H), 7.22-7.14 (m, 3H), 6.94 (d, J = 5.4 Hz, 1H), 5.76 (q, J = 6.4 Hz, 2H), 5.21 (p, J = 6.4 Hz, 1H), 4.68-4.52 (m, 1H), 3.88 (s, 3H), 2.69 (ddd, J = 10.4, 6.9, 4.7 Hz, 1H), 2.54 (hept, J = 7.0 Hz, 1H), 1.76-1.55 (m, 2H), 1.52-1.41 (m, 1H), 1.23 (d, J = 6.3 Hz, 3H), 1.16 (d, J = 7.4 Hz, 3H), 1.14 (d, J = 7.1 Hz, 6H), 1.10-1.02 (m, 1H), 1.01-0.90 (m, 1H), 0.81 (d, J = 5.2 Hz, 3H), 0.79 (d, J = 5.2 Hz, 3H). $^{13}$C NMR (101 MHz, CDCl$_3$) δ 176.20, 172.23, 162.84, 160.25, 145.54, 144.19, 142.19, 141.26, 128.63, 128.18, 126.49, 109.48, 89.91, 74.74, 56.12, 51.36, 48.17, 36.46, 33.83, 29.41, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 27.93, 22.72, 22.19, 18.66, 18.31, 18.15. |
| 215 | | HRMS-ESI m/z ([M + H]$^+$) calcd for C$_{29}$H$_{41}$N$_2$O$_8$, 545.2863; found, 545.2854 | $^1$H NMR (400 MHz, CDCl$_3$) δ 8.29 (d, J = 8.0 Hz, 1H), 8.27 (d, J = 5.4 Hz, 1H), 7.27-7.21 (m, 2H), 7.22-7.14 (m, 3H), 6.94 (d, J = 5.4 Hz, 1H), 5.93-5.73 (m, 2H), 5.25-5.16 (m, 1H), 4.67-4.52 (m, 1H), 4.09 (s, 2H), 3.89 (s, 3H), 3.58 (q, J = 7.0 Hz, 2H), 2.68 (ddd, J = 10.4, 6.9, 4.7 Hz, 1H), 1.76-1.56 (m, 2H), 1.53-1.41 (m, 1H), 1.23 (d, J = 6.3 Hz, 3H), 1.22 (t, J = 7.0 Hz, 3H), 1.15 (d, J = 7.1 Hz, 3H), 1.11-1.02 (m, 1H), 0.95 (dddd, J = 13.3, 10.9, 7.3, 5.0 Hz, 1H), 0.81 (d, J = 5.2 Hz, 3H), 0.79 (d, J = 5.2 Hz, 3H). $^{13}$C NMR (101 MHz, CDCl$_3$) δ 172.21, 170.03, 162.81, 160.19, 145.73, 143.94, 142.41, 141.26, 128.63, 128.19, 126.50, 109.62, 89.60, 74.80, 67.78, 67.17, 56.21, 51.37, 48.17, 36.47, 29.41, 27.94, 22.73, 22.19, 18.32, 18.15, 15.00. |
| 216 | | HRMS-ESI m/z ([M + H]$^+$) calcd for C$_{28}$H$_{29}$Cl$_2$N$_2$O$_6$, 559.1402; found, 559.1384 | $^1$H NMR (400 MHz, CDCl$_3$) δ 8.48 (d, J = 7.7 Hz, 1H), 8.35 (d, J = 5.4 Hz, 1H), 7.24-7.14 (m, 4H), 7.10 (dd, J = 6.5, 2.9 Hz, 3H), 7.02 (d, J = 5.5 Hz, 1H), 6.80 (dd, J = 8.2, 2.1 Hz, 1H), 5.20 (qd, J = 6.3, 5.0 Hz, 1H), 4.75-4.53 (m, 1H), 3.90 (s, 3H), 3.02-2.90 (m, 2H), 2.85 (dd, J = 12.3, 8.5 Hz, 1H), 2.37 (s, 3H), 1.30 (d, J = 7.2 Hz, 3H), 1.19 (d, J = 6.3 Hz, 3H). $^{13}$C NMR (101 MHz, CDCl$_3$) δ 171.97, 168.86, 162.50, 159.56, 146.67, 141.42, 139.98, 139.25, 137.62, 132.00, 130.91, 130.05, 129.97, 128.97, 128.53, 128.23, 126.97, 109.88, 73.35, 56.31, 52.70, 48.22, 37.40, 20.74, 18.28, 18.22. |
| 217 | | HRMS-ESI m/z ([M + H]$^+$) calcd for C$_{30}$H$_{33}$Cl$_2$N$_2$O$_6$, 587.1715; found, 587.1712 | $^1$H NMR (400 MHz, CDCl$_3$) δ 8.43 (d, J = 7.9 Hz, 1H), 8.34 (d, J = 5.4 Hz, 1H), 7.20 (d, J = 8.3 Hz, 1H), 7.17-7.13 (m, 3H), 7.13-7.08 (m, 3H), 7.00 (d, J = 5.4 Hz, 1H), 6.81 (dd, J = 8.2, 2.1 Hz, 1H), 5.19 (qd, J = 6.3, 4.8 Hz, 1H), 4.76-4.54 (m, 1H), 3.88 (s, 3H), 3.03-2.76 (m, 4H), 1.38-1.27 (m, 9H), 1.17 (d, J = 6.3 Hz, 3H). $^{13}$C NMR (101 MHz, CDCl$_3$) δ 174.66, 172.07, 162.49, 159.55, 146.56, 141.77, 140.02, 139.26, 137.82, 131.99, 130.92, 130.04, 129.96, 129.01, 128.58, 128.22, 126.96, 109.72, 73.24, 56.32, 52.71, 48.17, 37.43, 33.95, 18.80, 18.30, 18.25. |
| 218 | | HRMS-ESI m/z ([M + H]$^+$) calcd for C$_{29}$H$_{31}$Cl$_2$N$_2$O$_7$, 589.1508; found, 589.1490 | $^1$H NMR (400 MHz, CDCl$_3$) δ 8.35-8.24 (m, 2H), 7.23-7.16 (m, 4H), 7.14-7.09 (m, 2H), 7.07 (d, J = 2.1 Hz, 1H), 6.96 (d, J = 5.4 Hz, 1H), 6.79 (dd, J = 8.2, 2.1 Hz, 1H), 5.79-5.67 |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | (m, 2H), 5.29-5.18 (m, 1H), 4.72-4.60 (m, 1H), 3.91 (s, 3H), 3.08-2.91 (m, 2H), 2.86 (dd, J = 12.4, 8.7 Hz, 1H), 2.06 (s, 3H), 1.29 (d, J = 7.2 Hz, 3H), 1.23 (d, J = 6.3 Hz, 3H). $^{13}$C NMR (101 MHz, CDCl$_3$) δ 172.08, 170.25, 163.03, 160.35, 145.70, 144.09, 142.41, 139.89, 139.29, 131.98, 130.87, 130.05, 129.98, 128.90, 128.50, 128.27, 126.98, 109.65, 89.55, 73.46, 56.21, 52.76, 48.36, 37.45, 20.85, 18.29, 18.13. |
| 219 | | HRMS-ESI m/z ([M + H]$^+$) calcd for C$_{31}$H$_{35}$Cl$_2$N$_2$O$_7$, 617.1821; found, 617.1795 | $^1$H NMR (400 MHz, CDCl$_3$) δ 8.36 (d, J = 7.8 Hz, 1H), 8.28 (d, J = 5.3 Hz, 1H), 7.24-7.15 (m, 4H), 7.15-7.09 (m, 2H), 7.07 (d, J = 2.0 Hz, 1H), 6.95 (d, J = 5.4 Hz, 1H), 6.79 (dd, J = 8.2, 2.1 Hz, 1H), 5.82-5.67 (m, 2H), 5.29-5.18 (m, 1H), 4.74-4.58 (m, 1H), 3.88 (s, 3H), 3.09-2.91 (m, 2H), 2.85 (dd, J = 12.4, 8.7 Hz, 1H), 2.54 (hept, J = 7.0 Hz, 1H), 1.29 (d, J = 7.2 Hz, 3H), 1.23 (d, J = 6.3 Hz, 3H), 1.13 (d, J = 7.0 Hz, 6H). $^{13}$C NMR (101 MHz, CDCl$_3$) δ 176.22, 172.08, 163.01, 160.33, 145.56, 144.32, 142.06, 139.90, 139.29, 131.98, 130.87, 130.04, 129.97, 128.90, 128.50, 128.27, 126.97, 109.60, 89.93, 73.45, 56.15, 52.76, 48.36, 37.44, 33.84, 18.66, 18.28, 18.13. |
| 220 | | HRMS-ESI m/z ([M + H]$^+$) calcd for C$_{29}$H$_{33}$N$_2$O$_6$, 505.2338; found, 505.2328 | $^1$H NMR (400 MHz, CDCl$_3$) δ 8.51 (d, J = 7.9 Hz, 1H), 8.33 (d, J = 5.4 Hz, 1H), 7.21-7.13 (m, 5H), 7.03-6.94 (m, 3H), 6.92-6.84 (m, 2H), 5.20 (qd, J = 6.2, 4.7 Hz, 1H), 4.72-4.59 (m, 1H), 3.88 (s, 3H), 3.06-2.93 (m, 2H), 2.88 (dd, J = 11.9, 7.2 Hz, 1H), 2.38 (s, 3H), 1.30 (d, J = 7.2 Hz, 3H), 1.19 (d, J = 6.3 Hz, 3H). $^{13}$C NMR (101 MHz, CDCl$_3$) δ 172.05, 168.90, 162.41, 159.51, 146.68, 141.54, 140.39, 137.57, 136.51, 135.45, 129.05, 128.93, 128.89, 128.08, 126.65, 109.81, 73.53, 56.29, 53.09, 48.15, 37.93, 21.00, 20.75, 18.46, 18.39. |
| 221 | | HRMS-ESI m/z ([M + H]$^+$) calcd for C$_{30}$H$_{35}$N$_2$O$_7$, 535.2444; found, 535.2447 | $^1$H NMR (400 MHz, CDCl$_3$) δ 8.33 (d, J = 7.8 Hz, 1H), 8.28 (d, J = 5.4 Hz, 1H), 7.23-7.13 (m, 5H), 7.01-6.92 (m, 3H), 6.92-6.86 (m, 2H), 5.82-5.67 (m, 2H), 5.26-5.17 (m, 1H), 4.75-4.61 (m, 1H), 3.90 (s, 3H), 3.07-2.95 (m, 2H), 2.88 (dd, J = 11.5, 6.9 Hz, 1H), 2.25 (s, 3H), 2.05 (s, 3H), 1.30 (d, J = 7.2 Hz, 3H), 1.22 (d, J = 6.3 Hz, 3H). $^{13}$C NMR (101 MHz, CDCl$_3$) δ 172.16, 170.26, 162.95, 160.32, 145.70, 144.04, 142.53, 140.42, 136.45, 135.45, 129.00, 128.91, |

TABLE 2-continued

Analytical Data

| *Cmpd. No. | IR (cm$^{-1}$) | MASS | NMR ($^{1}$H, $^{13}$C or $^{19}$F) |
|---|---|---|---|
| | | | 128.86, 128.10, 126.64, 109.60, 89.57, 73.61, 56.19, 53.13, 48.31, 37.96, 20.99, 20.87, 18.40, 18.34. |
| 222 | | HRMS-ESI m/z ([M + H]$^{+}$) calcd for C$_{29}$H$_{32}$FN$_{2}$O$_{7}$, 539.2193; found, 539.2190 | $^{1}$H NMR (400 MHz, CDCl$_{3}$) δ 8.31 (d, J = 7.9 Hz, 1H), 8.29 (d, J = 5.4 Hz, 1H), 7.22-7.09 (m, 5H), 6.99-6.89 (m, 3H), 6.90-6.78 (m, 2H), 5.87-5.64 (m, 2H), 5.34-5.19 (m, 1H), 4.77-4.56 (m, 1H), 3.90 (s, 3H), 3.04 (dd, J = 12.7, 5.4 Hz, 1H), 2.95 (dt, J = 8.9, 5.5 Hz, 1H), 2.87 (dd, J = 12.7, 8.8 Hz, 1H), 2.05 (s, 3H), 1.28 (d, J = 7.2 Hz, 3H), 1.24 (d, J = 6.3 Hz, 3H). |
| 223 | | HRMS-ESI m/z ([M + H]$^{+}$) calcd for C$_{31}$H$_{36}$FN$_{2}$O$_{7}$, 567.2506; found, 567.2496 | $^{1}$H NMR (400 MHz, CDCl$_{3}$) δ 8.38 (d, J = 7.8 Hz, 1H), 8.28 (d, J = 5.4 Hz, 1H), 7.25-7.07 (m, 5H), 6.99-6.88 (m, 3H), 6.88-6.78 (m, 2H) 5.84-5.69 (m, 2H), 5.33-5.17 (m, 1H), 4.73-4.58(m, 1H), 3.88 (s, 3H), 3.04 (dd, J = 12.8, 5.4 Hz, 1H), 2.96 (dt, J = 8.8, 5.5 Hz, 1H), 2.87 (dd, J = 12.7, 8.8 Hz, 1H), 2.54 (hept, J = 7.0 Hz, 1H), 1.28 (d, J = 7.2 Hz, 3H), 1.23 (d, J = 6.3 Hz, 3H), 1.13 (d, J = 7.0 Hz, 6H). |
| 224 | | HRMS-ESI m/z ([M + H]$^{+}$) calcd for C$_{32}$H$_{33}$N$_{2}$O$_{6}$, 541.2338; found, 541.2336 | $^{1}$H NMR (400 MHz, CDCl$_{3}$) δ 8.52 (d, J = 7.6 Hz, 1H), 8.32 (d, J = 5.4 Hz, 1H), 7.81-7.62 (m, 3H), 7.45 (s, 1H), 7.43-7.34 (m, 2H), 7.22-7.09 (m, 6H), 6.96 (d, J = 5.5 Hz, 1H), 5.32-5.21 (m, 1H), 4.75-4.59 (m, 1H), 3.86 (s, 3H), 3.28-3.16 (m, 1H), 3.15-3.02 (m, 2H), 2.37 (s, 3H), 1.31 (d, J = 7.2 Hz, 3H), 1.22 (d, J = 6.3 Hz, 3H). $^{13}$C NMR (101 MHz, CDCl$_{3}$) δ 172.07, 168.92, 162.47, 159.53, 146.69, 141.53, 140.16, 137.60, 137.20, 133.46, 132.02, 129.06, 128.14, 127.76, 127.54, 127.54, 127.52, 127.51, 126.74, 125.83, 125.24, 109.83, 73.67, 56.29, 52.98, 48.21, 38.53, 20.78, 18.45, 18.41. |
| 225 | | HRMS-ESI m/z ([M + H]$^{+}$) calcd for C$_{33}$H$_{35}$N$_{2}$O$_{7}$, 571.2444; found, 571.2448 | $^{1}$H NMR (400 MHz, CDCl$_{3}$) δ 8.34 (d, J = 7.8 Hz, 1H), 8.27 (d, J = 5.3 Hz, 1H), 7.77-7.63 (m, 3H), 7.46-7.33 (m, 3H), 7.23-7.06 (m, 6H), 6.92 (d, J = 5.4 Hz, 1H), 5.81-5.69 (m, 2H), 5.36-5.23 (m, 1H), 4.77-4.60 (m, 1H), 3.87 (s, 3H), 3.23 (dd, J = 11.7, 4.3 Hz, 1H), 3.16-3.02 (m, 2H), 2.04 (s, 3H), 1.31 (d, J = 7.2 Hz, 3H), 1.25 (d, J = 6.3 Hz, 3H). $^{13}$C NMR (101 MHz, CDCl$_{3}$) δ 172.17, 170.27, 163.00, 160.33, 145.72, 144.07, 142.52, 140.19, 137.13, 133.43, 132.01, 129.00, 128.16, 127.75, 127.52, 127.51, 127.48, 126.73, 125.82, 125.24, 109.62, 89.59, 73.76, 56.19, 53.02, 48.36, 38.58, 20.87, 18.43, 18.33. |
| 226 | | HRMS-ESI m/z ([M + H]$^{+}$) calcd for C$_{35}$H$_{39}$N$_{2}$O$_{7}$, | $^{1}$H NMR (400 MHz, CDCl$_{3}$) δ 8.40 (d, J = 7.8 Hz, 1H), 8.27 (d, J = 5.3 Hz, 1H), 7.77-7.71 |

TABLE 2-continued

Analytical Data

| *Cmpd. No. | IR (cm$^{-1}$) | MASS | NMR ($^1$H, $^{13}$C or $^{19}$F) |
|---|---|---|---|
| | | 599.2757; found, 599.2756 | (m, 1H), 7.71-7.61 (m, 2H), 7.46-7.33 (m, 3H), 7.22-7.08 (m, 6H), 6.91 (d, J = 5.4 Hz, 1H), 5.78 (q, J = 6.4 Hz, 2H), 5.34-5.22 (m, 1H), 4.81-4.63 (m, 1H), 3.85 (s, 3H), 3.23 (dd, J = 11.7, 4.3 Hz, 1H), 3.17-3.02 (m, 2H), 2.53 (hept, J = 7.0 Hz, 1H), 1.31 (d, J = 7.2 Hz, 3H), 1.25 (d, J = 6.3 Hz, 3H), 1.13 (d, J = 7.0 Hz, 6H). $^{13}$C NMR (101 MHz, CDCl$_3$) δ 176.24, 172.18, 162.98, 160.32, 145.57, 144.32, 142.17, 140.20, 137.14, 133.43, 132.01, 129.00, 128.16, 127.75, 127.52, 127.51, 127.49, 126.73, 125.82, 125.23, 109.55, 89.97, 73.76, 56.14, 53.03, 48.36, 38.58, 33.86, 18.69, 18.42, 18.34. |
| 227 | (Thin film) 3382, 2937, 1676, 1507, 1175, 732, 699 | HRMS-ESI m/z ([M + H]$^+$) calcd for C$_{30}$H$_{35}$N$_2$O$_7$, 535.2439; found, 535.2441 | $^1$H NMR (400 MHz, CDCl$_3$) δ 8.55 (d, J = 7.8 Hz, 1H), 8.32 (d, J = 5.4 Hz, 1H), 7.37-7.22 (m, 7H), 7.22-7.08 (m, 3H), 7.02-6.96 (m, 1H), 5.17 (qd, J = 6.5, 4.8 Hz, 1H), 4.76-4.61 (m, 1H), 4.51-4.30 (m, 2H), 3.90 (s, 3H), 3.39 (d, J = 5.2 Hz, 2H), 2.73-2.65 (m, 2H), 2.39 (s, 3H), 2.21-2.07 (m, 1H), 1.46 (d, J = 7.1 Hz, 3H), 1.30 (d, J = 6.5 Hz, 3H). |
| 228 | (Thin film) 3381, 2938, 1770, 1676, 1508, 1175, 731 | HRMS-ESI m/z ([M + H]$^+$) calcd for C$_{30}$H$_{34}$FN$_2$O$_7$, 553.2345; found, 553.2358 | $^1$H NMR (400 MHz, CDCl$_3$) δ 8.67-8.41 (m, 1H), 8.31 (d, J = 5.5 Hz, 1H), 7.43-7.20 (m, 5H), 7.10-7.02 (m, 2H), 6.99 (d, J = 5.5 Hz, 1H), 6.97-6.89 (m, 2H), 5.14 (qd, J = 6.4, 4.9 Hz, 1H), 4.77-4.61 (m, 1H), 4.48-4.33 (m, 2H), 3.90 (s, 3H), 3.45-3.31 (m, 2H), 2.71-2.59 (m, 2H), 2.38 (s, 3H), 2.07 (tq, J = 7.6, 5.1 Hz, 1H), 1.46 (d, J = 7.2 Hz, 3H), 1.29 (d, J = 6.5 Hz, 3H). $^{13}$C NMR (101 MHz, CDCl$_3$) δ 171.89, 168.89, 162.44, 161.37 (d, J = 243.8 Hz), 159.49, 146.66, 141.52, 138.24, 137.55, 135.60 (d, J = 3.2 Hz), 130.49 (d, J = 7.8 Hz), 128.35, 127.63, 127.59, 115.10 (d, J = 21.1 Hz), 109.78, 73.08, 72.10, 68.24, 56.29, 48.18, 45.64, 32.63, 20.75, 18.63, 17.23. |
| 229 | (Thin film) 3382, 2978, 1770, 1508, 1175, 1041, 733 | HRMS-ESI m/z ([M + H]$^+$) calcd for C$_{32}$H$_{38}$FN$_2$O$_7$, 581.2658; found, 581.2662 | $^1$H NMR (400 MHz, CDCl$_3$) δ 8.45 (d, J = 7.9 Hz, 1H), 8.28 (d, J = 5.5 Hz, 1H), 7.37-7.29 (m, 3H), 7.29-7.22 (m, 1H), 7.15-7.08 (m, 2H), 6.98 (d, J = 5.5 Hz, 1H), 6.93-6.85 (m, 2H), 5.42 (qd, J = 6.6, 2.8 Hz, 1H), 4.61-4.50 (m, 1H), 4.50-4.33 (m, 2H), 3.90 (s, 3H), 2.99 (dd, J = 14.8, 5.5 Hz, 1H), 2.78 (dd, J = 14.8, 6.8 Hz, 1H), 2.42-2.34 (m, 3H), 2.34-2.23 (m, 1H), 2.21-2.15 (m, 1H), 1.35 (d, J = 6.5 Hz, 3H), 1.33 (s, 3H), 1.28 (d, J = 7.2 Hz, 3H), 1.26-1.23 (m, 3H). $^{13}$C NMR (101 MHz, CDCl$_3$) δ 171.90, 168.90, 162.35, 161.04 (d, J = 243.3 Hz), 159.47, 146.59, 141.49, 139.51, 138.24 |

TABLE 2-continued

Analytical Data

| *Cmpd. No. | IR (cm⁻¹) | MASS | NMR ($^1$H, $^{13}$C or $^{19}$F) |
|---|---|---|---|
| | | | (d, J = 3.1 Hz), 137.54, 130.12 (d, J = 7.6 Hz), 128.26, 127.11, 114.96 (d, J = 21.1 Hz), 109.74, 72.94, 63.38, 56.28, 53.80, 53.12, 48.14, 30.36, 29.28, 24.93, 24.84, 20.74, 18.23, 17.24. |
| 230 | (Thin film) 3382, 2977, 1771, 1507, 1175, 1040, 731 | HRMS-ESI m/z ([M + H]⁺) calcd for $C_{32}H_{39}N_2O_7$, 563.2752; found, 563.2759 | $^1$H NMR (400 MHz, CDCl$_3$) δ 8.45 (d, J = 7.9 Hz, 1H), 8.30 (d, J = 5.4 Hz, 1H), 7.33 (d, J = 4.4 Hz, 4H), 7.29-7.16 (m, 5H), 7.16-7.07 (m, 1H), 6.98 (d, J = 5.5 Hz, 1H), 5.44 (qd, J = 6.5, 2.8 Hz, 1H), 4.58-4.40 (m, 3H), 3.90 (s, 3H), 3.03 (dd, J = 14.8, 5.3 Hz, 1H) 2.81 (dd, J = 14.7, 7.1 Hz, 1H), 2.42-2.31 (m, 4H), 1.37 (d, J = 6.6 Hz, 3H), 1.34 (s, 3H), 1.30-1.16 (m, 6H). $^{13}$C NMR (101 MHz, CDCl$_3$) δ 171.96, 168.90, 162.32, 159.43, 146.61, 142.63, 141.58, 139.58, 137.49, 128.86, 128.28, 128.25, 127.12, 127.06, 125.58, 109.70, 73.09, 63.38, 56.27, 52.86, 48.12, 31.18, 29.27, 24.94, 24.88, 20.75, 18.23, 17.24. |
| 231 | (Thin film) 3381, 2983, 1770, 1676, 1508, 1176, 731 | HRMS-ESI m/z ([M + H]⁺) calcd for $C_{24}H_{30}FN_2O_7$, 477.2032; found, 477.2035 | $^1$H NMR (400 MHz, CDCl$_3$) δ 8.65-8.42 (m, 1H), 8.32 (d, J = 5.4 Hz, 1H), 7.17-7.04 (m, 2H), 7.04-6.88 (m, 3H), 5.09 (qd, J = 6.5, 4.6 Hz, 1H), 4.78-4.63 (m, 1H), 3.91 (s, 3H), 3.36-3.17 (m, 5H), 2.62 (d, J = 7.5 Hz, 2H), 2.39 (s, 3H), 2.03 (tq, J = 7.4, 5.2 Hz, 1H), 1.52 (d, J = 7.2 Hz, 3H), 1.28 (d, J = 6.5 Hz, 3H). |
| 232 | (Thin film) 3380, 2977, 1770, 1676, 1508, 1175, 1040, 730 | HRMS-ESI m/z ([M + H]⁺) calcd for $C_{26}H_{34}FN_2O_7$, 505.2345; found, 505.2351 | $^1$H NMR (400 MHz, CDCl$_3$) δ 8.45 (d, J = 7.9 Hz, 1H), 8.28 (d, J = 5.5 Hz, 1H), 7.21-7.04 (m, 2H), 6.98 (d, J = 5.5 Hz, 1H), 6.96-6.81 (m, 2H), 5.33 (qd, J = 6.5, 2.8 Hz, 1H), 4.61-4.48 (m, 1H), 3.90 (s, 3H), 3.16 (s, 3H), 2.85 (dd, J = 14.8, 5.3 Hz, 1H), 2.71 (dd, J = 14.8, 7.1 Hz, 1H), 2.38 (s, 3H), 2.24-2.15 (m, 1H), 1.36-1.23 (m, 6H), 1.20 (s, 3H), 1.15 (s, 3H). $^{13}$C NMR (101 MHz, CDCl$_3$) δ 171.88, 168.90, 162.35, 161.05 (d, J = 243.2 Hz), 159.47, 146.59, 141.49, 138.13 (d, J = 3.3 Hz), 137.54, 130.11 (d, J = 7.7 Hz), 114.95 (d, J = 21.0 Hz), 109.75, 72.82, 56.28, 52.25, 48.85, 48.14, 30.47, 29.28, 24.31, 24.09, 20.74, 18.24, 17.23. |
| 233 | (Thin film) 3376, 2979, 1773, 1508, 1126, 952, 733 | HRMS-ESI m/z ([M + H]⁺) calcd for $C_{33}H_{40}FN_2O_9$, 627.2712; found, 627.2724 | $^1$H NMR (400 MHz, CDCl$_3$) δ 8.37 (d, J = 7.8 Hz, 1H), 8.26 (d, J = 5.4 Hz, 1H), 7.39-7.22 (m, 5H), 7.15-7.01 (m, 2H), 7.01-6.88 (m, 3H), 5.83 (d, J = 0.9 Hz, 2H), 5.23-5.11 (m, 1H), 4.77-4.62 (m, 1H), 4.49-4.31 (m, 2H), 4.10 (s, 2H), 3.90 (s, 3H), 3.59 (q, J = 7.0 Hz, 2H), 3.38 (d, J = 5.1 Hz, 2H), 2.73-2.60 (m, 2H), 2.09 (tq, J = 7.5, 5.1 Hz, 1H), 1.48 (d, J = 7.2 Hz, 3H), 1.30 (d, J = 6.4 Hz, 3H), 1.27-1.18 (m, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | $^{13}$C NMR (101 MHz, CDCl$_3$) δ 172.01, 170.06, 162.98, 161.38 (d, J = 243.8 Hz), 160.24, 145.75, 144.03, 142.35, 138.22, 135.57 (d, J = 3.2 Hz), 130.48 (d, J = 7.8 Hz), 128.36, 127.62, 127.59, 115.12 (d, J = 21.2 Hz), 109.68, 89.63, 73.09, 72.14, 68.25, 67.80, 67.19, 56.22, 48.36, 45.65, 32.64, 18.54, 17.25, 15.01. |
| 234 | (Thin film) 3379, 2978, 1735, 1676, 1503, 1126, 952, 700 | HRMS-ESI m/z ([M + H]$^+$) calcd for C$_{33}$H$_{41}$N$_2$O$_9$, 609.2807; found, 609.2815 | $^1$H NMR (400 MHz, CDCl$_3$) δ 8.39 (d, J = 7.8 Hz, 1H), 8.26 (d, J = 5.3 Hz, 1H), 7.39-7.22 (m, 7H), 7.22-7.08 (m, 3H), 6.94 (d, J = 5.4 Hz, 1H), 5.89-5.77 (m, 2H), 5.18 (qd, J = 6.5, 4.9 Hz, 1H), 4.77-4.62 (m, 1H), 4.51-4.35 (m, 2H), 4.10 (s, 2H), 3.90 (s, 3H), 3.59 (q, J = 7.0 Hz, 2H), 3.41 (d, J = 5.2 Hz, 2H), 2.75-2.66 (m, 2H), 2.21-2.10 (m, 1H), 1.48 (d, J = 7.2 Hz, 3H), 1.31 (d, J = 6.5 Hz, 3H), 1.22 (t, J = 7.0 Hz, 3H). $^{13}$C NMR (101 MHz, CDCl$_3$) δ 172.02, 170.06, 162.95, 160.22, 145.76, 144.00, 142.40, 139.99, 138.32, 129.14, 128.37, 128.33, 127.59, 127.53, 126.06, 109.66, 89.63, 73.05, 72.30, 68.46, 67.80, 67.18, 56.21, 48.34, 45.52, 33.45, 18.60, 17.17, 15.01. |
| 235 | (Thin film) 3387, 2977, 1736, 1677, 1508, 1129 | HRMS-ESI m/z ([M + H]$^+$) calcd for C$_{35}$H$_{44}$FN$_2$O$_9$, 655.3025; found, 655.3028 | $^1$H NMR (400 MHz, CDCl$_3$) δ 8.33-8.25 (m, 1H), 8.23 (d, J = 5.4 Hz, 1H), 7.39-7.29 (m, 4H), 7.29-7.21 (m, 1H), 7.17-7.08 (m, 2H), 6.97-6.84 (m, 3H), 5.81 (s, 2H), 5.44 (qd, J = 6.6, 2.3 Hz, 1H), 4.61-4.49 (m, 1H), 4.49-4.38 (m, 2H), 4.09 (s, 2H), 3.90 (s, 3H), 3.59 (q, J = 7.0 Hz, 2H), 3.00 (dd, J = 14.8, 5.4 Hz, 1H), 2.79 (dd, J = 14.9, 6.8 Hz, 1H), 2.28 (ddd, J = 6.8, 5.4, 2.9 Hz, 1H), 1.37 (d, J = 6.5 Hz, 3H), 1.34 (s, 3H), 1.28 (d, J = 7.2 Hz, 3H), 1.26 (d, J = 1.4 Hz, 3H), 1.22 (t, J = 7.0 Hz, 3H). $^{13}$C NMR (101 MHz, CDCl$_3$) δ 171.99, 170.07, 162.89, 161.05 (d, J = 243.6 Hz), 160.23, 145.69, 144.06, 142.29, 139.50, 138.31 (d, J = 3.2 Hz), 130.11 (d, J = 7.7 Hz), 128.27, 127.09, 114.97 (d, J = 21.0 Hz), 109.64, 89.65, 76.99, 72.98, 67.79, 67.19, 63.38, 56.21, 53.20, 48.31, 30.32, 29.28, 24.95, 24.80, 18.09, 17.21, 15.00. |
| 236 | (Thin film) 3377, 2976, 1731, 1676, 1502, 1128, 953, 732 | HRMS-ESI m/z ([M + H]$^+$) calcd for C$_{35}$H$_{45}$N$_2$O$_9$, 637.3120; found, 637.3126 | $^1$H NMR (400 MHz, CDCl$_3$) δ 8.35-8.18 (m, 2H), 7.33 (d, J = 4.4 Hz, 4H), 7.29-7.16 (m, 5H), 7.16-7.07 (m, 1H), 6.93 (d, J = 5.4 Hz, 1H), 5.81 (s, 2H), 5.45 (qd, J = 6.5, 2.9 Hz, 1H), 4.56-4.39 (m, 3H), 4.09 (s, 2H), 3.89 (s, 3H), 3.59 (q, J = 7.0 Hz, 2H), 3.04 (dd, J = 14.8, 5.2 Hz, 1H), 2.83 (dd, J = 14.8, 7.1 Hz, 1H), 2.40-2.31 (m, 1H), 1.38 (d, J = 6.5 Hz, 3H), 1.35 (s, 3H), 1.28 (s, 3H), 1.26-1.19 (m, 6H). $^{13}$C NMR (101 MHz, CDCl$_3$) δ |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 172.03, 170.05, 162.86, 160.20, 145.71, 143.98, 142.69, 142.42, 139.58, 128.86, 128.28, 128.26, 127.11, 127.06, 125.58, 109.61, 89.65, 73.11, 67.79, 67.18, 63.39, 56.20, 52.93, 48.29, 31.13, 29.28, 24.92, 24.90, 18.09, 17.20, 15.01. |
| 237 | (Thin film) 3379, 2980, 1735, 1675, 1508, 1125, 952 | HRMS-ESI m/z ([M + H]$^+$) calcd for C$_{27}$H$_{36}$FN$_2$O$_9$, 551.2399; found, 551.2402 | $^1$H NMR (400 MHz, CDCl$_3$) δ 8.39 (d, J = 7.7 Hz, 1H), 8.27 (d, J = 5.4 Hz, 1H), 7.15-7.03 (m, 2H), 7.03-6.91 (m, 3H), 5.83 (d, J = 0.7 Hz, 2H), 5.16-5.03 (m, 1H), 4.71 (p, J = 7.2 Hz, 1H), 4.10 (s, 2H), 3.91 (s, 3H), 3.59 (q, J = 7.0 Hz, 2H), 3.36-3.19 (m, 5H), 2.68-2.59 (m, 2H), 2.04 (ddt, J = 12.5, 7.2, 5.2 Hz, 1H), 1.54 (d, J = 7.2 Hz, 3H), 1.30 (d, J = 6.5 Hz, 3H), 1.23 (t, J = 7.0 Hz, 3H). $^{13}$C NMR (101 MHz, CDCl$_3$) δ 172.04, 170.07, 163.00, 161.40 (d, J = 243.8 Hz), 160.24, 145.76, 144.03, 142.36, 135.58 (d, J = 3.3 Hz), 130.48 (d, J = 7.8 Hz), 115.15 (d, J = 21.1 Hz), 109.69, 89.63, 72.07, 70.87, 67.80, 67.20, 58.76, 56.23, 48.38, 45.56, 32.66, 18.62, 17.16, 15.01. |
| 238 | (Thin film) 3379, 2977, 1731, 1676, 1508, 1157, 953 | HRMS-ESI m/z ([M + H]$^+$) calcd for C$_{29}$H$_{40}$FN$_2$O$_9$, 579.2712; found, 579.2728 | $^1$H NMR (400 MHz, CDCl$_3$) δ 8.28 (d, J = 7.8 Hz, 1H), 8.23 (d, J = 5.4 Hz, 1H), 7.20-7.07 (m, 2H), 6.98-6.83 (m, 3H), 5.82 (s, 2H), 5.40-5.31 (m, 1H), 4.58-4.47 (m, 1H), 4.10 (s, 2H), 3.90 (s, 3H), 3.59 (q, J = 7.0 Hz, 2H), 3.17 (s, 3H), 2.87 (dd, J = 14.8, 5.2 Hz, 1H), 2.80-2.66 (m, 1H), 2.29-2.13 (m, 1H), 1.34 (d, J = 6.6 Hz, 3H), 1.28 (d, J = 7.2 Hz, 3H), 1.23 (t, J = 7.0 Hz, 3H), 1.21 (s, 3H), 1.16 (s, 3H). $^{13}$C NMR (101 MHz, CDCl$_3$) δ 171.97, 170.07, 162.89, 161.05 (d, J = 243.4 Hz), 160.23, 145.69, 144.04, 142.30, 138.20 (d, J = 3.2 Hz), 130.10 (d, J = 7.6 Hz), 114.95 (d, J = 21.1 Hz), 109.65, 89.65, 76.45, 72.86, 67.79, 67.19, 56.22, 52.34, 48.86, 48.31, 30.42, 24.27, 24.09, 18.10, 17.20, 15.00. |
| 239 | (Thin film) 3376, 2983, 1736, 1676, 1508, 1201, 969, 731 | HRMS-ESI m/z ([M + H]$^+$) calcd for C$_{31}$H$_{36}$FN$_2$O$_8$, 583.2450; found, 583.2452 | $^1$H NMR (400 MHz, CDCl$_3$) δ 8.36 (d, J = 7.7 Hz, 1H), 8.26 (d, J = 5.3 Hz, 1H), 7.40-7.20 (m, 5H), 7.12-7.01 (m, 2H), 6.93 (ddd, J = 8.7, 7.0, 2.1 Hz, 3H), 5.82-5.70 (m, 2H), 5.16 (qd, J = 6.5, 4.9 Hz, 1H), 4.71 (p, J = 7.3 Hz, 1H), 4.51-4.33 (m, 2H), 3.90 (s, 3H), 3.38 (d, J = 5.1 Hz, 2H), 2.66 (d, J = 7.5 Hz, 2H), 2.07 (s, 4H), 1.48 (d, J = 7.2 Hz, 3H), 1.30 (d, J = 6.5 Hz, 3H). $^{13}$C NMR (101 MHz, CDCl$_3$) δ 172.03, 170.27, 163.03, 161.38 (d, J = 243.8 Hz), 160.31, 145.71, 144.05, 142.50, 138.22, 135.57 (d, J = 3.3 Hz), 130.48 (d, J = 7.8 Hz), 128.35, 127.62, |

TABLE 2-continued

| *Cmpd. No. | IR (cm$^{-1}$) | MASS | NMR ($^1$H, $^{13}$C or $^{19}$F) |
|---|---|---|---|
| | | | 127.59, 115.12 (d, J = 21.2 Hz), 109.59, 89.58, 73.08, 72.11, 68.25, 56.19, 48.37, 45.65, 32.65, 20.87, 18.54, 17.25. |
| 240 | (Thin film) 3380, 2983, 1735, 1675, 1503, 1201, 968, 731 | HRMS-ESI m/z ([M + H]$^+$) calcd for C$_{31}$H$_{37}$N$_2$O$_8$, 565.2544; found, 565.2551 | $^1$H NMR (400 MHz, CDCl$_3$) δ 8.38 (d, J = 7.8 Hz, 1H), 8.27 (d, J = 5.3 Hz, 1H), 7.38-7.22 (m, 7H), 7.22-7.06 (m, 3H), 6.94 (d, J = 5.4 Hz, 1H), 5.75 (d, J = 1.8 Hz, 2H), 5.18 (qd, J = 6.4, 4.8 Hz, 1H), 4.79-4.64 (m, 1H), 4.50-4.32 (m, 2H), 3.90 (s, 3H), 3.41 (d, J = 5.2 Hz, 2H), 2.7 (dd, J = 7.5, 2.0 Hz, 2H), 2.21-2.10 (m, 1H), 2.07 (s, 3H), 1.48 (d, J = 7.2 Hz, 3H), 1.31 (d, J = 6.4 Hz, 3H). $^{13}$C NMR (101 MHz, CDCl$_3$) δ 172.05, 170.27, 163.00, 160.29, 145.71, 144.02, 142.55, 139.99, 138.32, 129.14, 128.37, 128.33, 127.59, 127.53, 126.06, 109.56, 89.59, 73.05, 72.27, 68.46, 56.18, 48.35, 45.53, 33.46, 20.88, 18.61, 17.18. |
| 241 | (Thin film) 3377, 2978, 1731, 1676, 1508, 1201, 1041 | HRMS-ESI m/z ([M + H]$^+$) calcd for C$_{33}$H$_{40}$FN$_2$O$_8$, 611.2763; found, 611.2765 | $^1$H NMR (400 MHz, CDCl$_3$) δ 8.32-8.18 (m, 2H), 7.39-7.29 (m, 4H), 7.29-7.19 (m, 1H), 7.17-7.07 (m, 2H), 6.98-6.83 (m, 3H), 5.74 (s, 2H), 5.44 (qd, J = 6.5, 2.9 Hz, 1H), 4.62-4.50 (m, 1H), 4.50-4.37 (m, 2H), 3.90 (s, 3H), 3.00 (dd, J = 14.8, 5.4 Hz, 1H), 2.79 (dd, J = 14.9, 6.9 Hz, 1H), 2.28 (ddd, J = 6.9, 5.5, 2.9 Hz, 1H), 2.07 (s, 3H), 1.37 (d, J = 6.5 Hz, 3H), 1.34 (s, 3H), 1.28 (d, J = 7.1 Hz, 3H), 1.26 (s, 3H). $^{13}$C NMR (101 MHz, CDCl$_3$) δ 172.02, 170.28, 162.94, 161.05 (d, J = 243.4 Hz), 160.32, 145.65, 144.08, 142.45, 139.51, 138.31 (d, J = 3.3 Hz), 130.12 (d, J = 7.7 Hz), 128.27, 127.09, 114.97 (d, J = 21.1 Hz), 109.55, 89.62, 77.00, 72.97, 63.38, 56.18, 53.20, 48.32, 30.33, 29.28, 24.94, 24.80, 20.87, 18.10, 17.22. |
| 242 | (Thin film) 3381, 2978, 1731, 1675, 1502, 1201, 1041, 730 | HRMS-ESI m/z ([M + H]$^+$) calcd for C$_{33}$H$_{41}$N$_2$O$_8$, 593.2857; found, 593.2861 | $^1$H NMR (400 MHz, CDCl$_3$) δ 8.31-8.20 (m, 2H), 7.33 (d, J = 4.3 Hz, 4H), 7.29-7.16 (m, 5H), 7.16-7.08 (m, 1H), 6.93 (d, J = 5.4 Hz, 1H), 5.80-5.67 (m, 2H), 5.45 (qd, J = 6.5, 2.9 Hz, 1H), 4.58-4.39 (m, 3H), 3.90 (s, 3H), 3.04 (dd, J = 14.8, 5.2 Hz, 1H), 2.83 (dd, J = 14.8, 7.2 Hz, 1H), 2.36 (ddd, J = 7.1, 5.2, 2.9 Hz, 1H), 2.06 (s, 3H), 1.38 (d, J = 6.6 Hz, 3H), 1.35 (s, 3H), 1.29 (s, 3H), 1.23 (d, J = 7.2 Hz, 3H). $^{13}$C NMR (101 MHz, CDCl$_3$) δ 172.06, 170.27, 162.91, 160.28, 145.66, 144.01, 142.69, 142.58, 139.58, 128.86, 128.28, 128.25, 127.10, 127.06, 125.58, 109.50, 89.62, 77.06, 73.09, 63.38, 56.16, 52.92, 48.30, 31.14, 24.92, 24.89, 20.87, 18.10, 17.21. |
| 243 | (Thin film) 3381, 2983, | HRMS-ESI m/z ([M + H]$^+$) calcd | $^1$H NMR (400 MHz, CDCl$_3$) δ 8.37 (d, J = 7.7 Hz, 1H), 8.27 |

TABLE 2-continued

| *Cmpd. No. | IR (cm$^{-1}$) | MASS | NMR ($^1$H, $^{13}$C or $^{19}$F) |
|---|---|---|---|
| | 1735, 1674, 1508, 1201, 969 | for C$_{25}$H$_{32}$FN$_2$O$_8$, 507.2137; found, 507.2139 | (d, J = 5.3 Hz, 1H), 7.16-7.03 (m, 2H), 7.03-6.88 (m, 3H), 5.80-5.71 (m, 2H), 5.10 (qd, J = 6.4, 4.7 Hz, 1H), 4.80-4.66 (m, 1H), 3.91 (s, 3H), 3.39-3.18 (m, 5H), 2.72-2.50 (m, 2H), 2.14-1.95 (m, 4H), 1.54 (d, J = 7.2 Hz, 3H), 1.30 (d, J = 6.5 Hz, 3H). $^{13}$C NMR (101 MHz, CDCl$_3$) δ 172.07, 170.28, 163.05, 161.40 (d, J = 243.8 Hz), 160.32, 145.71, 144.06, 142.52, 135.59 (d, J = 3.2 Hz), 130.48 (d, J = 7.7 Hz), 115.15 (d, J = 21.1 Hz), 109.59, 89.59, 72.04, 70.88, 58.76, 56.19, 48.39, 45.56, 32.67, 20.88, 18.63, 17.17. |
| 244 | (Thin film) 3381, 2978, 1732, 1676, 1509, 1202, 1042 | HRMS-ESI m/z ([M + H]$^+$) calcd for C$_{27}$H$_{36}$FN$_2$O$_8$, 535.2450; found, 535.2450 | $^1$H NMR (400 MHz, CDCl$_3$) δ 8.33-8.25 (m, 1H), 8.24 (d, J = 5.4 Hz, 1H), 7.19-7.07 (m, 2H), 7.00-6.83 (m, 3H), 5.74 (s, 2H), 5.35 (qd, J = 6.5, 2.9 Hz, 1H), 4.60-4.48 (m, 1H), 3.91 (s, 3H), 3.17 (s, 3H), 2.87 (dd, J = 14.8, 5.3 Hz, 1H), 2.72 (dd, J = 14.8, 7.1 Hz, 1H), 2.26-2.16 (m, 1H), 2.07 (s, 3H), 1.34 (d, J = 6.6 Hz, 3H), 1.29 (d, J = 7.2 Hz, 3H), 1.21 (s, 3H), 1.17 (s, 3H). $^{13}$C NMR (101 MHz, CDCl$_3$) δ 171.99, 170.28, 162.94, 161.05 (d, J = 243.4 Hz), 160.32, 145.65, 144.08, 142.45, 138.20 (d, J = 3.3 Hz), 130.11 (d, J = 7.7 Hz), 114.96 (d, J = 21.0 Hz), 109.56, 89.62, 76.46, 72.84, 56.18, 52.35, 48.86, 48.32, 30.44, 24.27, 24.08, 20.87, 18.11, 17.21. |
| 245 | | HRMS-ESI m/z ([M + H]$^+$) calcd for C$_{27}$H$_{37}$N$_2$O$_8$, 517.2550; found, 517.2555 | $^1$H NMR (400 MHz, CDCl$_3$) δ 8.26 (d, J = 7.7 Hz, 1H), 8.25 (d, J = 5.4 Hz, 1H), 7.37-7.08 (m, 5H), 6.93 (d, J = 5.3 Hz, 1H), 5.82-5.66 (m, 2H), 5.36 (qd, J = 6.6, 2.9 Hz, 1H), 4.55-4.45 (m, 1H), 3.90 (s, 3H), 3.19 (s, 3H), 2.90 (dd, J = 14.7, 5.0 Hz, 1H), 2.75 (dd, J = 14.7, 7.4 Hz, 1H), 2.29 (ddd, J = 7.7, 5.1, 2.9 Hz, 1H), 2.07 (s, 3H), 1.35 (d, J = 6.5 Hz, 3H), 1.24 (d, J = 7.2 Hz, 3H), 1.22 (s, 3H), 1.19 (s, 3H). $^{13}$C NMR (101 MHz, CDCl$_3$) δ 172.02, 170.26, 162.91, 160.28, 145.67, 144.01, 142.56, 128.84, 128.27, 128.25, 125.59, 109.52, 89.61, 76.52, 72.95, 56.18, 52.04, 48.88, 48.30, 31.25, 24.39, 24.05, 20.87, 18.11, 17.20. |
| 246 | (Thin film) 3382, 2939, 1771, 1676, 1509, 1218 | HRMS-ESI m/z ([M + H]$^+$) calcd for C$_{30}$H$_{33}$F$_2$N$_2$O$_7$, 571.2250; found, 571.2266 | $^1$H NMR (400 MHz, CDCl$_3$) δ 8.52 (d, J = 7.8 Hz, 1H), 8.31 (d, J = 5.4 Hz, 1H), 7.32-7.17 (m, 2H), 7.11-6.98 (m, 5H), 6.97-6.89 (m, 2H), 5.14 (qd, J = 6.4, 4.9 Hz, 1H), 4.77-4.62 (m, 1H), 4.45-4.27 (m, 2H), 3.90 (s, 3H), 3.35 (dd, J = 5.2, 1.6 Hz, 2H), 2.69-2.59 (m, 2H), 2.38 (s, 3H), 2.07 (ddq, J = 8.2, 6.7, 5.1 Hz, 1H), 1.48 (d, J = 7.2 Hz, 3H), 1.28 (d, J = 6.4 |

TABLE 2-continued

Analytical Data

| *Cmpd. No. | IR (cm$^{-1}$) | MASS | NMR ($^{1}$H, $^{13}$C or $^{19}$F) |
|---|---|---|---|
| | | | Hz, 3H).<br>$^{13}$C NMR (101 MHz, CDCl$_3$) δ 171.90, 168.89, 162.47, 162.27 (d, J = 245.6 Hz), 161.39 (d, J = 244.0 Hz), 159.50, 146.66, 141.49, 137.56, 135.54 (d, J = 3.3 Hz), 134.00 (d, J = 3.2 Hz), 130.47 (d, J = 7.8 Hz), 129.31 (d, J = 8.1 Hz), 115.18 (d, J = 21.4 Hz), 115.13 (d, J = 21.1 Hz), 109.80, 72.34, 72.01, 68.30, 56.29, 48.19, 45.58, 32.66, 20.74, 18.61, 17.20. |
| 247 | (Thin film) 3382, 2979, 1770, 1676, 1509, 1218 | HRMS-ESI m/z ([M + H]$^+$) calcd for C$_{32}$H$_{37}$F$_2$N$_2$O$_7$, 599.2563; found, 599.2579 | $^1$H NMR (400 MHz, CDCl$_3$) δ 8.44 (d, J = 7.9 Hz, 1H), 8.28 (d, J = 5.4 Hz, 1H), 7.34-7.20 (m, 3H), 7.16-7.07 (m, 2H), 7.07-6.95 (m, 3H), 6.95-6.82 (m, 2H), 5.41 (qd, J = 6.5, 2.8 Hz, 1H), 4.61-4.47 (m, 1H), 4.39 (q, J = 11.0 Hz, 2H), 3.90 (s, 3H), 2.94 (dd, J = 14.8, 5.6 Hz, 1H), 2.78 (dd, J = 14.8, 6.8 Hz, 1H), 2.37 (s, 3H), 1.34 (d, J = 6.6 Hz, 3H), 1.32 (s, 3H), 1.28 (d, J = 7.2 Hz, 3H), 1.24 (s, 3H).<br>$^{13}$C NMR (101 MHz, CDCl$_3$) δ 171.89, 168.90, 162.37, 162.01 (d, J = 244.8 Hz), 161.06 (d, J = 243.5 Hz), 159.48, 146.59, 141.47, 138.10 (d, J = 3.2 Hz), 137.55, 135.14 (d, J = 3.0 Hz), 130.09 (d, J = 7.7 Hz), 128.81 (d, J = 8.0 Hz), 115.08 (d, J = 21.3 Hz), 114.99 (d, J = 21.1 Hz), 109.76, 77.14, 72.79, 62.75, 56.29, 52.94, 48.15, 30.42, 24.89, 24.86, 20.74, 18.20, 17.23. |
| 248 | (Thin film) 3382, 2954, 1771, 1677, 1506, 1175 | HRMS-ESI m/z ([M + H]$^+$) calcd for C$_{38}$H$_{39}$N$_2$O$_7$, 515.2752; found, 515.2764 | $^1$H NMR (400 MHz, CDCl$_3$) δ 8.57 (d, J = 7.9 Hz, 1H), 8.32 (d, J = 5.4 Hz, 1H), 7.34-7.23 (m, 2H), 7.23-7.07 (m, 3H), 7.00 (d, J = 5.5 Hz, 1H), 5.12 (qd, J = 6.5, 4.6 Hz, 1H), 4.71 (dq, J = 8.0, 7.1 Hz, 1H), 3.90 (s, 3H), 3.40-3.25 (m, 4H), 2.71-2.61 (m, 2H), 2.39 (s, 3H), 2.09 (ddt, J = 9.8, 5.2, 3.3 Hz, 1H), 1.76-1.62 (m, 1H), 1.52 (d, J = 7.2 Hz, 3H), 1.48-1.38 (m, 2H), 1.29 (d, J = 6.4 Hz, 3H), 0.90 (d, J = 1.7 Hz, 3H), 0.88 (d, J = 1.7 Hz, 3H).<br>$^{13}$C NMR (101 MHz, CDCl$_3$) δ 171.95, 168.90, 162.42, 159.47, 146.67, 141.57, 140.17, 137.52, 129.15, 128.33, 126.01, 109.75, 72.39, 69.48, 69.04, 56.28, 48.18, 45.45, 38.54, 33.47, 25.07, 22.67, 22.60, 20.75, 18.81, 17.03. |
| 249 | (Thin film) 3382, 2938, 1736, 1676, 1508, 1219, 1202, 827 | HRMS-ESI m/z ([M + H]$^+$) calcd for C$_{31}$H$_{35}$F$_2$N$_2$O$_8$, 601.2356; found, 601.2360 | $^1$H NMR (400 MHz, CDCl$_3$) δ 8.35 (d, J = 7.7 Hz, 1H), 8.26 (d, J = 5.3 Hz, 1H), 7.32-7.19 (m, 2H), 7.13-6.98 (m, 4H), 6.98-6.87 (m, 3H), 5.75 (d, J = 0.9 Hz, 2H), 5.15 (qd, J = 6.5, 4.9 Hz, 1H), 4.71 (p, J = 7.2 Hz, 1H), 4.46-4.27 (m, 2H), 3.91 (s, 3H), 3.37 (d, J = 5.2 Hz, 2H), 2.78-2.52 (m, 2H), 2.13-2.00 (m, 4H), 1.49 (d, J = 7.2 Hz, 3H), 1.30 (d, J = 6.5 Hz, 3H). |

TABLE 2-continued

| | | Analytical Data | |
|---|---|---|---|
| *Cmpd. No. | IR (cm$^{-1}$) | MASS | NMR ($^1$H, $^{13}$C or $^{19}$F) |
| | | | $^{13}$C NMR (101 MHz, CDCl$_3$) δ 172.04, 170.27, 163.04, 162.27 (d, J = 245.5 Hz), 161.39 (d, J = 244.0 Hz), 160.32, 145.71, 144.07, 142.47, 135.51 (d, J = 3.3 Hz), 133.99 (d, J = 3.1 Hz), 130.45 (d, J = 7.8 Hz), 129.31 (d, J = 8.1 Hz), 115.19 (d, J = 21.3 Hz), 115.14 (d, J = 21.1 Hz), 109.60, 89.59, 72.35, 72.01, 68.29, 56.19, 48.37, 45.60, 32.68, 20.87, 18.53, 17.22. |
| 250 | (Thin film) 3381, 2979, 1733, 1676, 1508, 1202, 1041, 827 | HRMS-ESI m/z ([M + H]$^+$) calcd for C$_{33}$H$_{39}$F$_2$N$_2$O$_8$, 629.2669; found, 629.2686 | $^1$H NMR (400 MHz, CDCl$_3$) δ 8.31-8.19 (m, 2H), 7.32-7.23 (m, 2H), 7.17-7.07 (m, 2H), 7.07-6.97 (m, 2H), 6.97-6.84 (m, 3H), 5.73 (s, 2H), 5.43 (qd, J = 6.5, 2.8 Hz, 1H), 4.61-4.49 (m, 1H), 4.40 (q, J = 11.0 Hz, 2H), 3.90 (s, 3H), 2.96 (dd, J = 14.8, 5.5 Hz, 1H), 2.79 (dd, J = 14.8, 6.8 Hz, 1H), 2.28 (ddd, J = 6.8, 5.5, 2.8 Hz, 1H), 2.07 (s, 3H), 1.35 (d, J = 6.6 Hz, 3H), 1.33 (s, 3H), 1.29 (d, J = 7.2 Hz, 3H), 1.26 (d, J = 1.0 Hz, 3H). $^{13}$C NMR (101 MHz, CDCl$_3$) δ 172.01, 170.28, 162.95, 162.00 (d, J = 244.8 Hz), 161.06 (d, J = 243.6 Hz), 160.32, 145.65, 144.09, 142.42, 138.17 (d, J = 3.3 Hz), 135.13 (d, J = 3.1 Hz), 130.09 (d, J = 7.7 Hz), 128.78 (d, J = 8.0 Hz), 115.08 (d, J = 21.3 Hz), 114.99 (d, J = 21.1 Hz), 109.56, 89.62, 77.11, 72.81, 62.75, 56.18, 53.04, 48.33, 30.38, 24.87, 24.85, 20.87, 18.08, 17.21. |
| 251 | (Thin film) 3381, 2955, 1736, 1677, 1509, 1202, 1003 | HRMS-ESI m/z ([M + H]$^+$) calcd for C$_{29}$H$_{40}$FN$_2$O$_8$, 563.2763; found, 563.2769 | $^1$H NMR (400 MHz, CDCl$_3$) δ 8.38 (d, J = 7.7 Hz, 1H), 8.27 (d, J = 5.4 Hz, 1H), 7.15-7.03 (m, 2H), 7.03-6.89 (m, 3H), 5.80-5.69 (m, 2H), 5.11 (qd, J = 6.5, 4.6 Hz, 1H), 4.79-4.66 (m, 1H), 3.91 (s, 3H), 3.39-3.24 (m, 4H), 2.64 (d, J = 7.0 Hz, 2H), 2.14-1.96 (m, 4H), 1.76-1.61 (m, 1H), 1.54 (d, J = 7.2 Hz, 3H), 1.49-1.38 (m, 2H), 1.30 (d, J = 6.5 Hz, 3H), 0.90 (d, J = 1.6 Hz, 3H), 0.88 (d, J = 1.6 Hz, 3H). $^{13}$C NMR (101 MHz, CDCl$_3$) δ 172.07, 170.27, 163.03, 161.37 (d, J = 243.7 Hz), 160.31, 145.70, 144.06, 142.53, 135.74 (d, J = 3.2 Hz), 130.48 (d, J = 7.7 Hz), 115.10 (d, J = 21.1 Hz), 109.57, 89.59, 72.24, 69.54, 68.90, 56.19, 48.38, 45.59, 38.53, 32.68, 25.08, 22.65, 22.60, 20.88, 18.66, 17.12. |
| 252 | (Thin film) 3382, 2953, 1735, 1676, 1503, 1201, 1003, 969 | HRMS-ESI m/z ([M + H]$^+$) calcd for C$_{29}$H$_{41}$N$_2$O$_8$, 545.2857; found, 545.2871 | $^1$H NMR (400 MHz, CDCl$_3$) δ 8.39 (d, J = 7.8 Hz, 1H), 8.27 (d, J = 5.4 Hz, 1H), 7.32-7.23 (m, 2H), 7.23-7.09 (m, 3H), 6.94 (d, J = 5.4 Hz, 1H), 5.79-5.69 (m, 2H), 5.14 (qd, J = 6.5, 4.6 Hz, 1H), 4.80-4.66 (m, 1H), 3.91 (s, 3H), 3.41-3.27 (m, 4H), |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 2.75-2.59 (m, 2H), 2.16-2.01 (m, 4H), 1.74-1.64 (m, 1H), 1.54 (d, J = 7.2 Hz, 3H), 1.47-1.38 (m, 2H), 1.31 (d, J = 6.4 Hz, 3H), 0.90 (d, J = 1.7 Hz, 3H), 0.88 (d, J = 1.7 Hz, 3H). $^{13}$C NMR (101 MHz, CDCl$_3$) δ 172.09, 170.27, 163.00, 160.30, 145.71, 144.03, 142.58, 140.16, 129.15, 128.35, 126.02, 109.55, 89.60, 72.40, 69.50, 69.05, 56.18, 48.37, 45.46, 38.54, 33.48, 25.08, 22.67, 22.61, 20.88, 18.72, 17.05. |
| 253 | (Thin film) 3383, 2979, 1735, 1676, 1508, 1219, 1127, 828 | HRMS-ESI m/z ([M + H]$^+$) calcd for C$_{33}$H$_{39}$F$_2$N$_2$O$_9$, 645.2618; found, 645.2625 | $^1$H NMR (400 MHz, CDCl$_3$) δ 8.37 (d, J = 7.8 Hz, 1H), 8.26 (dd, J = 5.4, 1.0 Hz, 1H), 7.33-7.16 (m, 3H), 7.16-6.84 (m, 6H), 5.82 (d, J = 0.9 Hz, 2H), 5.22-5.05 (m, 1H), 4.77-4.62 (m, 1H), 4.46-4.26 (m, 2H), 4.10 (s, 2H), 3.90 (s, 3H), 3.59 (qd, J = 7.0, 1.0 Hz, 2H), 3.36 (d, J = 5.1 Hz, 2H), 2.74-2.56 (m, 2H), 2.15-1.99 (m, 1H), 1.49 (dd, J = 7.2, 1.0 Hz, 3H), 1.30 (dd, J = 6.4, 1.0 Hz, 3H), 1.22 (td, J = 7.1, 1.0 Hz, 3H). $^{13}$C NMR (101 MHz, CDCl$_3$) δ 172.02, 170.07, 163.00, 162.28 (d, J = 245.5 Hz), 161.40 (d, J = 244.0 Hz), 160.25, 145.76, 144.05, 142.32, 135.50 (d, J = 3.3 Hz), 133.98 (d, J = 3.2 Hz), 130.45 (d, J = 7.7 Hz), 129.31 (d, J = 8.0 Hz), 115.19 (d, J = 21.4 Hz), 115.15 (d, J = 21.2 Hz), 109.70, 89.64, 72.36, 72.04, 68.30, 67.80, 67.20, 56.23, 48.37, 45.60, 32.66, 18.52, 17.21, 15.01. |
| 254 | (Thin film) 3377, 2981, 1755, 1732, 1675, 1501, 1473, 1200 | HRMS-ESI m/z ([M + H]$^+$) calcd for C$_{32}$H$_{37}$Cl$_2$N$_2$O$_8$, 647.1921; found, 647.1925 | $^1$H NMR (400 MHz, CDCl$_3$) δ 8.31-8.22 (m, 2H), 7.38 (d, J = 2.6 Hz, 1H), 7.26 (s, 1H), 7.23 (d, J = 6.0 Hz, 3H), 7.17-7.11 (m, 2H), 7.02 (d, J = 8.8 Hz, 1H), 6.94 (d, J = 5.4 Hz, 1H), 5.76-5.72 (m, 2H), 5.58 (qd, J = 6.6, 3.0 Hz, 1H), 4.61-4.47 (m, 1H), 3.91 (s, 3H), 3.24 (dd, J = 14.9, 5.3 Hz, 1H), 2.94 (dd, J = 14.9, 6.8 Hz, 1H), 2.50 (ddd, J = 6.9, 5.3, 2.9 Hz, 1H), 2.07 (s, 3H), 1.48 (d, J = 6.5 Hz, 3H), 1.42 (s, 3H), 1.31 (s, 3H), 1.28 (d, J = 7.2 Hz, 3H) |
| 255 | (Thin film) 3380, 2981, 1733, 1675, 1499, 1200 | HRMS-ESI m/z ([M + H]$^+$) calcd for C$_{26}$H$_{33}$N$_2$O$_7$, 485.2282; found, 485.2284 | $^1$H NMR (400 MHz, CDCl$_3$) δ 8.38 (d, J = 7.8 Hz, 1H), 8.27 (d, J = 5.4 Hz, 1H), 7.29-7.20 (m, 2H), 7.20-7.13 (m, 1H), 7.13-7.09 (m, 2H), 6.94 (d, J = 5.3 Hz, 1H), 5.82-5.70 (m, 2H), 5.11-4.99 (m, 1H), 4.81-4.78 (m, 1H), 4.77-4.68 (m, 1H), 4.67 (dt, J = 1.8, 0.8 Hz, 1H), 3.91 (s, 3H), 2.82 (dd, J = 13.6, 5.5 Hz, 1H), 2.65 (dd, J = 13.5, 9.5 Hz, 1H), 2.55 (dt, J = 9.5, 5.8 Hz, 1H), 2.07 (s, 3H), 1.72-1.62 (m, 3H), 1.53 (d, J = 7.1 Hz, 3H), 1.29 (d, J = 6.4 Hz, 3H). |
| 256 | (Thin film) 3378, 2936, 1734, 1675, | HRMS-ESI m/z ([M + H]$^+$) calcd for C$_{28}$H$_{39}$N$_2$O$_9$, | $^1$H NMR (400 MHz, CDCl$_3$) δ 8.39 (d, J = 7.8 Hz, 1H), 8.27 (d, J = 5.4 Hz, 1H), 7.12-7.01 |

TABLE 2-continued

Analytical Data

| *Cmpd. No. | IR (cm$^{-1}$) | MASS | NMR ($^1$H, $^{13}$C or $^{19}$F) |
|---|---|---|---|
| | 1511, 1201 | 547.265; found, 547.2687 | (m, 2H), 6.95 (d, J = 5.4 Hz, 1H), 6.89-6.73 (m, 2H), 5.76 (d, J = 6.4 Hz, 1H), 5.74 (d, J = 6.4 Hz, 1H), 5.13 (qd, J = 6.5, 4.7 Hz, 1H), 4.73 (p, J = 7.3 Hz, 1H), 3.91 (s, 3H), 3.78 (s, 3H), 3.39- 3.19 (m, 4H), 2.70-2.52 (m, 2H), 2.13-1.96 (m, 1H), 2.07 (s, 3H), 1.62-1.49 (m, 2H), 1.54 (d, J = 7.2 Hz, 3H), 1.31 (d, J = 6.5 Hz, 3H), 0.91 (t, J = 7.4 Hz, 3H). |
| 257 | (Thin film) 3377, 2974, 1751, 1732, 1675, 1511, 1202 | HRMS-ESI m/z ([M + H]$^+$) calcd for C$_{30}$H$_{43}$N$_2$O$_9$, 575.2963; found, 575.3002 | $^1$H NMR (400 MHz, CDCl$_3$) δ 8.30 (d, J = 7.8 Hz, 1H), 8.25 (d, J = 5.4 Hz, 1H), 7.16-7.05 (m, 2H), 6.93 (d, J = 5.4 Hz, 1H), 6.84-6.73 (m, 2H), 5.77-5.71 (m, 2H), 5.38 (qd, J = 6.6, 2.8 Hz, 1H), 4.55 (p, J = 7.2 Hz, 1H), 3.90 (s, 3H), 3.77 (s, 3H), 3.28 (td, J = 6.5, 2.9 Hz, 2H), 2.89 (dd, J = 14.8, 5.3 Hz, 1H), 2.70 (dd, J = 14.9, 7.0 Hz, 1H), 2.19 (ddt, J = 7.2, 3.4, 1.8 Hz, 1H), 2.07 (s, 3H), 1.53 (h, J = 7.1 Hz, 2H), 1.35 (d, J = 6.6 Hz, 3H), 1.29 (d, J = 7.2 Hz, 3H), 1.21 (s, 3H), 1.15 (s, 3H), 0.92 (t, J = 7.4 Hz, 3H). |
| 258 | (Thin film) 3376, 2936, 1735, 1676, 1502, 1202 | HRMS-ESI m/z ([M + H]$^+$) calcd for C$_{35}$H$_{45}$N$_2$O$_9$, 637.312; found, 637.313 | $^1$H NMR (400 MHz, CDCl$_3$) δ 8.39 (d, J = 7.8 Hz, 1H), 8.27 (d, J = 5.4 Hz, 1H), 7.26 (dd, J = 8.0, 6.8 Hz, 2H), 7.22-7.14 (m, 3H), 6.98-6.91 (m, 2H), 6.83 (d, J = 2.2 Hz 1H), 6.77 (d, J = 8.3 Hz, 1H), 5:82-5.62 (m, 2H), 5.19-5.02 (m, 1H), 4.78-4.56 (m, 1H), 3.93 (d, J = 4.7 Hz, 2H), 3.90 (s, 3H), 3.79 (s, 3H), 3.36-3.15 (m, 4H), 2.63-2.53 (m, 2H), 2.07 (s, 3H), 2.03-1.93 (m, 1H), 1.58-1.50 (m, 2H), 1.48 (d, J = 7.1 Hz, 3H), 1.28 (d, J = 6.4 Hz, 3H), 0.89 (t, J = 7.4 Hz, 3H). |
| 259 | (Thin film) 3382, 2974, 1757, 1733, 1676, 1502, 1202 | HRMS-ESI m/z ([M + H]$^+$) calcd for C$_{37}$H$_{49}$N$_2$O$_9$, 665.3433; found, 665.3449 | $^1$H NMR (400 MHz, CDCl$_3$) δ 8.30 (d, J = 7.8 Hz, 1H), 8.24 (d, J = 5.4 Hz, 1H), 7.30-7.21 (m, 2H), 7.21-7.13 (m, 3H), 6.98 (dd, J = 8.3, 2.3 Hz, 1H), 6.90 (d, J = 5.4 Hz, 1H), 6.88 (d, J = 2.2 Hz, 1H), 6.74 (d, J = 8.3 Hz, 1H), 5.75 (d, J = 6.5 Hz, 1H), 5.73 (d, J = 6.5 Hz, 1H), 5.35 (qd, J = 6.6, 2.8 Hz, 1H), 4.53 (p, J = 7.2 Hz, 1H), 3.92 (s, 2H), 3.89 (s, 3H), 3.77 (s, 3H), 3.31-3.19 (m, 2H), 2.83 (dd, J = 14.8, 5.6 Hz, 1H), 2.64 (dd, J = 14.8, 6.9 Hz, 1H), 2.19-2.10 (m, 1H), 2.06 (s, 3H), 1.50 (h, J = 7.1 Hz, 2H), 1.32 (d, J = 6.5 Hz, 3H), 1.22 (d, J = 7.0 Hz, 3H), 1.18 (s, 3H), 1.12 (s, 3H), 0.90 (t, J = 7.4 Hz, 3H). |
| 260 | (Thin film) 3377, 2937, 1770, 1733, 1676, 1507, 1200, 1174 | HRMS-ESI m/z ([M + H]$^+$) calcd for C$_{29}$H$_{33}$N$_2$O$_6$, 505.2333; found, 505.2341 | $^1$H NMR (400 MHz, CDCl$_3$) δ 8.56 (s, 1H), 8.33 (d, J = 5.4 Hz, 1H), 7.32-6.99 (m, 11H), 4.95 (qd, J = 6.5, 3.1 Hz, 1H), 4.77-4.67 (m, 1H), 3.91 (s, 3H), 2.82-2.46 (m, 4H), 2.39 (s, 3H), 2.23-2.13 (m, 1H), 1.54 (d, J = 7.2 Hz, 3H), 1.26 (d, J = 6.3 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| 261 | (Thin film) 3382, 2965, 1771, 1732, 1682, 1506, 1199, 1174 | HRMS-ESI m/z ([M + H]$^+$) calcd for C$_{31}$H$_{37}$N$_2$O$_6$, 533.2646; found, 533.2649 | $^1$H NMR (400 MHz, CDCl$_3$) δ 8.56 (s, 1H), 8.33 (d, J = 5.6 Hz, 1H), 7.31-6.98 (m, 11H), 5.01-4.92 (m, 1H), 4.66 (dd, J = 9.3, 4.6 Hz, 1H), 3.91 (s, 3H), 2.81-2.47 (m, 5H), 2.16 (dd, J = 7.9, 5.1 Hz, 1H), 1.26 (d, J = 6.5 Hz, 3H), 1.04 (dd, J = 6.9, 1.6 Hz, 6H), 1.00 (d, J = 6.9 Hz, 3H). |
| 262 | IR (thin flim) 3376, 2936, 1771, 1732, 1677, 1507, 1199. | HRMS-ESI m/z ([M + H]$^+$) calcd for C$_{30}$H$_{35}$N$_2$O$_6$, 519.249; found, 519.2491 | $^1$H NMR (400 MHz, CDCl$_3$) δ 8.54 (d, J = 7.6 Hz, 1H), 8.32 (d, J = 5.3 Hz, 1H), 7.31-6.95 (m, 11H), 5.97 (d, J = 9.7 Hz, 1H), 5.04-4.87 (m, 2H), 4.77-4.50 (m, 2H), 3.91 (s, 3H), 2.82-2.47 (m, 5H), 2.39 (s, 3H), 1.30-1.21 (m, 6H). |
| 263 | IR (thin flim) 3383, 2940, 1770, 1734, 1676, 1588, 1508, 1202, 1176 | HRMS-ESI m/z ([M + H]$^+$) calcd for C$_{29}$H$_{31}$F$_2$N$_2$O$_6$, 541.2145; found, 541.2145 | $^1$H NMR (400 MHz, CDCl$_3$) δ 8.51 (s, 1H), 8.33 (d, J = 5.4 Hz, 1H), 7.26-7.15 (m, 2H), 7.03-6.99 (m, 1H), 6.93-6.68 (m, 6H), 5.02-4.85 (m, 1H), 4.81-4.56 (m, 1H), 3.92 (s, 3H), 2.79-2.43 (m, 5H), 2.38 (s, 3H), 1.55 (d, J = 7.2 Hz, 3H), 1.26 (d, J = 6.5 Hz, 3H). |
| 264 | (Thin film) 3382, 2940, 1770, 1733, 1674, 1507, 1217, 1175. | HRMS-ESI m/z ([M + H]$^+$) calcd for C$_{29}$H$_{31}$F$_2$N$_2$O$_6$, 541.2145; found, 541.2156 | $^1$H NMR (400 MHz, CDCl$_3$) δ 8.52 (s, 1H), 8.32 (d, J = 5.4 Hz, 1H), 7.11-6.88 (m, 9H), 4.96-4.87 (m, 1H), 4.76-4.62 (m, 1H), 3.93 (d, J = 8.3 Hz, 3H), 2.74-2.40 (m, 5H), 2.38 (d, J = 0.9 Hz, 3H), 1.54 (d, J = 7.2 Hz, 3H), 1.25 (d, J = 6.6 Hz, 3H). |
| 265 | (Thin film) 3383, 2938, 1735, 1755, 1676, 1504, 1202, 1041, 1004 | HRMS-ESI m/z ([M + H]$^+$) calcd for C$_{30}$H$_{35}$N$_2$O$_7$, 535.2439; found, 535.2451 | $^1$H NMR (400 MHz, CDCl$_3$) δ 8.38 (d, J = 7.8 Hz, 1H), 8.27 (d, J = 5.4 Hz, 1H), 7.30-7.03 (m, 10H), 6.95 (d, J = 5.4 Hz, 1H), 5.80-5.71 (m, 2H), 5.07-4.91 (m, 1H), 4.83-4.62 (m, 1H), 3.91 (s, 3H), 2.80-2.47 (m, 5H), 2.07 (s, 3H), 1.56 (d, J = 7.2 Hz, 3H), 1.28 (d, J = 6.4 Hz, 3H). |
| 266 | (Thin film) 3382, 2964, 1757, 1733, 1681, 1503, 1312, 1202 | HRMS-ESI m/z ([M + H]$^+$) calcd for C$_{32}$H$_{39}$N$_2$O$_7$, 563.2752; found, 563.2759 | $^1$H NMR (400 MHz, CDCl$_3$) δ 8.44 (d, J = 9.5 Hz, 1H), 8.27 (d, J = 5.4 Hz, 1H), 7.31-7.01 (m, 10H), 6.95 (d, J = 5.4 Hz, 1H), 5.77 (d, J = 6.4 Hz, 1H) 5.74 (d, J = 6.4 Hz, 1H), 4.98 (ddt, J = 9.7, 6.4, 3.3 Hz, 1H), 4.71 (dd, J = 9.3, 4.6 Hz, 1H), 3.91 (s, 3H), 2.80-2.47 (m, 5H), 2.38-2.24 (m, 1H), 2.06 (s, 3H), 1.27 (d, J = 6.5 Hz, 3H), 1.12-0.95 (m, 6H). |
| 267 | (Thin film) 3378, 2939, 1735, 1675, 1585, 1504, 1487, 1248, 1202 | HRMS-ESI m/z ([M + H]$^+$) calcd for C$_{30}$H$_{33}$F$_2$N$_2$O$_7$, 571.225; found, 571.2263 | $^1$H NMR (400 MHz, CDCl$_3$) δ 8.35 (d, J = 7.8 Hz, 1H), 8.28 (dd, J = 5.4, 1.7 Hz, 1H), 7.21 (ddt, J = 13.7, 8.0, 4.0 Hz, 2H), 6.96 (d, J = 5.4 Hz, 1H), 6.95-6.69 (m, 6H), 5.78-5.73 (m, 2H), 4.94 (qd, J = 6.4, 3.0 Hz, 1H), 4.71 (dt, J = 19.5, 7.4 Hz, 1H), 3.92 (s, 3H), 2.87-2.41 (m, 5H), 2.07 (s, 3H), 1.56 (d, J = 7.2 Hz, 3H), 1.28 (d, J = 5.5 Hz, 3H). |
| 268 | (Thin film) 3383, 2939, 1735, 1676, 1508, 1218, 1203 | HRMS-ESI m/z ([M + H]$^+$) calcd for C$_{30}$H$_{33}$F$_2$N$_2$O$_7$, 571.225; found, 571.225 | $^1$H NMR (400 MHz, CDCl$_3$) δ 8.35 (d, J = 7.7 Hz, 1H), 8.27 (d, J = 5.4 Hz, 1H), 7.11-6.87 (m, 9H), 5.75 (s, 2H), 4.94 (tt, J = 7.0, 3.5 Hz, 1H), 4.73 (dq, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | J = 14.7, 7.3 Hz, 1H), 2.76-2.41 (m, 5H), 2.17 (s, 3H), 2.07 (s, 3H), 1.56 (d, J = 7.2 Hz, 3H), 1.27 (d, J = 6.5 Hz, 3H). |
| 269 | (Thin film) 3377, 2936, 1756, 1734, 1678, 1503, 1202 | HRMS-ESI m/z ([M + H]$^+$) calcd for C$_{31}$H$_{37}$N$_2$O$_7$, 549.2595; found, 549.2601 | $^1$H NMR (400 MHz, CDCl$_3$) δ 8.40 (d, J = 8.6 Hz, 1H), 8.27 (d, J = 5.2 Hz, 1H), 7.29-7.02 (m, 10H), 6.95 (d, J = 5.5 Hz, 1H), 5.80-5.72 (m, 2H), 4.98 (dd, J = 6.6, 2.9 Hz, 1H), 4.72 (dt, J = 7.0, 1.7 Hz, 1H), 3.91 (s, 3H), 2.81-2.47 (m, 5H), 2.07 (s, 3H), 2.05-1.75 (m, 2H), 1.26 (d, J = 4.0 Hz, 3H), 1.04 (t, J = 7.4 Hz, 3H). |
| 270 | | HRMS-ESI m/z ([M + H]$^+$) calcd for C$_{31}$H$_{37}$N$_2$O$_8$, 565.2544; found, 565.2533 | $^1$H NMR (400 MHz, CDCl$_3$) δ 8.55 (s, 1H), 8.33 (d, J = 5.4 Hz, 1H), 7.17 (dt, J = 13.6, 7.9 Hz, 2H), 7.00 (d, J = 5.4 Hz, 1H), 6.77-6.58 (m, 6H), 4.96 (dd, J = 6.5, 2.9 Hz, 1H), 4.82-4.64 (m, 1H), 3.91 (s, 3H), 3.78 (s, 3H), 3.76 (s, 3H), 2.74 (dd, J = 14.1, 6.4 Hz, 1H), 2.67-2.45 (m, 4H), 2.38 (s, 3H) 1.55 (d, 3H) 1.26 (d, J = 64 Hz, 3H). $^{13}$C NMR (126 MHz, CDCl$_3$) δ 171.94, 168.92, 162.48, 159.64, 159.58, 159.49, 146.68, 141.93, 141.80, 141.53, 137.55, 129.37, 129.32, 121.51, 121.33, 114.92, 114.88, 111.31, 111.23, 109.78, 72.27, 56.28, 55.14, 55.12, 48.26, 46.64, 31.59, 22.66, 20.75, 16.54, 14.12. |
| 271 | | ESIMS m/z 579.3 ([M + H]$^+$) | $^1$H NMR (400 MHz, CDCl$_3$) δ 8.55 (s, 1H), 8.33 (d, J = 5.4 Hz, 1H), 7.17 (dt, J = 14.2, 7.9 Hz, 2H), 7.00 (d, J = 5.5 Hz, 1H), 6.76-6.59 (m, 6H), 5.05-4.92 (m, 1H), 4.75-4.62 (m, 1H), 3.91 (s, 3H), 3.78 (s, 3H), 3.76 (s, 3H), 2.73 (dd, J = 14.1, 6.6 Hz, 1H), 2.55 (dtd, J = 27.9, 13.7, 7.1 Hz, 4H), 2.38 (s, 3H), 2.08-1.95 (m, 1H), 1.88 (dq, J = 14.1, 7.2 Hz, 1H), 1.26 (d, J = 6.5 Hz, 3H), 1.03 (t, J = 7.5 Hz, 3H). $^{13}$C NMR (126 MHz, CDCl$_3$) δ 171.25, 168.91, 162.67, 159.64, 159.57, 159.50, 146.69, 141.95, 141.83, 141.59, 137.54, 129.37, 129.30, 121.51, 121.32, 114.90, 114.89, 111.33, 111.22, 109.76, 72.22, 56.28, 55.14, 55.12, 53.47, 46.68, 31.59, 22.66, 20.76, 16.60, 14.13, 9.77. |
| 272 | | ESIMS m/z 565.3 ([M + H]$^+$) | $^1$H NMR (400 MHz, CDCl$_3$) δ 8.56 (s, 1H), 8.33 (d, J = 5.4 Hz, 1H), 7.08-6.93 (m, 5H), 6.85-6.76 (m, 4H), 4.94 (dd, J = 6.5, 3.0 Hz, 1H), 4.72 (dd, J = 7.9, 7.1 Hz, 1H), 3.91 (s, 3H), 3.79 (s, 3H), 3.77 (s, 3H), 2.71-2.42 (m, 4H), 2.39 (s, 3H), 2.10-2.01 (m, 1H), 1.54 (d, J = 7.2 Hz, 3H), 1.25 (d, J = 1.7 Hz, 3H). $^{13}$C NMR (126 MHz, CDCl$_3$) δ 171.99, 168.93, 162.46, 159.49, 157.89, 157.86, 146.67, 141.54, 137.54, 132.37, 132.17, 129.99, |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | 129.82, 113.83, 113.78, 109.77, 72.28, 56.29, 55.23, 55.22, 48.24, 47.16, 34.86, 34.53, 29.27, 20.76, 16.42. |
| 273 | | HRMS-ESI m/z ([M + H]$^+$) calcd for C$_{30}$H$_{39}$N$_2$O$_7$, 537.2595; found, 537.2574 | $^1$H NMR (400 MHz, CDCl$_3$) δ 8.56 (s, 1H), 8.32 (d, J = 5.5 Hz, 1H), 7.07-6.92 (m, 5H), 6.86-6.73 (m, 4H), 4.96 (dt, J = 8.6, 4.3 Hz, 1H), 4.75-4.56 (m, 1H), 3.91 (s, 3H), 3.79 (s, 3H), 3.77 (s, 3H), 2.71-2.41 (m, 5H), 2.39 (s, 3H), 2.07-1.96 (m, 1H), 1.87 (tq, J = 13.7, 7.3, 6.7 Hz, 1H), 1.24 (d, J = 6.5 Hz, 3H), 1.02 (t, J = 7.5 Hz, 3H). |
| 274 | | HRMS-ESI m/z ([M + H]$^+$) calcd for C$_{32}$H$_{39}$N$_2$O$_9$, 595.2658; found, 595.265 | $^1$H NMR (300 MHz, CDCl$_3$) δ 8.38 (d, J = 7.8 Hz, 1H), 8.28 (d, J = 5.4 Hz, 1H), 7.18 (dt, J = 10.4, 7.9 Hz, 2H), 6.95 (d, J = 5.4 Hz, 1H), 6.77-6.58 (m, 6H), 5.79-5.70 (m, 2H), 4.97 (qd, J = 6.4, 3.0 Hz, 1H), 4.85-4.61 (m, 1H), 3.91 (s, 3H), 3.79 (s, 3H), 3.77 (s, 3H), 2.81-2.45 (m, 5H), 2.18 (t, J = 7.2 Hz, 1H), 2.07 (s, 3H), 1.57 (d, J = 7.3 Hz, 3H), 1.28 (d, J = 6.5 Hz, 3H). $^{13}$C NMR (126 MHz, CDCl$_3$) δ 171.29, 168.92, 162.64, 159.49, 157.89, 157.85, 146.67, 141.59, 137.53, 132.39, 132.19, 130.00, 129.81, 113.83, 113.76, 109.75, 72.23, 56.29, 55.22, 55.21, 53.44, 47.19, 34.85, 34.56, 31.59, 20.77, 16.47, 9.76. |
| 275 | | HRMS-ESI m/z ([M + H]$^+$) calcd for C$_{33}$H$_{41}$N$_2$O$_9$, 609.2807; found, 609.2822. | $^1$H NMR (300 MHz, CDCl$_3$) δ 8.40 (d, J = 8.3 Hz, 1H), 8.28 (d, J = 5.4 Hz, 1H), 7.23-7.11 (m, 2H), 6.95 (d, J = 5.4 Hz, 1H), 6.76-6.58 (m, 7H), 5.79-5.71(m, 2H), 4.99 (dt, J = 6.7, 3.4 Hz, 1H), 4.72 (ddd, J = 8.3, 7.0, 5.3 Hz, 1H), 3.91 (s, 3H), 3.79 (s, 3H), 3.76 (s, 3H), 2.81-2.45 (m, 4H), 2.25-2.13 (m, 1H), 2.06 (s, 3H), 1.95-1.78 (m, 1H), 1.27 (d, J = 6.5 Hz, 3H), 1.05 (t, J = 7.5 Hz, 3H). $^{13}$C NMR (126 MHz, CDCl$_3$) δ 171.42, 170.28, 163.24, 160.36, 159.64, 159.58, 145.70, 144.10, 142.50, 141.92, 141.79, 129.38, 129.31, 121.49, 121.32, 114.92, 114.89, 111.28, 111.20, 109.56, 89.65, 72.27, 56.18, 55.14, 55.11, 53.63, 46.64, 35.95, 35.59, 25.91, 20.87, 16.57, 9.87. |
| 276 | | ESIMS m/z 595.7 ([M + H]$^+$) | $^1$H NMR (300 MHz, CDCl$_3$) δ 8.39 (d, J = 7.7 Hz, 1H), 8.27 (d, J = 5.4 Hz, 1H), 7.09-6.98 (m, 2H), 7.02-6.91 (m, 3H), 6.86-6.72 (m, 4H), 5.77 (d, J = 6.4 Hz, 1H), 5.74 (d, J = 6.4 Hz, 1H), 4.96 (qd, J = 6.6, 3.2 Hz, 1H), 4.83-4.67 (m, 1H), 3.91 (s, 3H), 3.79 (s, 3H), 3.77 (s, 3H), 2.68 (dd, J = 14.2, 6.8 Hz, 1H), 2.55 (q, J = 6.1 Hz, 2H), 2.46 (dd, J = 13.7, 6.6 Hz, 1H), 2.07 (s, 3H), 2.17-2.00 (m, 1H), 1.60-1.53 (m, 3H), 1.26 (d, J = 6.5 Hz, 3H). |

TABLE 2-continued

Analytical Data

| *Cmpd. No. | IR (cm$^{-1}$) | MASS | NMR ($^1$H, $^{13}$C or $^{19}$F) |
|---|---|---|---|
| | | | $^{13}$C NMR (126 MHz, CDCl$_3$) δ 172.14, 170.30, 163.03, 160.32, 157.91, 157.88, 145.70, 144.08, 142.53, 132.35, 132.16, 129.98, 129.82, 113.84, 113.79, 109.56, 89.62, 72.32, 56.19, 55.23 (2C), 48.41, 47.15, 34.87, 34.56, 20.89, 18.77, 16.43. |
| 277 | (Thin film) 3380, 2935, 1755, 1732, 1676, 1510, 1243, 1200 | ESIMS m/z 609.8 ([M + H]$^+$) | $^1$H NMR (300 MHz, CDCl$_3$) δ 8.41 (d, J = 8.2 Hz, 1H), 8.27 (d, J = 5.3 Hz, 1H), 7.08-6.93 (m, 5H), 6.85-6.75 (m, 4H), 5.75 (s, 2H), 4.97 (dd, J = 6.4, 3.0 Hz, 1H), 4.78-4.65 (m, 1H), 3.91 (s, 3H), 3.79 (d, J = 0.7 Hz, 3H), 3.77 (s, 3H), 2.74-2.39 (m, 5H), 2.07 (s, 3H), 2.07-1.96 (m, 1H), 1.87 (dt, J = 14.1, 7.3 Hz, 1H), 1.26 (d, J = 6.5 Hz, 3H), 1.04 (t, J = 7.5 Hz, 3H). |
| 278 | (Thin film) 3382, 2977, 1756, 1731, 1675, 1510, 1201, 1038 | HRMS-ESI m/z ([M + H]$^+$) calcd for C$_{31}$H$_{43}$N$_2$O$_9$, 587.2963; found, 587.2958 | $^1$H NMR (400 MHz, CDCl$_3$) δ 8.29 (d, J = 8.0 Hz, 1H), 8.25 (d, J = 5.4 Hz, 1H), 7.12-7.06 (m, 2H), 6.93 (d, J = 5.3 Hz, 1H), 6.83-6.71 (m, 2H), 5.76-5.72 (m, 2H), 5.36 (qd, J = 6.7, 2.8 Hz, 1H), 4.62-4.50 (m, 1H), 3.90 (s, 3H), 3.77 (s, 3H), 3.27-3.11 (m, 2H), 2.87 (dd, J = 14.7, 5.3 Hz, 1H), 2.70 (dd, J = 14.8, 7.2 Hz, 1H), 2.24-2.14 (m, 1H), 2.07 (s, 3H), 1.36 (d, J = 6.5 Hz, 3H), 1.30 (d, J = 7.2 Hz, 3H), 1.20 (s, 3H), 1.16 (s, 3H), 1.03-0.91 (m, 1H), 0.55-0.42 (m, 2H), 0.22-0.12 (m, 2H). |
| 279 | (Thin film) 3377, 2983, 1734, 1677, 1501, 1245 | HRMS-ESI m/z ([M + H]$^+$) calcd for C$_{33}$H$_{39}$F$_2$N$_2$O$_9$, 645.2618; found, 645.2621 | $^1$H NMR (400 MHz, CDCl$_3$) δ 8.32 (d, J = 7.8 Hz, 1H), 8.25 (d, J = 5.4 Hz, 1H), 7.14 (d, J = 8.6 Hz, 2H), 7.08-6.97 (m, 1H), 6.93 (d, J = 5.5 Hz, 1H), 6.80 (d, J = 8.7 Hz 2H), 6.78-6.68 (m, 2H), 5.77-5.71 (m, 2H), 5.55 (qd, J = 6.5, 2.9 Hz, 1H), 4.69-4.54 (m, 1H), 3.91 (s, 3H), 3.78 (s, 3H), 3.12 (dd, J = 14.9, 5.8 Hz, 1H), 2.87 (dd, J = 14.9, 6.3 Hz, 1H), 2.38 (td, J = 6.1, 2.9 Hz, 1H), 2.07 (s, 3H), 1.46 (d, J = 6.6 Hz, 3H), 1.37 (s, 3H), 1.35 (d, J = 7.3 Hz, 3H), 1.22 (s, 3H). |
| 280 | (Thin film) 3386, 2936, 1738, 1676, 1509, 1244, 1201, 1037 | HRMS-ESI m/z ([M + H]$^+$) calcd for C$_{29}$H$_{39}$N$_2$O$_9$, 559.265; found, 559.265 | $^1$H NMR (400 MHz, CDCl$_3$) δ 8.23 (d, J = 7.7 Hz, 1H), 8.11 (d, J = 5.4 Hz, 1H), 6.95-6.86 (m, 2H), 6.79 (d, J = 5.4 Hz, 1H), 6.71-6.57 (m, 2H), 5.67-5.51 (m, 2H), 4.98 (qd, J = 6.4, 4.6 Hz, 1H), 4.57 (p, J = 7.2 Hz, 1H), 3.75 (s, 3H), 3.62 (s, 3H), 3.23 (dd, J = 9.7, 5.8 Hz, 1H), 3.17 (dd, J = 9.7, 5.2 Hz, 1H), 3.08-2.94 (m, 2H), 2.52-2.38 (m, 2H), 1.96-1.86 (m, 1H), 1.91 (s, 3H), 1.38 (d, J = 7.2 Hz, 3H), 1.15 (d, J = 6.5 Hz, 3H), 0.92-0.77 (m, 1H), 0.39-0.28 (m, 2H), 0.07--0.06 (m, 2H). |
| 281 | (Thin film) 3380, 2936, 1734, 1675, 1501, 1200, | HRMS-ESI m/z ([M + H]$^+$) calcd for C$_{36}$H$_{45}$N$_2$O$_9$, 649.312; found, | $^1$H NMR (400 MHz, CDCl$_3$) δ 8.38 (d, J = 7.8 Hz, 1H), 8.27 (d, J = 5.4 Hz, 1H), 7.30-7.22 (m, 3H), 7.21-7.15 (m, 2H), |

TABLE 2-continued

Analytical Data

| *Cmpd. No. | IR (cm⁻¹) | MASS | NMR (¹H, ¹³C or ¹⁹F) |
|---|---|---|---|
| | | 1002 649.3135 | 6.99-6.91 (m, 2H), 6.83 (d, J = 2.2 Hz, 1H), 6.77 (d, J = 8.3 Hz, 1H), 5.82-5.70 (m, 2H), 5.14-5.06 (m, 1H), 4.77-4.63 (m, 1H), 3.98-3.91 (m, 2H), 3.90 (s, 3H), 3.79 (s, 3H), 3.36 (dd, J = 9.7, 5.8 Hz, 1H), 3.31 (dd, J = 9.7, 5.1 Hz, 1H), 3.18-3.07 (m, 2H), 2.64-2.47 (m, 2H), 2.07 (s, 3H), 2.05-1.95 (m, 1H), 1.48 (d, J = 7.1 Hz, 3H), 1.28 (d, J = 6.5 Hz, 3H), 1.04-0.92 (m, 1H), 0.54-0.36 (m, 2H), 0.18-0.10 (m, 2H). |
| 282 | (Thin film) 3380, 2939, 1736, 1674, 1510, 1200 | HRMS-ESI m/z ([M + H]⁺) calcd for $C_{31}H_{34}F_2N_2O_9$, 617.2305; found, 617.2313 | ¹H NMR (400 MHz, CDCl₃) δ 8.33 (d, J = 7.8 Hz, 1H), 8.25 (d, J = 5.4 Hz, 1H), 7.07 (d, J = 8.6 Hz, 2H), 6.99 (ddd, J = 10.7, 8.9, 5.3 Hz, 1H), 6.94 (d, J = 5.4 Hz, 1H), 6.85-6.78 (m, 2H), 6.59-6.47 (m, 2H), 5.74 (s, 2H), 5.21 (qd, J = 6.4, 4.7 Hz, 1H), 4.73 (p, J = 7.2 Hz, 1H), 3.97-3.86 (m, 2H), 3.91 (s, 3H), 3.78 (s, 3H), 2.82-2.69 (m, 2H), 2.33-2.21 (m, 1H), 2.06 (s, 3H), 1.51 (d, J = 7.2 Hz, 3H), 1.40 (d, J = 6.5 Hz, 3H). |
| 283 | | HRMS-ESI m/z ([M + H]⁺) calcd for $C_{23}H_{29}N_2O_6$, 429.2025; found, 429.2029 | ¹H NMR (400 MHz, CDCl₃) δ 8.55 (d, J = 8.1 Hz, 1H), 8.33 (d, J = 5.4 Hz, 1H), 7.30-7.25 (m, 2H), 7.25-7.18 (m, 1H), 7.17-7.09 (m, 2H), 7.00 (d, J = 5.5 Hz, 1H), 5.12 (dq, J = 8.3, 6.4 Hz, 1H), 4.72 (p, J = 7.3 Hz, 1H), 3.89 (s, 3H), 2.65 (ddd, J = 11.6, 8.2, 3.9 Hz, 1H), 2.39 (s, 3H), 1.92-1.78 (m, 1H), 1.67-1.54 (m, 1H), 1.52 (d, J = 7.2 Hz, 3H), 1.06 (d, J = 6.3 Hz, 3H), 0.72 (t, J = 7.3 Hz, 3H). ¹³C NMR (101 MHz, CDCl₃) δ 172.27, 168.83, 162.39, 159.48, 146.65, 141.62, 140.86, 137.53, 128.62, 128.38, 126.70, 109.77, 75.49, 56.26, 52.95, 48.21, 24.49, 20.71, 18.68, 18.23, 11.83. |

*Cmpd. No. - Compound Number
*¹H NMR were run at 400 MHz unless noted otherwise
*¹³C NMR were run at 101 MHz unless noted otherwise
*¹⁹F NMR were run at 376 MHz unless noted otherwise

TABLE 3

Biological Testing Rating Scale
Rating Table for Biological Activity

| % Disease Control | Rating |
|---|---|
| 80-100 | A |
| More than 0-Less than 80 | B |
| Not Tested | C |
| No activity noticed in this bioassay | D |

TABLE 4

Biological Activity - High-Volume Cereal Activity at 100 ppm

| Cmpd. No. | PUCCRT* | | SEPTTR* | |
|---|---|---|---|---|
| | 1DP* | 3DC* | 1DP* | 3DC* |
| 91 | A | A | B | A |
| 92 | A | A | A | A |
| 93 | A | A | B | A |
| 94 | A | A | B | B |
| 95 | A | A | B | B |
| 96 | A | A | A | B |
| 97 | B | B | B | B |
| 98 | A | A | A | A |
| 99 | B | B | D | B |
| 100 | B | D | D | B |
| 101 | A | B | A | D |

TABLE 4-continued

Biological Activity - High-Volume Cereal Activity at 100 ppm

| Cmpd. No. | PUCCRT* 1DP* | PUCCRT* 3DC* | SEPTTR* 1DP* | SEPTTR* 3DC* |
|---|---|---|---|---|
| 102 | A | A | B | A |
| 103 | A | B | A | B |
| 104 | D | B | D | B |
| 105 | A | B | B | B |
| 106 | B | B | D | B |
| 107 | B | D | D | D |
| 108 | A | D | D | B |
| 109 | B | D | D | D |
| 110 | A | D | D | D |
| 112 | B | D | B | D |
| 113 | A | A | B | A |
| 114 | B | B | D | B |
| 115 | A | A | D | A |
| 116 | B | A | B | B |
| 117 | A | A | A | B |
| 118 | B | A | A | B |
| 119 | D | D | D | B |
| 120 | D | B | D | B |
| 121 | A | B | A | B |
| 122 | B | D | D | D |
| 123 | D | B | D | A |
| 125 | B | B | B | B |
| 126 | B | D | B | D |
| 127 | B | D | B | B |
| 128 | A | D | A | B |
| 129 | A | B | A | B |
| 130 | A | D | A | B |
| 131 | A | B | A | B |
| 132 | A | A | B | A |
| 133 | A | D | B | B |
| 134 | A | B | A | B |
| 135 | A | B | B | B |
| 136 | B | B | D | A |
| 137 | D | B | D | B |
| 138 | D | D | D | D |
| 139 | B | D | B | B |
| 140 | D | B | B | B |
| 141 | B | B | A | B |
| 143 | A | B | A | B |
| 145 | B | D | A | B |
| 146 | B | D | B | B |
| 147 | A | D | A | D |
| 148 | B | D | B | D |
| 149 | A | D | A | D |
| 150 | A | D | A | D |
| 151 | A | D | A | D |
| 152 | A | B | D | D |
| 153 | A | D | B | B |
| 154 | A | D | A | D |
| 155 | D | D | D | D |
| 160 | A | D | B | D |
| 162 | A | A | A | A |
| 163 | A | A | B | B |
| 164 | A | A | A | A |
| 165 | B | A | A | B |
| 166 | A | A | B | B |
| 167 | A | A | A | A |
| 168 | A | A | A | A |
| 169 | A | A | A | A |
| 170 | B | D | B | B |
| 171 | D | B | B | B |
| 172 | C | C | C | C |
| 173 | C | C | C | C |
| 174 | C | C | C | C |
| 175 | C | C | C | C |
| 176 | C | C | C | C |
| 177 | C | C | C | C |
| 178 | C | C | C | C |
| 179 | C | C | C | C |
| 180 | C | C | C | C |
| 181 | C | C | C | C |
| 182 | C | C | C | C |
| 183 | C | C | C | C |
| 184 | C | C | C | C |
| 185 | C | C | C | C |
| 186 | C | C | C | C |
| 187 | C | C | C | C |
| 188 | C | C | C | C |
| 189 | C | C | C | C |
| 190 | C | C | C | C |
| 191 | C | C | C | C |
| 192 | C | C | C | C |
| 193 | C | C | C | C |
| 194 | C | C | C | C |
| 195 | C | C | C | C |
| 196 | C | C | C | C |
| 197 | C | C | C | C |
| 198 | C | C | C | C |
| 199 | C | C | C | C |
| 200 | C | C | C | C |
| 201 | C | C | C | C |
| 202 | C | C | C | C |
| 203 | C | C | C | C |
| 204 | C | C | C | C |
| 205 | C | C | C | C |
| 206 | C | C | C | C |
| 207 | C | C | C | C |
| 208 | C | C | C | C |
| 209 | C | C | C | C |
| 210 | C | C | C | C |
| 211 | C | C | C | C |
| 212 | C | C | C | C |
| 213 | C | C | C | C |
| 214 | C | C | C | C |
| 215 | C | C | C | C |
| 216 | C | C | C | C |
| 217 | C | C | C | C |
| 218 | C | C | C | C |
| 219 | C | C | C | C |
| 220 | C | C | C | C |
| 221 | C | C | C | C |
| 222 | C | C | C | C |
| 223 | C | C | C | C |
| 224 | C | C | C | C |
| 225 | C | C | C | C |
| 226 | C | C | C | C |
| 227 | C | C | C | C |
| 228 | C | C | C | C |
| 229 | C | C | C | C |
| 230 | C | C | C | C |
| 231 | C | C | C | C |
| 232 | C | C | C | C |
| 233 | C | C | C | C |
| 234 | C | C | C | C |
| 235 | C | C | C | C |
| 236 | C | C | C | C |
| 237 | C | C | C | C |
| 238 | C | C | C | C |
| 239 | C | C | C | C |
| 240 | C | C | C | C |
| 241 | C | C | C | C |
| 242 | C | C | C | C |
| 243 | C | C | C | C |
| 244 | C | C | C | C |
| 245 | C | C | C | C |
| 246 | C | C | C | C |
| 247 | C | C | C | C |
| 248 | C | C | C | C |
| 249 | C | C | C | C |
| 250 | C | C | C | C |
| 251 | C | C | C | C |
| 252 | C | C | C | C |
| 253 | C | C | C | C |
| 254 | C | C | C | C |
| 255 | C | C | C | C |
| 256 | C | C | C | C |
| 257 | C | C | C | C |
| 258 | C | C | C | C |

TABLE 4-continued

Biological Activity - High-Volume Cereal Activity at 100 ppm

| Cmpd. No. | PUCCRT* 1DP* | PUCCRT* 3DC* | SEPTTR* 1DP* | SEPTTR* 3DC* |
|---|---|---|---|---|
| 259 | C | C | C | C |
| 260 | C | C | C | C |
| 261 | C | C | C | C |
| 262 | C | C | C | C |
| 263 | C | C | C | C |
| 264 | C | C | C | C |
| 265 | C | C | C | C |
| 266 | C | C | C | C |
| 267 | C | C | C | C |
| 268 | C | C | C | C |
| 269 | C | C | C | C |
| 270 | C | C | C | C |
| 271 | C | C | C | C |
| 272 | C | C | C | C |
| 273 | C | C | C | C |
| 274 | C | C | C | C |
| 275 | C | C | C | C |
| 276 | C | C | C | C |
| 277 | C | C | C | C |
| 278 | C | C | C | C |
| 279 | C | C | C | C |
| 280 | C | C | C | C |
| 281 | C | C | C | C |
| 282 | C | C | C | C |
| 283 | C | C | C | C |
| 284 | A | A | B | D |

*PUCCRT—Wheat Brown Rust (*Puccinia triticina*)
*SEPTTR—Wheat Leaf Blotch (*Zymoseptoria tritici*)
*1DP—1 Day Protectant
*3DC—Day Curative

TABLE 5

Biological Activity - Low-Volume Cereal Activity at 121.5 g/H

| Cmpd. No. | PUCCRT* 1DP* | PUCCRT* 3DC* | SEPTTR* 1DP* | SEPTTR* 3DC* |
|---|---|---|---|---|
| 91 | C | C | C | C |
| 92 | C | C | C | C |
| 93 | C | C | C | C |
| 94 | C | C | C | C |
| 95 | C | C | C | C |
| 96 | C | C | C | C |
| 97 | C | C | C | C |
| 98 | C | C | C | C |
| 99 | C | C | C | C |
| 100 | C | C | C | C |
| 101 | C | C | C | C |
| 102 | C | C | C | C |
| 103 | C | C | C | C |
| 104 | C | C | C | C |
| 105 | C | C | C | C |
| 106 | C | C | C | C |
| 107 | C | C | C | C |
| 108 | C | C | C | C |
| 109 | C | C | C | C |
| 110 | C | C | C | C |
| 112 | C | C | C | C |
| 113 | C | C | C | C |
| 114 | C | C | C | C |
| 115 | C | C | C | C |
| 116 | C | C | C | C |
| 117 | C | C | C | C |
| 118 | C | C | C | C |
| 119 | C | C | C | C |
| 120 | C | C | C | C |
| 121 | C | C | C | C |
| 122 | C | C | C | C |
| 123 | C | C | C | C |
| 125 | C | C | C | C |
| 126 | C | C | C | C |
| 127 | C | C | C | C |
| 128 | C | C | C | C |
| 129 | C | C | C | C |
| 130 | C | C | C | C |
| 131 | C | C | C | C |
| 132 | C | C | C | C |
| 133 | C | C | C | C |
| 134 | C | C | C | C |
| 135 | C | C | C | C |
| 136 | C | C | C | C |
| 137 | C | C | C | C |
| 138 | C | C | C | C |
| 139 | C | C | C | C |
| 140 | C | C | C | C |
| 141 | C | C | C | C |
| 143 | C | C | C | C |
| 145 | C | C | C | C |
| 146 | C | C | C | C |
| 147 | C | C | C | C |
| 148 | C | C | C | C |
| 149 | C | C | C | C |
| 150 | C | C | C | C |
| 151 | C | C | C | C |
| 152 | C | C | C | C |
| 153 | C | C | C | C |
| 154 | C | C | C | C |
| 155 | C | C | C | C |
| 160 | C | C | C | C |
| 162 | A | A | A | A |
| 163 | C | C | C | C |
| 164 | A | A | B | B |
| 165 | C | C | C | C |
| 166 | C | C | C | C |
| 167 | A | A | A | B |
| 168 | A | A | A | B |
| 169 | A | A | A | A |
| 170 | C | C | C | C |
| 171 | C | C | C | C |
| 172 | A | B | B | B |
| 173 | A | B | A | A |
| 174 | A | B | A | B |
| 175 | A | A | D | B |
| 176 | A | B | D | D |
| 177 | A | B | A | B |
| 178 | B | B | B | B |
| 179 | A | D | B | A |
| 180 | B | D | B | D |
| 181 | A | B | B | B |
| 182 | B | B | D | D |
| 183 | B | D | D | D |
| 184 | A | A | A | A |
| 185 | B | B | B | D |
| 186 | D | D | B | D |
| 187 | B | B | B | B |
| 188 | A | A | A | A |
| 189 | A | A | A | B |
| 190 | A | A | A | A |
| 191 | A | A | A | A |
| 192 | A | A | A | A |
| 193 | A | A | A | B |
| 194 | A | B | A | A |
| 195 | A | A | A | A |
| 196 | A | B | A | A |
| 197 | A | A | A | A |
| 198 | B | B | A | A |
| 199 | A | A | A | A |
| 200 | A | A | A | A |
| 201 | B | B | A | B |
| 202 | B | B | A | A |
| 203 | A | B | A | A |
| 204 | B | B | A | A |
| 205 | A | A | A | A |

TABLE 5-continued

| Biological Activity - Low-Volume Cereal Activity at 121.5 g/H | | | | |
|---|---|---|---|---|
| | PUCCRT* | | SEPTTR* | |
| Cmpd. No. | 1DP* | 3DC* | 1DP* | 3DC* |
| 206 | A | A | A | A |
| 207 | A | A | A | A |
| 208 | A | B | A | B |
| 209 | B | D | B | B |
| 210 | A | B | A | A |
| 211 | B | D | A | A |
| 212 | A | A | A | A |
| 213 | A | A | A | A |
| 214 | A | A | A | A |
| 215 | A | A | A | A |
| 216 | B | B | A | B |
| 217 | D | D | B | B |
| 218 | B | B | A | B |
| 219 | B | B | B | B |
| 220 | B | B | A | A |
| 221 | A | B | A | A |
| 222 | A | D | A | A |
| 223 | A | B | A | A |
| 224 | B | D | B | B |
| 225 | B | B | B | B |
| 226 | B | D | B | B |
| 227 | B | B | A | B |
| 228 | B | B | A | B |
| 229 | B | D | A | B |
| 230 | A | B | A | A |
| 231 | B | B | B | B |
| 232 | B | D | B | B |
| 233 | A | B | B | B |
| 234 | A | A | B | A |
| 235 | A | B | A | B |
| 236 | A | B | A | B |
| 237 | A | A | B | B |
| 238 | A | B | B | B |
| 239 | A | B | A | B |
| 240 | A | A | B | A |
| 241 | A | B | A | A |
| 242 | A | A | A | A |
| 243 | A | A | B | B |
| 244 | A | A | B | A |
| 245 | A | A | D | B |
| 246 | B | B | A | B |
| 247 | B | D | B | B |
| 248 | A | B | D | B |
| 249 | A | B | A | B |
| 250 | B | B | B | D |
| 251 | A | B | B | A |
| 252 | A | A | A | A |
| 253 | A | B | A | B |
| 254 | A | B | A | A |
| 255 | A | A | B | A |
| 256 | A | A | D | D |
| 257 | A | D | D | B |
| 258 | B | B | B | B |
| 259 | B | D | D | B |
| 260 | A | B | A | B |
| 261 | A | B | B | B |
| 262 | A | B | B | D |
| 263 | B | B | B | B |
| 264 | B | D | B | D |
| 265 | A | B | A | B |
| 266 | A | B | B | D |
| 267 | B | D | B | B |
| 268 | A | A | B | B |
| 269 | A | B | A | A |
| 270 | A | B | B | D |
| 271 | B | D | B | D |
| 272 | B | B | A | D |
| 273 | B | B | A | B |
| 274 | A | B | B | D |
| 275 | A | B | B | D |
| 276 | A | D | A | B |
| 277 | A | B | A | D |
| 278 | A | B | B | B |
| 279 | A | B | B | A |
| 280 | A | A | B | A |
| 281 | A | B | B | A |
| 282 | A | D | B | B |
| 283 | A | A | B | A |
| 284 | C | C | C | C |

*PUCCRT—Wheat Brown Rust (*Puccinia triticina*)
*SEPTTR—Wheat Leaf Blotch (*Zymoseptoria tritici*)
*1DP—1 Day Protectant
*3DC—3 Day Curative

TABLE 6

| Biological Activity - Disease Control at 25 ppm | | |
|---|---|---|
| | PHAKPA* | |
| Cmpd. No. | 1DP* | 3DC* |
| 169 | A | B |
| 240 | A | B |
| 242 | B | D |

*PHAKPA—Asian Soybean Rust (*Phakopsora pachyrhizi*)
*1DP—1 Day Protectant
*3DC—3 Day Curative

What is claimed is:

1. A compound of Formula I

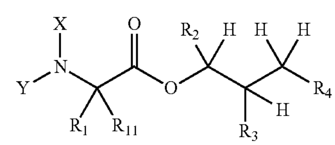

I wherein

X is hydrogen or $C(O)R_5$;

Y is hydrogen, $C(O)R_5$, or Q;

Q is $R_1$ is $CH_2OCH_3$, or hydrogen or alkyl, where alkyl is optionally substituted with 0, 1 or multiple $R_8$;

$R_2$ is methyl;

$R_3$ is chosen from $C(O)OCH_3$ or alkyl, alkenyl, or aryl, each optionally substituted with 0, 1 or multiple $R_8$;

$R_4$ is chosen from alkyl or aryl, each optionally substituted with 0, 1 or multiple $R_8$;

$R_5$ is alkoxy, optionally substituted with 0, 1, or multiple $R_8$;

$R_6$ is chosen from hydrogen or alkoxy, where alkoxy is optionally substituted with 0, 1, or multiple $R_8$;

$R_7$ is chosen from hydrogen, $C(O)R_9$, or $CH_2OC(O)R_9$;

$R_8$ is chosen from hydrogen, alkyl, aryl, halo, alkenyl, or phenoxy, each optionally substituted with 0, 1, or multiple $R_{10}$, $R_9$ is chosen from alkyl, alkoxy, or aryl, each optionally substituted with 0, 1, or multiple $R_8$;

$R_{10}$ is chosen from alkyl, aryl, halo, haloalkyl, haloaryl, alkenyl, or alkoxy; and $R_{11}$ is chosen from hydrogen or methyl.

2. A compound according to claim 1, wherein X and Y are hydrogen.

3. A compound according to claim 2, wherein $R_1$ and $R_{11}$ are independently chosen from hydrogen or methyl.

4. A compound according to claim 2, wherein $R_3$ is independently chosen from alkyl or aryl, each optionally substituted with 0, 1 or multiple $R_8$.

5. A compound according to claim 2, wherein $R_1$ and $R_{11}$ are independently chosen from hydrogen or methyl, and $R_3$ is independently chosen from alkyl or aryl, each optionally substituted with 0, 1 or multiple $R_8$.

6. A compound according to claim 1, wherein X is $C(O)R_5$ and Y is hydrogen.

7. A compound according to claim 6, wherein $R_1$ and $R_{11}$ are independently chosen from hydrogen or methyl.

8. A compound according to claim 6, wherein $R_3$ is independently chosen from alkyl or aryl, each optionally substituted with 0, 1 or multiple $R_8$.

9. A compound according to claim 6, wherein $R_1$ and $R_{11}$ are independently chosen from hydrogen or methyl, and $R_3$ is independently chosen from alkyl or aryl, each optionally substituted with 0, 1 or multiple $R_8$.

10. A compound according to claim 1, wherein X is hydrogen and Y is Q.

11. A compound according to claim 10, wherein $R_7$ is hydrogen.

12. A compound according to claim 11, wherein $R_6$ is $OCH_3$.

13. A compound according to claim 12, wherein $R_1$ and $R_{11}$ are independently chosen from hydrogen or methyl.

14. A compound according to claim 12, wherein $R_3$ is independently chosen from alkyl or aryl, each optionally substituted with 0, 1 or multiple $R_8$.

15. A compound according to claim 12, wherein $R_1$ and $R_{11}$ are independently chosen from hydrogen or methyl, and $R_3$ is independently chosen from alkyl or aryl, each optionally substituted with 0, 1 or multiple $R_8$.

16. A compound according to claim 10, wherein $R_7$ is $C(O)R_9$, or $CH_2OC(O)R_9$.

17. A compound according to claim 16, wherein $R_1$ and $R_{11}$ are independently chosen from hydrogen or methyl.

18. A compound according to claim 16, wherein $R_3$ is independently chosen from alkyl or aryl, each optionally substituted with 0, 1 or multiple $R_8$.

19. A compound according to claim 16, wherein $R_1$ and $R_{11}$ are independently chosen from hydrogen or methyl, and $R_3$ is independently chosen from alkyl or aryl, each optionally substituted with 0, 1 or multiple $R_8$.

* * * * *